(12) United States Patent
Kim et al.

(10) Patent No.: US 11,685,791 B2
(45) Date of Patent: *Jun. 27, 2023

(54) ANTIBODY BINDING SPECIFICALLY TO N-TERMINAL REGION OF LYSYL-TRNA SYNTHETASE EXPOSED ON CELL MEMBRANE

(71) Applicant: Zymedi Co., Ltd., Incheon (KR)

(72) Inventors: Sunghoon Kim, Seoul (KR); Hyunbo Shim, Seoul (KR); Nam Hoon Kwon, Gyeonggi-do (KR); Daeyoung Han, Gyeonggi-do (KR)

(73) Assignee: Zymedi Co., Ltd., Incheon (KR)

( * ) Notice: Subject to any disclaimer, the term of this patent is extended or adjusted under 35 U.S.C. 154(b) by 536 days.

This patent is subject to a terminal disclaimer.

(21) Appl. No.: 16/498,505

(22) PCT Filed: Mar. 27, 2018

(86) PCT No.: PCT/KR2018/003594
§ 371 (c)(1),
(2) Date: Sep. 27, 2019

(87) PCT Pub. No.: WO2018/182284
PCT Pub. Date: Oct. 4, 2018

(65) Prior Publication Data
US 2020/0102402 A1     Apr. 2, 2020

(30) Foreign Application Priority Data

Mar. 27, 2017 (KR) .................. 10-2017-0038775
Sep. 15, 2017 (KR) .................. 10-2017-0118890
Sep. 15, 2017 (KR) .................. 10-2017-0118917

(51) Int. Cl.
*C07K 16/40* (2006.01)
*C12N 15/52* (2006.01)
*G01N 33/574* (2006.01)

(52) U.S. Cl.
CPC .............. *C07K 16/40* (2013.01); *C12N 15/52* (2013.01); *G01N 33/574* (2013.01)

(58) Field of Classification Search
CPC ....... C07K 16/40; C12N 15/52; G01N 33/574
See application file for complete search history.

(56) References Cited

U.S. PATENT DOCUMENTS

| | | | |
|---|---|---|---|
| 8,962,560 B2 | 2/2015 | Greene et al. | |
| 9,511,085 B2 | 12/2016 | Kim et al. | |
| 2005/0277157 A1 | 12/2005 | Rose et al. | |
| 2013/0243745 A1* | 9/2013 | Greene ................. | A61P 29/00 514/6.9 |
| 2016/0377619 A1 | 12/2016 | Kim et al. | |
| 2021/0070880 A1* | 3/2021 | Kwon ................ | A61K 39/0005 |

FOREIGN PATENT DOCUMENTS

| | | |
|---|---|---|
| JP | 2012-500256 A | 1/2012 |
| JP | 2013532965 A | 8/2013 |
| KR | 10-2010-0040583 A | 4/2010 |
| KR | 10-2015-0079476 A | 7/2015 |
| WO | 2010021415 A1 | 2/2010 |
| WO | 2011153277 A2 | 12/2011 |
| WO | 2019054819 A1 | 3/2019 |

OTHER PUBLICATIONS

Almagro & Fransson, Humanization of antibodies, Frontiers in Bioscience 2008; 13: 1619-33 (Year: 2008).*
Oct. 1, 20206—(AU) Examination Report—App No. 2018244677.
Nov. 4, 2020—(JP) Office Action—App No. 2019-553434.
Park et al. "Human lysyl-tRNA synthetase is secreted to trigger proinflammatory response" PNAS, vol. 102, No. 18, May 3, 2005, pp. 6356-6361.
Yoshifuji et al. "Anti-aminoacyl-tRNA synthetase antibodies in clinical course prediction of interstitial lung disease complicated with idiopathic inflammatory myopathies" Autoimunity, May 2006; 39(3): 233-241.
Aug. 22, 2018 (WO)—International Search Report PCT/KR2018/003594.
Kim et al. "Chemical inhibition of prometastic lysyl-tRNA synthetase-maminin receptor interaction" Nature Chemical Biology, vol. 10, Jan. 2014.
Jeon et al. "Function of membranous lysyl-tRNA synthetase and its implication for tumorigenesis" Biochimica et Biophysica Acta 1864 (2016) 1707-1713.
Dec. 18, 2020 (EP) European Search Report Application No. 18777477.3.

* cited by examiner

*Primary Examiner* — Peter J Reddig
*Assistant Examiner* — Cheng Lu
(74) *Attorney, Agent, or Firm* — Banner & Witcoff, Ltd.

(57) ABSTRACT

The present invention relates to an antibody binding specifically to an N-terminal region of lysyl-tRNA synthetase which is exposed on the cell membrane and a use thereof.

8 Claims, 35 Drawing Sheets
(18 of 35 Drawing Sheet(s) Filed in Color)
Specification includes a Sequence Listing.

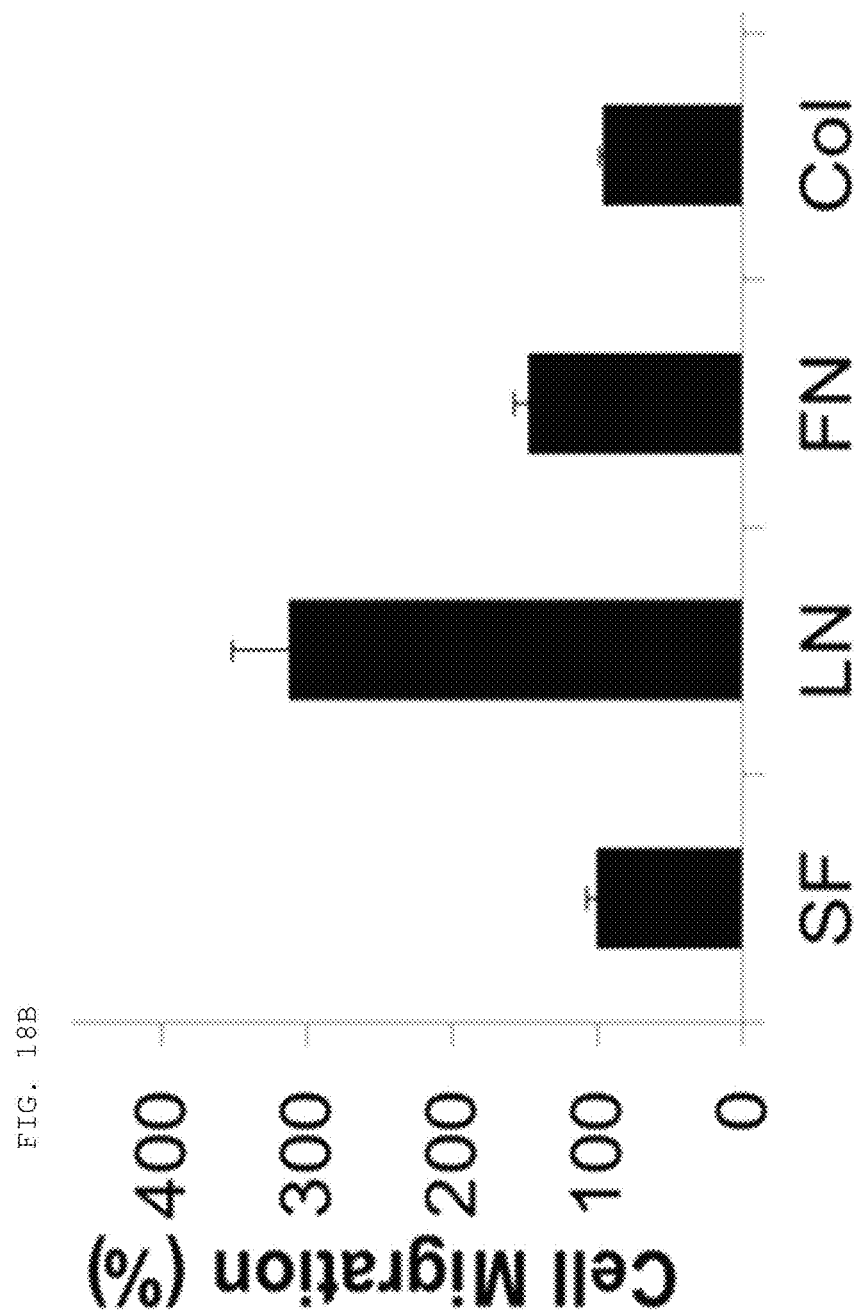

FIG. 20C

ANTIBODY BINDING SPECIFICALLY TO N-TERMINAL REGION OF LYSYL-TRNA SYNTHETASE EXPOSED ON CELL MEMBRANE

RELATED APPLICATION DATA

This application is a National Stage Application under 35 U.S.C. 371 of co-pending PCT application number PCT/KR2018/003594 designating the United States and filed Mar. 27, 2018; which claims the benefit of Korean Patent Application No. 10-2017-0038775 filed Mar. 27, 2017, Korean Patent Application No. 10-2017-0118890 filed Sep. 15, 2017 and Korean Patent Application No. 10-2017-0118917 filed Sep. 15, 2017, the entire specifications of which are incorporated herein by reference in their entireties.

SEQUENCE LISTING

The instant application contains a Sequence Listing which has been filed electronically in ASCII format and is hereby incorporated by reference in its entirety. Said ASCII copy, created on Dec. 12, 2019, is named 009041_00002_US_SL.txt and is 232,975 bytes in size.

TECHNICAL FIELD

The present invention relates to an antibody or fragment thereof specifically binding to an extracellularly exposed lysyl-tRNA synthetase N-terminal region and use thereof and, more specifically, to an antibody or fragment thereof having particular complementary determining region (CDR) sequences defined in the present specification and specifically binding to an epitope containing the sequence of SEQ ID NO: 97 in the lysyl-tRNA synthetase (KRS) N-terminus, to use of the antibody or fragment thereof for inhibition of cancer metastasis, to use of the antibody or fragment thereof for cancer diagnosis, and to a pharmaceutical composition for the prevention or treatment of an immune cell migration-related disease.

BACKGROUND ART

Recent studies have established that human lysyl-tRNA synthetase (KPS) generally present in the cytosol translocates to the plasma membrane (cell membrane) to interact with a 67-kDa laminin receptor (67LR) present on the plasma membrane, thereby promoting the migration of tumor (or cancer) cells to affect cancer metastasis (Dae Gyu Kim et al., Chemical inhibition of prometastatic lysyl-tRNA synthetaselaminin receptor interaction, Nat Chem Biol. 2014 January; 10(1): 2934, Dae Gye Kim et. al. Interaction of two translational components, lysyl-tRNA synthetase and p40/37LRP, in plasma membrane promotes laminin-dependent cell migration, FASEB J. (2012)26, 4142-4159). Human KRS (Genbank Accession No. NP_005539.1, etc) comprises an N-terminal extension (1-72), an anticodon-binding domain (73-209), and a catalytic domain (220-597). Human KRS is an enzyme essential for protein synthesis, and normally resides within the multi-tRNA synthetase complex (MSC) in the cytosol. However, after the introduction of laminin signal, p38 MAPK phosphorylates KRS at the T52 residues, and KRS translocates to the cell membrane, where KRS protects 67LR from ubiquitin-mediated degradation. It has also been reported that KRS translocated to the cell membrane accelerates cancer metastasis by stabilizing and interacting with 67LR associated with cancer metastasis.

Meanwhile, immune cells are involved in a primary defense mechanism in the body, but excessive activation of immune cells has been recently reported as one of main pathogeneses. Increased mobility of immune cells are normally observed upon the activation of inflammatory immune cells, and specifically, such immune cell migration and invasion are reported to be closely involved in disease pathology in the following diseases.

For instance, a cardiovascular disease whose lesions occur in the heart and major arteries, includes atherosclerosis and a coronary artery disease (Ross R et al., New Engl J Med, 1999:340(2):115-26, Poli G et al., Redox Biol 2013; 1(1):125-30, Libby P et al., Circulation 2002; 5; 105(9): 1135-43). Atherosclerosis is an inflammatory disease triggered by cholesterol, and is caused by atheroma composed of cholesterol deposited on the inner membrane of an artery and immune cells migrating from the blood to the inside of an artery. That is, atheroma is formed by migration of immune cells, such as monocytes, to a site where oxidized cholesterol cause inflammation. The formation of atheroma roughens the interior surface of blood vessels and thickens the wall of blood vessels, and thus the inner diameter of the blood vessels becomes narrowed, resulting in circulatory disturbances. The bursting of fibrous membranes surrounding atheroma causes thrombi in the blood vessels and bleeding in atheroma, and thus the inner diameter of the blood vessels becomes rapidly narrowed or the blood vessels become blocked. This occurs mainly in blood vessels supplying blood to the heart, blood vessels supplying blood to the brain, blood vessels supplying blood to kidneys, and peripheral blood vessels, thereby causing an ischemic heart disease, an ischemic cerebrovascular disease (stroke), kidney failure, and a limb ischemic arterial disease. It has been known in the past that CC chemokine ligand 2 (CCL2, MCP-1), which causes an inflammatory response by inducing the migration of monocytes, plays an important role in the occurrence and development of such cardiovascular diseases, and therefore, new measures to treat such cardiovascular diseases by inhibiting the action of CCL2 and the resultant migration of monocytes have been suggested (Gu L et al., Mol Cell, 1998; 2(2):275-81, Aiello R J et al., Arterioscler Thromb Vasc Biol 1999; 19(6):1518-25, Gosling J1 et al., Clin Invest 1999; 103(6):773-8, Harrington J R et al., Stem Cells 2000; 18(1):65-6, Ikeda U et al., Clin Cardiol 2002; 25(4):143-7).

Pulmonary arterial hypertension (PAH) is classified as Group 1 in the clinical classification system (ESC Guidelines, European Heart Journal 2015) of the World Health Organization (WHO), and is a rare disease clinically characterized by difficulty in breathing, an increase in mean pulmonary artery pressure (mPAP, mPAP>25 mm Hg), and right ventricular dysfunction. Several pre-existing factors, such as heredity, infection, and related diseases, are involved in such pulmonary arterial hypertension, but the immune response resulting from endothelial cell injury has been known to act as a key pathological factor (Huertas et al., Circulation, 129:1332-1340, 2014). As for such a phenomenon, a series of processes according to the invasion and dysfunction of immune cells has been known to be deeply associated with pathological phenomena, and especially, the interaction between immune cells and vascular endothelial cells is known to be important in PAH. It has also been reported that the invasion of monocytes and macrophages accelerates the progress of Alport syndrome.

In fibrosis-related diseases, the continued (chronic) inflammatory responses activate the wound-healing program, leading to fibrosis. After tissue injury, inflammatory immune cells, such as monocytes/macrophages, neutrophils, eosinophils, and mast cells, invade the injured site rapidly while being activated, and secrete various cytokines, which in turn activate surrounding fibroblasts, epithelial cells, or smooth muscle cells into myoblast type cells, and these myoblast type cells produce and secrete extracellular matrix proteins in large quantities, ultimately causing the accumulation of extracellular matrix proteins in large quantities, and resulting in scar formation and tissue fibrosis or hypertrophy (Gurtner G C et al., Trends Cell Biol. 15: 599-607, 2005). This pathology is one of the fundamental causes of: scar formation in skin tissues, caused by skin wounds due to cuts, burns, bedsores, and the like; or sclerosing fibrosis of liver, kidney, vascular, and pulmonary tissues. Fibrosis is also shown to be a major pathological characteristic in chronic autoimmune diseases, such as scleroderma, rheumatoid arthritis, Crohn's disease, ulcerative colitis, myelofibrosis, and systemic lupus erythematosus. It has also been known that the activation of inflammatory immune cells contribute to pathology in atopic diseases, asthma, COPD, psoriasis, kelloid, proliferative retinopathy, and the like.

Especially in the wound-healing program, fibroblasts activated into myoblast type cells are called myofibroblasts. Since myofibroblasts are at the center of all the disease pathologies associated with fibrosis, eliminating molecular or immunological mechanisms inducing the activity of myofibroblasts is a key element of disease treatment. It has been widely known that many types of innate immunity or adaptive immunity are important in the activation and differentiation of fibroblasts, and therefore, eliminating an inflammatory response in the wound site is a key factor in stopping tissue remodeling into fibrosis and maintaining normal tissue morphology. However, since the inflammatory response is not easily eliminated in practice, understanding the mechanisms of innate and adaptive immunity to find key mediators is important in slowing fibrosis.

In some cases, monocytes, macrophages, and the like contribute to wound healing, but secrete reactive oxygen, nitrogen, and the like, and thus have harmful effects on surrounding cells. Therefore, monocytes and macrophages, if not rapidly removed, cause more tissue injury, resulting in fibrosis. Therefore, restricting monocytes and macrophages, which respond first in the early stages of the disease, is considered a therapeutic strategy for various chronic inflammation- and fibrotic-related diseases.

It has been known that when the wound healing mechanism triggers a fibrosis response, the platelet-derived growth factor (PDGF) associated with hemagglutination recruits other inflammatory immune cells into the wound site and TGF-β1 accelerates extracellular matrix synthesis from local fibroblasts. It has been however reported that the factors involved in hemagglutination induce fibrosis even when the factors are deficient.

Meanwhile, the fact that Myc-KRS41-597 (ΔN) with a deletion of 40 terminal residues in N-terminal extension (N-ext) is not localized on the plasma membrane indicates that the KRS N-ext region is an essential region in the translocation of KRS to the cell membrane. As for cancer metastasis, specifically, the KRS N-ext region has been known to be involved in the binding of KRS and 67LR in the interaction thereof. To use this fact for therapeutic or diagnostic purposes, it is necessary to specifically target a particular site (especially, KRS N-ext) in the KRS protein according to the characteristics of several domains constituting the KRS protein.

However, despite the importance of aminoacyl-tRNA synthetases (ARSs) including KRS as biomarkers, ARSs are similar in view of the protein structure, and thus the antibodies obtained via immunization of animals with a ARS protein show a cross reactivity, for example, binding with other ARSs, and in many cases, high-sensitive antibodies are not even produced.

In the diseases caused by excessive activation of immune cells as mentioned above, target factors for preventing the translocation (and invasion) of immune cells have been conventionally suggested, and attempts have been made to devise therapeutic methods to treat diseases regulating the target factors, but respective limitations thereof are being reported. Therefore, for effective disease treatment, it is still a critical challenge to establish what the key mediator is and what strategy will control the key mediator, in the mitigation of immune cells.

DETAILED DESCRIPTION OF THE INVENTION

Technical Problem

While studying to construct an antibody specifically binding to an extracellularly exposed KRS N-terminal region, the present inventors verified that antibodies having particular complementary determining region (CDR) sequences defined in the present specification showed very high binding specificity and affinity to the KRS N-terminal region as well as inhibited cancer metastasis in vivo. Furthermore, the present inventors verified that an increase in KRS level in the cellular membrane of immune cells (monocytes/macrophages) is an important pathological phenomenon in immune cell migration- and invasion-related diseases, and thus KRS has a particular correlation with laminin (especially, laminin subtype α4β2γ1), and verified that KRS N-terminus binding antibodies provided in the present invention reduced the KRS level increased on the cell membrane of immune cells and actually inhibited the migration and infiltration of immune cells, and thus had an effect of treating related diseases, and therefore the present inventors completed the present invention.

Therefore, an aspect of the present invention is to provide an antibody or fragment thereof specifically binding to an epitope containing the sequence of SEQ ID NO: 97 in the lysyl-tRNA synthetase (KRS) N-terminus.

Another aspect of the present invention is to provide a polynucleotide encoding the antibody or fragment thereof of the present invention, a recombinant expression vector comprising the polynucleotide, and a cell transformed with the recombinant vector.

Still another aspect of the present invention is to provide a method for producing an antibody or fragment thereof specifically binding to an extracellularly exposed lysyl-tRNA synthetase (KRS) N-terminal region, the method comprising: (a) transforming host cells with the recombinant expression vector; (b) incubating the transformed host cells to produce an antibody or fragment thereof; and (c) collecting the antibody or fragment thereof produced in the host cells.

Still another aspect of the present invention is to provide a pharmaceutical composition comprising the antibody or fragment thereof of the present invention as an active ingredient for inhibition of cancer metastasis.

Still another aspect of the present invention is to provide a pharmaceutical composition consisting of the antibody or fragment thereof of the present invention for inhibition of cancer metastasis.

Still another aspect of the present invention is to provide a pharmaceutical composition essentially consisting of the antibody or fragment thereof of the present invention for inhibition of cancer metastasis.

Still another aspect of the present invention is to provide a composition comprising the antibody or fragment thereof of the present invention as an active ingredient for cancer diagnosis.

Still another aspect of the present invention is to provide a composition consisting of the antibody or fragment thereof of the present invention for cancer diagnosis.

Still another aspect of the present invention is to provide a composition essentially consisting of the antibody or fragment thereof of the present invention for cancer diagnosis.

Still another aspect of the present invention is to provide a pharmaceutical composition comprising the antibody or fragment thereof of the present invention as an active ingredient for the prevention or treatment of an immune cell migration-related disease.

Still another aspect of the present invention is to provide a pharmaceutical composition consisting of the antibody or fragment thereof of the present invention for the prevention or treatment of an immune cell migration-related disease.

Still another aspect of the present invention is to provide a pharmaceutical composition essentially consisting of the antibody or fragment thereof of the present invention for the prevention or treatment of an immune cell migration-related disease.

Still another aspect of the present invention is to provide use of the antibody or fragment thereof of the present invention for preparing an agent for inhibition of cancer metastasis.

Still another aspect of the present invention is to provide a method for inhibiting cancer metastasis in a subject in need thereof, the method comprising administering the antibody or fragment thereof of the present invention to the subject in an amount effective for inhibiting cancer metastasis.

Still another aspect of the present invention is to provide use of the antibody or fragment thereof of the present invention for preparing an agent for cancer diagnosis.

Still another aspect of the present invention is to provide a method for diagnosing cancer in a subject in need thereof, the method comprising administering the antibody or fragment thereof of the present invention to the subject in an amount effective for diagnosing cancer.

Still another aspect of the present invention is to provide use of the antibody or fragment thereof of the present invention for preparing an agent for the treatment of an immune cell migration-related disease.

Still another aspect of the present invention is to provide a method for treating an immune cell migration-related disease in a subject in need thereof, the method comprising administering the antibody or fragment thereof of the present invention to the subject in an amount effective for treating an immune cell migration-related disease.

Technical Solution

In accordance with an aspect of the present invention, there is provided an antibody or fragment thereof specifically binding to an epitope containing the sequence of SEQ ID NO: 97 in the lysyl-tRNA synthetase (KRS) N-terminus.

In accordance with another aspect of the present invention, there is provided a polynucleotide encoding the antibody or fragment thereof of the present invention, a recombinant expression vector comprising the polynucleotide, and a cell transformed with the recombinant vector.

In accordance with still another aspect of the present invention, there is provided a method for producing an antibody or fragment thereof specifically binding to an extracellularly exposed lysyl-tRNA synthetase (KRS) N-terminal region, the method comprising: (a) transforming host cells with the recombinant expression vector; (b) incubating the transformed host cells to produce an antibody or fragment thereof; and (c) collecting the antibody or fragment thereof produced in the host cells.

In accordance with still another aspect of the present invention, there is provided a pharmaceutical composition comprising the antibody or fragment thereof of the present invention as an active ingredient for inhibition of cancer metastasis.

In accordance with still another aspect of the present invention, there is provided a pharmaceutical composition consisting of the antibody or fragment thereof of the present invention for inhibition of cancer metastasis.

In accordance with still another aspect of the present invention, there is provided a pharmaceutical composition essentially consisting of the antibody or fragment thereof of the present invention for the inhibition of cancer metastasis.

In accordance with still another aspect of the present invention, there is provided a composition comprising the antibody or fragment thereof of the present invention as an active ingredient for cancer diagnosis.

In accordance with still another aspect of the present invention, there is provided a composition consisting of the antibody or fragment thereof of the present invention for cancer diagnosis.

In accordance with still another aspect of the present invention, there is provided a composition essentially consisting of the antibody or fragment thereof of the present invention as an active ingredient for cancer diagnosis.

In accordance with still another aspect of the present invention, there is provided a pharmaceutical composition comprising the antibody or fragment thereof of the present invention as an active ingredient for the prevention or treatment of an immune cell migration-related disease.

In accordance with still another aspect of the present invention, there is provided a pharmaceutical composition consisting of the antibody or fragment thereof of the present invention for the prevention or treatment of an immune cell migration-related disease.

In accordance with still another aspect of the present invention, there is provided a pharmaceutical composition essentially consisting of the antibody or fragment thereof of the present invention for the prevention or treatment of an immune cell migration-related disease.

In accordance with still another aspect of the present invention, there is provided use of the antibody or fragment thereof of the present invention for preparing an agent for inhibition of cancer metastasis.

In accordance with still another aspect of the present invention, there is provided a method for inhibiting cancer metastasis in a subject in need thereof, the method comprising administering the antibody or fragment thereof of the present invention to the subject in an amount effective for inhibiting cancer metastasis.

In accordance with still another aspect of the present invention, there is provided use of the antibody or fragment thereof of the present invention for preparing an agent for cancer diagnosis.

In accordance with still another aspect of the present invention, there is provided a method for diagnosing cancer in a subject in need thereof, the method comprising administering the antibody or fragment thereof of the present invention to the subject in an amount effective for diagnosing cancer.

In accordance with still another aspect of the present invention, there is provided use of the antibody or fragment thereof of the present invention for preparing an agent for treatment of an immune cell migration-related disease.

In accordance with still another aspect of the present invention, there is provided a method for treating an immune cell migration-related disease in a subject in need thereof, the method comprising administering the antibody or fragment thereof of the present invention to the subject in an amount effective for treating an immune cell migration-related disease.

Hereinafter, the present invention will be described in detail.

As used herein, the term "extracellularly exposed lysyl-tRNA synthetase (KRS) N-terminal region" refers to a particular sequence exposed to the extracellular space or on the surface of the cell membrane when KM produced in cells is translocated to the cell membrane (or plasma membrane), and may normally refer to a partial or full-length sequence of a 1- to 72-amino acid region in the KRS N-terminus. In addition, there is sequence similarity across species in the KRS N-terminal region, and especially, the KRS N-terminal region may contain the amino acid sequence defined by SEQ ID NO: 97. Preferably, the KRS N-terminal region contains the sequence defined by SEQ ID NO: 75 for humans, the sequence defined by SEQ ID NO: 113 for mice, and the sequence defined by SEQ ID NO: 114 for rats.

As used herein, the term "KRS" refers to the full-length polypeptide known as lysyl-tRNA synthetase or any KRS fragment sequence comprising the N-terminal region. As described above, the antibodies or fragments thereof according to the present invention specifically detect the extracellularly exposed KRS N-terminal region, and thus also can detect the foregoing KRS full-length polypeptide or any KRS fragment sequence containing the N-terminal region. The specific sequence of KRS is not particularly limited as long as the sequence contains the polypeptide defined by SEQ ID NO: 75 and is known as lysyl-tRNA synthetase in the art. For instance, KRS of the present invention includes: a sequence derived from a human (*Homo sapiens*) and known as NCBI (Genbank) Accession No. NP_005539.1 or the like; a sequence derived from a mouse (*Mus musculus*) and known as NCBI (Genbank) Accession No. NP_444322.1 or the like; and a sequence derived from a rat (*Rattus norvegicus*) and known as NCBI (Genbank) Accession No. XP 006255692.1 or the like, and besides, reference may be made to the following sequence information, but is not limited thereto: XP_005004655.1 (guinea-pig: *Cavia porcellus*), XP_021503253.1 (gerbil, *Meriones unguiculatus*), XP_002711778.1 (rabbit, *Oryctolagus cuniculus*), XP_536777.2 (dog, *Canis lupus familiaris*), XP_003126904.2 (swine, *Sus scrofa*), XP_011755768.1 (monkey, *Macaca nemestrina*), XP_008984479.1 (marmoset, *Callithrix jacchus*), XP_019834275.1 (cow, *Bos indicus*), and XP_511115.2 (chimpanzee, Pan troglodytes). Most preferably, KRS may be a polypeptide consisting of the amino acid sequence defined by SEQ ID NO: 76 (Genbank Accession No. NP_005539.1).

In the present invention, the antibody is also called immunoglobulin (Ig) and is a generic term for proteins that are involved in biological immunity by selectively acting on antigens. A whole antibody found in nature usually consists of two pairs of light chain (LC) and heavy chain (HC), each of which is a polypeptide composed of several domains, or has two pairs of HC/LC as a basic unit. There are five types of heavy chains constituting mammalian antibodies, which are denoted by the Greek letters: α, δ, ε, γ, and μ, and different types of heavy chains constitute different types of antibodies: IgA, IgD, IgE, IgG and IgM, respectively. There are two types of light chains constituting mammalian antibodies, which are denoted by λ and κ.

The heavy and light chains of antibodies are structurally divided into a variable region and a constant region according to the variability of amino acid sequence. The constant region of the heavy chain is composed of three or four heavy chain constant regions, such as CH1, CH2, and CH3 (IgA, IgD, and IgG antibodies) and CH4 (IgE and IgM antibodies), according to the type of antibody, and the light chain has one constant region CL. The variable regions of the heavy and light chains are each composed of one domain of a heavy chain variable region (VH) or a light chain variable region (VL). The light chain and the heavy chain are linked to each other by one covalent disulfide linkage while variable regions and constant regions thereof are arranged in parallel, and two heavy chain molecules, which are linked with the light chains, are linked to each other by two covalent disulfide linkages, thereby forming a whole antibody. The whole antibody specifically binds to an antigen through the variable regions of the heavy and light chains. The whole antibody is composed of two pairs of heavy and light chains (HC-LC), and thus one whole antibody molecule has divalent mono-specificity in which one whole antibody molecule binds to two same antigens through two variable regions.

The variable regions of the antibody, which comprise antigen-binding sites, are each divided into framework regions (FRs) with low sequence variability and complementary determining regions (CDRs), which are hypervariable regions with high sequence variability. In VH and VL, three CDRs and four FRs are arranged in the order of FR1-CDR1-FR2-CDR2-FR3-CDR3-FR4 in a direction from the N-terminal to the C-terminal. CDRs, which have the highest sequence variability in the variable regions of the antibody, are sites that directly bind to an antigen, and are very important in antigen specificity of the antibody.

The present invention provides an antibody or fragment thereof specifically binding to an epitope containing the sequence of SEQ ID NO: 97 in the lysyl-tRNA synthetase (KRS) N-terminus.

As used herein, the "epitope" refers to a protein determinant capable of specifically binding to an antibody. An epitope is usually composed of surface groups of molecules, such as amino acids or sugar side chains, and usually have specific three-dimensional structural characteristics as well as specific charge characteristics. Conformational and non-conformational epitopes are distinguished from each other in that the binding to the conformational epitopes but not the non-conformational epitopes is lost in the presence of denaturing solvents. An epitope may comprise amino acid residues directly involved in the binding (also called immunogenic component of the epitope) and other amino acid residues not directly involved in the binding, for example, amino acid residues effectively blocked by the specific antigen binding peptide (in other words, the amino acid residue being within the footprint of the specific antigen binding peptide).

Preferably, the epitope is a site to which the N3 monoclonal antibody of the present invention derived from the KRS N-terminal sequence binds, and the specific sequence thereof is not particularly limited as long as the sequence is a consecutive region comprising amino acids (klsknelkrrlka) defined by SEQ ID NO: 97, and may usually consist of a 13-52 amino acid sequence, more preferably, a 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 amino acid sequence, comprising the amino acid sequence of SEQ ID NO: 97.

Preferably, the epitope of the present invention may include the amino acid sequences defined by SEQ ID NO: 75, SEQ ID NO: 98, SEQ ID NO: 99, SEQ ID NO: 100, and SEQ ID NO: 101, which are derived from the human KRS N-terminus; the amino acid sequences defined by SEQ ID NO: 113, SEQ ID NO: 103, SEQ ID NO: 104, SEQ ID NO: 105, and SEQ ID NO: 106, which are derived from the mouse KRS N-terminus; and the amino acid sequences defined by SEQ ID NO: 114, SEQ ID NO: 108, SEQ ID NO: 109, SEQ ID NO: 110, and SEQ ID NO: 111, which are derived from the rat KRS N-terminus. The epitope may be more preferably the amino acid sequence at positions 15 to 29 in the human KRS N-terminal region defined by SEQ ID NO: 75 (SEQ ID NO: 75, SEQ ID NO: 98, SEQ ID NO: 99, SEQ ID NO: 100, and SEQ ID NO: 101), and most preferably the amino acid sequence at positions 15 to 42 in the human KRS N-terminal region defined by SEQ ID NO: 75 (SEQ ID NO: 101).

The "antibody or fragment thereof specifically binding to an extracellularly exposed KRS N-terminal region" provided in the present invention comprises:

a heavy chain variable region (VH) comprising: heavy chain complementary determining region 1 (CDR1) containing the amino acid sequence selected from the group consisting of SEQ ID NO: 1, SEQ ID NO: 13, SEQ ID NO: 25, and SEQ ID NO: 37; heavy chain complementary determining region 2 (CDR2) containing the amino acid sequence selected from SEQ ID NO: 3, SEQ ID NO: 15, SEQ ID NO: 27, and SEQ ID NO: 39; and heavy chain complementary determining region 3 (CDR3) containing the amino acid sequence selected from SEQ ID NO: 5, SEQ ID NO: 17, SEQ ID NO: 29, and SEQ ID NO: 41; and a light chain variable region (VL) comprising: light chain complementary determining region 1 (CDR1) containing the amino acid sequence selected from the group consisting of SEQ ID NO: 7, SEQ ID NO: 19, SEQ ID NO: 31, and SEQ ID NO: 43; light chain complementary determining region 2 (CDR2) containing the amino acid sequence selected from SEQ ID NO: 9, SEQ ID NO: 21, SEQ ID NO: 33, and SEQ ID NO: 45; and light chain complementary determining region 3 (CDR3) containing the amino acid sequence selected from SEQ ID NO: 11, SEQ ID NO: 23, SEQ ID NO: 35, and SEQ ID NO: 47.

The antibodies composed of the CDR sequences have excellent ability to specifically bind to the extracellularly exposed KRS N-terminal region. This feature is well described in the examples of the present specification. In an example of the present invention, to construct scFv fragments specifically binding to the extracellularly exposed KRS N-terminal region, a total of five experimental steps starting from primary screening through scFv phage library screening to indirect ELISA (secondary screening), western blotting (tertiary screening), immunoprecipitation (quaternary screening), and immunofluorescent staining (quinary screening) were performed to select scFv fragments showing high binding specificity and binding affinity in view of KRS N-terminal binding. A total of 1920 scFv clones were selected in the primary screening through scFv phage library screening, but four types of fragments, N3 scFv, N5 scFv, N7 scFv, and N9 scFv, which have the highest specificity, were finally selected through the five steps of screening. In addition, the scFv fragments were converted into IgG antibodies, thereby constructing N3 IgG, N5 IgG, N7 IgG, and N9 IgG antibodies, and these antibodies were also verified to show high binding specificity in view of KRS N-terminal binding.

The antibodies or fragments thereof specifically binding to the extracellularly exposed KRS N-terminal region according to the present invention are antibodies having the following CDR conformations of heavy and light variable regions, wherein (i), (ii), (iii), and (iv) below indicate CDR combinations of N3, N5, N7, and N9 antibodies in respective examples:

(1) a heavy chain variable region comprising heavy chain complementary determining region 1 containing the amino acid sequence defined by SEQ ID NO: 1, heavy chain complementary determining region 2 containing the amino acid sequence defined by SEQ ID NO: 3, and heavy chain complementary determining region 3 containing the amino acid sequence defined by SEQ ID NO: 5, and a light chain variable region comprising light chain complementary determining region 1 containing the amino acid sequence defined by SEQ ID NO: 7, light chain complementary determining region 2 containing the amino acid sequence defined by SEQ ID NO: 9, and light chain complementary determining region 3 containing the amino acid sequence defined by SEQ ID NO: 11;

(2) a heavy chain variable region comprising heavy chain complementary determining region 1 containing the amino acid sequence defined by SEQ ID NO: 13, heavy chain complementary determining region 2 containing the amino acid sequence defined by SEQ ID NO: 15, and heavy chain complementary determining region 3 containing the amino acid sequence defined by SEQ ID NO: 17, and a light chain variable region comprising light chain complementary determining region 1 containing the amino acid sequence defined by SEQ ID NO: 19, light chain complementary determining region 2 containing the amino acid sequence defined by SEQ ID NO: 21, and light chain complementary determining region 3 containing the amino acid sequence defined by SEQ ID NO: 23;

(3) a heavy chain variable region comprising heavy chain complementary determining region 1 containing the amino acid sequence defined by SEQ ID NO: 25, heavy chain complementary determining region 2 containing the amino acid sequence defined by SEQ ID NO: 27, and heavy chain complementary determining region 3 containing the amino acid sequence defined by SEQ ID NO: 29, and a light chain variable region comprising light chain complementary determining region 1 containing the amino acid sequence defined by SEQ ID NO: 31, light chain complementary determining region 2 containing the amino acid sequence defined by SEQ ID NO: 33, and light chain complementary determining region 3 containing the amino acid sequence defined by SEQ ID NO: 35; and (4) a heavy chain variable region comprising heavy chain complementary determining region 1 containing the amino acid sequence defined by SEQ ID NO: 37, heavy chain complementary determining region 2 containing the amino acid sequence defined by SEQ ID NO: 39, and heavy chain complementary determining region 3 containing the amino acid sequence defined by SEQ ID NO: 41, and a light chain variable region comprising light chain complementary determining region 1 containing the amino acid sequence defined by SEQ ID NO: 43, light chain complementary determining region 2 containing the amino acid sequence defined by SEQ ID NO: 45, and light chain complementary determining region 3 containing the amino acid sequence defined by SEQ ID NO: 47.

Most preferably, the antibodies or fragments thereof according to the present invention are characterized by comprising the following heavy chain and light chain variable regions: In the antibodies or fragments thereof, the heavy chain variable region contains the amino acid sequence selected from the group consisting of SEQ ID NO: 49 (N3 SEQ ID NO: 53 (N5 SEQ ID NO: 57 (N7 VH), and SEQ ID NO: 61 (N9 VH), and the light chain variable region contains the amino acid sequence selected from the group consisting of SEQ ID NO: 51 (N3 VL), SEQ ID NO: 55 (N5 VL), SEQ ID NO: 59 (N7 VL), and SEQ ID NO: 63 (N9 VL).

The antibody comprising the heavy chain variable region (VH) and the light chain variable region (VL) may be an antibody comprising a heavy chain containing the amino acid sequence selected from the group consisting of SEQ ID NO: 77, SEQ ID NO: 81, SEQ ID NO: 85, and SEQ ID NO: 89 and a light chain containing the amino acid sequence selected from the group consisting of SEQ ID NO: 79, SEQ ID NO: 83, SEQ ID NO: 87, and SEQ ID NO: 91.

Most preferably, the antibodies may be antibodies comprising: a heavy chain containing the amino acid sequence defined by SEQ ID NO: 77 and a light chain containing the amino acid sequence defined by SEQ ID NO: 79; a heavy chain containing the amino acid sequence defined by SEQ ID NO: 81 and a light chain containing the amino acid sequence defined by SEQ ID NO: 83; a heavy chain containing the amino acid sequence defined by SEQ ID NO: 85 and a light chain containing the amino acid sequence defined by SEQ ID NO: 87; and a heavy chain containing the amino acid sequence defined by SEQ ID NO: 89 and a light chain containing the amino acid sequence defined by SEQ ID NO: 91.

The "antibody specifically binding to the extracellularly exposed KRS N-terminal region" according to the present invention is not limited to the type thereof as long as the antibody has the above CDR combinations or VH and VL combinations. As a specific example, the antibody may be selected from the group consisting of IgG, IgA, IgM, IgE, and IgD antibodies, and may be preferably an IgG antibody.

The antibodies of the present invention may be monoclonal antibodies or polyclonal antibodies as long as the antibodies have the above CDR combinations or VH and Vt combinations that specifically bind to the KRS N-terminal region, but are preferably monoclonal antibodies, which are a group of antibodies each having substantially identical amino acid sequences in heavy and light chains.

The antibody of the present invention may be derived from any animals including mammals including humans, and birds, and may be preferably derived from humans. However, the antibody of the present invention may be a chimeric antibody including a portion of the antibody derived from humans and a portion of the antibody derived from a different species of animal. That is, the present invention includes all of chimeric antibodies, humanized antibodies, and human antibodies, and may be preferably human antibodies.

In addition, the fragment of the antibody of the present invention refers to an antibody fragment that retains antigen-specific binding ability of a whole antibody. Preferably, the fragment retains at least 20%, 50%, 70%, 80%, 90%, 95%, or 100% of the KRS N-terminal binding affinity of the mother antibody. Specifically, the fragment may be in the form of Fab, F(ab)$_2$, Fab', F(ab')$_2$, Fv, diabody, scFv, or the like.

Fab (fragment, antigen-binding) is an antigen-binding fragment of an antibody, and is composed of a heavy chain and a light chain each consisting of one variable domain and one constant domain. F(ab')$_2$ is a fragment produced by pepsin hydrolysis of an antibody, and F(ab')$_2$ has a form in which two Fab molecules are linked via disulfide bonds at the heavy-chain hinge region. F(ab') is a monomeric antibody fragment in which a heavy-chain hinge is added to a Fab separated from F(ab')$_2$ fragment by the reduction of disulfide bonds thereof. Fv (variable fragment) is an antibody fragment composed of only respective variable regions of the heavy and light chains. scFv (single chain variable fragment) is a recombinant antibody fragment in which a heavy chain variable region (VH) and a light chain variable region (VL) are linked to each other via a flexible peptide linker. The diabody refers to a fragment in which VH and VL of scFv are linked by a very short linker and thus cannot be bound to each other, and bind to VL and VH of another scFv in the same form, respectively, to form a dimer.

For the purposes of the present invention, the fragment of the antibody is not limited to the structure or conformation thereof as long as the fragment of the antibody retains binding specificity to the KRS N-terminal region, but may be preferably scFv. The scFv according to the present invention has a CDR conformation or VH and VL, conformation specific to the KRS N-terminal region, and the sequence thereof is not particularly limited as long as the C-terminal of VH and the N-terminal of VL are linked through a linker. The linker is not particularly limited to the type thereof as long as it is known as a linker applied to scFv in the art, but may be a peptide containing the amino acid sequence defined by SEQ ID NO: 65. Specifically, the scFv of the present invention may contain the amino acid sequence selected from the group consisting of SEQ ID NO: 67 (N3 scFv), SEQ ID NO: 69 (N5 scFv), SEQ ID NO: 71 (N7 scFv), and SEQ ID NO: 73 (N9 scFv).

The antibody or fragment thereof of the present invention may comprise a conservative amino acid substitution (also called a conservative variant of the antibody) that does not substantially change biological activity thereof.

In addition, the foregoing antibody or fragment thereof of the present invention may be conjugated to an enzyme, a fluorescent material, a radioactive material, and a protein, but is not limited thereto. Also, methods of conjugating the above materials to the antibody have been well known in the art.

The present invention provides a polynucleotide encoding the foregoing antibody or fragment thereof according to the present invention.

In the present specification, the polynucleotide may be described as an oligonucleotide or a nucleic acid, and includes: DNA or RNA analogues (e.g., peptide nucleic acids and non-naturally occurring nucleotide analogues) generated using DNA molecules (e.g., cDNA or genomic DNA), RNA molecules (e.g., mRNA), or nucleotide analogues; and hybrids thereof. The polynucleotide may be single-stranded or double-stranded.

The polynucleotide refers to a nucleotide sequence encoding an antibody composed of heavy and light chains each having a CDR conformation or VH and VL conformation specific to the KRS N-terminal region. The polynucleotide of the present invention is not particularly limited to the sequence thereof as long as the sequence encodes the antibody or fragment thereof of the present invention. The polynucleotides encoding the foregoing CDR sequences in the above-described antibodies according to the present invention are not particularly limited to the sequences thereof, but may preferably contain the nucleotide sequence defined by SEQ ID NO: 2 (heavy chain CDR1), SEQ ID NO: 4 (heavy chain CDR2), SEQ ID NO: 6 (heavy chain CDR3), SEQ ID NO: 8 (light chain CDR1), SEQ ID NO: 10 (light chain CDR2), SEQ ID NO: 12 (light chain CDR3), SEQ ID NO: 14 (heavy chain CDR1), SEQ ID NO: 16 (heavy chain CDR2), SEQ ID NO: 18 (heavy chain CDR3), SEQ ID NO: 20 (light chain CDR1), SEQ ID NO: 22 (light chain CDR2), SEQ ID NO: 24 (light chain CDR3), SEQ ID NO: 26 (heavy chain CDR1), SEQ ID NO: 28 (heavy chain CDR2), SEQ ID NO: 30 (heavy chain CDR3), SEQ ID NO: 32 (light chain CDR1), SEQ ID NO: 34 (light chain CDR2), SEQ ID NO: 36 (light chain CDR3), SEQ ID NO: 38 (heavy chain CDR1), SEQ ID NO: 40 (heavy chain CDR2), SEQ ID NO: 42 (heavy chain CDR3), SEQ ID NO: 44 (light chain CDR1), SEQ ID NO: 46 (light chain CDR2), or SEQ ID NO: 48 (light chain CDR3).

In addition, the polynucleotides encoding the foregoing VH and VL in the antibody according to the present invention are not particularly limited to the sequences thereof, but may preferably contain the nucleotide sequence defined by SEQ ID NO: 50 (VH), SEQ ID NO: 52 (VL), SEQ ID NO: 54 (VH), SEQ ID NO: 56 (VL), SEQ ID NO: 58 (VH), SEQ ID NO: 60 (VL), SEQ ID NO: 62 (VH), or SEQ ID NO: 64 (VL).

In addition, the polynucleotide encoding the fragment of the antibody may preferably contain the nucleotide sequence of any one selected from the group consisting of SEQ ID NO: 68, SEQ ID NO: 70, SEQ ID NO: 72, and SEQ ID NO: 74, which encode scFv fragments according to the present invention.

The polynucleotides encoding the antibody or fragment thereof of the present invention may be obtained by a method known in the art. For example, on the basis of DNA sequences encoding a part or the entirety of the heavy and light chains of the antibody or corresponding amino acid sequences, the polynucleotides may be synthesized by the oligonucleotide synthesis methods that are known in the art, e.g., a polymerase chain reaction (PCR) method.

The present invention provides a recombinant expression vector comprising the polynucleotide encoding the antibody or fragment thereof according to the present invention.

As used herein, the "recombinant", used interchangeably with "genetic manipulation", and refers to the construction of a gene in the form that does not exist in nature, by using molecular cloning experiment techniques, such as gene transformation, cleavage, or linkage.

As used herein, the term "expression" refers to the production of proteins or nucleic acids in cells.

As used herein, the term "recombinant expression vector" is a vector that can express a target protein or nucleic acid (RNA) in a suitable host cell, and refers to a gene construct comprising essential control elements that are operably linked to be capable of expressing a polynucleotide (gene) insert. The term "operably linked" refers to the functional linkage of a nucleic acid expression control sequence and a nucleic acid sequence encoding a target protein or RNA so as to perform general functions, which means the linkage therebetween so as to allow a gene to be expressed by the expression control sequence. The expression control sequence refers to a DNA sequence that controls the expression of an operably linked polynucleotide sequence in a particular host cell. Such an expression control sequence includes a promoter for transcription, any operator sequence for controlling transcription, a sequence for encoding a proper mRNA ribosomal binding site, a sequence for controlling the termination of transcription and translation, an initiation codon, a termination codon, a polyadenylation A signal, an enhancer, and the like.

The recombinant expression vector of the present invention is not particularly limited to the type thereof as long as the vector is ordinarily used in a field of cloning, and examples of the recombinant expression vector include a plasmid vector, a cosmid vector, a bacteriophage vector, and a viral vector, but are not limited thereto. Examples of the plasmid may include *Escherichia coli*-derived plasmids (pBR322, pBR325, pUC118, pUC119, and pET-22b(+)), *Bacillus subtilis*-derived plasmids (pUB110 and pTP5), and yeast-derived plasmids (YEp13, YEp24, and YCp50), and examples of the virus may include: animal viruses, such as retrovirus, adenovirus, or vaccinia virus; and insect viruses, such as baculovirus.

The recombinant expression vector according to the present invention means a gene construct that is operably linked so as to be capable of expressing, in a suitable host cell, a polynucleotide encoding the antibody or fragment thereof composed of heavy and light chains having the foregoing CDR or VH and VL conformations capable of specifically binding the KRS N-terminal region.

The polynucleotides encoding heavy and light chains of the antibody according to the present invention may be contained in separate recombinant expression vectors, respectively, or may be contained in one recombinant expression vector.

The Present Invention Provides Cells Transformed with the Above-Described Recombinant Expression Vector.

The cells of the present invention are not particularly limited to the type thereof as long as the cells can be used to express a polynucleotide encoding an antibody or a fragment thereof contained in the recombinant expression vector of the present invention. The cells (host cells) transformed with the recombinant expression vector according to the present invention may be prokaryotic cells (e.g., *E. coli*), eukaryotic cells (e.g., yeast or other fungi), plant cells (e.g., tobacco or tomato plant cells), animal cells (e.g., human cells, monkey cells, hamster cells, rat cells, mouse cells, or insect cells), or hybridomas derived therefrom. Preferably, the cells may be derived from mammals including humans.

Exemplary prokaryotes suitable for the present purpose include Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescens*, and *Shigella*, as well as Bacilli, e.g., *B. subtilis* and *B. licheniformis, Pseudomonas*, e.g., *P. aeruginosa*, and *Streptomyces*. The cells of the present invention are not particularly limited as long as the cells can express the vector of the present invention, but may be preferably *E. coli*.

*Saccharomyces cerevisiae* is most frequently used as a eukaryote for the cells of the present invention. However, a number of other genera, species, and strains can be used, but are not limited to, for example, *Schizosaccharomyces pompe; Kluyveromyces* hosts, such as, *K lactis, K. fragilis* (ATCC 12,424), *K. bulgaricus* (ATCC 16,045), *K. wickeramii* (ATCC 24,178), *K. waltii* (ATCC 56,500), *K. droso-*

*philarum* (ATCC 36,906), *K. thermotolerans*, and *K. marxianus*; *Yarrowia* (EP 402,226); *Pichia pastoris* (EP 183,070); *Candida*; *Trichoderma reesia* (EP 244,234); *Neurospora crassa*; *Schwanniomyces*, such as *Schwanniomyces occidentalis*; and filamentous fungi, for example, *Neurospora, Penicillium, Tolypocladium*, and *Aspergillus* hosts, such as *A. nidulans* and *A. niger*.

The term "transformation" refers to a modification of the genotype of a host cell due to the introduction of exotic polynucleotides, and refers to an introduction of an exotic polynucleotide into a host cell regardless of a method used for the transformation. The exotic polynucleotide introduced into the host cell is incorporated into and maintained in the genome of the host cell, or is maintained without the incorporation thereinto, and the present invention includes both.

The recombinant expression vector capable of expressing the antibody or fragment thereof specifically binding to the KRS N-terminal region according to the present invention can be introduced into cells for producing the antibody or fragment thereof, by a method known in the art, for example, but is not limited to, transient transfection, microinjection, transduction, cell fusion, calcium phosphate precipitation, liposome-mediated transfection, DEAE dextran-mediated transfection, polybrene-mediated transfection, electroporation, gene gun, and known methods for introducing nucleic acids into cells, and then can transform the cells.

The present invention provides a method for preparing an antibody or fragment thereof specifically binding to an extracellularly exposed lysyl-tRNA synthetase (KRS) N-terminal region, the method comprising:

(a) transforming host cells with the recombinant expression vector;

(b) incubating the transformed host cells to produce an antibody or fragment thereof; and (c) collecting the antibody or fragment thereof produced in the host cells.

In step (a), in order to produce the antibody or fragment thereof according to the present invention, host cells are transformed with the recombinant expression vector, in which the polynucleotide encoding the antibody or fragment thereof is operably linked.

A person skilled in the art can perform the present step by selecting a suitable transformation method according to the selected host cells and recombinant expression vector as described above. The recombinant expression vectors comprising nucleotide sequences of heavy and light chains may be co-transformed in the same host cell to allow the heavy and light chains to be expressed in one cell, or the recombinant expression vectors comprising nucleotide sequences of heavy and light chains may be transformed in separate host cells to allow the heavy and light chains to be separately expressed.

In step (b), the transformed host cells are incubated to produce polypeptides of heavy and light chains of the antibody or fragment of the antibody according to the present invention from the recombinant expression vector introduced into the host cells.

The medium composition, incubation conditions, and incubation time for incubating the host cells may be appropriately selected according to a method ordinarily used in the art. The antibody molecules produced in the host cell may be accumulated in the cellular cytoplasm, may be secreted outside the cell or in the culture medium by a suitable signal sequence, or may be targeted using a periplasm or the like. It is also preferable that the antibody according to the present invention has a functional conformation through protein refolding using a method known in the art so as to maintain binding specificity to the KRS N-terminal. As for the production of IgG type antibody, heavy and light chains may be expressed in separate cells and then contacted with each other in a separate step to constitute the whole antibody, or heavy and light chains may be expressed in the same cell to form the whole antibody inside the cell.

In step (c), the antibody or fragment thereof produced in the host cells is obtained.

A person skilled in the art can properly select and control the collection method considering characteristics of polypeptides of the antibody or fragment thereof produced in the host cells, characteristics of the host cells, the mode of expression, or the targeting or not of the polypeptide. For example, the antibody or fragment thereof secreted into the culture medium can be collected by obtaining the culture medium, in which the host cells are cultured, removing impurities through centrifugation, and the like. In order to, as necessary, excrete the antibody present in specific organelles or cytoplasm in the cells to the outside of the cells and collect the antibody, the cells may be lysed within an extent that does not affect the functional structure of the antibody or the fragment thereof. The obtained antibody may be further subjected to a process of further removing impurities and carrying out concentration, through chromatography, filtration using a filter, dialysis, or the like.

The polypeptide in the manufacturing (production) method of the present invention may be the antibody or fragment thereof itself of the present invention, and a polypeptide to which another amino acid sequence other than the antibody or fragment thereof of the present invention is further bound. In this case, the amino acid sequence may be removed from the antibody or fragment thereof of the present invention by using a method well known to a person skilled in the art.

The antibody or fragment thereof of the present invention specifically binds to the KRS N-terminal region, and thus is useful in the diagnostic analysis for detecting and quantifying KRS proteins in, for example, particular cells, tissues, or serum. Especially, the extracellularly exposed KRS N-terminal region can be specifically detected without cell lysis. Therefore, the present invention provides a method for specific detection of an extracellularly exposed lysyl-tRNA synthetase (KRS) N-terminal region, the method comprising: contacting the antibody or fragment thereof with a sample; and detecting the antibody or fragment thereof.

The detection method of the present invention may comprise a step of preparing a sample, which is to be measured for the presence or absence of KRS (or extracellularly exposed KRS N-terminal peptide) and the concentration thereof by using the antibody or fragment thereof according to the present invention (step (1)), before contacting the antibody or fragment thereof according to the present invention with the sample.

A person skilled in the art may suitably select a known protein detection method using an antibody and prepare a sample suitable for the selected method. In addition, the sample may be cells or tissues obtained by biopsy, blood, whole blood, serum, plasma, saliva, cerebrospinal fluid, or the like, which is collected from a subject to be examined for the presence or absence of cancer (especially breast cancer or lung cancer) or cancer metastasis. Examples of the protein detection method using the antibody include, but are not limited to, western blotting, immune blotting, dot blotting, immunohistochemistry, enzyme-linked immunosorbent assay (ELISA), radioimmunoassay, competitive binding assay, immunoprecipitation, and the like. For example, for western blotting, a preparation may be made by adding a buffer suitable for electrophoresis to a sample or cell lysate, followed by boiling, and for immunohistochemistry, a treatment may be performed by immobilizing and blocking cells or tissue slices, followed by blocking.

Next, a step of contacting the antibody or fragment thereof according to the present invention with the sample prepared in the above-described step is performed (step (2)).

The antibody according to the present invention is an antibody or fragment thereof that has the above-described CDR or VH and VL conformations and specifically binds to the KRS N-terminal region, and specific types and sequence organization thereof are as described above.

The antibody or fragment thereof may be labeled with a general detectable moiety, for "detection" thereof. For instance, the antibody or fragment thereof may be labeled with a radioisotope or fluorescent label by using the technique described in literature [Current Protocols in Immunology, Volumes 1 and 2, 1991, Coligen et al., Ed. Wiley-Interscience, New York, N.Y., Pubs]. In addition, various enzyme-substrate labels are usable, and examples of the enzymatic label include: luciferase, such as *Drosophila* luciferase and bacterial luciferase (U.S. Pat. No. 4,737,456), luciferin, 2,3-dihydrophthalazine dionise, malate dehydrogenase, urase, peroxidase such as horseradish peroxidase (HRPO), alkaline phosphatase, β-galactosidase, glucoamylase, lysozyme, saccharide oxidase (e.g., glucose oxidase, galactose oxidase, and glucose-6-phosphate dehydrogenase), heterocyclic oxidase (e.g., uricase and xanthine oxidase), lactoperoxidase, microperoxidase, and the like. Techniques for conjugating enzymes to antibodies are described in, for example, literature [O'Sullivan et al., 1981, Methods for the Preparation of Enzyme-Antibody Conjugates for use in Enzyme Immunoassay, in Methods in Enzym. (J. Langone & H. Van Vunakis, eds.), Academic press, N. Y., 73: 147-166]. The labels may be directly or indirectly conjugated to antibodies using various known techniques. For instance, the antibody may be conjugated to biotin, and any labels pertaining to three classes of widespread categories cited above may be conjugated to avidin or vice versa. Biotin may selectively bind to avidin, and therefore, this label may be conjugated to an antibody in such an indirect manner. Alternatively, in order to attain the indirect conjugation of a label to an antibody, the antibody may be conjugated to a small hapten (e.g., dioxin), and one of different types of labels recited above may be conjugated to an anti-hapten antibody (e.g., anti-dioxin antibody). Therefore, the indirect conjugation of a label to an antibody can be attained.

As used herein, the "contacting" is used in a general sense thereof, and refers to the mixing, binding, or touching of two or more substances. The contacting may be performed in vitro or in another container, or may be performed in situ, in vivo, in the subject, in the tissue, or in the cell.

Next, a step of detecting the antibody or fragment thereof according to the present invention from the sample after the execution of step (2) is performed (step (3)).

The "detection" is performed on a complex of the antibody or fragment thereof according to the present invention and an antigen, the complex being formed in the sample, and refers to the detection of the presence or absence of the KRS N-terminal peptide (or a protein including the peptide, for example, KRS) or the measurement (including qualitative measurement, quantitative measurement, or both) of the level of the peptide. Therefore, the detection method of the present invention may further comprise a step of removing extra antibodies or fragments thereof, which did not form the complex together with the KRS N-terminal region, after the execution of step (2) before step (3) to be described later.

When the antibody or fragment thereof used in step (2) described above contains a detectable moiety, such as fluorescence, radioactive isotope, or enzyme, which directly labels the antibody or fragment thereof, the detection may be carried out by a detection method for the corresponding moiety, known in the art. For instance, radioactivity may be measured by, for example, scintillation counting, and fluorescence may be quantified using a fluorometer.

When the antibody or fragment thereof, per se, used in step (2) described above does not contain the foregoing detectable moiety, the indirect detection using a secondary antibody labeled with fluorescence, radioactivity, enzyme, or the like may be carried out. The secondary antibody binds to the antibody or fragment thereof (primary antibody) according to the present invention.

Recent studies established that human lysyl-tRNA synthetase (KRS) present in the cytosol translocates to the plasma membrane (cell membrane) to interact with a 67-kDa laminin receptor (67LR) present on the plasma membrane, thereby promoting the migration of tumor (or cancer) cells to affect cancer metastasis (Dae Gyu Kim et al., Chemical inhibition of prometastatic lysyl-tRNA synthetaselaminin receptor interaction, Nat Chem Biol. 2014 January; 10(1): 2934.). Here, the KRS N terminal extension (N-ext) region has been known to be essential in the translocation of KRS to the cell membrane. As for cancer metastasis, specifically, the KRS N-ext region has been known to be involved in the binding of KRS and 67LR in the interaction thereof.

The antibodies and fragments thereof according to the present invention are excellent in specific binding ability to the KRS N-ext region. Actually, the antibodies and fragments thereof according to the present invention bind to the KRS N-ext region, and thus inhibit the binding (interaction) with a laminin receptor, thereby showing excellent ability to inhibit cancer metastasis. This is well described in the examples of the invention. An example in the present specification verified that as a result of administering the antibody according to the present invention into in vivo cancer metastasis models with induced cancer, the antibody of the present invention showed excellent cancer metastasis-inhibiting ability in a dose-dependent manner. Especially, the cancer metastasis inhibitory ability of the antibody of the present invention was very excellent even compared with YH16899 compound, which is known to inhibit cancer metastasis by inhibiting the interaction between the laminin receptor (67LR) and KRS.

Therefore, the present invention provides a pharmaceutical composition for inhibition of cancer metastasis and a composition for cancer diagnosis, each of the compositions comprising the foregoing antibody or fragment thereof of the present invention as an active ingredient for inhibition of cancer metastasis.

Furthermore, the present invention provides a pharmaceutical composition for inhibition of cancer metastasis and a composition for cancer diagnosis, each the compositions consisting of the foregoing antibody or fragment thereof of the present invention.

Furthermore, the present invention provides a pharmaceutical composition for inhibition of cancer metastasis and a composition for cancer diagnosis, each the compositions essentially consisting of the foregoing antibody or fragment thereof of the present invention.

The cancer is not particularly limited to the type thereof as long as the cancer is known as a malignant tumor in the art, and example thereof may be selected from the group consisting of breast cancer, large intestine cancer, lung cancer, small cell lung cancer, gastric cancer, liver cancer, blood cancer, bone cancer, pancreatic cancer, skin cancer, head or neck cancer, cutaneous or intraocular melanoma, uterine cancer, ovarian cancer, rectal cancer, anal cancer, colon cancer, breast cancer, fallopian tube carcinoma, endometrial carcinoma, cervical cancer, vaginal cancer, vulvar carcinoma, Hodgkin's disease, esophageal cancer, small intestine cancer, endocrine cancer, thyroid cancer, parathyroid carcinoma, adrenal cancer, soft tissue sarcoma, uterine cancer, penis cancer, prostate cancer, chronic or acute leukemia, lymphocyte lymphoma, bladder cancer, kidney or ureter cancer, renal cell carcinoma, renal pelvic carcinoma, CNS tumor, primary CNS lymphoma, spinal cord tumor, brain stem glioma, and pituitary adenoma. Preferably, the cancer may be breast cancer or pulmonary cancer.

The present invention provides a pharmaceutical composition comprising the antibody or fragment thereof of the present invention as an active ingredient for the prevention or treatment of an immune cell migration-related disease.

Furthermore, the present invention provides a pharmaceutical composition consisting of the antibody or fragment thereof of the present invention for the prevention or treatment of an immune cell migration-related disease.

Furthermore, the present invention provides a pharmaceutical composition essentially consisting of the antibody or fragment thereof of the present invention for the prevention or treatment of an immune cell migration-related disease.

As used herein, the term "immune cells" preferably refers to monocytes or macrophages.

As used herein, the term "immuno cell migration-related disease" is not particularly limited to the specific type thereof as long as it is known in the art that excessive migration (and invasion) of immune cells is the main pathogenesis of the disease, and examples thereof may be selected from the group consisting of a cardiovascular disease, a fibrotic disease, a chronic inflammatory disease, and Alport syndrome.

The cardiovascular disease is not particularly limited to the following specific types of cardiovascular diseases and may be selected from the group consisting of pulmonary arterial hypertension, atherosclerosis, angina pectoris, myocardial infarction, ischemic cerebrovascular disease, arteriosclerosis, and mesenteric sclerosis.

The fibrotic disease is not particularly limited to the following specific types of the fibrotic diseases, and may be selected from the group consisting of scleroderma, rheumatoid arthritis, Crohn's disease, ulcerative colitis, myelofibrosis, pulmonary fibrosis, hepathic fibrosis, liver cirrhosis, kidney fibrosis, myofibrosis, cardiac fibrosis, systemic lupus erythematosus, hereditary fibrosis, infectious fibrosis (especially fibrosis caused by continuous infection), irritant fibrosis (fibrosis caused by repetitive exposure to irritant materials, such as tobacco and toxic materials), fibrosis caused by chronic autoimmune, fibrosis caused by antigen incompatibility during organ transplantation, fibrosis by hyperlipidemia, fibrosis by obesity, diabetic fibrosis, fibrosis by hypertension, and occlusion caused by fibrosis in stent insertion.

The chronic inflammatory disease may be selected from the group consisting of asthma, atopic dermatitis, eczema, psoriasis, osteoarthritis, gout, psoriatic arthritis, cirrhosis, nonalcoholic steatohepatitis, chronic obstructive pulmonary disease, rhinitis, diabetic retinopathy, diabetic renal failure, diabetic neuropathy, and multiple sclerosis.

The pharmaceutical composition according to the present invention may comprise the antibody or fragment thereof of the present invention alone or may further comprise at least one pharmaceutically acceptable carrier. As used herein, the term "pharmaceutically acceptable" refers to a non-toxic composition that is physiologically acceptable, does not inhibit action of an active ingredient when administered to humans, and does not normally cause an allergic response or similar responses, such as gastroenteric troubles and dizziness.

In the pharmaceutical composition according to the present invention, the antibody or fragment thereof may be administered in several oral and parental dosage forms during clinical administration. The antibody or fragment thereof, when formulated, may be prepared using a diluent or an excipient, such as a filler, an extender, a binder, a wetting agent, a disintegrant, or a surfactant, which is normally used. Solid formulations for oral administration include a tablet, a pill, a powder, granules, a capsule, a troche, and the like. These solid formulations may be prepared by mixing the antibody or fragment thereof of the present invention or a pharmaceutically acceptable salt thereof with at least one excipient, for example, starch, calcium carbonate, sucrose or lactose, or gelatin. In addition, lubricants, such as magnesium stearate and talc, may be used besides to the simple excipients. Liquid formulations for oral administration include a suspension, a solution for internal use, an emulsion, a syrup, and the like. Besides simple diluents that are frequently used, such as water and liquid paraffin, several excipients, for example, a wetting agent, a sweetener, an aroma, a preservative, and the like may be contained in the liquid formulations.

Exemplary formulations for parenteral administration include a sterile aqueous solution, a non-aqueous solvent, a suspension solvent, an emulsion, a freeze-drying agent, and a suppository. The composition for treatment of the present invention may be prepared in the form of a freeze-dried cake or an aqueous solution in order to mix and store any physiologically acceptable carrier, excipient, or stabilizer (Remington: The Science and Practice of Pharmacy, 19th Edition, Alfonso, R., ed, Mack Publishing Co. (Easton, Pa.: 1995)) and an antibody with preferable purity. The acceptable carrier, excipient, or stabilizer is non-toxic to a user at the used dose and concentration, and examples thereof include: buffers, for example, phosphoric acid, citric acid, and other organic acids; antioxidants including ascorbic acid; low-molecular weight (less than about 10 residues) polypeptides; proteins, for example, serum albumin, gelatin, or immunoglobulin; hydrophilic polymers, for example, polyvinyl pyrrolidone; amino acids, for example, glycine, glutamine, asparagine, arginine, or lysine; monosaccharides, disaccharides, and other carbohydrates including glucose, mannose, or dextrin; chelating agents, for example, EDT; sugar alcohols, for example, mannitol or sorbitol; salt-forming counter ions, for example, sodium; and (or) non-ionic surfactants, for example, Tween, pluronics, or polyethylene glycol (PEG).

The antibody of the present invention may be administered in a pharmaceutically effective amount to a subject fighting against cancer or an immune cell migration-related disease. As used herein, the term "pharmaceutically effective amount" refers to an amount showing a higher response compared with negative control, and preferably refers to an amount sufficient to treat cancer, an amount sufficient to inhibit cancer metastasis, and an amount sufficient to treat an immune cell migration-related disease. The total effective amount of the antibody or fragment thereof of the present invention may be administered to a patient as a single dose, or may be administered by a fractionated treatment protocol, in which multiple doses are administered for a long period of time. The dose of the antibody or fragment thereof of the present invention to the human body may be normally 0.01-100 mg/kg/week, preferably 0.1-20 mg/kg/week, and more preferably 5-10 mg/kg/week. However, as for the dose of the antibody or fragment thereof of the present invention, an effective dose thereof with respect to a patient is determined in consideration of various factors, for example, the route of administration of the pharmaceutical composition, the number of times of treatment, a patient's age, body weight, health condition, and sex, the severity of disease, the diet, and the excretion rate, and therefore, considering this fact, a person skilled in the art could determine a suitable effective amount of the antibody or fragment thereof of the present invention according to the particular use as a cancer metastasis inhibitor. The pharmaceutical composition according to the present invention is not particularly limited to the dosage form, route of administration, and administration method thereof as long as the composition shows effects of the present invention.

The route of administration of the composition of the present invention may be a known antibody administration method, for example, the injection or infusion by an intravenous, intraperitoneal, intracranial, subcutaneous, intramuscular, intraocular, intraarterial, cerebrospinal, or intralesional route, or the injection or infusion by the sustained release system described below. For example, the antibody of the present invention may be administered systemically or locally.

The pharmaceutical composition of the present invention may be used alone or in combination with surgery, hormone therapy, chemotherapy, and methods using biological response controller, for cancer prevention or treatment.

The pharmaceutical composition of the present invention may also be used alone or in combination with surgery, hormone therapy, chemotherapy, and methods using biological response controller, for prevention or treatment of an immune cell migration-related disease.

The diagnosis and prognosis of cancer (or cancer metastasis) according to the present invention may be evaluated by detecting KRS proteins (especially, extracellularly exposed KRS N-terminal region) in the biological sample, and the diagnosis and prognosis of the immune cell migration-related disease according to the present invention may be evaluated by detecting KRS proteins (especially, extracellularly exposed KRS N-terminal region) in the biological sample.

As used herein, the term "diagnosis" refers to identifying the presence or characteristics of a pathological condition. In the present invention, the diagnosis is to identify the occurrence or the likelihood (risk) of cancer or/and cancer metastasis or an immune cell migration-related disease.

The term "detection" is as described above, and the biological sample includes blood and other liquid samples having biological origins, biopsy specimens, solid tissue samples such as tissue culture, or cells derived therefrom. More specifically, examples of the biological sample may include, but are not limited to, tissues, extracts, cell lysates, whole blood, plasma, serum, saliva, ocular fluid, cerebrospinal fluid, sweat, urine, milk, ascites fluid, synovial fluid, peritoneal fluid, and the like. The sample may be obtained from animals, preferably mammals, and most preferably humans. The sample may be pre-treated before use for detection. Examples of the pretreatment may include filtration, distillation, extraction, concentration, interference ingredient deactivation, reagent addition, and the like. In addition, nucleic acids and proteins isolated from the sample may be used for detection.

The antibody or fragment thereof according to the present invention may be provided as a diagnostic kit. The kit is not particularly limited to the type thereof as long as the kit is known in the art as an assay kit that provides a peptide having an antibody or a particular binding domain as a component, and examples thereof include a kit for western blotting, ELISA, radioimmunoassay, radioimmunodiffusion, Ouchterlony immunodiffusion, rocket immunoelectrophoresis, immunohistochemistry, immunoprecipitation assay, complement fixation assay, FACS, a protein chip, or the like.

The antibody or fragment thereof of the present invention may be used in a kit, i.e., a packaged combination of reagents in predetermined amounts with instructions for performing the diagnostic assay. Where the antibody is labeled with an enzyme, the kit may include substrates and cofactors required by the enzyme (e.g., a substrate precursor which provides the chromophore or fluorophore). In addition, other additives may be included such as stabilizers, buffers (e.g., a block buffer or lysis buffer) and the like. The relative amounts of various reagents may be varied widely to provide concentrations in solution of the reagents which substantially optimize the sensitivity of the assay. The reagents may be provided as dry powders, usually lyophilized, including excipients which on dissolution will provide a reagent solution having an appropriate concentration.

The present invention provides use of the antibody or fragment thereof of the present invention for preparing an agent for the inhibition of cancer metastasis.

The present invention provides a method for inhibiting cancer metastasis in a subject in need thereof, the method comprising administering the antibody or fragment thereof of the present invention to the subject in an amount effective for inhibiting cancer metastasis.

The present invention provides use of the antibody or fragment thereof of the present invention for preparing an agent for cancer diagnosis.

The present invention provides a method for diagnosing cancer in a subject in need thereof, the method comprising administering the antibody or fragment thereof of the present invention to the subject in an amount effective for diagnosing cancer.

The present invention provides use of the antibody or fragment thereof of the present invention for preparing an agent for the treatment of an immune cell migration-related disease.

The present invention provides a method for treating an immune cell migration-related disease in a subject in need thereof, the method comprising administering the antibody or fragment thereof of the present invention to the subject in an amount effective for treating the immune cell migration-related disease.

As used herein, term "effective amount" refers to an amount to show an effect of alleviation, treatment, prevention, detection, or diagnosis of cancer or an effect of inhibiting or reducing cancer metastasis, and refers to an amount to show an effect of alleviation, treatment, prevention, detection, or diagnosis of an immune cell migration-related disease. Term "subject" may be an animal, preferably a mammal, especially an animal including a human being, and may be cells, a tissue, an organ, or the like derived from an animal. The subject may be a patient in need of the effect.

As used herein, term "treatment" broadly refers to alleviating cancer, a cancer-related disease, or an immune cell migration-related disease, and may include healing or substantially preventing such a disease or alleviating a condition of the disease, and may include alleviating, healing, or preventing one or most of the symptoms resulting from cancer or a cancer-related disease, but is not limited thereto.

As used herein, the term "comprising" is used synonymously with "containing" or "being characterized", and does not exclude additional ingredients or steps not mentioned in the composition or method. The term "consisting of" means excluding additional elements, steps, or ingredients not otherwise specified. The term "essentially consisting of" means including the mentioned elements or steps as well as any element or step that does not substantially affect basic characteristics of the mentioned elements or steps in the scope of compositions or methods.

Advantageous Effects

The antibodies or fragments thereof according to the present invention have particular complementary determining regions (CDRs) defined in the present specification and a very excellent specific binding ability to an extracellularly exposed KRS N-terminal region. Furthermore, the antibodies or fragments thereof according to the present invention is specifically targeted to the KRS N-terminal region in vivo, and thus inhibit the interaction between the laminin receptor and the KRS N-terminal region, thereby exerting an excellent effect on the inhibition of cancer metastasis, and can control the migration of immune cells, thereby exerting a very remarkable effect on the prevention, alleviation, and treatment of an immune cell migration-related disease.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A shows the results, wherein cells having KRS N-terminal region exposed on the cell membrane were constructed through myc-KRS T52D (active mutant) expression and it was investigated whether N3, N5, N7, and N9 scFv clones bound to the exposed region (KRS: meaning myc-KRS T52D). FIG. 3B shows that in the inactive mutant (myc-KRS T52A) or WT-KRS (laminin untreated) expression group, no detection signals were observed in spite of the treatment with N3, N5, N7, and N9 scFv clones since the KRS N-terminal region was not exposed on the cell membrane.

FIG. 5A shows the western blotting results of confirming the KRS binding ability of N3 IgG and N5 IgG as representatives among the antibodies of the present invention. FIG. 5B shows the immunoprecipitation results of confirming KRS binding ability of N3 IgG and N5 IgG as representatives among the antibodies of the present invention.

FIG. 6A shows the SPR results of quantitatively confirming KRS N-terminus binding ability of N3 IgG. FIG. 6B shows the SPR results of quantitatively confirming KRS N-terminus binding ability of N5 IgG.

FIG. 7A shows the results, wherein the cells transformed to express WT-KRS were treated with laminin to extracellularly expose KRS N-terminal region, and then treated with the antibody of the present invention, N3 IgG, to investigate the binding of N3 IgG to the exposed region through immunofluorescence staining. FIG. 7B shows the results, wherein the cells having extracellularly exposed KRS N-terminal region were constructed through T52D-KRS (active mutant, myc tagged KRS) expression, and then treated with the antibody of the present invention, N3 IgG, to investigate the binding of N3 IgG to the exposed region through immunofluorescence staining. It was also confirmed through an experiment to impart permeability to the cell membrane that the antibody of the present invention translocates into cells and can bind with KRS protein present inside the cells. FIG. 7C shows the results, wherein the cells transformed to express WT-KRS were treated with laminin to extracellularly expose KRS N-terminal region, and then treated with the antibody of the present invention, N5 IgG, to investigate the binding of N5 IgG to the exposed region through immunofluorescence staining (N5 IgG: green).

FIG. 9A shows the results of confirming that cell migration was suppressed by the treatment with the antibody of the present invention N3 IgG. FIG. 9B shows the results of confirming that the antibody of the present invention N3 IgG significantly suppressed cell migration in a dose-dependent manner.

FIGS. 18A-18B show results of cell migration. FIG. 18A shows the transwell migration assay results of comparing the effects of collagen, fibronectin, and laminin on immune cell (monocyte/macrophage) migration, and provides microscopic images of migrating cells. FIG. 18B is a graph showing cell counts measured (quantified) on the microscopic images of FIG. 18A.

FIG. 19A shows the transwell migration assay results of comparing the effects of various laminin subtypes (LN111, LN211, LN221, LN411, LN421, LN511, and LN521) on immune cell (monocyte/macrophage) migration, and provides microscopic images of migrating cells. FIG. 19B is a graph showing the cell count measured (quantified) on the microscopic images of FIG. 19A. FIG. 19C shows the western blotting results of confirming that KRS increased on the monocyte/macrophage membrane by LN421 treatment.

FIGS. 20A-20C show results of cell migration. FIG. 20A shows the Transwell migration assay results of comparing the inhibitory effects of the antibody of the present invention, N3 IgG, on LN421-specific monocyte/macrophage migration, and provides microscopic images of migrating cells. FIG. 20B is a graph showing the cell counts measured (quantified) on the microscopic images of FIG. 20 A. FIG. 20C shows the western blotting results of confirming that the KRS level increased by LN421 treatment in the monocyte/macrophage membrane was reduced by the treatment with the antibody of the present invention, N3 IgG.

FIG. 21A shows a change in right ventricular end-systolic pressure (RVESP) by the administration of the antibody of the present invention, N3 IgG, in pulmonary arterial hypertension (PAR) models (Mock IgG: negative control, Ab 1 mpk: N3 antibody 1 mpk, Ab 10 mpk: N3 antibody 10 mpk, sildenafil: positive control). FIG. 21B shows a change in left ventricular end-systolic pressure (LVESP) by the administration of the antibody of the present invention, N3 IgG, in pulmonary arterial hypertension (PAH) models (Mock IgG: negative control, Ab 1 mpk: N3 IgG 1 mpk, Ab 10 mpk: N3 IgG 10 mpk, sildenafil: positive control).

MODE FOR CARRYING OUT THE INVENTION

Figure 1:
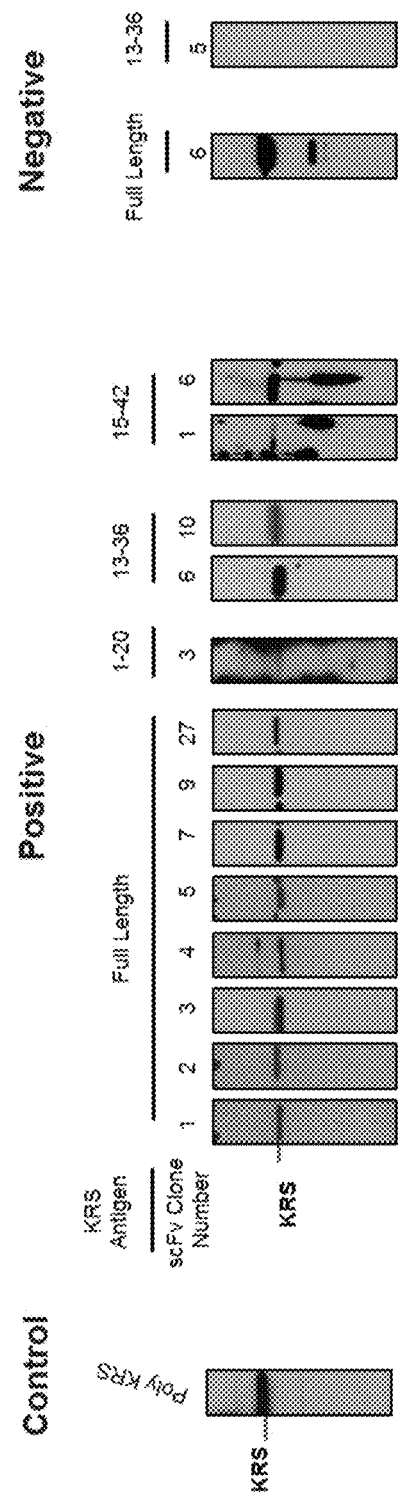
FIG. 1 shows the results of selecting, through western blotting (WB), scFv phage clones binding to KRS full-length sequence or KRS N-terminal fragments.

Hereinafter, the present invention will be described in detail.

However, the following examples are merely for illustrating the present invention and are not intended to limit the scope of the present invention.

Example 1 sdFv Library Screening

<1-1> Screening of scFv Phages Primary Screening

In order to select scFv antibodies specifically binding to only the KRS N-terminal region (SEQ ID NO: 75) extracellularly exposed when KRS translocates to the cell membrane by the laminin signal, in the KRS full-length sequence (SEQ ID NO: 76), phage display panning was performed using the scFv phage library derived from HA-tagged human B cells. The scFv display phage library (Library size: app. 7.6×10$^9$ Library produced by prof. Hyunbo Shim) used in the present experiment is disclosed in Korean Patent No. 10-0961392. As shown in Table 1 below, the KRS full-length sequences and KRS fragments with particular different regions of the N-terminus were used as antigen proteins for phage display panning.

To an immuno-tube containing 1 ml of 1×PBS solution, 1-10 μg of antigen proteins were added and incubated at 37° C. for 1 h at 200 rpm, thereby coating the inner surface of the tube with antigens. The antigen solution was drained, and uncoated antigens were removed by washing once with tap water. To prevent non-specific binding between antigen proteins and phages, the immuno-tube and scFv library were separately incubated with 1×PBST (0.05% tween20-containing PBS) containing 3% skim milk at room temperature for 1 h. After the skim milk was removed from the immuno-tube, scFv library was added and incubated at 150 rpm for 1 h at 37° C., thereby binding scFv phages to the antigens. After the scFv phages were incubated in the tube, unbound scFv phages were removed by washing two or five times with 1×PBST.

ScFv phages specifically binding to the respective KRS antigens were isolated within 10 min by addition of 1 ml of triethylamine (100 mM) at room temperature, and neutralized with Tris (1 M, pH 7.4). The filtered scFv phages were added to ER2537 *E. coli* cultured to OD<1, followed by infection with incubation at 120 rpm for 1 h and 30 min at 37° C. *E. coli* infected with the phages was centrifuged to partially remove the culture supernatant, followed by re-dispersion, and then spread on 15 cm-diameter agarose plate containing ampicillin and glucose (2%). The next day, 5 ml of SB medium was applied to collect all of the cells grown in the plate, and glycerol (50%) was added to 0.5 times the total volume, followed by mixing, and then the mixture was dispensed in 1 ml portions and stored at −80° C. (scFv panning stock). Then, 20 μl of the prepared stock was seeded in 20 ml of SB solution, followed by incubation, and then constructed into scFv phage library (1 ml) for the next step of phage panning by using helper phages. The above procedure for isolating phages expressing scFv specific to antigens was repeated two or three times.

<1-2> Screening of Specifically Binding scFv Antibodies Through ELISA_Secondary Screening It was investigated through indirect ELISA whether scFv-expressed phages selected in Example <1-1> bound to the foregoing full-length KRS or N-terminal fragments.

The scFv product obtained by three rounds of panning was diluted, and applied on 10 cm-diameter agarose plate. The next day, respective colonies were selected, and incubated in 96-well plate containing 200 μl of SB medium. After the colonies were checked to grow well overall, IPTG (1 mM) was added, followed by incubation at 30° C. for 16 h, thereby inducing scFv production. The next day, the 96-well plate was centrifuged to isolate only cells, and then the cells were lysed with TES solution, followed by re-centrifugation, thereby separating only the supernatant. The obtained supernatant was subjected to indirect ELISA to select scFv specifically binding to antigens. The plates were coated with KRS full-length antigens or the N-terminal fragment antigens, respectively, incubated with the culture supernatant containing scFv, and then incubated with anti-HA-HRP antibody (Roche Applied Science) as a secondary antibody. The color development was performed using tetramethyl benzimidine (TMB, Thermo scientific), and then stopped using $H_2SO_4$ (1 M), and the absorbance was read at 450 nm using ELISA reader. ELISA was performed on control (blank) and the above-described antigens (Ag) at the same time to select only colonies with positive values. Out of the total of 1920 colonies subjected to ELISA, 93 colonies were selected as being positive (see Table 1).

TABLE 1

| | Antigen (KRS fragment) | | | | | | | | | |
|---|---|---|---|---|---|---|---|---|---|---|
| | Full | 1-20 | 13-36 | 31-46 | 1-29 | 5-34 | 10-38 | 15-42 | 24-49 | Total |
| Panning Outcomes | 288 | 384 | 384 | 192 | 192 | 192 | 96 | 96 | 96 | 1920 |
| HITS | 51 | 8 | 20 | 2 | 1 | 1 | 0 | 8 | 2 | 93 |

<1-3> Sequencing

Sequences were analyzed to filter out the same Ab with overlapping CDR sequences out of 93 colonies selected through ELISA screening in Example <1-2>. Sequencing was specifically performed by the following method: After E. coli retaining scFv clones was cultured, phagemids were obtained by miniprep. The phagemids were sequenced using Omp primer (Hye young Yang, et. al., 2009, Mol. Cells 27, 225-235). The sequence thus obtained was used to verify the sequences of CDR regions of the phagemids by Bioedit program. Out of these, the clones with overlapping CDR sequences were eliminated to verify scFv clones of respective independent CDR sequences.

TABLE 2

| | Antigen (KRS fragment) | | | | | | | | | |
|---|---|---|---|---|---|---|---|---|---|---|
| | Full | 1-20 | 13-36 | 31-46 | 1-29 | 5-34 | 10-38 | 15-42 | 24-49 | Total |
| HITS | 51 | 8 | 20 | 2 | 1 | 1 | 0 | 8 | 2 | 93 |
| Different Clones | 10 | 8 | 11 | 1 | 1 | 1 | 0 | 4 | 2 | 38 |

As a result of screening antibodies with overlapping CDR sequences through sequencing, 38 scFv clones with different CDR sequences were obtained as shown in Table 2.

<1-4> Screening of Specifically Binding scFv Antibodies Through Western Blotting_Tertiary Screening It was investigated through western blotting whether 38 scFv clones isolated in Example <1-3> specifically bound to KRS.

The scFv positive single-colony clones were incubated in 5 ml of kanamycin-containing SB medium (Bactotrytone 30 g, yeast extract 20 g, MOPS buffer 10 g/L) to start seed culture, and after incubation overnight, the culture was transferred to 500 ml of kanamycin-containing SB medium. When the OD value at 600 nm reached about 0.5, IPTG was added to reach 1 mM, followed by incubation at 30° C. overnight, thereby expressing scFv proteins in the periplasm of E. coli. The next day, E. coli obtained through centrifugation were suspended in 1×TES buffer (50 mM Tris, 1 mM EDTA, 20% Sucrose, pH 8.0), and then 0.2×TES was added by 1.5 times, followed by mixing, and then supernatant was taken through centrifugation, thereby extracting the periplasm.

Finally, 5 mM $MgSO_4$ was added to the scFv antibodies extracted from the periplasm, and the resultant material was mixed with Ni-NTA beads previously equilibrated with PBS, followed by stirring for 1 h in a cold storage to bind the antibody to the Ni-NTA beads. Thereafter, affinity chromatography was performed to sufficiently wash out the non-bound proteins with PBS. After further sufficient washing with a buffer containing 5 mM imidazole, the bound scFv antibodies were eluted using 200 mM imidazole buffer. The eluted antibodies were dialyzed, and the purity thereof was checked by electrophoresis. The protein quantification was performed by BCA assay, and the amount of purified antibodies was recorded, and then a certain amount thereof was dispensed and then frozen stored.

As described above, the scFv antibodies extracted from the periplasm were used to investigate using western blotting whether the scFv antibodies bound to the full-length KRS or respective KRS N-terminal fragments. Then, 30 μg of HCT116 cell lysate was electrophoresed through SDS PAGE, transferred onto PVDF membrane, and then blocked with 3% skim milk. Thereafter, the extracted scFv antibodies were added at 1.0 μg/μl, followed by incubation for 1 h. The unbound scFv antibodies were washed out, and for detection, the scFv binding with antigens were incubated with anti-HA secondary antibodies linked with horseradish peroxidase (HRP), and film sensitization was carried out using ECL reagent as a substrate in a dark room. The sensitized bands were compared with standard molecule markers to identify bands corresponding to sizes of the full-length KRS and the respective fragments.

Through the western blotting, scFv clones with highly weak bands (faint bands) and non-specific bands (double bands) were ruled out. Therefore, 13 scFv clones were selected, and these results are shown in FIG. 1.

<1-5> Screening of Specifically Binding scFv Antibodies Through Immunoprecipitation_Quaternary Screening Immunoprecipitation was performed to investigate whether the scFv clones selected in Example <1-4> actually bound to native KRS. The purified scFv clones and HCT116 cell lysate were subjected to Ag-Ab binding, and immunoprecipitation was performed utilizing scFv HA-tag.

Specifically, HCT116 cells were lysed in 20 mM Tris-HCl buffer (pH 7.4, lysis buffer) containing 150 mM NaCl, 0.5% Triton X-100, 0.1% SDS and a protease inhibitor. Each scFv (5 μg) was added to 500 μg of HCT116 cell lysate, and then incubated at 4° C. overnight. Then 30 μl of anti-HA agarose beads were added, followed by incubation at 4° C. for 4 h. The supernatant was removed through centrifugation. The precipitate thus obtained was dissolved in SDS-sample buffer, and boiled for 7 min. The dissolving and boiling step was repeated twice.

Each of the immunoprecipitated samples prepared through the above-described procedure was electrophoresed through SDS PAGE, transferred onto PVDF membrane, and then blocked with 3% skim milk. Thereafter, KRS polyclonal antibodies (rabbit, Neomics, Co. Ltd. #NMS-01-0005) were added, followed by incubation for 1 h. After the unbound antibodies were washed out, anti-rabbit secondary antibodies (ThermoFisher Scientific, #31460) were added, followed by incubation. After incubation with the secondary antibodies, film sensitization was carried out using ECL reagent as a substrate in a dark room. The sensitized bands were compared with standard molecule markers to identify bands corresponding to sizes of the full-length KRS and the respective fragments.

Figure 2:
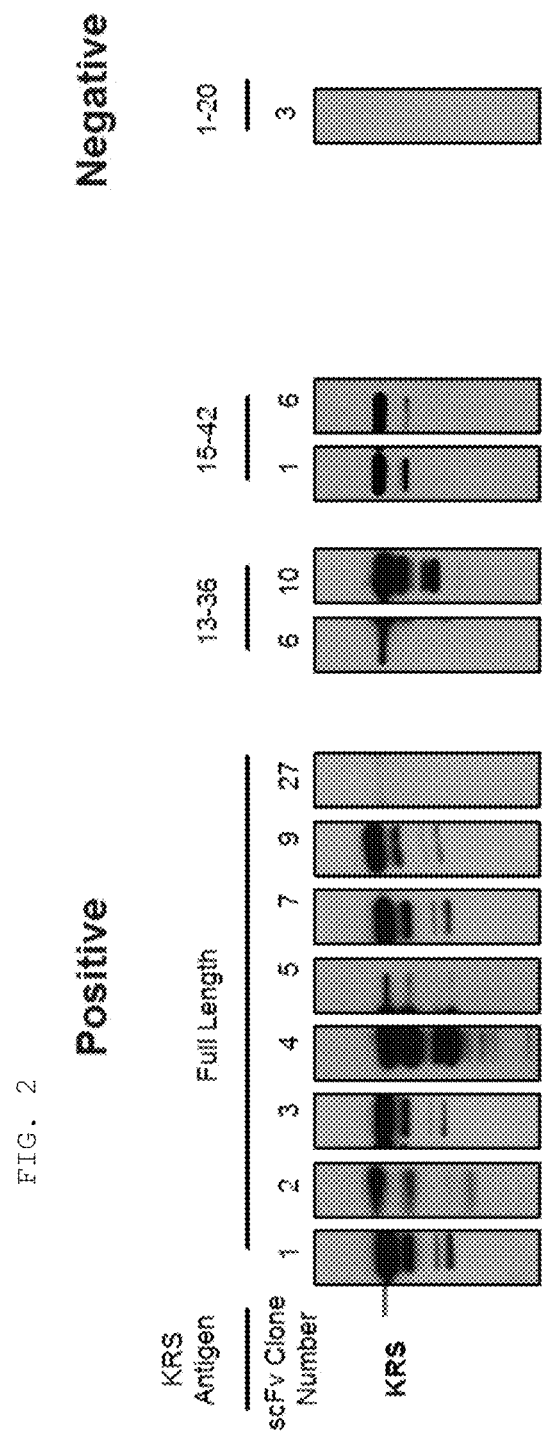
FIG. 2 shows the results of selecting, through immunoprecipitation (IP), scFv phage clones binding to KRS full-length sequence or KRS N-terminal fragments.

Therefore, 12 scFv clones were selected, and these results are shown in FIG. 2.

<1-6> Screening of Specifically Binding scFv Antibodies Through Immunofluorescence_Quinary Screening Immunofluorescence was performed to investigate whether the scFv clones selected in Example <1-5> actually bound to the KRS N-terminal region exposed on the cell membrane. In order to make a phenomenon in which KRS is exposed on the membrane, KRS-T52D mutant (active mutant) was used. Specifically, A549 cells were seeded on glass coverslip (1×10⁵ cell, 12 well plate-based), and after 24 h, myc-KRS WT/myc-KRS T52D (active mutant)/myc-KRS T52A (inactive mutant) were overexpressed, respectively. After incubation for 24 h, the cells were incubated using serum-free media (RPMI 1640 media) at 37° C. for 1 h. Thereafter, the cells were treated with 10 μg/ml laminin (L2020; Sigma) and then incubated at 37° C. for 1 h. Each of myc-KRS T52D (active mutant) and myc-KRS T52A (inactive mutant) vectors was constructed using pcDNA3-myc-KRS WT vector as a backbone through site-directed mutagenesis (QuikChange □ Site-Directed Mutagenesis kit, Agilent, #200523).

The prepared samples were washed with PBS (4° C.), fixed by the treatment with 4% paraformaldehyde for 10 min, and then washed. The samples were blocked with CAS block for 10 min, and treated with the scFv and Myc antibodies for 2 h. Thereafter, the unbound antibodies were washed out, and incubated with secondary antibodies for 1 h in a dark room. DAPI staining was performed for 10 min before mounting.

Figure 3A:
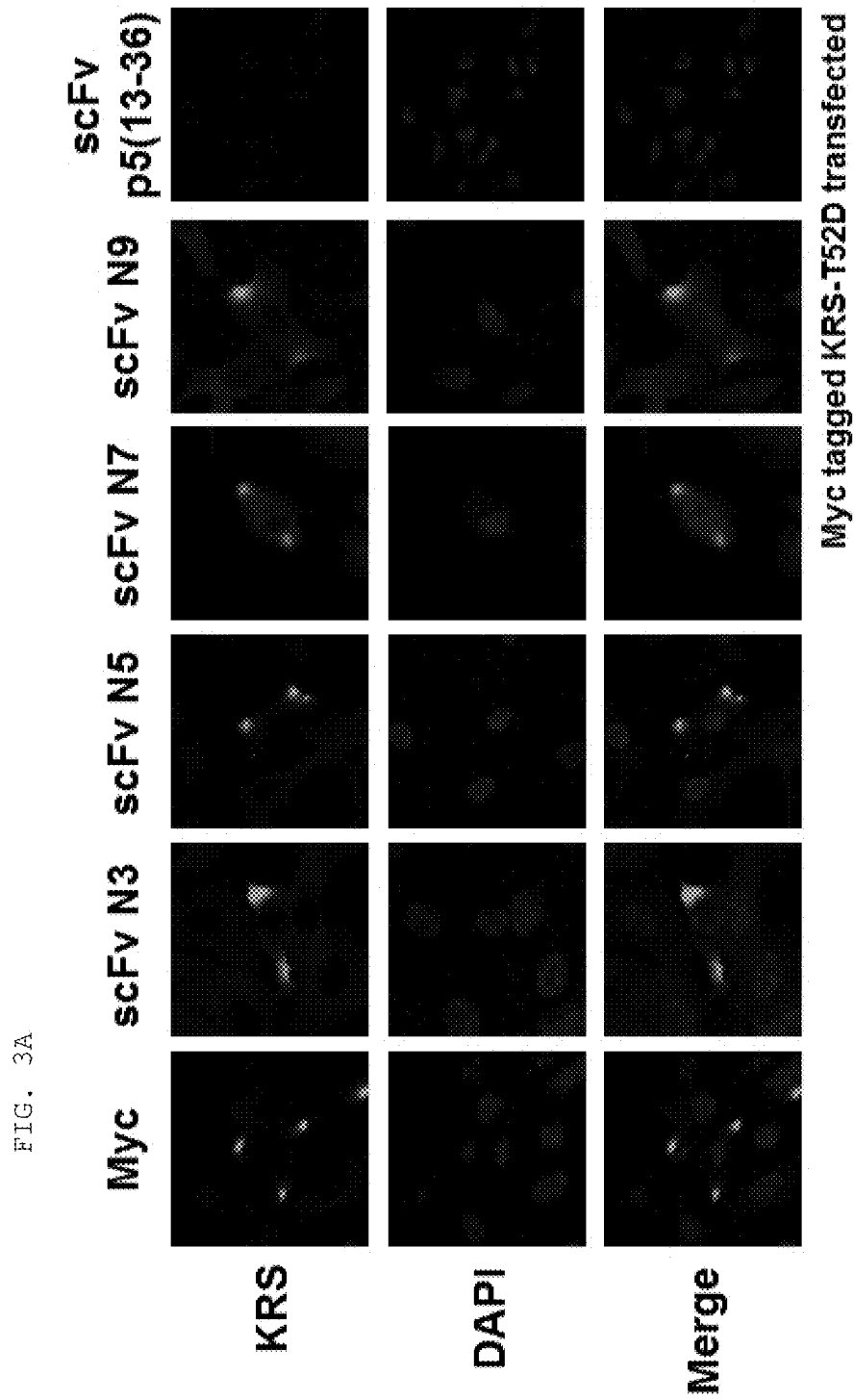
FIGS. 3A-3B show scFv staining of WT and mutant myc-KRS.
Figure 3B:
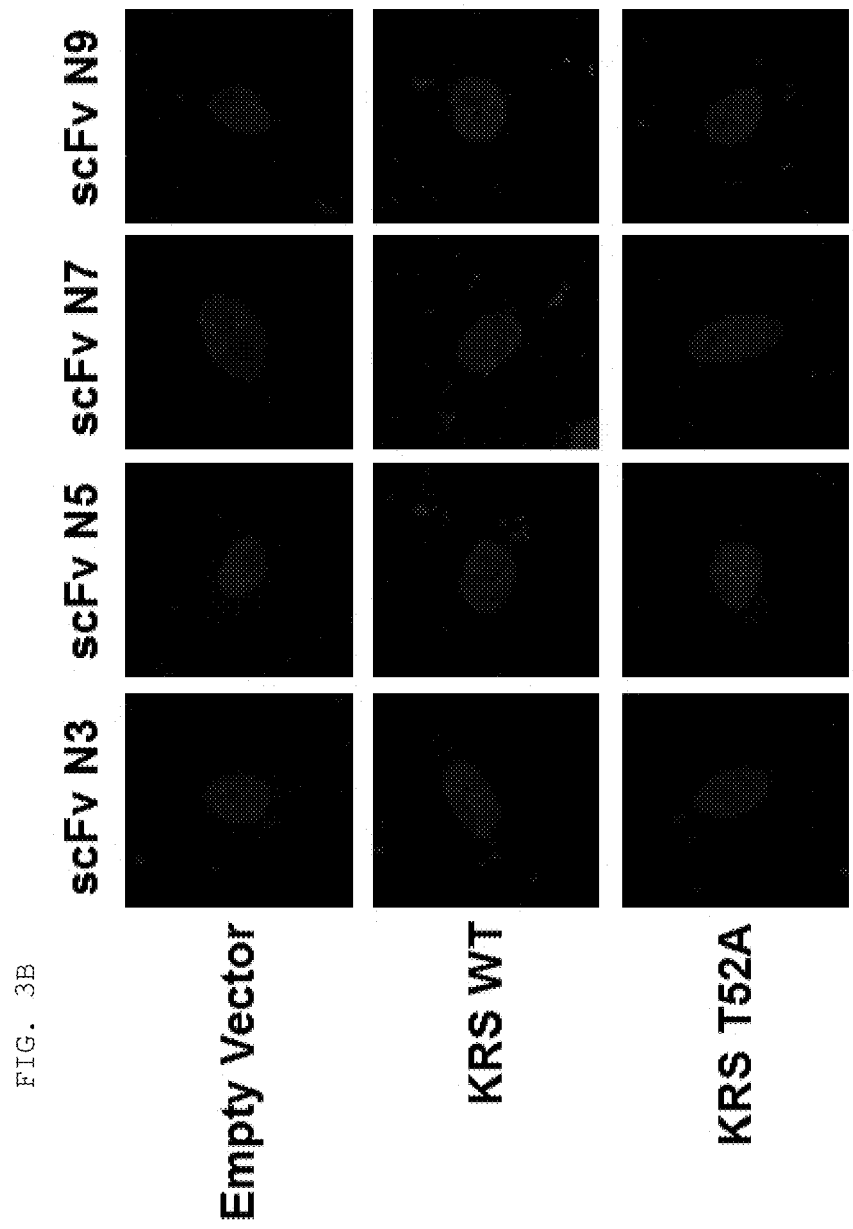
Figure 3C:
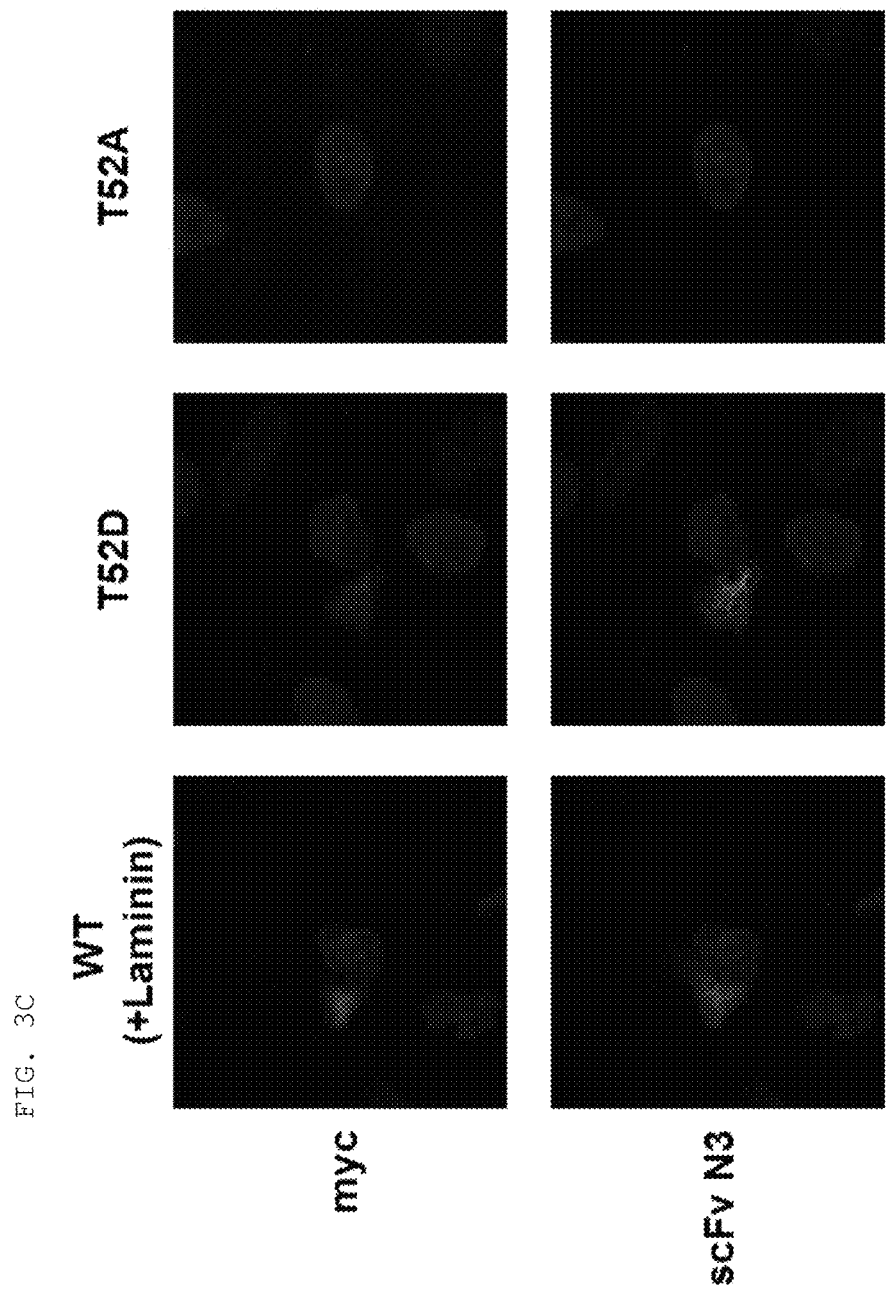
FIG. 3C shows that when cells transformed with myc-labeled WT-KRS, T52D, and T52A were treated with laminin and scFv staining was performed, staining was observed at similar sites in the membrane localization of WT-KRS by laminin and T52D mutant and the transformed myc was also stained at the same site, but staining was not observed in T52A (scFv: green, myc: red).

As shown in FIGS. 3A-3C, the experimental results showed that a total of four scFv clones (N3, N5, N7, and N9) not binding to the inactive mutant (T52A) and WT-KRS (laminin untreated) but binding only active mutant cells were selected. When laminin treatment was carried out for inducing the membrane localization of WT-KRS and scFv staining was performed, similar staining regions were observed in WT-KRS and T52D mutant.

It was confirmed that these clones specifically bind to the cell surface (tip).

<1-7> Verification of Specific Binding Ability to KRS N-Terminus

To investigate whether the scFv clones (N3, N5, N7, and N9) finally selected through Example <1-6> actually bound to KRS N-terminus, full-length KRS (denoted by F, SEQ ID NO: 76), a KRS fragment with deletion in amino acids at positions 1-71 in the N-terminus (defined by SEQ ID NO: 1), and a KRS fragment composed of amino acid residues 1-200 in the N-terminus (defined by SEQ ID NO: 2) were used to conduct western blotting.

A549 cells were transformed by the method as described in Example <1-6> using polynucleotides encoding full-length KRS and KRS fragments. Thereafter, the cells were lysed, and western blotting was performed by the same method as described in Example <1-4>.

Figure 4:
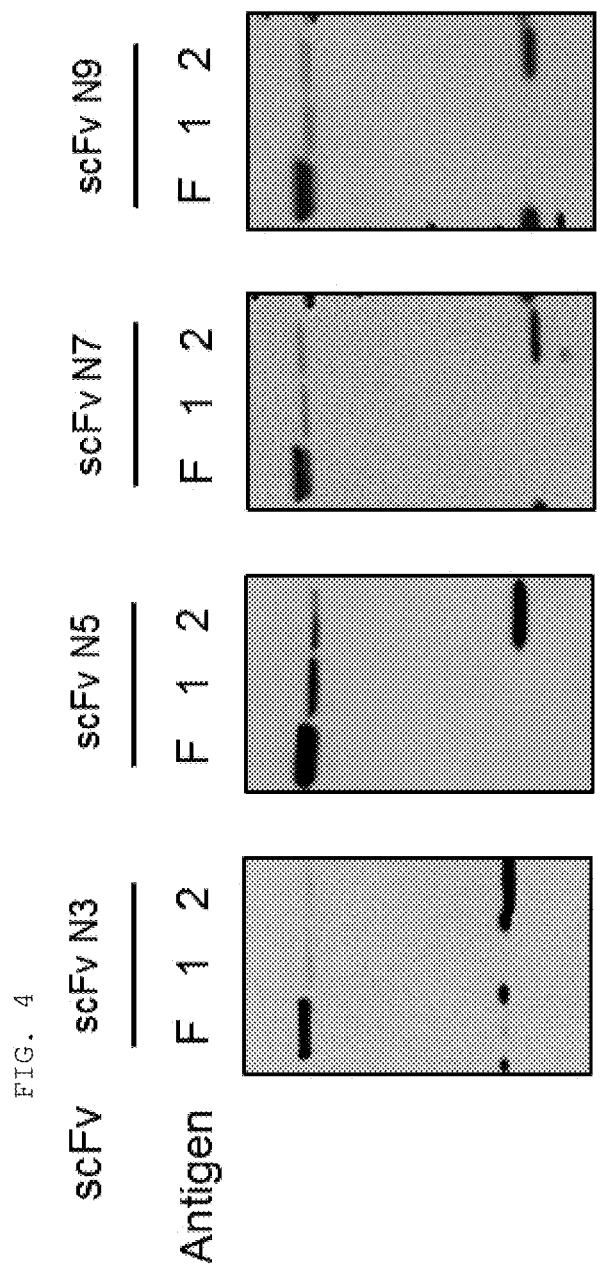
FIG. 4 shows the western blotting results of confirming whether N3, N5, N7, and N9 scFv clones specifically bound to KRS N-terminus by using full-length KRS (denoted by F, SEQ ID NO: 76), a KRS fragment with deletion of amino acids at positions 1-71 in the N-terminus (denoted by 1), and a KRS fragment composed of amino acid residues 1-200 in the N-terminus (denoted by 2).

As shown in FIG. 4, the results confirmed that all the selected scFv clones (N3, N5, N7, and N9) showed bands in only the fragment with amino acids at 1-200 in the N-terminus while showing no bands in fragment 1 without amino acids at positions 1-72 in the N-terminus. It was therefore verified that all of the scFv N3, N5, N7, and N9 clones specifically bound to the KRS N-terminus.

<1-8> Sequencing of KRS N-Terminal Binding Specific scFv Clones

The scFv clones (N3, N5, N7, and N9) finally selected through Example <1-6> were analyzed for CDR conformation and VH and VL sequences thereof. Sequencing was performed by the same method as described in Example <1-3>.

As a result of sequencing, N3 scFv consists of the amino acid sequence defined by SEQ ID NO: 67, which contains the linker sequence of SEQ ID NO: 65 in the middle thereof. In addition, N3 VH consists of the amino acid sequence defined by SEQ ID NO: 49 and N3 VL consists of the amino acid sequence defined by SEQ ID NO: 51. As a result of sequencing respective CDRs contained in VH and VL of N3, N3 VH comprises heavy chain CDR1 defined by SEQ ID NO: 1, heavy chain CDR2 defined by SEQ ID NO: 3, and heavy chain CDR3 defined by SEQ ID NO: 5, and N3 VL comprises light chain CDR1 defined by SEQ ID NO: 7, light chain CDR2 defined by SEQ ID NO: 9, and light chain CDR3 defined by SEQ ID NO: 11.

N5 scFv consists of the amino acid sequence defined by SEQ ID NO: 69, which contains the linker sequence of SEQ ID NO: 65 in the middle thereof. In addition, N5 VH consists of the amino acid sequence defined by SEQ ID NO: 53 and N5 VL consists of the amino acid sequence defined by SEQ ID NO: 55. N5 VH comprises heavy chain CDR1 defined by SEQ ID NO: 13, heavy chain CDR2 defined by SEQ ID NO: 15, and heavy chain CDR3 defined by SEQ ID NO: 17, and N5 VL comprises light chain CDR1 defined by SEQ ID NO: 19, light chain CDR2 defined by SEQ ID NO: 21, and light chain CDR3 defined by SEQ ID NO: 23.

N7 scFv consists of the amino acid sequence defined by SEQ ID NO: 71, which contains the linker sequence of SEQ ID NO: 65 in the middle thereof. In addition, N7 VH consists of the amino acid sequence defined by SEQ ID NO: 57 and N7 VL consists of the amino acid sequence defined by SEQ ID NO: 59. N7 VH comprises heavy chain CDR1 defined by SEQ ID NO: 25, heavy chain CDR2 defined by SEQ ID NO: 27, and heavy chain CDR3 defined by SEQ ID NO: 29, and N7 VL comprises light chain CDR1 defined by SEQ ID NO: 31, light chain CDR2 defined by SEQ ID NO: 33, and light chain CDR3 defined by SEQ ID NO: 35.

N9 scFv consists of the amino acid sequence defined by SEQ ID NO: 73, which contains the linker sequence of SEQ ID NO: 65 in the middle thereof. In addition, N9 VH consists of the amino acid sequence defined by SEQ ID NO: 61 and N9 VL consists of the amino acid sequence defined by SEQ ID NO: 63. N9 VH comprises heavy chain CDR1 defined by SEQ ID NO: 37, heavy chain CDR2 defined by SEQ ID NO: 39, and heavy chain CDR3 defined by SEQ ID NO: 41, and N9 VL comprises light chain CDR1 defined by SEQ ID NO: 43, light chain CDR2 defined by SEQ ID NO: 45, and light chain CDR3 defined by SEQ ID NO: 47.

Example 2

Conversion of scFv Antibodies into IgG Antibodies and Evaluation of Specific Binding Ability Thereof <2-1> Conversion of scFv Antibodies into IgG Antibodies First, the polynucleotides encoding scFv were amplified via PCR from N3, N5, N7, and N9 phage genomes. The nucleotide sequences of the primers used to amplify a gene of VH region of the scFv antibodies: Forward (AGA GAG TGT ACA CTC CCA GGC GGC CGA GGT GCA G, SEQ ID NO: 93), Reverse (CGC CGC TGG GCC CTT GGT GGA GGC TGA GCT CAC GGT GAC CAG, SEQ ID NO: 94). The nucleotide sequences of the primers used to amplify a gene of VL region of the scFv antibodies: Forward (AAG CGG CCG CCA CCA TGG GAT GGA GCT GTA TCA TCC TCT TCT TGG TAG CAA CAG CTA CAG GTG TAC ACT CCC AGT CTG TGC TGA CTC AG, SEQ ID NO: 95), Reverse (CGC CGC CGT ACG TAG GAC CGT CAG CTT GGT, SEQ ID NO: 96)

PCR was performed with each phage DNA (50 ng) as a template by using the primers (10 pmol each) in conditions of: 95° C./3 min; 95° C./30 s, 60° C./30 s, 72° C./30 s, 30 cycles; and 72° C./5 min, thereby amplifying the VH or VL gene of N3, N5, N7, or N9 scFv. The PCR product was inserted into the pcDNA3.4 vector used in IgG production using restriction enzymes. IgG heavy and light chain proteins were individually encoded in separate plasmids.

The constructed vectors comprising DNA encoding heavy and light chains of each of IgGs (hereinafter, called N3 IgG, N5 IgG, N7 IgG, and N9 IgG, respectively) containing scFv variable regions were co-transformed in freestyle 293F cells to express the heavy and light chains together in cells. The transformed 293F cells were incubated in conditions of 37° C. and 8% $CO_2$ for 7 days, and the supernatant was obtained. The supernatant was filtered through a cellulose acetate membrane filter (pore size 0.22 µm, Corning), and purified using CaptivA™ PriMAB protein A column (Repligen, USA). The concentrations of the obtained antibodies were measured using BCA kit (Pierce, 23225), and the IgG antibody proteins produced in reduction and non-reduction conditions were analyzed.

<2-2> Verification of KRS Binding Ability of Converted IgG_Western Blotting and Immunoprecipitation The KRS binding ability of the IgGs constructed in Example <2-1> was investigated by western blotting (WB) and immunoprecipitation. Western blotting was performed in the same manner as described in Example <1-4> and immunoprecipitation was performed in the same manner as described in Example <1-5>.

Figure 5A:
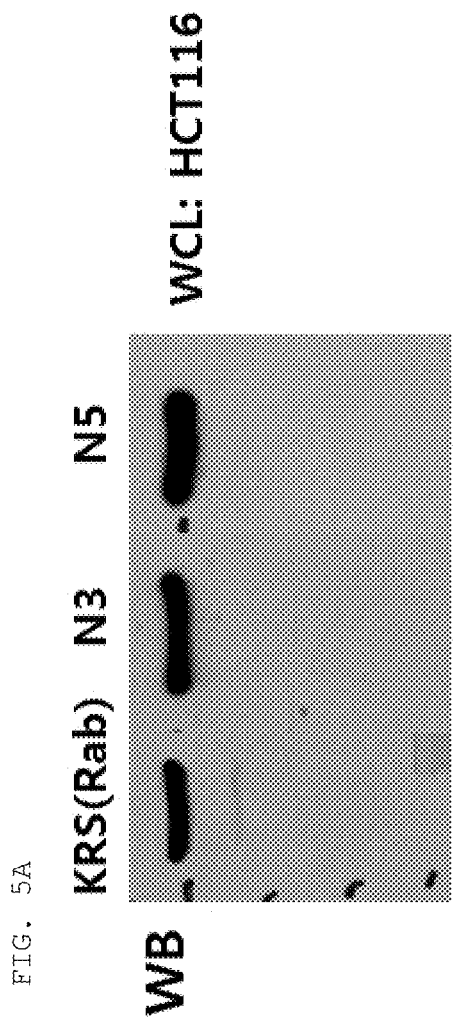
FIGS. 5A-5B show KRS binding ability.
Figure 5B:
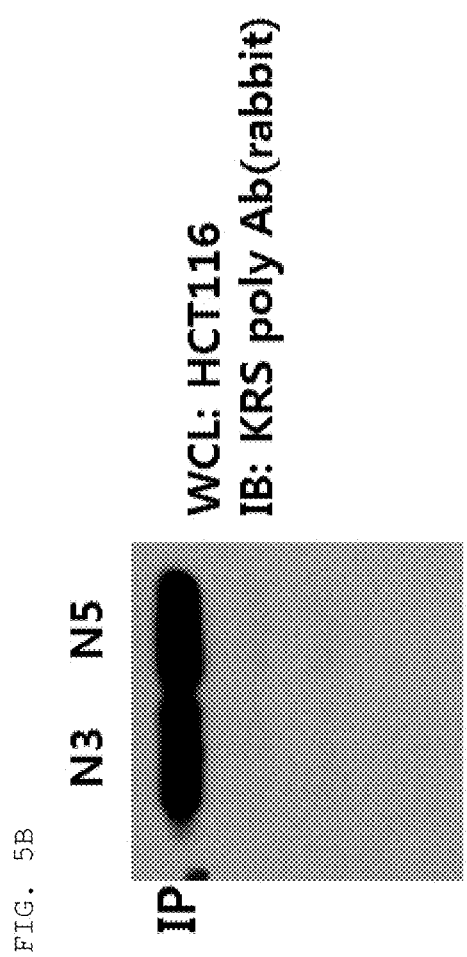

The results verified that the IgGs constructed in the present invention bound to KRS, and FIGS. 5A-5B shows these results using N3 IgG and N5 IgG as representatives.

<2-3> Verification of KRS N-Terminus-Specific Binding Ability of Converted IgGs_SPR The quantitative binding ability of the purified antibody proteins (N3 IgG and N5 IgG) to the antigen (KRS 1-207 aa) were measured using Biacore 2000 SPR (surface plasmon resonance) (GE healthcare, US) biosensor. After KRS was immobilized on a sensor chip (CM5, GE healthcare, US), antibody proteins (6.25-100 nM), which were serially diluted with HES buffer solution (10 mM HEPES, pH 7.4, 150 mM NaCl, 3 mM EDTA, 0.005% surfactant P20), were allowed to flow at a rate of 30 µl/min for 3 min, and 1 M NaCl/20 mM NaOH was allowed to flow at a rate of 30 µl/min for 3 min, thereby inducing the dissociation of proteins bound to the antigen. Mock IgG was used as control. Specific experiment conditions are as follows:

Immobilized Antigen: KRS
Immobilized level: 185 RU
Antibody: N3 IgG and N5 IgG
Running buffer: HBS-N buffer
Regeneration: 2 M NaCl, 20 mM NaOH (flow 30 ul/min 1 min)

TABLE 3

|  | ka (1/Ms) | kd (1/s) | KD (M) |
| --- | --- | --- | --- |
| N3 IgG | 1.09E+05 | 0.009055 | 8.34E-08 |
| N5 IgG | 3.13E+06 | 0.003282 | 1.05E-09 |

Figure 6A:
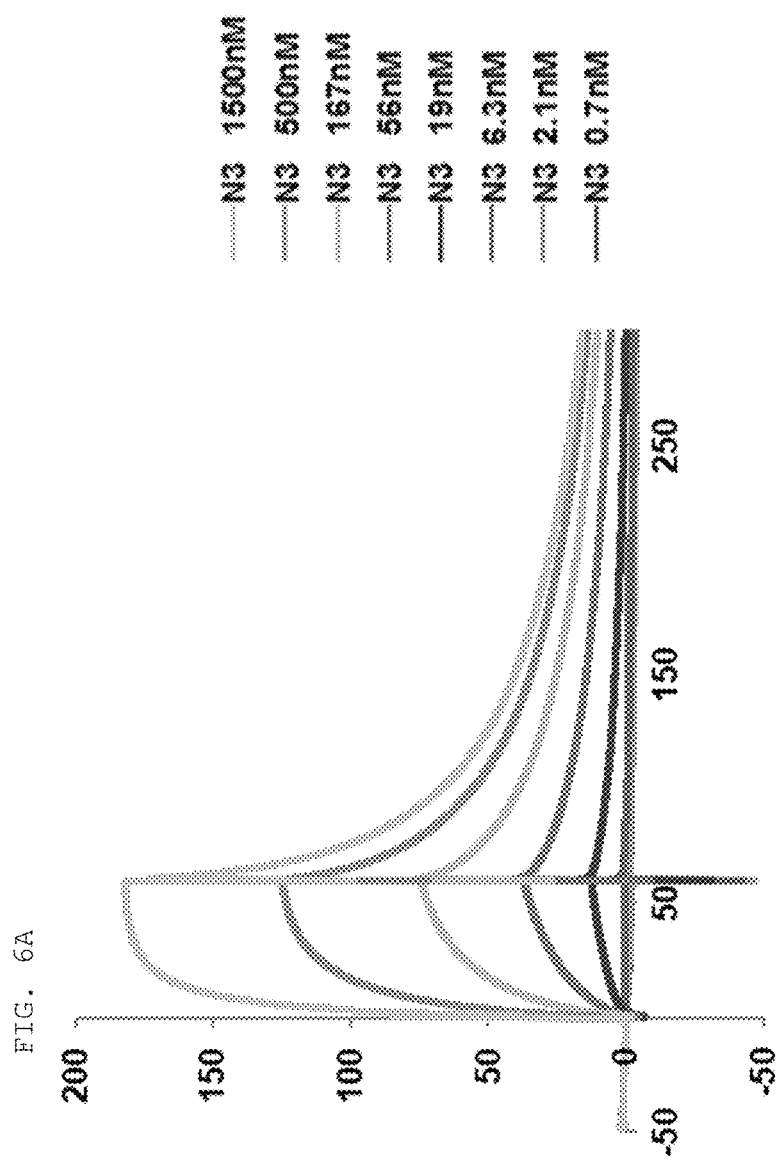
FIGS. 6A-6B show KRS N-terminus binding ability.
Figure 6B:
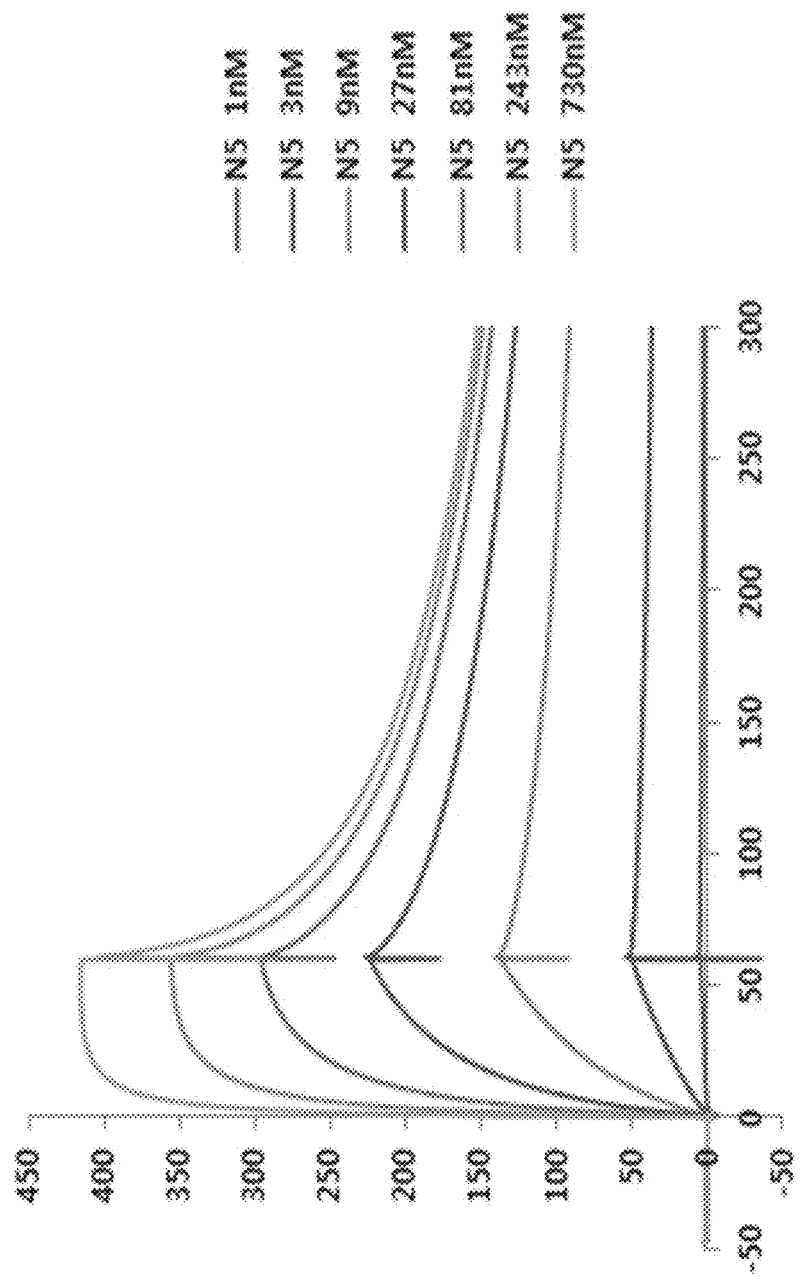

Table 3 shows kinetic rate constants and equilibrium dissociation constants measured for N3 IgG and N5 IgG by using Biacore 2000 SPR. The affinity was obtained from the kinetic rate constants (ka and kd) and equilibrium dissociation constants (KD) by using BIA evaluation ver. 3.2 software. FIGS. 6A-6B show SPR graph results of N3 IgG and N5 IgG, respectively. It was confirmed from FIGS. 6A-6B and Table 3 that N3 IgG and N5 IgG of the present invention has high specific binding ability to the KRS N-terminal region. No binding signals were observed in mock IgG as control.

<2-4> Verification of KRS N-Terminus Specific Binding Ability of Converted IgG Immunofluorescence Staining To investigate whether the IgGs constructed in the present invention actually bound to the region of KRS exposed on the cell membrane, immunofluorescence was performed. Immunofluorescence staining was performed by the same method as described in Example <1-6> by using N3 IgG and N5 IgG as representatives.

Figure 7A:
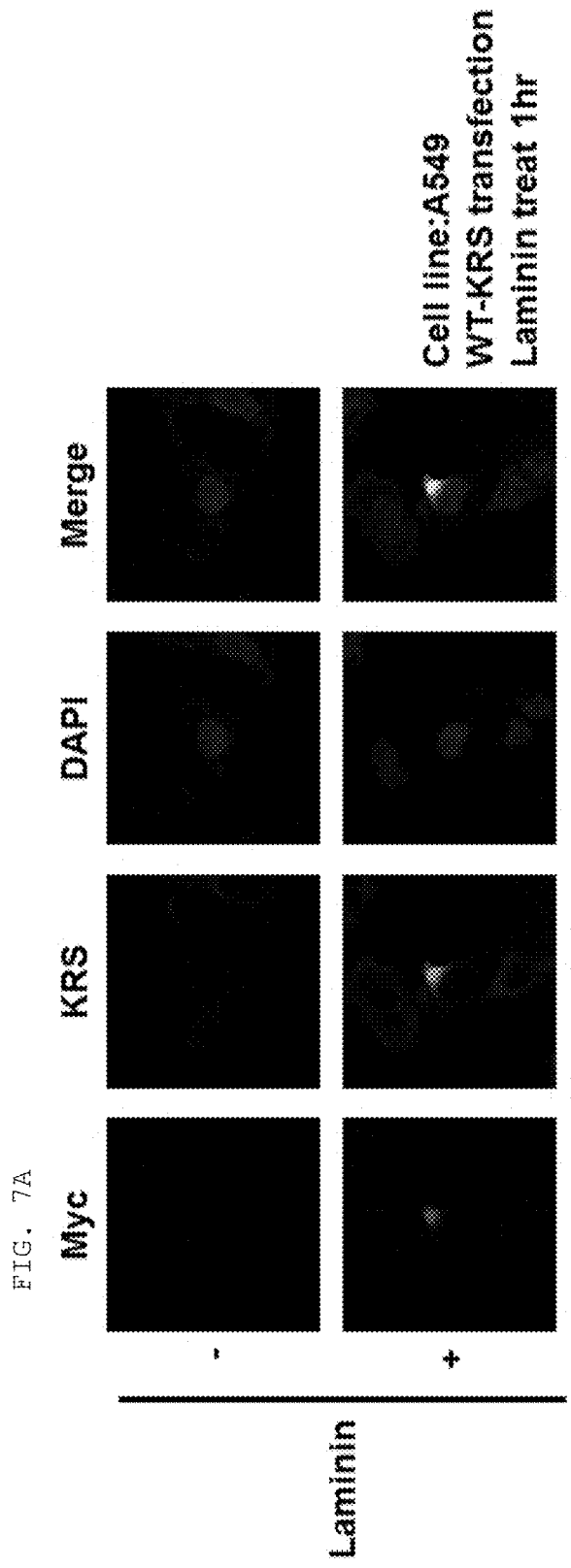
FIGS. 7A-7C show immunofluorescence staining.
Figure 7B:
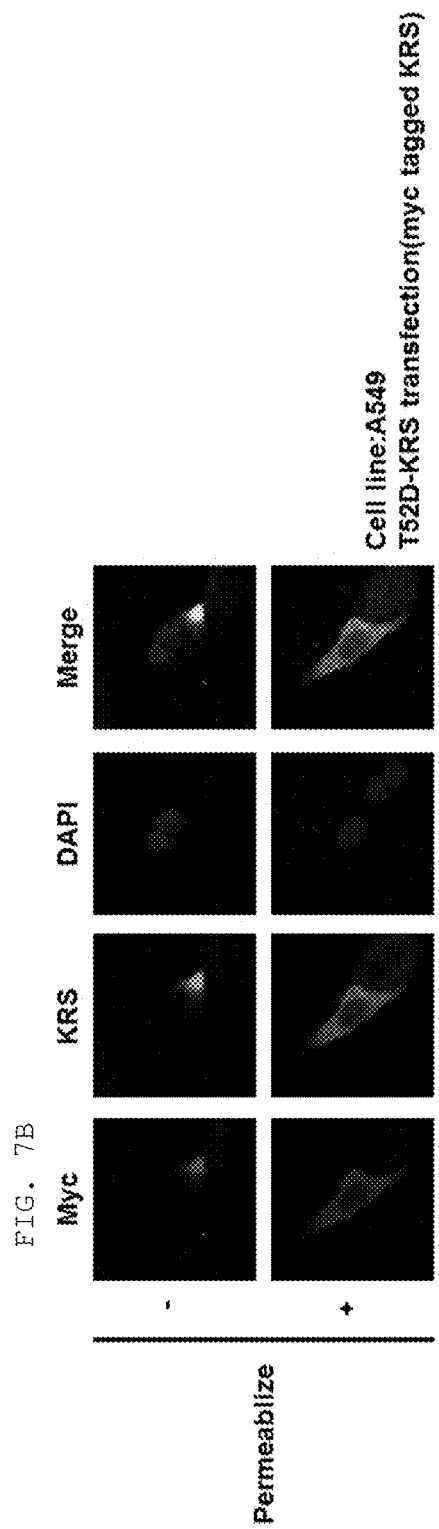
Figure 7C:
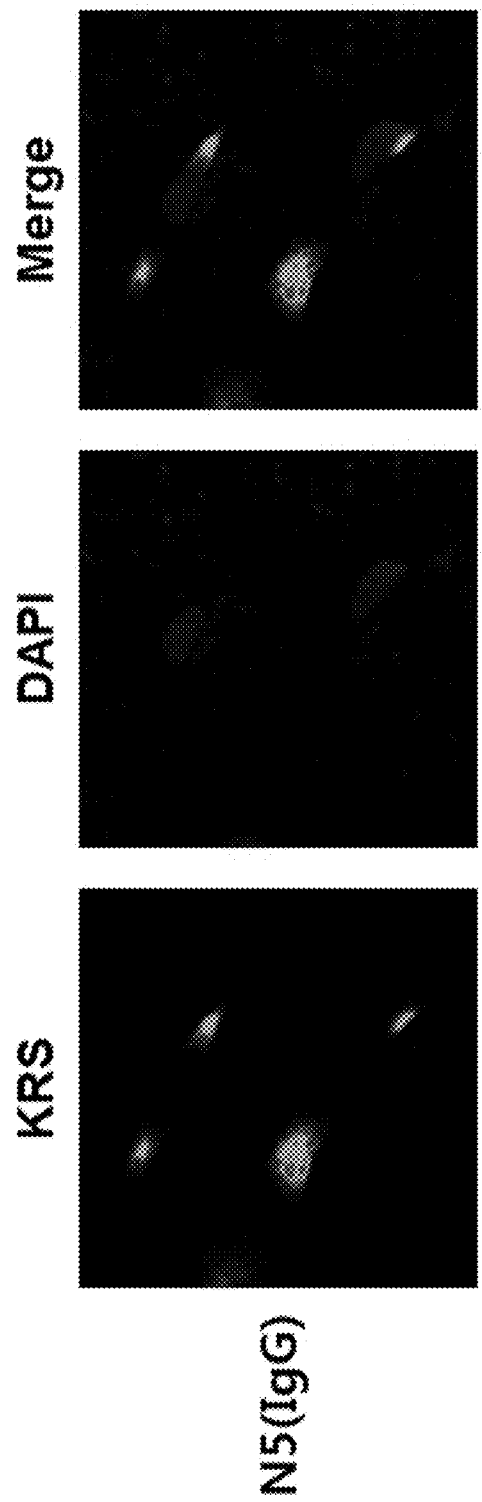

As shown in FIG. 7A, the results confirmed that N3 IgG favorably bound specifically to the extracellularly exposed KRS N-terminal region when the membrane localization of WT-KRS was induced by laminin treatment. As shown in FIG. 7B, the experiment using T52D-KRS (active mutant, myc tagged KRS) also showed that the antibody of the present invention favorably bound to the extracellularly exposed KRS N-terminal region, and when the experimental cells became permeabilized, the KRS proteins present in cytosol were detected at high sensitivity. It was also confirmed as shown in FIG. 7C that N5 IgG favorably bound specifically to extracellularly exposed KRS N-terminal region when the membrane localization of WT-KRS was induced by laminin treatment.

It was therefore verified that the antibodies provided in the present invention have high binding specificity to an extracellularly exposed KRS N-terminal region.

Example 3

Verification of Inhibitory Effect on Cancer Metastasis
<3-1> Cytotoxicity Evaluation MTT assay was performed on N3 IgG as a representative. A549 cells were seeded in 96-well plates (5,000 cell/well) and incubated. The cells were washed with serum-free media, and then treated with human mock IgG and N3 IgG of 0, 50, 100, 500 nM (in serum-free media). After 24-h incubation, MTT solution was added with 50 μg/well, followed by incubation for 4 h. After MTT solution was removed, the wells were treated with 100 ul of DMSO, and then the absorbance was measured at 570 nm.

Figure 8:
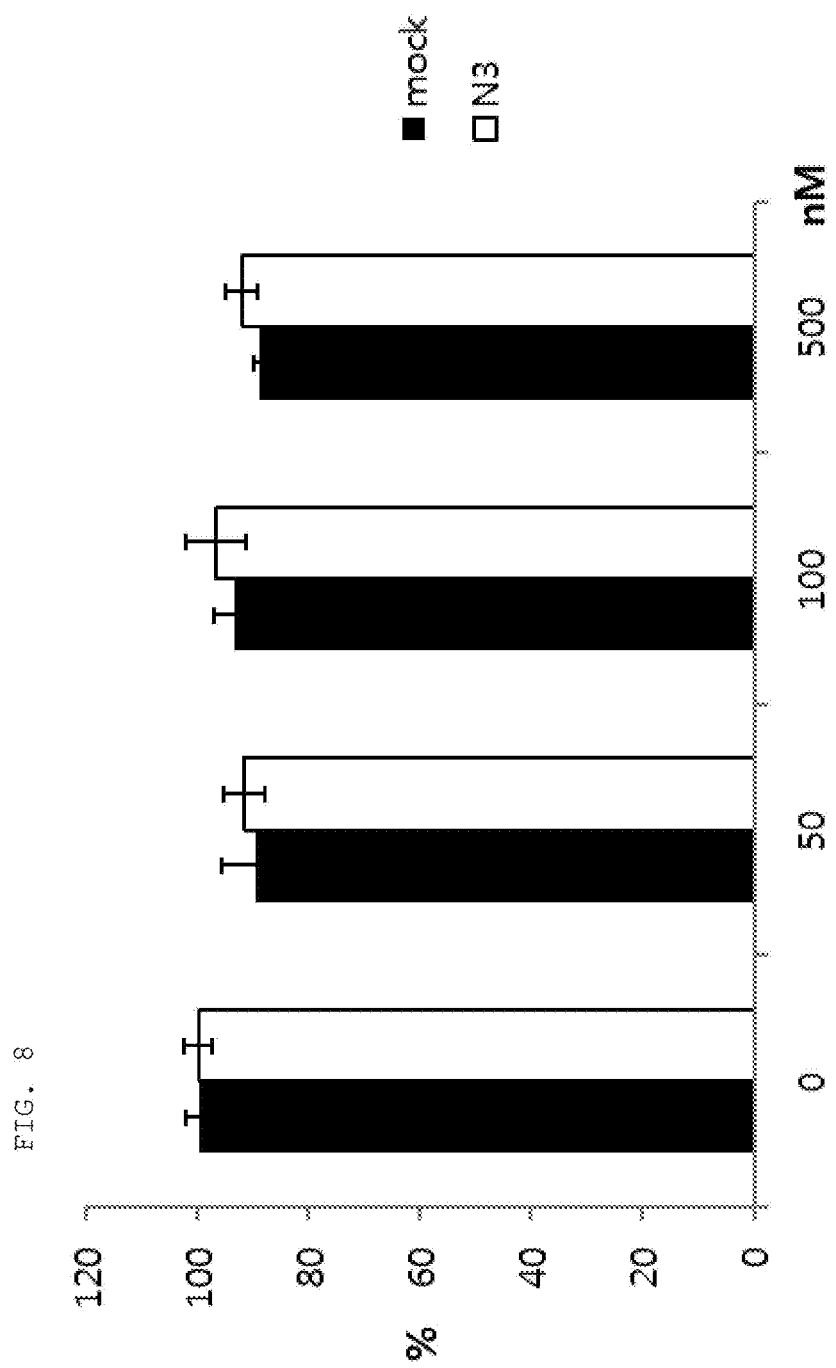
FIG. 8 shows the MTT assay results of confirming that the antibody of the present invention N3 IgG had no cytotoxicity.

As shown in FIG. 8, the experimental results confirmed that the antibody of the present invention shows no cytotoxicity.

<3-2> Cell Migration Assay

Cell migration was measured using a 24-well Transwell chamber with polycarbonate membrane (8.0 μm pore size, Costar) as disclosed in the prior art (Park, S. G. et al., Human lysyl-tRNA synthetase is secreted to trigger pro-inflammatory response, Proc. Natl. Acad. Sci. USA 102, 6356-6361 (2005)). In the Transwell chamber, the lower well was coated with 10 μg of laminin (in gelatin) and dried with UV. Thereafter, A549 cells were suspended in serum-free RPIM media, and then placed at a concentration of 1×10$^5$ cells per well in the upper chamber. The chamber was treated with N3 IgG or human mock IgG (control) at 100 nM or 500 nM, followed by incubation for 24 h. Thereafter, the chamber was washed twice with PBS, and treated with 70% MeOH (in PBS) for 30 min. The chamber was again washed twice with PBS, and treated with Hematoxylin solution for 30 min. The chamber was washed three times with DW, and the membrane in the chamber was cut and mounted on the slide glass.

Figure 9A:
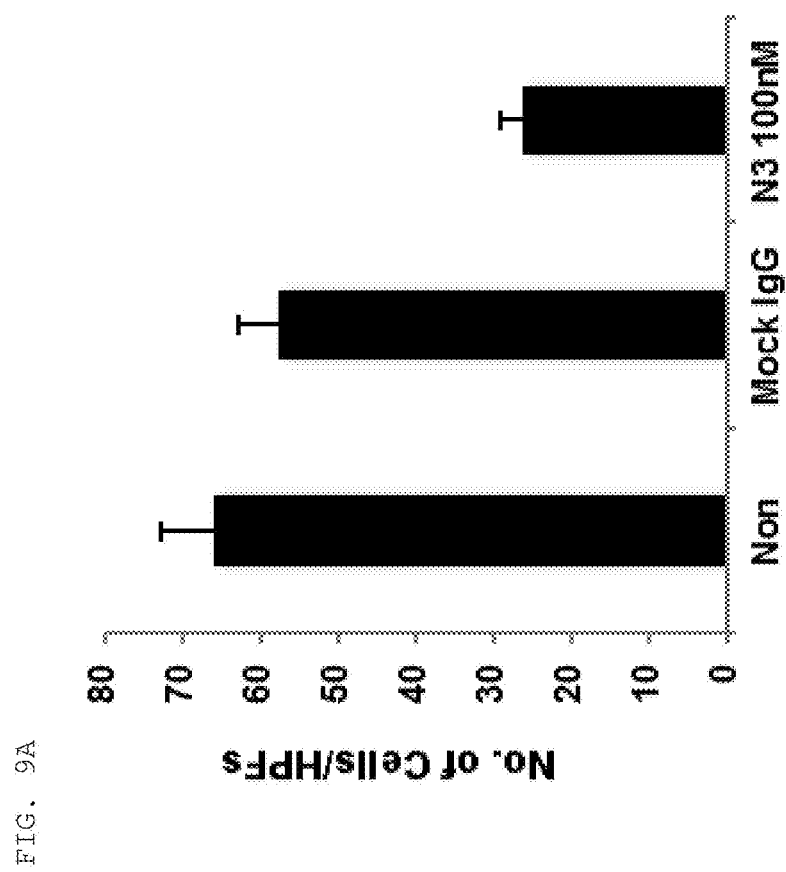
FIGS. 9A-9B show results of cell migration suppression.
Figure 9B:
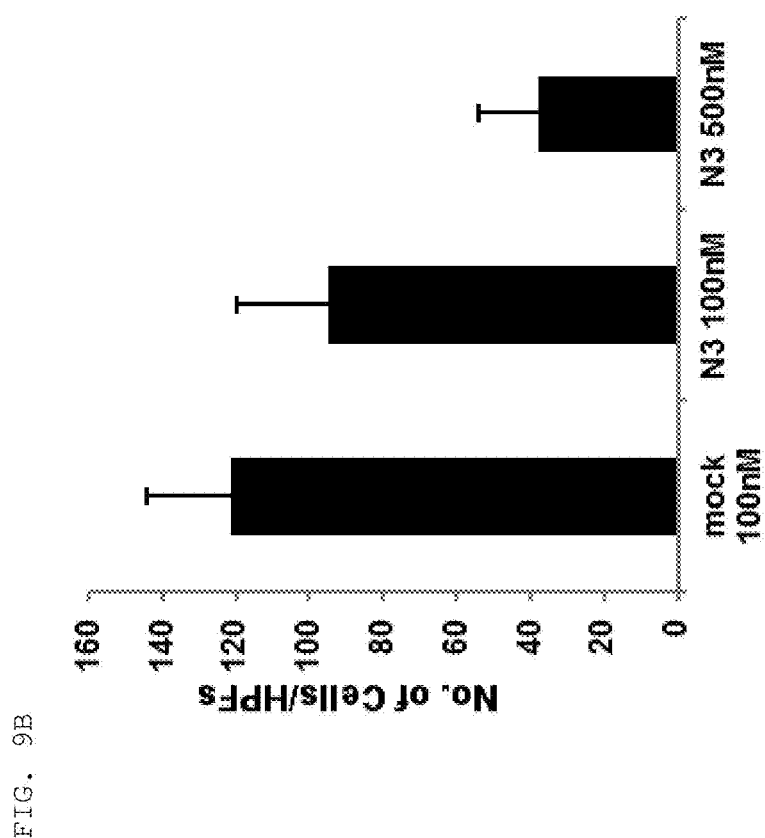
Figure 10:
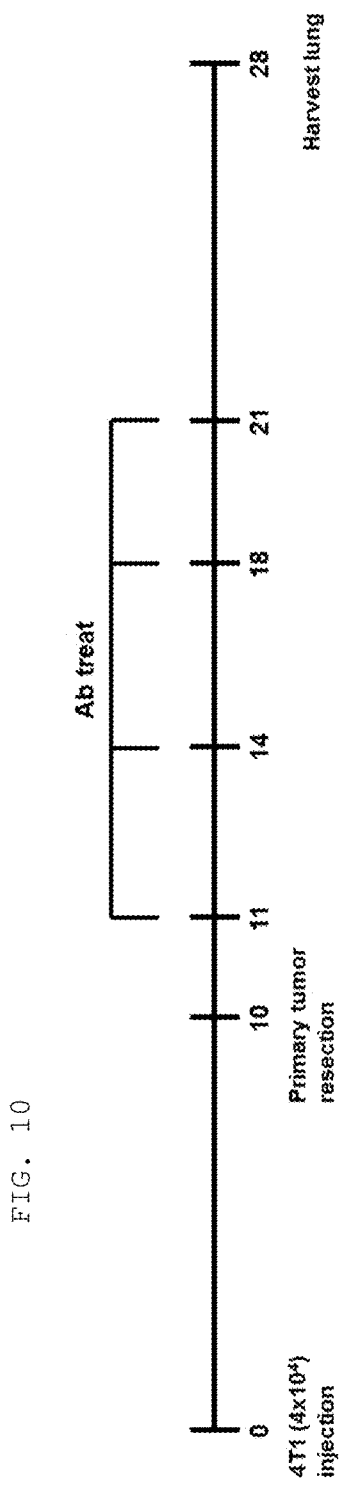
FIG. 10 schematically shows an experimental schedule of construction of mouse cancer metastasis models, administration of therapeutic substance (antibody or YH16899), and observation of lung metastasis in the mouse models, in an experiment using in vivo cancer metastasis models.

As shown in FIG. 9A, the experimental results showed that N3 IgG significantly inhibited the migration of A549 cells. The experimental results also showed that this cell migration inhibitory effect was dose-dependent (see FIG. 9B).

<3-3> Evaluation of Cancer Metastasis Inhibitory Effect in In-Vivo Cancer Metastasis Models Since KRS can accelerate cell migration through 67LR associated with cancer metastasis, tumor (cancer) animal models were constructed using mouse breast cancer 4T-1 cells (Korean Cell Line Bank), which are well metastasizable to the lung. Orthotopic breast cancer animal models were constructed by injecting 4×10$^4$ 4 T1 cells into the fat pad of six 7-week old BALB/cAnCr mice (Doo Yeol Biotech).

The cancer was injected into the mammary fat pad, and after 10 days (Day 10), cancer tissues were resected from the fat pad. After one day (Day 11), N3 IgG (10 mg/kg) was administered twice a week for two weeks at intervals of 3 days (a total of four times, Days 11, 14, 18, and 21) via tail vein i.v. injection, and the same dose of control mock IgG (Thermo #31154) was also administered. One week after the completion of the entire antibody dosing schedule, that is, 28 days after cancer injection, the mice were sacrificed to take lung tissue. Upon autopsy of lung tissue, the lung was inflated by injection of a saline solution into the bronchus through a syringe, collected, and then stored in Bouin's solution (Sigma #HT10132) for 24 h. Thereafter, the metastasis nodules in each lobe of the lung were counted through a microscope.

Figure 11:
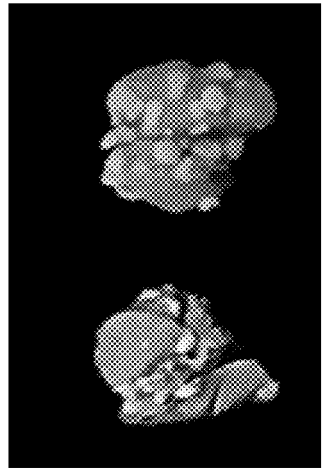
FIG. 11 shows mouse lung specimens capable of confirming that caner metastasis to lungs were significantly suppressed by the administration of the antibody of the present invention, N3 IgG, in in-vivo cancer metastasis models. The degrees of progression and severity of cancer metastasis could be evaluated from the count and condition of nodules generated in the lung specimens.
Figure 11:
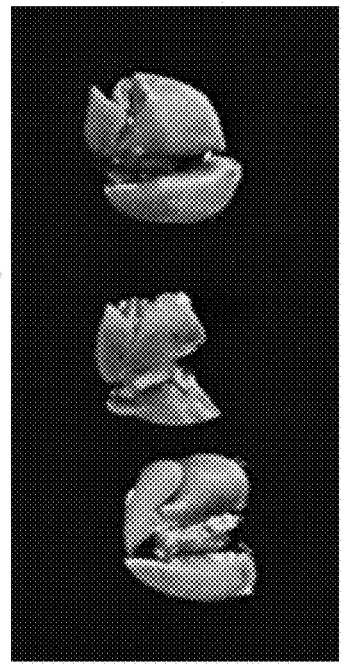
Figure 12:
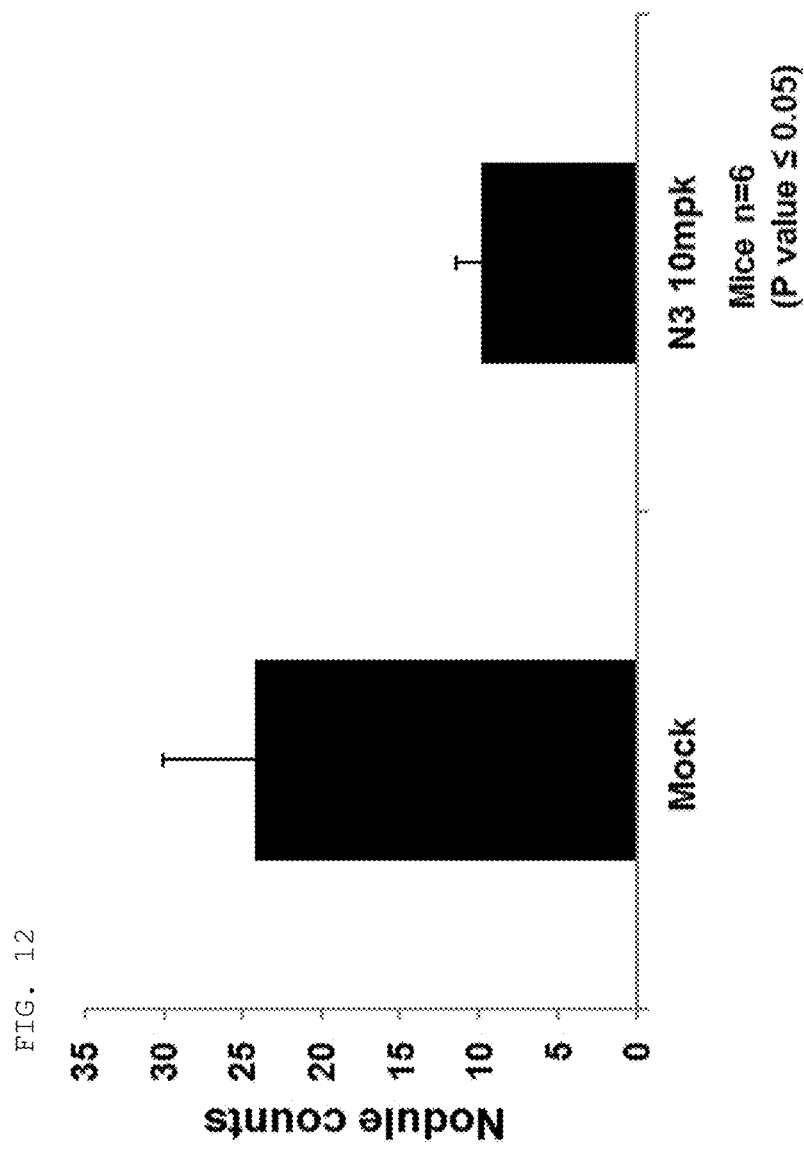
FIG. 12 shows the results of confirming that the generation of lung nodules was significantly suppressed by the administration of the antibody of the present invention, N3 IgG, compared with control, in in-vivo cancer metastasis models (i.e., cancer metastasis to lungs were significantly suppressed).
Figure 13:
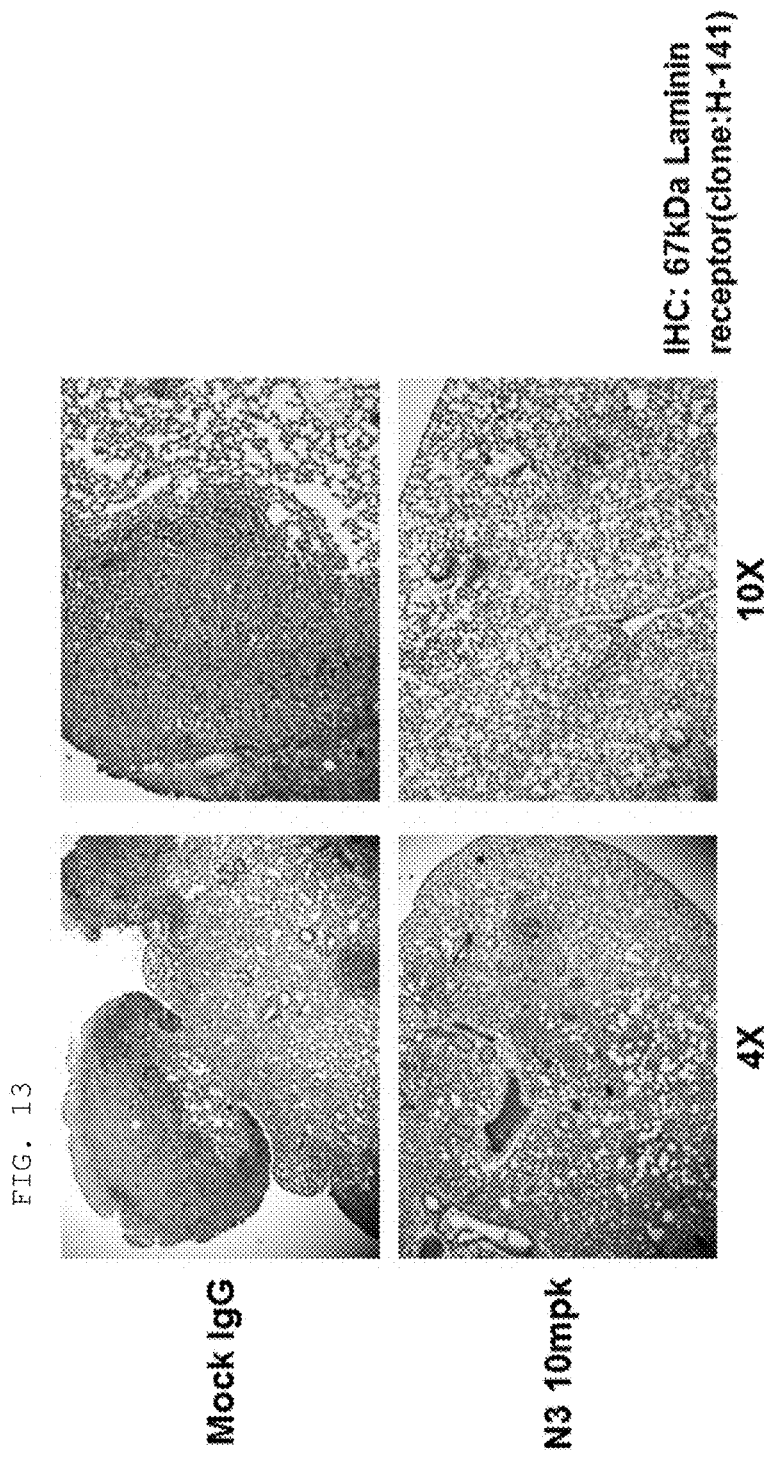
FIG. 13 comparatively shows the lung tissues in control and the N3 IgG treatment group, and confirmed that a significantly large amount of laminin receptors were expressed in the metastasis nodule sites in control compared with the group treated with the antibody of the present invention.

As shown in FIGS. 11 and 12, the experimental results confirmed that many nodules were generated in the lung due to cancer metastasis in control, and such nodules were significantly suppressed in the N3 IgG treatment group. FIG. 13 comparatively shows the lung tissues in control and the N3 IgG treatment group, and confirmed that a significantly large amount of laminin receptors were expressed in the metastasis nodule sites in control compared with the group treated with the antibody of the present invention.

<3-4> Effect Comparison with Anti-Cancer Metastasis Compound (YH16899) in In-Vivo Cancer Metastasis Models It has been known in the foregoing literature "Dae Gyu Kim et al., (2014)" that the YH16899 compound has an effect on cancer metastasis inhibition by suppressing the interaction between 67LR and KRS. Then, the cancer metastasis inhibitory effect was compared between YH16899 and N3 IgG, the antibody of the present invention. The construction of in-vivo tumor models and the observation of lung metastasis condition were carried out by the same method as in Example <3-3>. YH16899 was orally administered at 100 mpk every day. N3 IgG was intravenously injected at difference concentrations (1 mpk, 10 mpk) through mouse tails.

Figure 14:
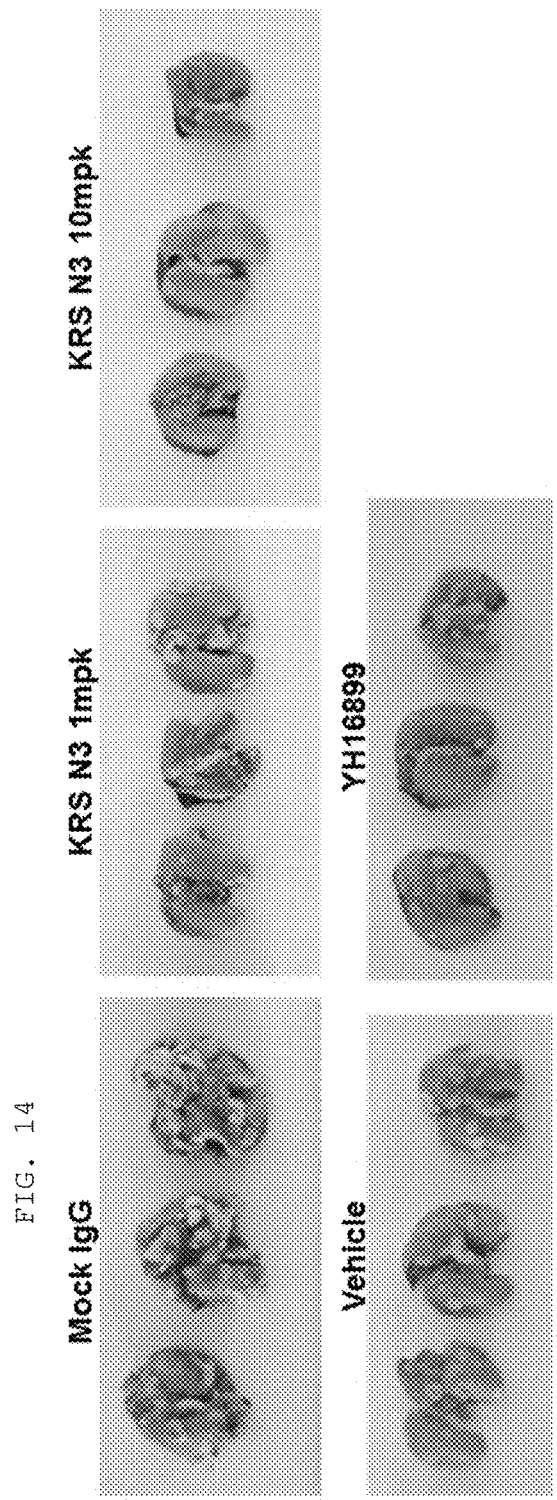
FIG. 14 shows the lung specimens of control, YH16899 treatment group, N3 IgG treatment group, and shows the results that the generation of lung nodules was significantly suppressed in the YH16899 treatment group and the N3 IgG treatment group compared with control.
Figure 15:
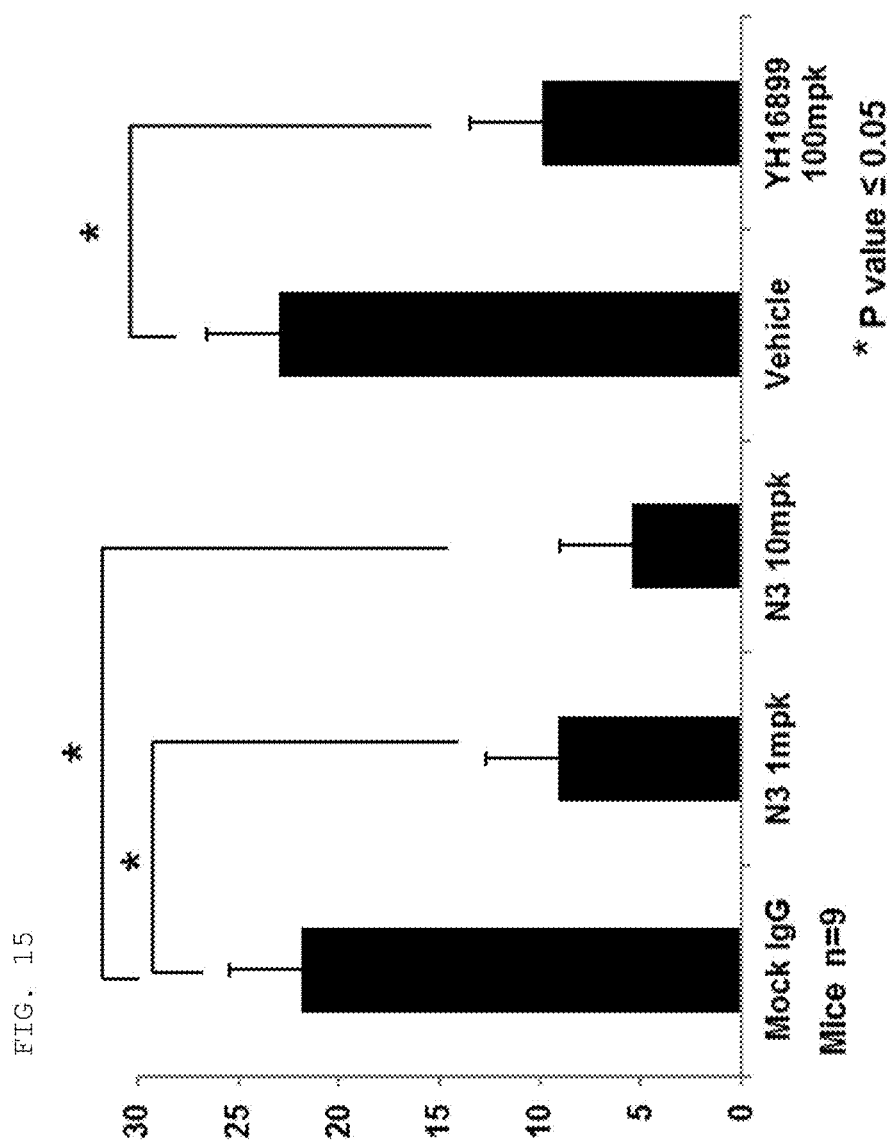
FIG. 15 shows the lung metastasis inhibition efficiency (efficiency of inhibiting lung nodule formation) of the cancer metastasis inhibitor substances according to the treatment concentration in the YH16899 treatment group and the N3 IgG treatment group.

As shown in FIGS. 14 and 15, the experimental results confirmed that the lung nodule count was significantly reduced in a dose-dependent manner in the N3 IgG treatment group, and the treatment with merely 1 mpk of N3 IgG significantly inhibited cancer metastasis compared with YH16899 (100 mpk) treatment groups.

Example 4

Verification of Binding Sites of KRS Antibodies
<4-1> Human KRS Binding Sites of KRS Monoclonal Antibodies To investigate human KRS binding sites of N3 IgG among the KRS antibodies constructed above, surface plasmon resonance (SPR) was performed as below.

First, N3 IgG antibody was immobilized to Biacore T200 (GE Healthcare) equipped with Series S sensor chip CM5 (GE Healthcare) by using an amine coupling kit (GE Healthcare). Then, the peptides shown in Table 4 below dissolved in PBS solution at corresponding concentrations were allowed to flow for 60 s. Then, PBS was allowed to flow for 5 min. Then, the binding ability was analyzed by Biacore T200 Evaluation software v2.0 (GE Healthcare).

TABLE 4

| Peptide informaiton | | | | |
|---|---|---|---|---|
| Name | Sequence information | Species | MW | SEQ ID NO |
| F1 (1-29) | MAAVQAAEVKVDGSEPKLSE ELKRPIKA | H | 3168 | 98 |
| F2 (5-34) | QAAEVKVDGSEPKLSEELKR PIKEKKVA | H | 3351 | 99 |

TABLE 4 -continued

Peptide informaiton

| Name | Sequence information | Species | MW | SEQ ID NO |
|---|---|---|---|---|
| F3 (10-38) | KVDGSEPELSENELERRLKA EKKVAEKEA | H | 3310 | 100 |
| F4 (15-42) | EPKLSKNELKRRLKAEKKVA EKEAKQKE | H | 3337 | 101 |
| F5 (24-49) | KRRLKAEKKVAEKEAKQKEL SEKQLS | H | 3084 | 102 |
| mF1 (1-28) | MAILQESEVEVDGEQKLSKN ELKRRLKA | M | 3230 | 103 |
| mF2 (3-34) | QESEVEVDGEQKLSKNELKR RLKAEKKLA | M | 3383 | 104 |
| mF3 (10-37) | KVDGEQKLSKNELKPRLKAE KKLAEKEA | M | 3268 | 105 |
| mF4 (15-41) | QELSENELERRLKAEKKLAE KEAKQEE | M | 3253 | 106 |
| mF5 (24-48) | RRLKAEKELAEKEAKQKELS EKQLN | M | 2997 | 107 |
| rF1 (1-28) | MAILREGEVELDGEPKLSKN ELKRRLKA | R | 3211 | 108 |
| rF2 (3-34) | REGEVELDGEPKLSKNELKR RLKAEKKLA | R | 3364 | 109 |
| rF3 (10-37) | KLDGEPKLSKNELKRRLKAE KKLAEKEA | R | 3251 | 110 |
| rF4 (15-41) | PKLSKNELKRRLKAEKKLAE KEAKQKE | R | 3222 | 111 |
| rF5 (24-48) | RRLKAEKKLAEKEAKQKELS EKQLN | R | 2997 | 112 |

Figure 16:
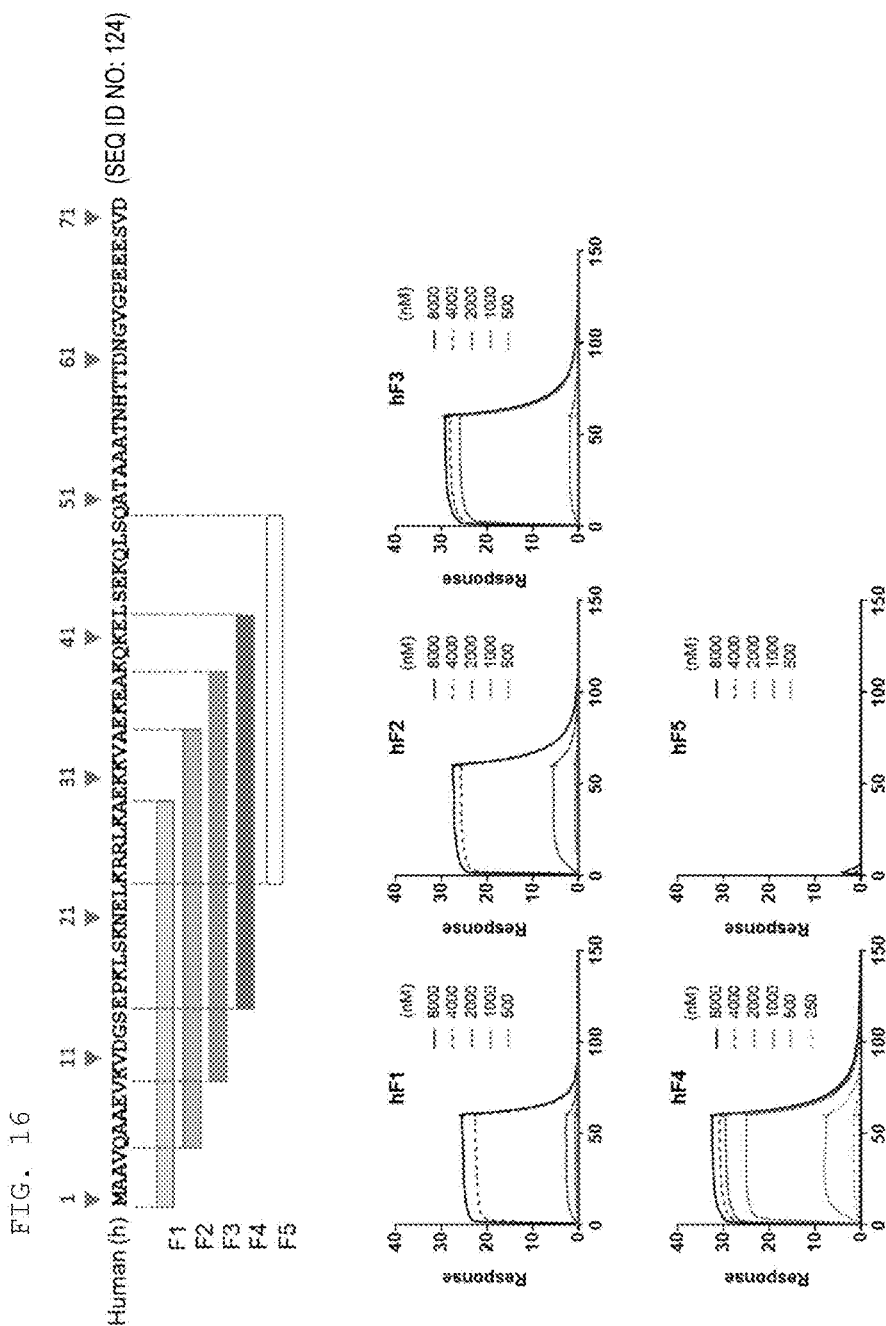
FIG. 16 shows the SPR results of quantitatively confirming the binding ability of N3 IgG to human (h) KRS N-terminal peptide fragments (F1, F2, F3, F4, and F5) (gray bars below the sequence indicate the binding ability of N3 antibody to corresponding regions (F1 to F5), and the darker the bar, the stronger the binding ability).

As shown in FIG. 16, the results depicted that N3 IgG antibody bound to epitopes F1, F2, F3, and F4, but not epitope F5. In addition, the binding ability to epitope F4 was strongest, and the binding ability to F3, F2, and F1 was stronger in that order.

These results could confirm that the main binding site of N3 IgG antibody corresponds to amino acid resides at positions 15 to 29 in the KRS N-terminal region.

<4-2> Interspecies Cross Activity of KRS Monoclonal Antibody

The above example validated the human KRS binding site of the KRS antibody N3 IgG, and to investigate whether N3 IgG showed cross activity with other species mouse (m) and rat (r), surface plasmon resonance (SPR) was performed as below.

In the same manner as the experimental method described in Example 4-1 above, N3 IgG antibody was immobilized on the chip by using an amine coupling kit (GE Healthcare). Then, the peptides shown in Table 4 above dissolved in PBS solution at corresponding concentrations were allowed to flow for 60 s, and PBS was allowed to flow for 5 min. Then, the binding ability was analyzed by Biacore T200 Evaluation software v2.0 (GE Healthcare).

Figure 17:
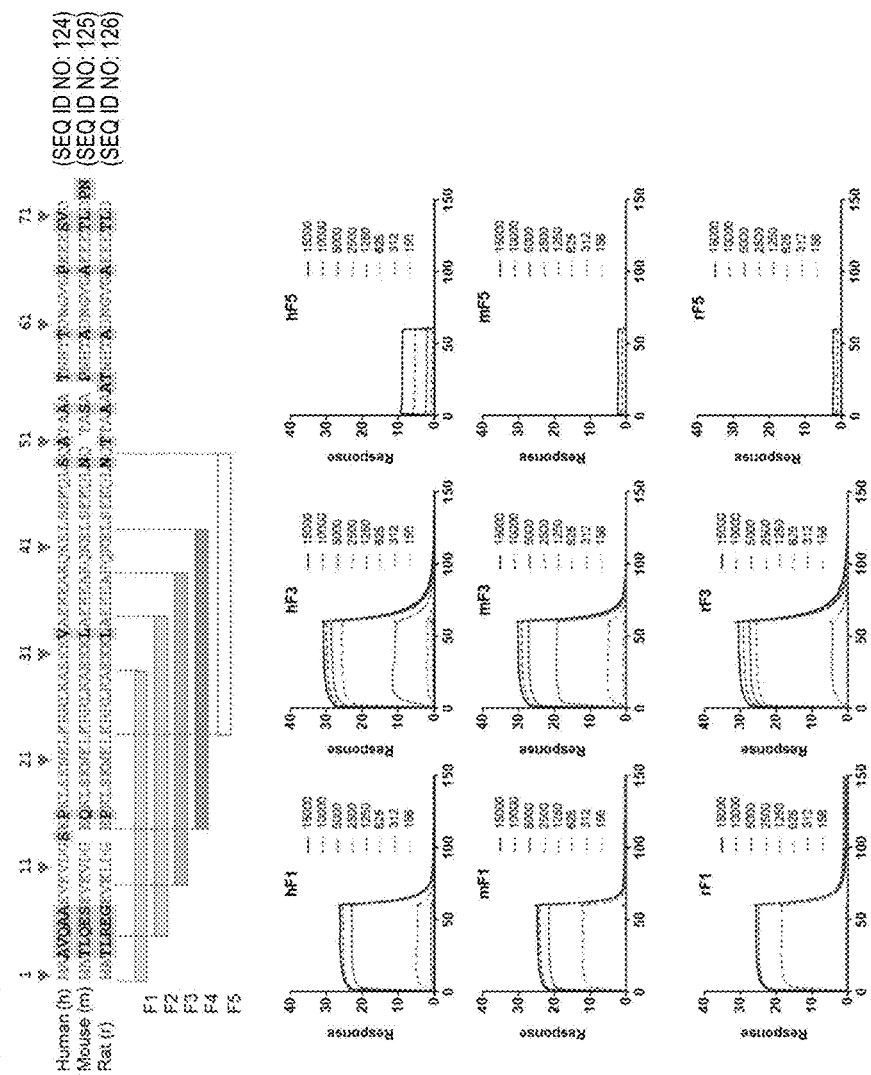
FIG. 17 shows the SPR results of quantitatively confirming the binding ability of N3 IgG to KRS N-terminal peptide fragments (F1, F3, and F5) of human (h), mouse (m), and rat (r) (gray bars below the sequences indicate the binding ability of N3 antibody to corresponding regions (F1 to F5), and the darker the bar, the stronger the binding ability).

As shown in FIG. 17, the results depicted that the N3 IgG antibody bound to epitopes F1, F2, F3, and F4 of human (h), mouse (m), and rat (r) but not epitope F5. The stronger binding ability to epitope F3 than F1 was the same among human, mouse, and rat (F2 and F4 data not shown)

These results could confirm that the N3 IgG antibody is capable of interspecies cross activity.

Example 5

Verification of Laminin Signal Role in Immune Cell Migration and Invasion

It was investigated which of several extracellular matrixes constituting blood vessels accelerated the migration and invasion of monocytes/macrophages. Specific experimental methods for Transwell migration assay using collagen, fibronectin, and laminin as extracellular matrixes were as below. Transwell (Corning, #3421-5 mm) was coated with gelatin (0.5 mg/ml), and then RAW 264.7 cells ($1 \times 10^5$ cells/well) were seeded in the top chamber. Each serum-free DMEM (500 µl) containing laminin (laminin mixture, Biolamina), fibronectin, or collagen (10 µg/ml) was placed in the bottom chamber. After 24 h, non-migrating cells present on the upper part of the membrane were removed by cotton swabs. The cells in the bottom chamber were fixed by treatment with 70% methanol for 30 min, and then stained with 50% hematoxylin for 30 min. After the staining, the membrane was taken and mounted on the slide, and then the migrating cells present on the bottom surface of the membrane were observed and quantified through a high-resolution microscope.

Figure 18A:
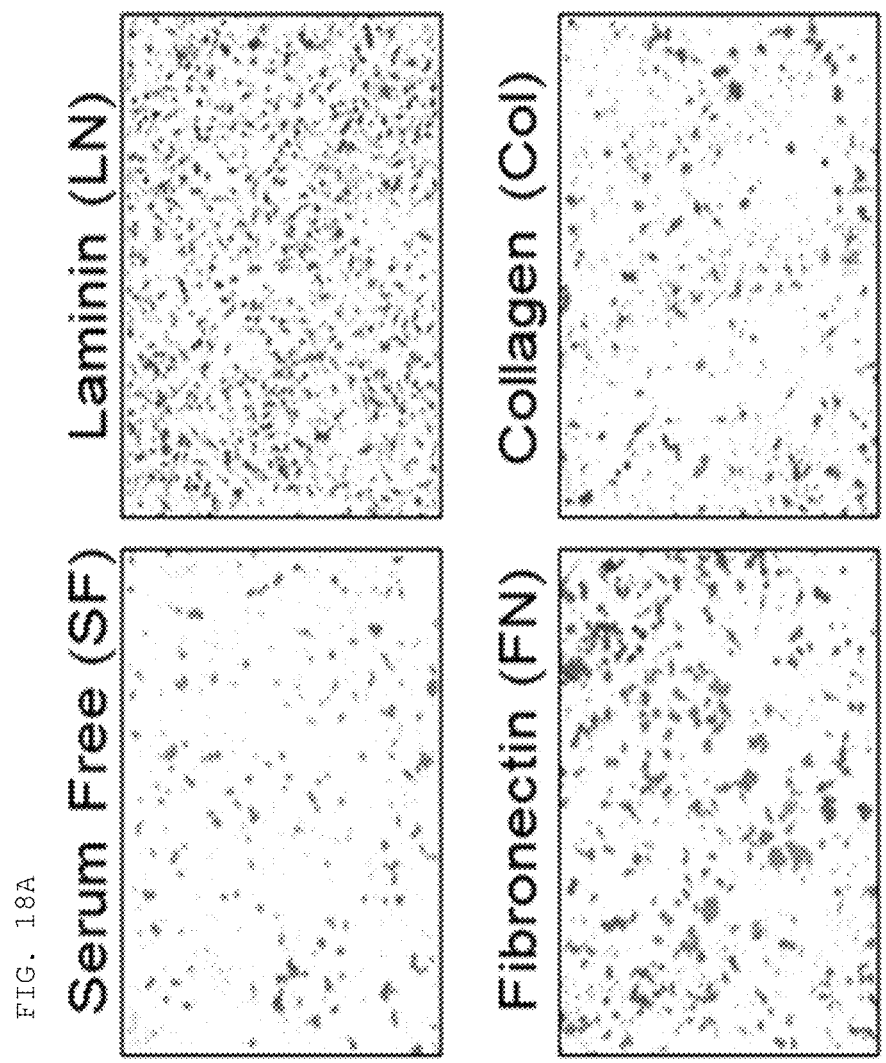

As shown in FIGS. 18A and 18B, the experimental results confirmed that out of several extracellular matrixes, laminin accelerated monocyte/macrophage migration most strongly.

Example 6

Immune Cell Migration and Invasion Effects by Laminin Subtypes

The effects of laminin subtypes on the immune cell migration and invasion were evaluated. Transwell migration assay was performed by the same method as in Example 5 using LN111, LN211, LN221, LN411, LN421, LN511, and LN521 (10 µg/ml) as various laminin subtype proteins (purchased from Biolamina). Specific sequences of the laminin subtypes may be referenced α4 chain of SEQ ID NO: 115, α2 chain of SEQ ID NO: 121, α5 chain of SEQ ID NO: 122, β2 chain of SEQ ID NO: 117, β1 chain of SEQ ID NO: 123, and γ1 chain of SEQ ID NO: 119, according to the chains constituting respective laminin subtypes.

RAW 264.7 cells ($2 \times 10^6$ cell) were incubated for 18 hr, treated with 1 µg/ml of each laminin subtype in serum-free DMEM, and then harvested at 0 h, 12 h, and 24 h. RAW 264.7 cell protein was separated into cytosol and membrane fractions by using the ProteoExtract Subcellular Proteome Extraction Kit (Calbiotech, cat #539790). The obtained protein was electrophoresed, transferred onto PVDF membrane (Milipore), and blocked with 3% skim milk. Thereafter, KRS polyclonal antibody (rabbit, Neomics, Co. Ltd. #NMS-01-0005) was added, followed by incubation for 1 h. After the unbound antibodies were washed out, anti-rabbit secondary antibodies (ThermoFisher Scientific, #31460) were added, followed by incubation. After incubation with the secondary antibodies, film sensitization was carried out using ECL reagent as a substrate in a dark room. The sensitized bands were compared with standard molecule markers to identify bands corresponding to KRS sizes. Na+/K+ ATPase (Abcam) and tubulin (Sigma) antibody were used for plasma membrane and cytosol marker identification, respectively.

Figure 19A:
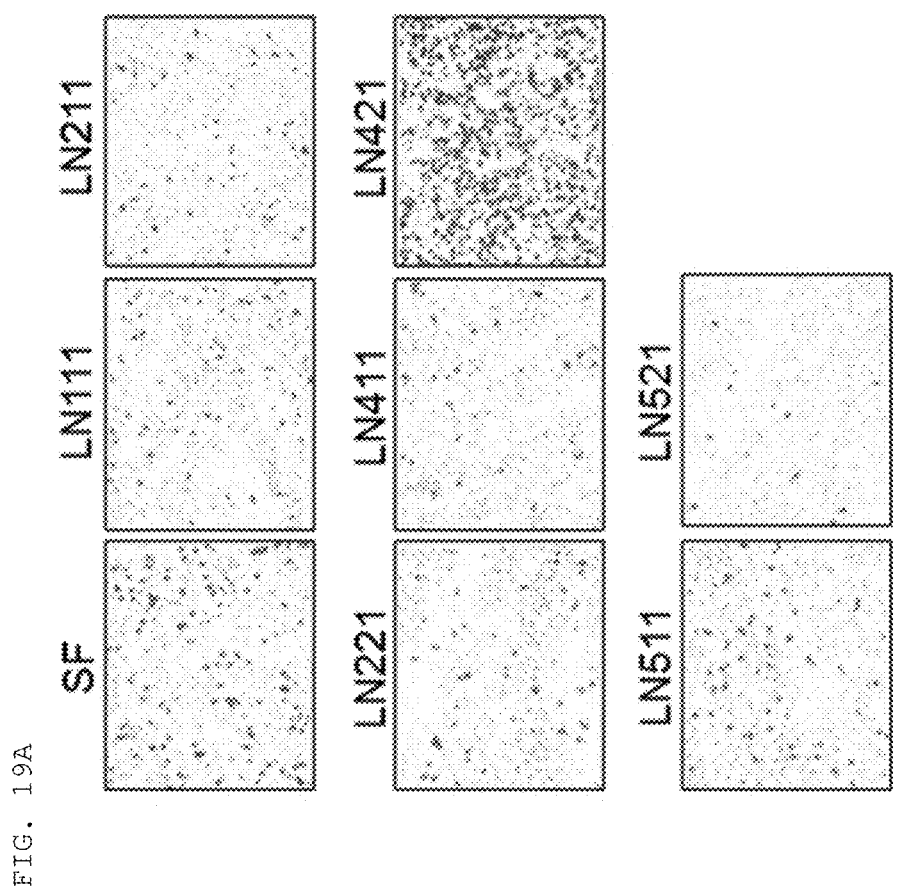
FIGS. 19A-19C show results of cell migration.
Figure 19B:
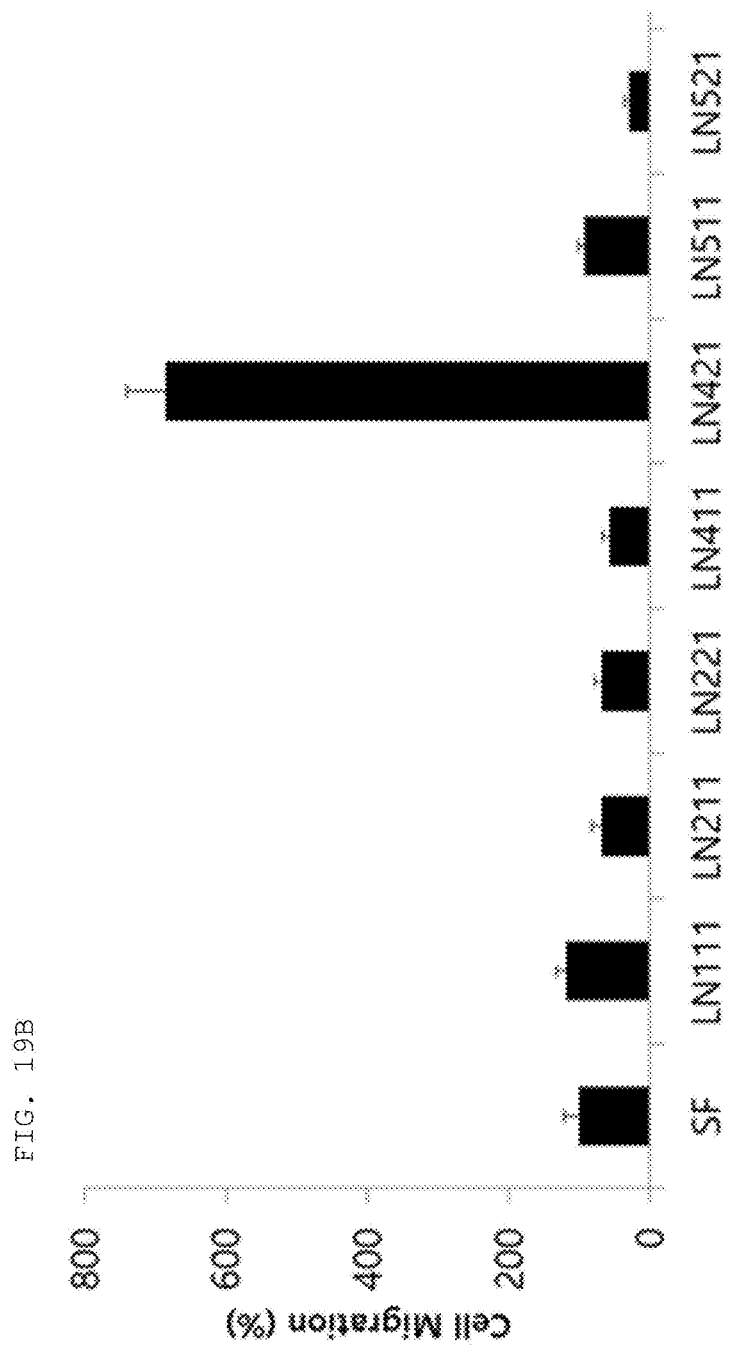
Figure 19C:
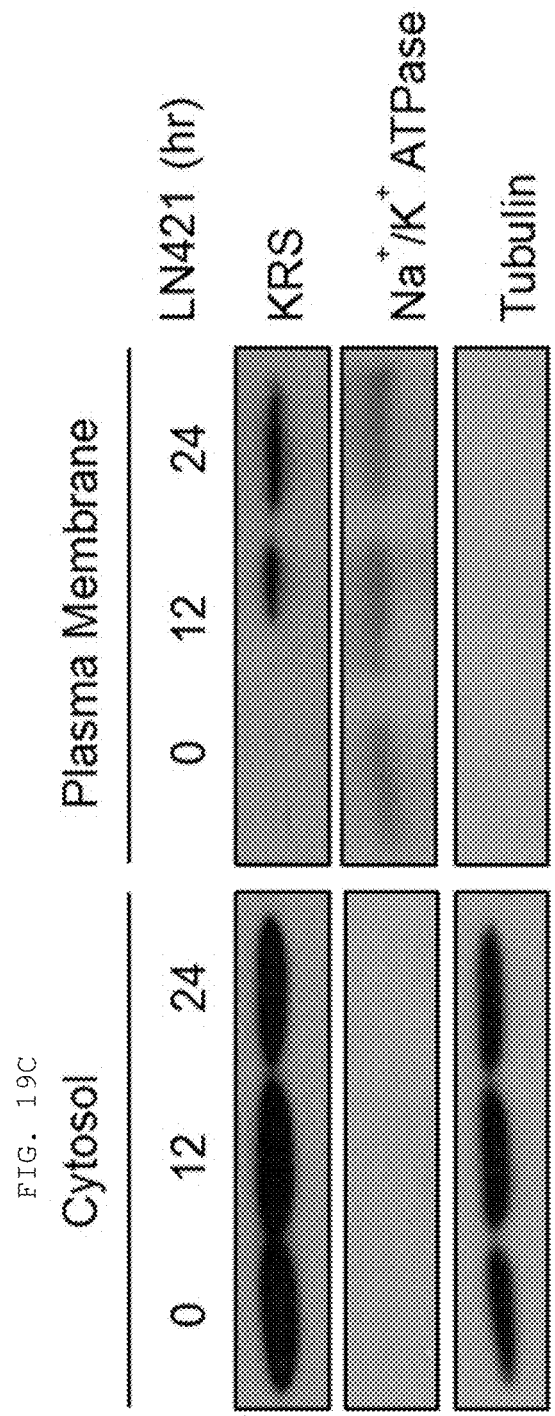

As shown in FIGS. 19A and 19B, the experiment results confirmed that monocytes/macrophages migrate by specifically responding to α4β2γ1 subtype (LN421) among all the tested laminin subtypes. That is, it was confirmed that monocytes/macrophages migrated and invaded specifically responding to LN421. As shown in FIG. 19C, it was confirmed that the treatment of monocytes/macrophages with LN421 increased the amount of KRS detected in the cellular membrane region but partly decreased the amount of KRS detected in the cytosol region. These results indicate that KRS, which is generally present in the cytosol region after expression inside monocytes/macrophages, translocates to the cellular membrane region by LN421 treatment, and that a KRS increase in the immune cell membrane region corresponds to an important pathological phenomenon in the diseases associated with immune cell migration and invasion.

Example 7

Construction of Antibody for Reducing Cellular Membrane KRS Level and Verification of Immune Cell Migration/Invasion Control Effect The effect on immune cell migration and invasion was investigated using N3 IgG antibody as a representative among the antibodies constructed in Example 1 above. Specific experimental methods were as follows. Transwell (Corning, #3421-5 mm) was coated with gelatin (0.5 mg/ml), and then RAW 264.7 cells ($1 \times 10^5$ cells/well) were seeded in the top chamber. Serum-free DMEM (500 μl) containing laminin 421 (1 μg/ml) was placed in the bottom chamber. The top chamber was treated with each antibody at 100 nM. After 24 h, immobilization with 70% methanol was carried out for 30 min, and then staining with 50% hematoxylin was carried out for 30 min. The non-migrating cells present on the upper part of the membrane were removed by cotton swabs, and then the membrane was taken and mounted on the slide. The migrating cells present on the bottom surface of the membrane were observed by a high-resolution microscope (FIG. 20A), and the cells were counted on the obtained images and plotted on the graph (FIG. 20B).

RAW 264.7 cells were treated with laminin 421 (1 μg/ml) and antibody (100 nM), incubated for 24 h, and harvested. Thereafter, the harvest was separated into the membrane and cytosol fractions by using the ProteoExtract Subcellular Proteome Extraction Kit (Calbiochem), sampled, and then subjected to western blotting with respect to KRS. Specific method thereof was as described in Example 6.

Figure 20A:
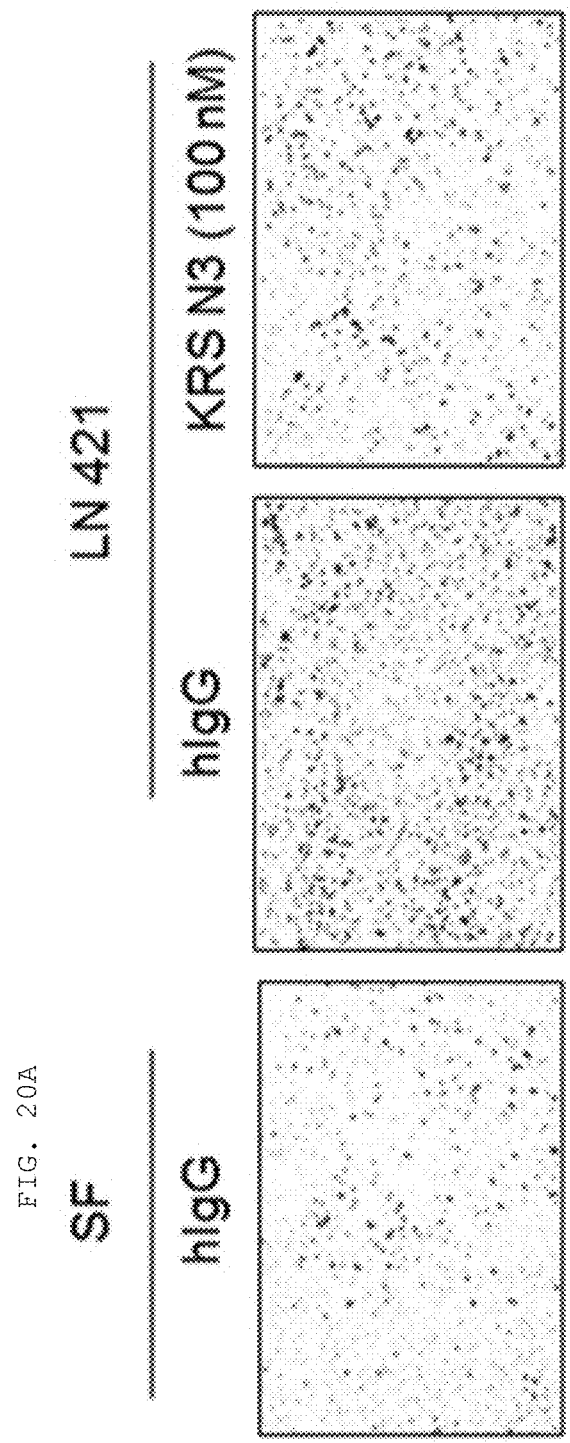
Figure 20B:
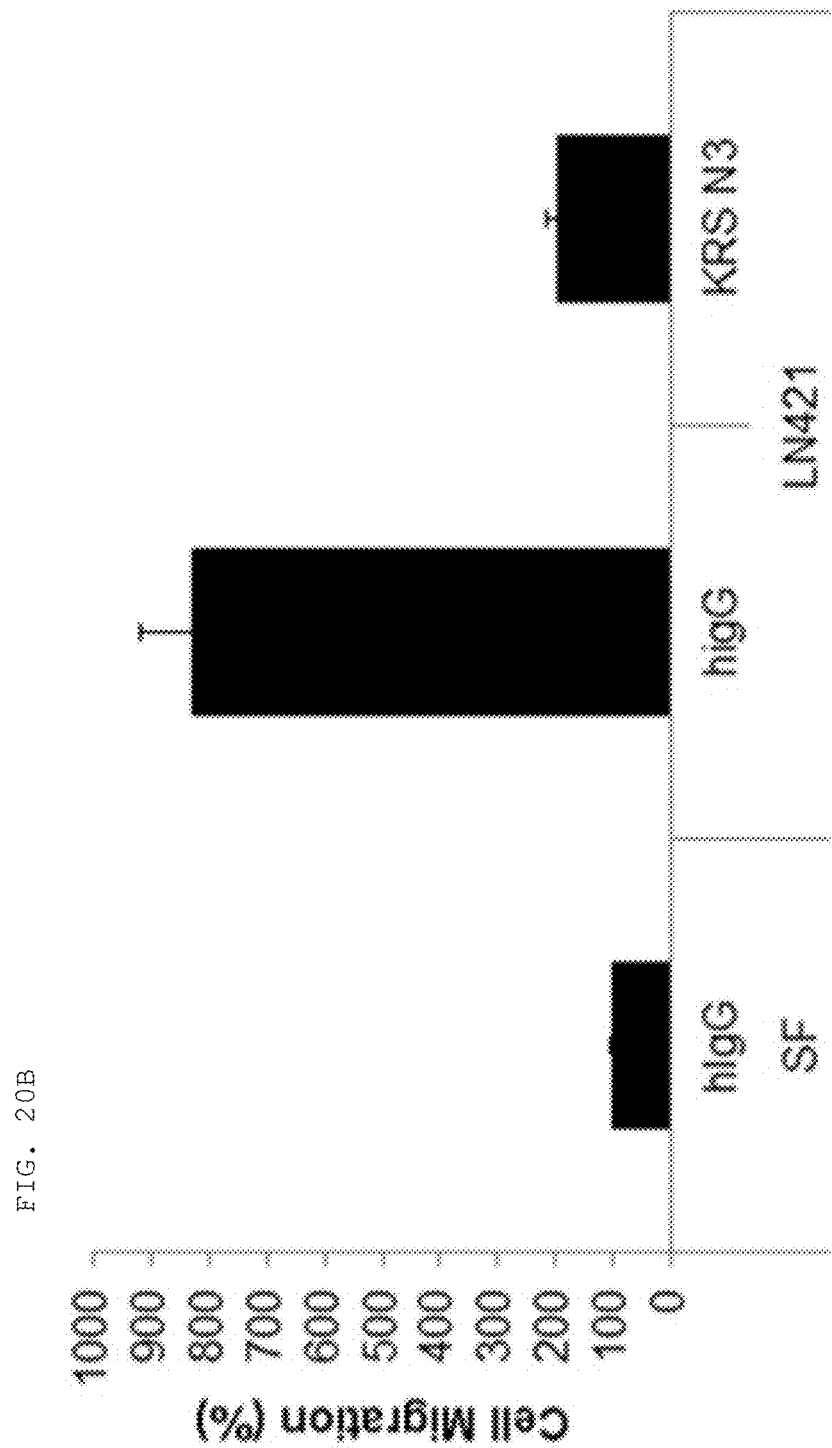
Figure 20C:
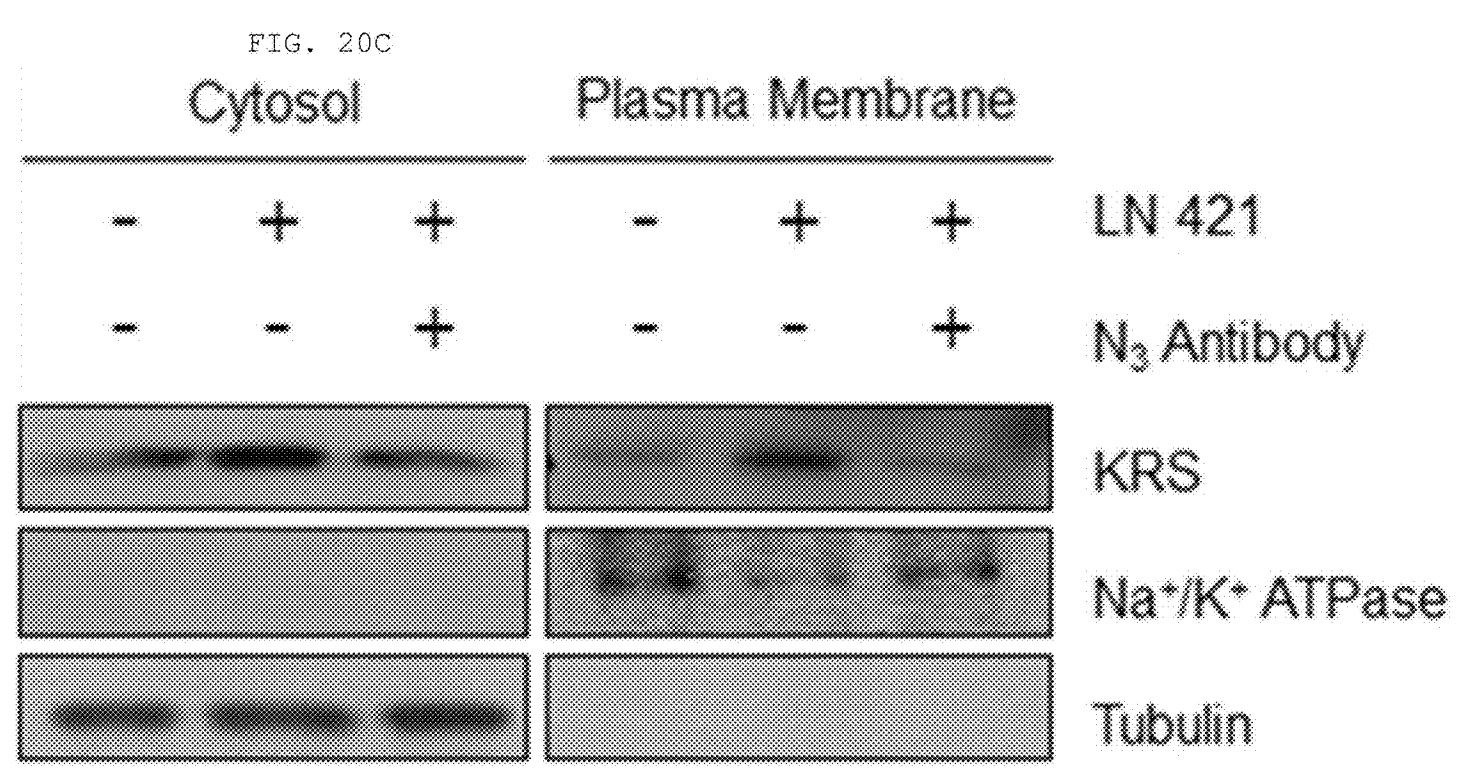

As shown in FIGS. 20A and 20B, the experimental results confirmed that the antibody of the present invention effectively inhibited specifically LN421-dependent monocyte/macrophage migration. As shown in FIG. 20c, it was confirmed that the LN421 treatment increased the KRS level in the monocyte/macrophage cell membrane and the treatment with N3 IgG antibody effectively reduced the KRS level in the cell membrane.

These results confirmed that the antibody of the present invention has possibility as a novel therapeutic agent for diseases involved in the migration of immune cells, such as monocytes/macrophages.

Example 8

Verification of Effect on Immune Cell Migration-Related Disease in In-Vivo Models As in the examples above, the following experiment was executed using N3 IgG antibody as a representative among the antibodies of the present invention.

[Methods]
1. Pulmonary Arterial Hypertension (PAH) Model Construction and Test Substance Administration To induce PAH in seven-week-old SD rats (Orient Bio), 60 mpk of monocrotaline (MCT) was subcutaneously injected. Thereafter, the rats were divided into four groups (five animals per group), and administered with 1 mpk of mock human IgG (Thermo Fisher Scientific, negative control), 1 mpk of N3 IgG, 10 mpk of N3 IgG 10, and 25 mpk of sildenafil (positive control) for three weeks. All antibodies were i.v. injected twice a week, and sildenafil was orally administered every day.

2. Blood Flow and Blood Pressure Measurement

After three weeks, the rats were anesthetized with isoflurane, and measured for blood flow and pressure by using a high-precision pneumatic measurement system (MPVS cardiovascular pressure and volume system, model name: MPVS Ultra, manufacturer: Millar Instruments). The right ventricular end-systolic pressure (RVESP), right ventricular end-diastolic pressure, left ventricular end-systolic pressure, left ventricular end-diastolic pressure were measured using an exclusive catheter (Mikro-Tip rat pressure catheter, manufacturer: Millar Instruments). The cardiac output was measured using a perivascular blood flow probe (Transonic Flow probes, manufacturer: Millar Instruments), and experimental method thereof was performed by the same method as disclosed in the following literature: Pacher P, Nagayama T, Mukhopadhyay P, Batkai S, Kass D A. Measurement of cardiac function using pressure-volume conductance catheter technique in mice and rats. Nat Protoc 2008; 3(9):1422-34.

3. Immunohistochemistry (IHC)

The collected lungs were fixed in paraformaldehyde (PFA) according to the ordinary procedure, and then paraffin-infiltrated and embedded through washing, dehydration, and clearing. The rat lung tissue paraffin blocks were micro-sectioned to a thickness of 6 μm, and slides were manufactured. Thereafter, staining was performed as below. The sample was first treated with xylene for 5 min three times, treated with 100% ethanol, 95% ethanol, 90% ethanol, and 70% ethanol, and DW in that order for 2 min, and washed with PBS for 5 min. After 0.3% $H_2O_2$ treatment, the sample was washed with PBS for 5 min twice. The sample was immersed in 0.01 M citrate buffer, heated, and washed with PBS-T (0.03% Tween 20). Thereafter, the sample was blocked (2% BSA & 2% goat serum in PBS) at room temperature for 30 min. The sample was stained with anti-CD68 antibody (1:200, ED1 clone, Abcam) at 4° C. overnight. The sample was washed with PBS-T for 5 min three times, and then treated with polymer-HRP anti-mouse envision kit (DAKO) at 4° C. for 1 h. The sample was washed with PBS-T three times, and then color-developed by the treatment with DAB substrate buffer and DAB chromogen 20. The stained tissue was treated with Mayer's hematoxylin (Sigma) for 1 min, and then treated with 70% ethanol, 90% ethanol, 95% ethanol, and 100% ethanol in that order for 2 min each twice. Last, the tissue was treated with xylene three times for 5 min, and then observed under an optical microscope.

[Results]
<2-1> Verification of Blood Pressure and Cardiac Output Changes.

The models of PAH, which is a disease having a close relation between immune cell invasion and pathological phenomena, were treated with N3 IgG antibody (1 mpk or 10 mpk) for 3 weeks (i.v., twice a week), and then measured for right ventricular end-systolic pressure (RVESP), right ventricular end-diastolic pressure (RVEDP), left ventricular end-systolic pressure (LVESP), left ventricular end-diastolic pressure (LVEDP), and cardiac output (CO). The results thereof are shown in Table 5.

TABLE 5

|  | MCT + Mock IgG (n = 4) | MCT + N3 Ab 1 mpk (n = 5) | MCT + N3 Ab 10 mpk (n = 5) | MCT + Sildenafil (n = 5) |
|---|---|---|---|---|
| RVESP (mmHg) | 62.5 ± 5.7 | 45.0 ± 8.1 | 41.2 ± 7.7 | 48.4 ± 9.6 |
| RVEDP (mmHg) | 2.8 ± 1.5 | 1.4 ± 2.2 | 3.8 ± 1.3 | 2.6 ± 1.3 |
| LVESP (mmHg) | 81.5 ± 11.4 | 95.8 ± 4.8 | 93.4 ± 11.3 | 83.2 ± 4.7 |
| LVEDP (mmHg) | 1.0 ± 0.8 | 2.6 ± 1.9 | 4.6 ± 3.9 | 3.6 ± 2.3 |
| CO (ml/min) | 58 ± 4.7 (n = 4) | 74.0 ± 0.9 (n = 5) | 59.8 ± 12.9 (n = 5) | 49.6 ± 17.7 (n = 4) |

(No CO measurement for one animal of MCT + mock IgG group, died from anesthesia, and one animal of sildenafil treatment group, died during surgery)

Pulmonary arterial hypertension causes the right ventricular-end pressure to rise due to narrowing of the pulmonary artery, resulting in right ventricular failure. In addition, the reward mechanism thereof is destroyed due to continuous hypertension, resulting in right ventricular hypertrophy followed by right ventricular dilation. This causes left ventricular compression due to ventricular septum movement, resulting in reductions in end-diastolic volume and cardiac output of the left ventricle (WooSeok Lee, et al., Clinical Characteristics and Prognostic Factors of Patients with Severe Pulmonary Hypertension, *Korean Circulation J* 2007; 37:265-270). Resultingly, the pulmonary arterial hypertension is mainly associated with the right ventricle, but also involved in functions of the left ventricle.

Figure 21A:
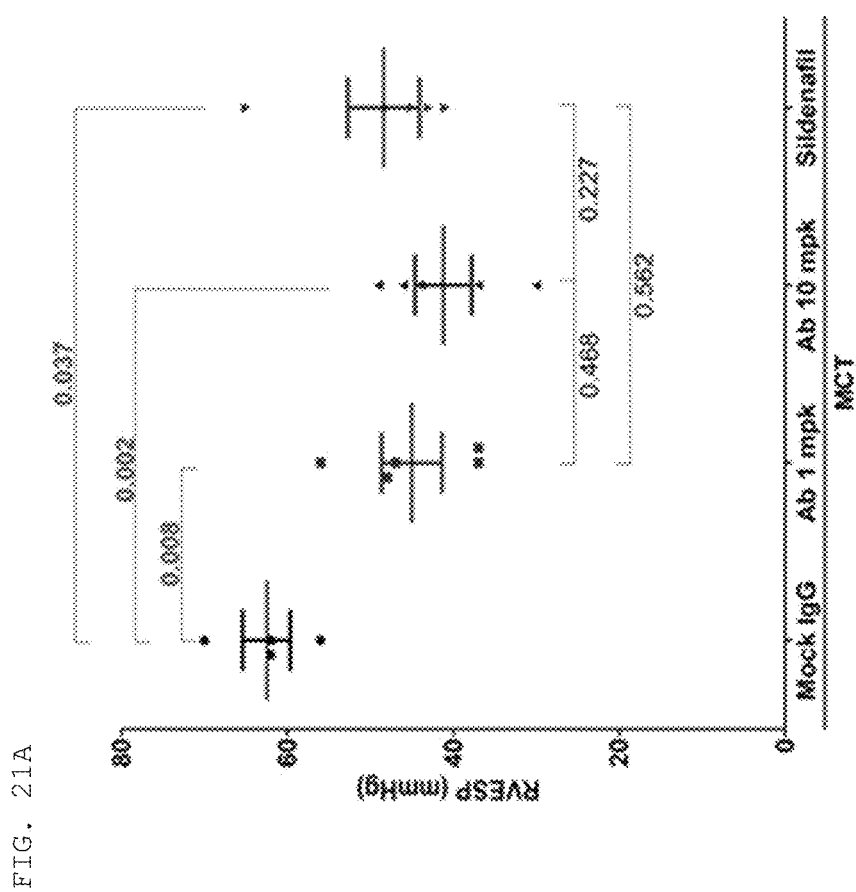
FIGS. 21A-21B show changes in right and left ventricular end-systolic pressure.

PAH patients showed a RVESP increase, which was also observed in the PAH animal models of the present experiment. In this regard, as shown in FIG. 21A, N3 antibody significantly reduced RVESP at both the concentrations thereof, and favorably reduced RVESP than especially sildenafil, the positive control drug.

Figure 21B:
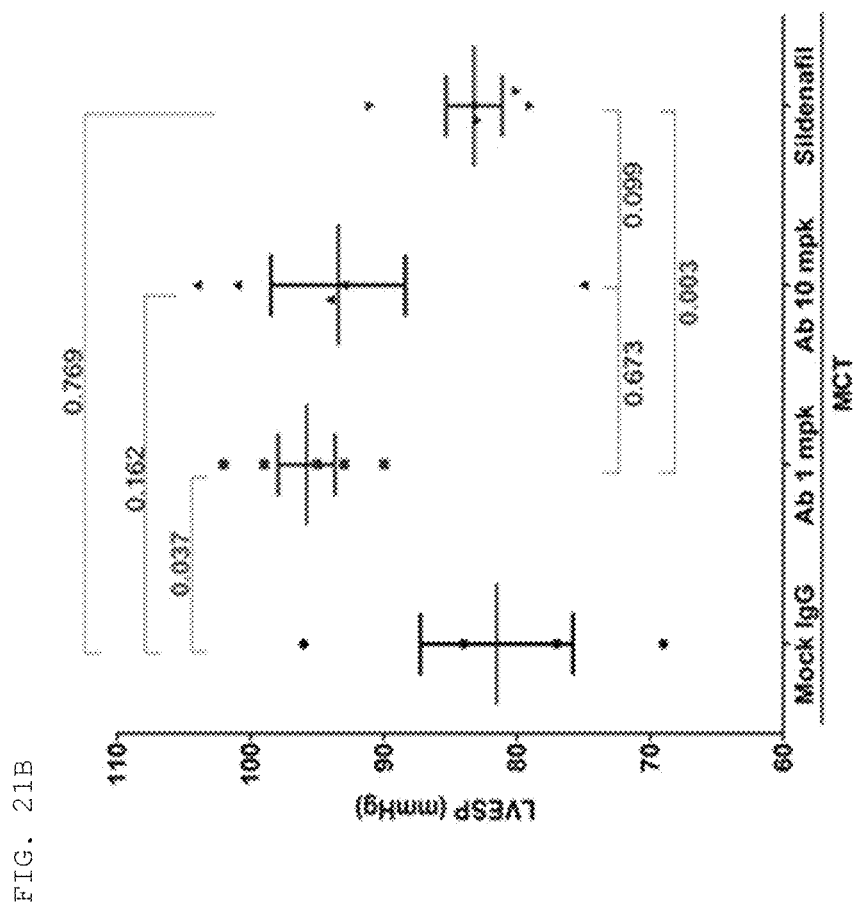

In addition, a reduction in left ventricular end-systolic pressure (LVESP) due to N3 IgG antibody administration was not observed, and rather, as shown in FIG. 21B, LVESP significantly increased in the group administered with the antibody of the present invention. Therefore, the antibody of the present invention is contrast with sildenafil used as an existing therapeutic agent for pulmonary arterial hypertension wherein sildenafil causes pulmonary arterial dilatation and systemic arterial dilatation, thereby risking a reduction in systemic blood pressure.

That is, it was confirmed that the antibody of the present invention showed a tendency of having a low effect on systemic artery pressure compared with sildenafil, and this effect is thought to be a favorable characteristic of a therapeutic agent considering that sildenafil administration may be a risk of developing hypotension in clinical sites. Moreover, severe pulmonary arterial hypertension causes systolic RV failure, which may be accompanied by low cardiac output and systemic hypotension.

Whereas, a treatment to alleviate pulmonary arterial hypertension by the antibody of the present invention is expected to increase the cardiac output and systemic blood pressure, thereby normalizing the blood pressure.

Overall, it was confirmed that the administration of the antibody of the present invention reduced the risk of side effects of existing therapeutic drugs and showed PAH symptom alleviation and treatment effects.

<8-2> Echocardiography

The D-shaped left ventricle finding indicating pressure overload in the right ventricle was observed in three animals in the MCT alone administration group (i.e., test substance non-administration PAH models) and three animals in the MCT+sildenafil administration group, but was not observed in the therapeutic antibody administration groups.

In addition, as shown in Table 6 below, the body weights of respective groups increased to similar degrees, with no significant difference. That is, the findings were not observed to indicate abnormal signs, including abnormal weight reduction, caused by the administration of the therapeutic antibody.

TABLE 6

|  | MCT + Mock IgG (n = 4) | MCT + Ab 1 mpk (n = 5) | MCT + Ab 10 mpk (n = 5) | MCT + Sildenafil (n = 5) |
|---|---|---|---|---|
| Absolute change (g) | 101.4 ± 14.2 | 113.5 ± 14.6 | 104.1 ± 12.3 | 104.1 ± 26.4 |
| Relative change (%) | 48.8 ± 7.8 | 43.6 ± 5.2 | 40.7 ± 5.0 | 49.8 ± 10.5 |

<8-3> Verification of Monocyte/Macrophage Migration and Infiltration Degrees

Figure 22:
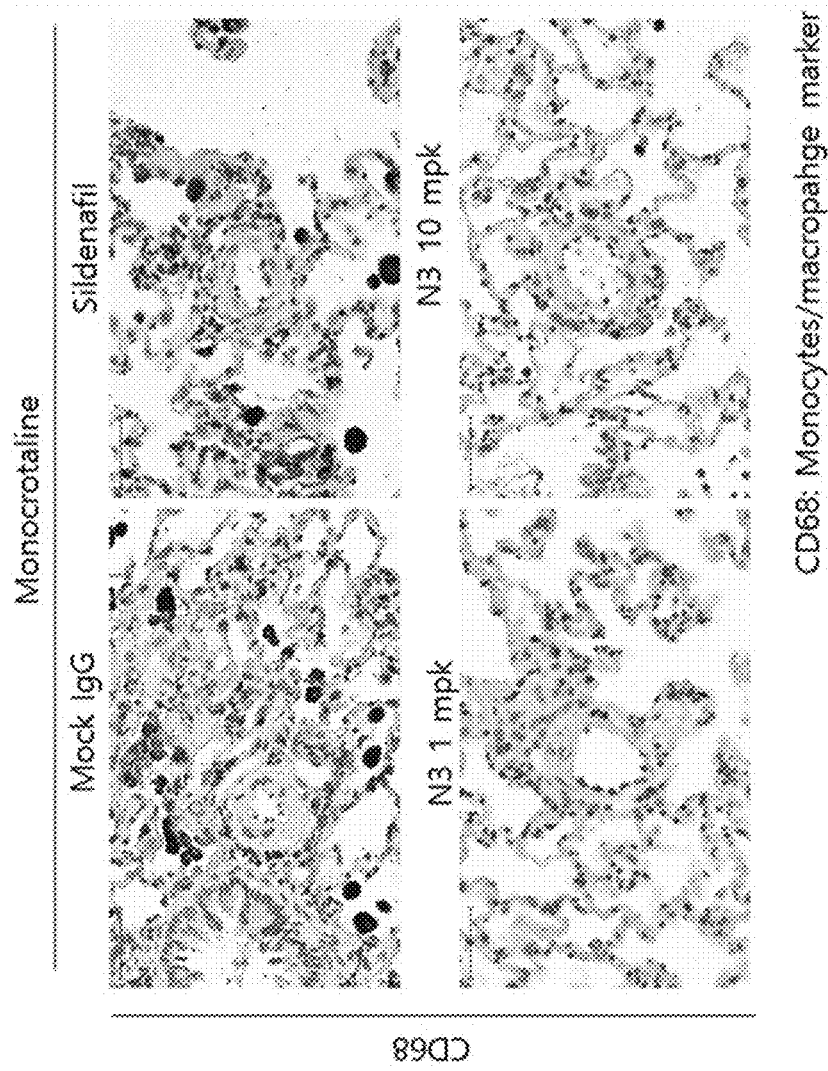
FIG. 22 shows the IHC staining results of confirming that the administration of the antibody of the present invention, N3 IgG, reduced immune cell migration and invasion in the pulmonary arterial hypertension (PAH) models.

IHC staining was performed with respect to CD68, which is a monocyte/macrophage marker, by using the lung tissues of each experimental group. As shown in FIG. 22, the experimental results confirmed that the groups treated with N3 IgG antibodies of the present invention explicitly reduced the monocyte/macrophage infiltration into lung tissues, and such an effect was significantly excellent than that of sildenafil.

INDUSTRIAL APPLICABILITY

As described above, the antibodies or fragments thereof according to the present invention have particular CDR (complementary determining region) sequences defined in the present specification and very excellent specific binding ability to the extracellularly exposed KRS N-terminal region, and thus can be used in the diagnosis of a disease (e.g., cancer) known to be accompanied by specific behaviors of KRS. Furthermore, the antibodies or fragments thereof according to the present invention are also specifically targeted to the KRS N-terminal region in vivo, and thus inhibit the interaction between the laminin receptor and the KRS N-terminal region to exert an excellent inhibitory effect on cancer metastasis, and therefore can be used as a therapeutic agent. Furthermore, the antibodies or fragments thereof according to the present invention can control the migration of immune cells, and thus can be very advantageously used in the prevention, alleviation, and treatment of immune cell migration-related diseases, and therefore have high industrial applicability.

The invention claimed is:

1. An antibody or fragment thereof specifically binding to an epitope consisting of a sequence of SEQ ID NO: 101, SEQ ID NO: 106, or SEQ ID NO: 111 in the lysyl-tRNA synthetase (KRS) N-terminus, wherein the antibody or fragment thereof specifically binds to an extracellularly exposed lysyl-tRNA synthetase (KRS) N-terminal region, wherein the antibody or fragment thereof comprises a heavy chain variable region and a light chain variable region which are selected from the group consisting of:

a heavy chain variable region comprising heavy chain complementary determining region 1 containing the amino acid sequence defined by SEQ ID NO: 1, heavy chain complementary determining region 2 containing the amino acid sequence defined by SEQ ID NO: 3, and heavy chain complementary determining region 3 containing the amino acid sequence defined by SEQ ID NO: 5, and a light chain variable region comprising light chain complementary determining region 1 containing the amino acid sequence defined by SEQ ID NO: 7, light chain complementary determining region 2 containing the amino acid sequence defined by SEQ ID NO: 9, and light chain complementary determining region 3 containing the amino acid sequence defined by SEQ ID NO: 11;

a heavy chain variable region comprising heavy chain complementary determining region 1 containing the amino acid sequence defined by SEQ ID NO: 13, heavy chain complementary determining region 2 containing the amino acid sequence defined by SEQ ID NO: 15, and heavy chain complementary determining region 3 containing the amino acid sequence defined by SEQ ID NO: 17, and a light chain variable region comprising light chain complementary determining region 1 containing the amino acid sequence defined by SEQ ID NO: 19, light chain complementary determining region 2 containing the amino acid sequence defined by SEQ ID NO: 21, and light chain complementary determining region 3 containing the amino acid sequence defined by SEQ ID NO: 23;

a heavy chain variable region comprising heavy chain complementary determining region 1 containing the amino acid sequence defined by SEQ ID NO: 25, heavy chain complementary determining region 2 containing the amino acid sequence defined by SEQ ID NO: 27, and heavy chain complementary determining region 3 containing the amino acid sequence defined by SEQ ID NO: 29, and a light chain variable region comprising light chain complementary determining region 1 containing the amino acid sequence defined by SEQ ID NO: 31, light chain complementary determining region 2 containing the amino acid sequence defined by SEQ ID NO: 33, and light chain complementary determining region 3 containing the amino acid sequence defined by SEQ ID NO: 35; and a heavy chain variable region comprising heavy chain complementary determining region 1 containing the amino acid sequence defined by SEQ ID NO: 37, heavy chain complementary determining region 2 containing the amino acid sequence defined by SEQ ID NO: 39, and heavy chain complementary determining region 3 containing the amino acid sequence defined by SEQ ID NO: 41, and a light chain variable region comprising light chain complementary determining region 1 containing the amino acid sequence defined by SEQ ID NO: 43, light chain complementary determining region 2 containing the amino acid sequence defined by SEQ ID NO: 45, and light chain complementary determining region 3 containing the amino acid sequence defined by SEQ ID NO: 47.

2. The antibody or fragment thereof of claim 1, wherein the antibody or fragment thereof comprises the heavy chain variable region containing the amino acid sequence selected from the group consisting of SEQ ID NO: 49, SEQ ID NO: 53, SEQ ID NO: 57, and SEQ ID NO: 61, and the light chain variable region containing the amino acid sequence selected from the group consisting of SEQ ID NO: 51, SEQ ID NO: 55, SEQ ID NO: 59, and SEQ ID NO: 63.

3. The antibody or fragment thereof of claim 1, wherein the antibody is selected from the group consisting of IgG, IgA, IgM, IgE, and IgD, and the fragment is selected from the group consisting of diabody, Fab, Fab', F(ab)2, F(ab')2, Fv, and scFv.

4. The antibody or fragment thereof of claim 3, wherein the scFv contains the amino acid sequence selected from the group consisting of SEQ ID NO: 67, SEQ ID NO: 69, SEQ ID NO: 71, and SEQ ID NO: 73.

5. A polynucleotide encoding the antibody or fragment thereof of claim 1.

6. A method for producing an antibody or fragment thereof specifically binding to an extracellularly exposed lysyl-tRNA synthetase (KRS) N-terminal region, the method comprising:
(a) transforming host cells with a recombinant expression vector comprising a polynucleotide encoding the antibody or fragment thereof of claim 1;
(b) incubating the transformed host cells to produce an antibody or fragment thereof; and
(c) collecting the antibody or fragment thereof produced in the host cells.

7. A method for specific detection of an extracellularly exposed lysyl-tRNA synthetase (KRS) N-terminal region, the method comprising:
contacting the antibody or fragment thereof of claim 1 with a sample; and
detecting the antibody or fragment thereof.

8. A method for diagnosing cancer in a subject in need thereof, the method comprising administering the antibody or fragment thereof claim 1 labelled with a detectable moiety to the subject in an amount effective for diagnosing cancer.

* * * * *

SEQUENCE LISTING

<160> NUMBER OF SEQ ID NOS: 126

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      N3 VH CDR1

<400> SEQUENCE: 1

Ser Tyr Asp Met Ser
1               5

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      N3 VH CDR1

<400> SEQUENCE: 2
agttatgata tgagc                                                         15

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      N3 VH CDR2

<400> SEQUENCE: 3

Ala Ile Ser Tyr Asp Asn Gly Asn Thr Tyr Tyr Ala Asp Ser Val Lys
1               5                   10                  15

Gly

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence: Synthetic
      N3 VH CDR2

<400> SEQUENCE: 4
gcgatctctt atgataatgg taatacatat tacgctgatt ctgtaaaagg t                 51

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      N3 VH CDR3

<400> SEQUENCE: 5

Met Ala Leu Asp Phe Asp Tyr
1               5

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic -continued

N3 VH CDR3

<400> SEQUENCE: 6
atggcgcttg atttcgacta c                                              21

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      N3 VL CDR1

<400> SEQUENCE: 7

Ser Ser Ser Asn Ile Gly Ser Asn Tyr Val Thr
1               5                   10

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      N3 VL CDR1

<400> SEQUENCE: 8
tcttcatcta atattggcag taattatgtc acc                                  33

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      N3 VL CDR2

<400> SEQUENCE: 9

Asp Asn Ser Asn Arg Pro Ser
1               5

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      N3 VL CDR2

<400> SEQUENCE: 10
gataatagta atcggccaag c                                              21

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      N3 VL CDR3

<400> SEQUENCE: 11

Ala Ser Trp Asp Asp Ser Leu Ser Ala
1               5

<210> SEQ ID NO 12
<211> LENGTH: 27
<212> TYPE: DNA
<213> ORGANISM: Artificial Sequence

```
<220> FEATURE:
<223> OTHER INFORMATION: Description of Artificial Sequence: Synthetic
      N3 VL CDR3

<400> SEQUENCE: 12
gcttcttggg atgatagcct gagtgct                                              27

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      N5 VH CDR1

<400> SEQUENCE: 13

Asp Tyr Ala Met Ser
1               5

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      N5 VH CDR1

<400> SEQUENCE: 14
gattatgcta tgagc                                                           15

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      N5 VH CDR2

<400> SEQUENCE: 15

Trp Ile Tyr Ser Gly Ser Gly Asn Lys Tyr Tyr Ala Asp Ser Val Lys
1               5                   10                  15

Gly

<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence: Synthetic
      N5 VH CDR2

<400> SEQUENCE: 16
tggatctatt ctggtagtgg taataaatat tacgctgatt ctgtaaaagg t                   51

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      N5 VH CDR3

<400> SEQUENCE: 17

Met Gly Leu Asp Phe Asp Tyr
1               5
```

```
<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      N5 VH CDR3

<400> SEQUENCE: 18
atgggtttgg atttcgacta c                                                    21

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      N5 VL CDR1

<400> SEQUENCE: 19

Ser Ser Ser Asn Ile Gly Asn Asn Tyr Val Ser
1               5                   10

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      N5 VL CDR1

<400> SEQUENCE: 20
tcttcatcta atattggcaa taattatgtc tcc                                        33

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      N5 VL CDR2

<400> SEQUENCE: 21

Asp Asp Asn Gln Arg Pro Ser
1               5

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      N5 VL CDR2

<400> SEQUENCE: 22
gatgataatc agcggccaag c                                                    21

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      N5 VL CDR3

<400> SEQUENCE: 23

Gly Thr Trp Asp Asp Ser Leu Ser Ala
1               5
```

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      N5 VL CDR3

<400> SEQUENCE: 24
ggtacttggg atgatagcct gagtgct                                        27

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      N7 VH CDR1

<400> SEQUENCE: 25

Asp Tyr Tyr Met Ser
1               5

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      N7 VH CDR1

<400> SEQUENCE: 26
gattattata tgagc                                                     15

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      N7 VH CDR2

<400> SEQUENCE: 27

Gly Ile Tyr Ser Gly Thr Gly Ser Ile Tyr Tyr Ala Asp Ser Val Glu
1               5                   10                  15

Gly

<210> SEQ ID NO 28
<211> LENGTH: 51
<212> TYPE: DNA
<213> ORGANISM: Artificial Sequence
<220> FEATURE:
<223> OTHER INFORMATION: Description of Artificial Sequence: Synthetic
      N7 VH CDR2

<400> SEQUENCE: 28
gggatctatt ctggtactgg tagtatatat tacgctgatt ctgtagaagg t             51

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      N7 VH CDR3

-continued

<400> SEQUENCE: 29

Pro Pro Tyr His Phe Asp Tyr
1               5

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      N7 VH CDR3

<400> SEQUENCE: 30
cctccgtatc atttcgacta c                                           21

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      N7 VL CDR1

<400> SEQUENCE: 31

Ser Ser Ser Asn Ile Gly Ser Asn Tyr Val Thr
1               5                   10

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      N7 VL CDR1

<400> SEQUENCE: 32
tcttcatcta atattggcag taattatgtc acc                               33

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      N7 VL CDR2

<400> SEQUENCE: 33

Ala Asp Ser Asn Arg Pro Ser
1               5

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      N7 VL CDR2

<400> SEQUENCE: 34
gctgatagta atcggccaag c                                           21

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic

N7 VL CDR3

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      N7 VL CDR3

<400> SEQUENCE: 36
ggtgcttggg attatagcct gagtggt                                              27

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      N9 VH CDR1

<400> SEQUENCE: 37

Asn Tyr Asp Met Ser
1               5

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: Synthetic
      N9 VH CDR1

<400> SEQUENCE: 38
aattatgata tgagc                                                           15

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      N9 VH CDR2

<400> SEQUENCE: 39

Trp Ile Tyr Ser Gly Asp Ser Ser Lys Tyr Tyr Ala Asp Ser Val Lys
1               5                   10                  15
Gly

<210> SEQ ID NO 40
<211> LENGTH: 51
<212> TYPE: DNA
<213> ORGANISM: Artificial Sequence
<220> FEATURE:
<223> OTHER INFORMATION: Description of Artificial Sequence: Synthetic
      N9 VH CDR2

<400> SEQUENCE: 40
tggatctatt ctggtgatag tagtaaatat tacgctgatt ctgtaaaagg t                   51

<210> SEQ ID NO 41
<211> LENGTH: 7

```
<212> TYPE: PRT
<213> ORGANISM: Artificial Sequence
<220> FEATURE:
<223> OTHER INFORMATION: Description of Artificial Sequence: Synthetic
      N9 VH CDR3

<400> SEQUENCE: 41

Glu Thr Arg Thr Phe Asp Tyr
1               5

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      N9 VH CDR3

<400> SEQUENCE: 42
gagacgcgga cgttcgacta c                                          21

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      N9 VL CDR1

<400> SEQUENCE: 43

Ser Ser Phe Asn Ile Gly Ser Asn Ala Val Tyr
1               5                   10

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic
      N9 VL CDR1

<400> SEQUENCE: 44
tcttcattta atattggcag taatgctgtc tac                              33

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      N9 VL CDR2

<400> SEQUENCE: 45

Tyr Asn Ser Gln Arg Pro Ser
1               5

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      N9 VL CDR2

<400> SEQUENCE: 46
tataatagtc agcggccaag c                                          21
```

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      N9 VL CDR3

<400> SEQUENCE: 47

Gly Ser Trp Asp Ala Ser Leu Ser Gly
1               5

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      N9 VL CDR3

<400> SEQUENCE: 48
ggctcttggg atgctagcct gagtggt                                             27

<210> SEQ ID NO 49
<211> LENGTH: 116
<212> TYPE: PRT
<213> ORGANISM: Artificial Sequence
<220> FEATURE:
<223> OTHER INFORMATION: Description of Artificial Sequence: Synthetic
      N3 VH

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser
        115

<210> SEQ ID NO 50
<211> LENGTH: 348
<212> TYPE: DNA
<213> ORGANISM: Artificial Sequence
<220> FEATURE:
<223> OTHER INFORMATION: Description of Artificial Sequence: Synthetic
      N3 VH

<400> SEQUENCE: 50
gaggtgcagc tgttggagtc tgggggaggc ttggtacagc ctggggggtc cctgagactc         60
tcctgtgcag cctctggatt cacctttagc agttatgata tgagctgggt ccgccaggct        120
ccagggaagg gctggagtg gtctcagcg atctcttatg ataatggtaa tacatattac        180
gctgattctg taaaaggtcg gttcaccatc tccagagaca attccaagaa cacgctgtat        240

```
ctgcaaatga acagcctgag agccgaggac acggccgtgt attactctgc gagaatggcg      300
cttgatttcg actactgggg ccagggtaca ctggtcaccg tgagctca                   348
```

<210> SEQ ID NO 51
<211> LENGTH: 110
<212> TYPE: PRT
<213> ORGANISM: Artificial Sequence
<220> FEATURE:
<223> OTHER INFORMATION: Description of Artificial Sequence: Synthetic
      N3 VL

<400> SEQUENCE: 51

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
            20                  25                  30

Tyr Val Thr Trp Tyr Gln Gln Leu Pro Gly Thr Ala Pro Lys Leu Leu
        35                  40                  45

Ile Tyr Asp Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Ala Tyr Val Phe Gly Gly Gly Thr Lys Leu Thr Val Leu
            100                 105                 110
```

<210> SEQ ID NO 52
<211> LENGTH: 330
<212> TYPE: DNA
<213> ORGANISM: Artificial Sequence
<220> FEATURE:
<223> OTHER INFORMATION: Description of Artificial Sequence: Synthetic
      N3 VL

<400> SEQUENCE: 52

```
cagtctgtgc tgactcagcc accctcagcg tctgggaccc ccgggcagag ggtcaccatc      60
tcttgtactg gctcttcatc taatattggc agtaattatg tcacctggta ccagcagctc     120
ccaggaacgg cccccaaact cctcatctat gataatagta atcggccaag cggggtccct     180
gaccgattct ctggctccaa gtctggcacc tcagcctccc tggccatcag tgggctccgg     240
tccgaggatg aggctgatta ttactgtgct cttgggatg atagcctgag tgcttatgtc      300
ttcggcggag gcaccaagct gacggtccta                                      330
```

<210> SEQ ID NO 53
<211> LENGTH: 116
<212> TYPE: PRT
<213> ORGANISM: Artificial Sequence
<220> FEATURE:
<223> OTHER INFORMATION: Description of Artificial Sequence: Synthetic
      N5 VH

<400> SEQUENCE: 53

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45
```

Ser Trp Ile Tyr Ser Gly Ser Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Leu Asp Phe Asp Tyr Trp Gly Gln Gly Thr Leu Val
            100                 105                 110

Thr Val Ser Ser
        115

<210> SEQ ID NO 54
<211> LENGTH: 348
<212> TYPE: DNA
<213> ORGANISM: Artificial Sequence
<220> FEATURE:
<223> OTHER INFORMATION: Description of Artificial Sequence: Synthetic
      N5 VH

<400> SEQUENCE: 54
gaggtgcagc tgttggagtc tgggggaggc ttggtacagc ctgggggtc cctgagactc        60 tcctgtgcag cctctggatt caccttagc gattatgcta tgagctgggt ccgccaggct       120
ccagggaaag gctggagtg gtctcatgg atctattctg gtagtggtaa taaatattac       180
gctgattctg taaaaggtcg gttcaccatc tccagagaca attccaagaa cacgctgtat       240
ctgcaaatga acagcctgag agccgaggac acggccgtgt attactgtgc gagaatgggt       300
ttggatttcg actactgggg ccagggtaca ctggtcaccg tgagctca                    348

<210> SEQ ID NO 55
<211> LENGTH: 110
<212> TYPE: PRT
<213> ORGANISM: Artificial Sequence
<220> FEATURE:
<223> OTHER INFORMATION: Description of Artificial Sequence: Synthetic
      N5 VL

<400> SEQUENCE: 55

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Asp Ser Leu
                85                  90                  95

Ser Ala Tyr Val Phe Gly Gly Gly Thr Lys Leu Thr Val Leu
            100                 105                 110

<210> SEQ ID NO 56
<211> LENGTH: 330
<212> TYPE: DNA
<213> ORGANISM: Artificial Sequence
<220> FEATURE:
<223> OTHER INFORMATION: Description of Artificial Sequence: Synthetic
      N5 VL

<400> SEQUENCE: 56

```
cagtctgtgc tgactcagcc accctcagcg tctgggaccc ccgggcagag ggtcaccatc     60
tcttgtactg gctcttcatc taatattggc aataattatg tctcctggta ccagcagctc    120
ccaggaacgg cccccaaact cctcatctat gatgataatc agcggccaag cggggtccct    180
gaccgattct ctggctccaa gtctggcacc tcagcctccc tggccatcag tgggctccgg    240
tccgaggatg aggctgatta ttactgtggt acttgggatg atagcctgag tgcttatgtc    300
ttcggcggag gcaccaagct gacggtccta                                     330
```

<210> SEQ ID NO 57
<211> LENGTH: 116
<212> TYPE: PRT
<213> ORGANISM: Artificial Sequence
<220> FEATURE:
<223> OTHER INFORMATION: Description of Artificial Sequence: Synthetic N7 VH

<400> SEQUENCE: 57

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
            20                  25                  30
Tyr Met Ser Trp Val Arg Gln Ala Pro Gly Lys Gly Leu Glu Trp Val
        35                  40                  45
Ser Gly Ile Tyr Ser Gly Thr Gly Ser Ile Tyr Tyr Ala Asp Ser Val
    50                  55                  60
Glu Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Ser
                85                  90                  95
Ala Arg Pro Pro Tyr His Phe Asp Tyr Trp Gly Gln Gly Thr Leu Val
            100                 105                 110
Thr Val Ser Ser
        115
```

<210> SEQ ID NO 58
<211> LENGTH: 348
<212> TYPE: DNA
<213> ORGANISM: Artificial Sequence
<220> FEATURE:
<223> OTHER INFORMATION: Description of Artificial Sequence: Synthetic N7 VH

<400> SEQUENCE: 58

```
gaggtgcagc tgttggagtc ggggggaggc ttggtacagc ctgggggtc cctgagactc      60
tcctgtgcag cctctggatt cacctttagc gattattata tgagctgggt ccgccaggct    120
ccagggaagg ggctggagtg ggtctcaggg atctattctg gtactggtag tatatattac    180
gctgattctg tagaaggtcg gttcaccatc tccagagaca attccaagaa cacgctgtat    240
ctgcaaatga acagcctgag agccgaggac acggccgtgt attactctgc gagacctccg    300
tatcatttcg actactgggg ccagggtaca ctggtcaccg tgagctca                 348
```

<210> SEQ ID NO 59
<211> LENGTH: 110
<212> TYPE: PRT
<213> ORGANISM: Artificial Sequence
<220> FEATURE:

<223> OTHER INFORMATION: Description of Artificial Sequence: Synthetic
     N7 VL

<400> SEQUENCE: 59

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
            20                  25                  30

Tyr Val Thr Trp Tyr Gln Gln Leu Pro Gly Thr Ala Pro Lys Leu Leu
        35                  40                  45

Ile Tyr Ala Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Tyr Ser Leu
                85                  90                  95

Ser Gly Tyr Val Phe Gly Gly Gly Thr Lys Leu Thr Val Leu
            100                 105                 110

<210> SEQ ID NO 60
<211> LENGTH: 330
<212> TYPE: DNA
<213> ORGANISM: Artificial Sequence
<220> FEATURE:
<223> OTHER INFORMATION: Description of Artificial Sequence: Synthetic
     N7 VL

<400> SEQUENCE: 60
cagtctgtgc tgactcagcc accctcagcg tctgggaccc ccgggcagag ggtcaccatc    60
tcttgtactg gctcttcatc taatattggc agtaattatg tcacctggta ccagcagctc   120
ccaggaacgg cccccaaact cctcatctat gctgatagta atcggccaag cggggtccct   180
gaccgattct ctggctccaa gtctggcacc tcagcctccc tggccatcag tgggctccgg   240
tccgaggacg aggctgatta ttactgtggt gcttgggatt atagcctgag tggttatgtc   300
ttcggcggag gcaccaagct gacggtccta                                    330

<210> SEQ ID NO 61
<211> LENGTH: 116
<212> TYPE: PRT
<213> ORGANISM: Artificial Sequence
<220> FEATURE:
<223> OTHER INFORMATION: Description of Artificial Sequence: Synthetic
     N9 VH

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Trp Ile Tyr Ser Gly Asp Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Glu Thr Arg Thr Phe Asp Tyr Trp Gly Gln Gly Thr Leu Val

Thr Val Ser Ser
    115

<210> SEQ ID NO 62
<211> LENGTH: 348
<212> TYPE: DNA
<213> ORGANISM: Artificial Sequence
<220> FEATURE:
<223> OTHER INFORMATION: Description of Artificial Sequence: Synthetic
      N9 VH

<400> SEQUENCE: 62
gaggtgcagc tgttggagtc tgggggaggc ttggtacagc ctggggggtc cctgagactc    60
tcctgtgcag cctctggatt cacctttagc aattatgata tgagctgggt ccgccaggct   120
ccagggaagg ggctggagtg ggtctcatgg atctattctg gtgatagtag taaatattac   180
gctgattctg taaaaggtcg gttcaccatc tccagagaca attccaagaa cacgctgtat   240
ctgcaaatga acagcctgag agccgaggac acggccgtgt attactctgc gagagagacg   300
cggacgttcg actactgggg ccagggtaca ctggtcaccg tgagctca                348

<210> SEQ ID NO 63
<211> LENGTH: 110
<212> TYPE: PRT
<213> ORGANISM: Artificial Sequence
<220> FEATURE:
<223> OTHER INFORMATION: Description of Artificial Sequence: Synthetic
      N9 VL

<400> SEQUENCE: 63

Gln Ser Val Leu Thr Gln Pro Pro Ser Ala Ser Gly Thr Pro Gly Gln
1               5                   10                  15

Arg Val Thr Ile Ser Cys Thr Gly Ser Ser Phe Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Tyr Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Ser Gly Tyr Val Phe Gly Gly Gly Thr Lys Leu Thr Val Leu
            100                 105                 110

<210> SEQ ID NO 64
<211> LENGTH: 330
<212> TYPE: DNA
<213> ORGANISM: Artificial Sequence
<220> FEATURE:
<223> OTHER INFORMATION: Description of Artificial Sequence: Synthetic
      N9 VL

<400> SEQUENCE: 64
cagtctgtgc tgactcagcc accctcagcg tctgggaccc ccgggcagag ggtcaccatc    60
tcttgtactg gctcttcatt taatattggc agtaatgctg tctactggta ccagcagctc   120
ccaggaacgg ccccaaact cctcatctat tataatagtc agcggccaag cggggtccct   180
gaccgattct ctggctccaa gtctggcacc tcagcctccc tggccatcag tgggctccgg   240
tccgaggatg aggctgatta ttactgtggc tcttgggatg ctagcctgag tggttatgtc    300
ttcggcggag gcaccaagct gacggtccta                                    330

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      linker for scFv

<400> SEQUENCE: 65

Gly Gly Gly Gly Ser Gly Gly Gly Gly Ser Gly Gly Gly Gly Ser
1               5                   10                  15

<210> SEQ ID NO 66
<211> LENGTH: 45
<212> TYPE: DNA
<213> ORGANISM: Artificial Sequence
<220> FEATURE:
<223> OTHER INFORMATION: Description of Artificial Sequence: Synthetic
      linker for scFv

<400> SEQUENCE: 66
ggtggaggcg gttcaggcgg aggtggatcc ggcggtggcg gatcg                    45

<210> SEQ ID NO 67
<211> LENGTH: 241
<212> TYPE: PRT
<213> ORGANISM: Artificial Sequence
<220> FEATURE:
<223> OTHER INFORMATION: Description of Artificial Sequence: Synthetic
      N3 scFv (VH+linker+VL)

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser

```
                195                 200                 205
Gly Leu Arg Ser Glu Asp Glu Ala Asp Tyr Tyr Cys Ala Ser Trp Asp
        210                 215                 220

Asp Ser Leu Ser Ala Tyr Val Phe Gly Gly Gly Thr Lys Leu Thr Val
225                 230                 235                 240

Leu

<210> SEQ ID NO 68
<211> LENGTH: 723
<212> TYPE: DNA
<213> ORGANISM: Artificial Sequence
<220> FEATURE:
<223> OTHER INFORMATION: Description of Artificial Sequence: Synthetic
      N3 scFv (VH+linker+VL)

<400> SEQUENCE: 68
gaggtgcagc tgttggagtc tgggggaggc ttggtacagc ctgggggtc cctgagactc      60 tcctgtgcag cctctggatt cacctttagc agttatgata tgagctgggt ccgccaggct    120
ccagggaagg ggctggagtg ggtctcagcg atctcttatg ataatggtaa acatattac    180 gctgattctg taaaaggtcg gttcaccatc tccagagaca attccaagaa cacgctgtat   240
ctgcaaatga acagcctgag agccgaggac acggccgtgt attactctgc gagaatggcg   300
cttgatttcg actactgggg ccagggtaca ctggtcaccg tgagctcagg tggaggcggt   360
tcaggcggag gtggatccgg cggtggcgga tcgcagtctg tgctgactca gccacccctca   420 gcgtctggga cccccgggca gagggtcacc atctcttgta ctggctcttc atctaatatt   480
ggcagtaatt atgtcacctg gtaccagcag ctcccaggaa cggcccccaa actcctcatc   540
tatgataata gtaatcggcc aagcggggtc cctgaccgat tctctggctc caagtctggc   600
acctcagcct ccctggccat cagtgggctc cggtccgagg atgaggctga ttattactgt   660
gcttcttggg atgatagcct gagtgcttat gtcttcggcg aggcaccaa gctgacggtc    720 cta                                                                 723

<210> SEQ ID NO 69
<211> LENGTH: 241
<212> TYPE: PRT
<213> ORGANISM: Artificial Sequence
<220> FEATURE:
<223> OTHER INFORMATION: Description of Artificial Sequence: Synthetic
      N5 scFv (VH+linker+VL)

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Trp Ile Tyr Ser Gly Ser Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Leu Asp Phe Asp Tyr Trp Gly Gln Gly Thr Leu Val
            100                 105                 110
```

Thr Val Ser Ser Gly Gly Gly Ser Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Asn Asn Tyr Val Ser Trp Tyr Gln Gln Leu Pro Gly Thr Ala Pro
                165                 170                 175

Lys Leu Leu Ile Tyr Asp Asp Asn Gln Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Arg Ser Glu Asp Glu Ala Asp Tyr Tyr Cys Gly Thr Trp Asp
    210                 215                 220

Asp Ser Leu Ser Ala Tyr Val Phe Gly Gly Gly Thr Lys Leu Thr Val
225                 230                 235                 240

Leu

<210> SEQ ID NO 70
<211> LENGTH: 723
<212> TYPE: DNA
<213> ORGANISM: Artificial Sequence
<220> FEATURE:
<223> OTHER INFORMATION: Description of Artificial Sequence: Synthetic
      N5 scFv (VH+linker+VL)

<400> SEQUENCE: 70
gaggtgcagc tgttggagtc tgggggaggc ttggtacagc ctggggggtc cctgagactc      60
tcctgtgcag cctctggatt cacctttagc gattatgcta tgagctgggt ccgccaggct     120
ccagggaaag gctggagtg gtctcatgg atctattctg gtagtggtaa taaatattac       180
gctgattctg taaaaggtcg gttcaccatc tccagagaca attccaagaa cacgctgtat     240
ctgcaaatga acagcctgag agccgaggac acggccgtgt attactgtgc gagaatgggt     300
ttggatttcg actactgggg ccagggtaca ctggtcaccg tgagctcagg tggaggcggt     360
tcaggcggag gtggatccgg cggtggcgga tcgcagtctg tgctgactca gccaccctca     420
gcgtctggga cccccgggca gagggtcacc atctcttgta ctggctcttc atctaatatt     480
ggcaataatt atgtctcctg gtaccagcag ctcccaggaa cggcccccaa actcctcatc     540
tatgatgata atcagcggcc aagcggggtc cctgaccgat tctctggctc caagtctggc     600
acctcagcct ccctggccat cagtgggctc cggtccgagg atgaggctga ttattactgt     660
ggtacttggg atgatagcct gagtgcttat gtcttcggcg aggcaccaa gctgacggtc     720 cta                                                                    723

<210> SEQ ID NO 71
<211> LENGTH: 241
<212> TYPE: PRT
<213> ORGANISM: Artificial Sequence
<220> FEATURE:
<223> OTHER INFORMATION: Description of Artificial Sequence: Synthetic
      N7 scFv (VH+linker+VL)

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
         35                  40                  45

Ser Gly Ile Tyr Ser Gly Thr Gly Ser Ile Tyr Tyr Ala Asp Ser Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Ser
                 85                  90                  95

Ala Arg Pro Pro Tyr His Phe Asp Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Gln Ser Val Leu Thr Gln Pro Pro Ser Ala Ser Gly Thr
        130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Ala Asp Ser Asn Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Arg Ser Glu Asp Glu Ala Asp Tyr Tyr Cys Gly Ala Trp Asp
    210                 215                 220

Tyr Ser Leu Ser Gly Tyr Val Phe Gly Gly Gly Thr Lys Leu Thr Val
225                 230                 235                 240

Leu

<210> SEQ ID NO 72
<211> LENGTH: 723
<212> TYPE: DNA
<213> ORGANISM: Artificial Sequence
<220> FEATURE:
<223> OTHER INFORMATION: Description of Artificial Sequence: Synthetic
      N7 scFv (VH+linker+VL)

<400> SEQUENCE: 72
gaggtgcagc tgttggagtc gggggggaggc ttggtacagc ctggggggtc cctgagactc      60
tcctgtgcag cctctggatt cacctttagc gattattata tgagctgggt ccgccaggct     120
ccagggaagg ggctggagtg ggtctcaggg atctattctg gtactggtag tatatattac     180
gctgattctg tagaaggtcg gttcaccatc tccagagaca attccaagaa cacgctgtat     240
ctgcaaatga acagcctgag agccgaggac acggccgtgt attactctgc gagacctccg     300
tatcatttcg actactgggg ccagggtaca ctggtcaccg tgagctcagg tggaggcggt     360
tcaggcggag gtggatccgg cggtggcgga tcgcagtctg tgctgactca gccaccctca     420
gcgtctggga cccccgggca gagggtcacc atctcttgta ctggctcttc atctaatatt     480
ggcagtaatt atgtcacctg gtaccagcag ctcccaggaa cggcccccaa actcctcatc     540
tatgctgata gtaatcggcc aagcggggtc cctgaccgat tctctggctc caagtctggc     600
acctcagcct ccctggccat cagtgggctc cggtccgagg acgaggctga ttattactgt     660
ggtgcttggg attatagcct gagtggttat gtcttcggcg aggcaccaa gctgacggtc     720 cta                                                                   723

<210> SEQ ID NO 73
<211> LENGTH: 241
<212> TYPE: PRT
<213> ORGANISM: Artificial Sequence
<220> FEATURE:
<223> OTHER INFORMATION: Description of Artificial Sequence: Synthetic N9 scFv (VH+linker+VL)

<400> SEQUENCE: 73

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Trp Ile Tyr Ser Gly Asp Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Glu Thr Arg Thr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Phe Asn Ile
145                 150                 155                 160

Gly Ser Asn Ala Val Tyr Trp Tyr Gln Gln Leu Pro Gly Thr Ala Pro
                165                 170                 175

Lys Leu Leu Ile Tyr Tyr Asn Ser Gln Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Arg Ser Glu Asp Glu Ala Asp Tyr Tyr Cys Gly Ser Trp Asp
    210                 215                 220

Ala Ser Leu Ser Gly Tyr Val Phe Gly Gly Gly Thr Lys Leu Thr Val
225                 230                 235                 240

Leu
```

<210> SEQ ID NO 74
<211> LENGTH: 723
<212> TYPE: DNA
<213> ORGANISM: Artificial Sequence
<220> FEATURE:
<223> OTHER INFORMATION: Description of Artificial Sequence: Synthetic N9 scFv (VH+linker+VL)

<400> SEQUENCE: 74

```
gaggtgcagc tgttggagtc tgggggaggc ttggtacagc ctgggggtc cctgagactc      60 tcctgtgcag cctctggatt caccttagc aattatgata tgagctgggt ccgccaggct     120
ccagggaagg ggctggagtg gtctcatgg atctattctg gtgatagtag taaatattac    180
gctgattctg taaaaggtcg gttcaccatc tccagagaca attccaagaa cacgctgtat    240
ctgcaaatga acagcctgag agccgaggac acggccgtgt attactctgc gagagagacg   300
```

-continued

```
cggacgttcg actactgggg ccagggtaca ctggtcaccg tgagctcagg tggaggcggt    360
tcaggcggag gtggatccgg cggtggcgga tcgcagtctg tgctgactca gccaccctca    420
gcgtctggga ccccggggca gagggtcacc atctcttgta ctggctcttc atttaatatt    480
ggcagtaatg ctgtctactg gtaccagcag ctcccaggaa cggcccccaa actcctcatc    540
tattataata gtcagcggcc aagcggggtc cctgaccgat tctctggctc caagtctggc    600
acctcagcct ccctggccat cagtgggctc cggtccgagg atgaggctga ttattactgt    660
ggctcttggg atgctagcct gagtggttat gtcttcggcg aggcaccaa gctgacggtc     720
cta                                                                  723
```

<210> SEQ ID NO 75
<211> LENGTH: 52
<212> TYPE: PRT
<213> ORGANISM: Artificial Sequence
<220> FEATURE:
<223> OTHER INFORMATION: Description of Artificial Sequence: Synthetic
      membrane exposed Lysyl-tRNA synthetase N-term

<400> SEQUENCE: 75

Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
            20                  25                  30

Val Ala Glu Lys Glu Ala Lys Gln Lys Glu Leu Ser Glu Lys Gln Leu
        35                  40                  45

Ser Gln Ala Thr
    50

<210> SEQ ID NO 76
<211> LENGTH: 597
<212> TYPE: PRT
<213> ORGANISM: Artificial Sequence
<220> FEATURE:
<223> OTHER INFORMATION: Description of Artificial Sequence: Synthetic
      Lysyl-tRNA synthetase(KRS) full

<400> SEQUENCE: 76

Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
            20                  25                  30

Val Ala Glu Lys Glu Ala Lys Gln Lys Glu Leu Ser Glu Lys Gln Leu
        35                  40                  45

Ser Gln Ala Thr Ala Ala Ala Thr Asn His Thr Thr Asp Asn Gly Val
    50                  55                  60

Gly Pro Glu Glu Glu Ser Val Asp Pro Asn Gln Tyr Tyr Lys Ile Arg
65                  70                  75                  80

Ser Gln Ala Ile His Gln Leu Lys Val Asn Gly Glu Asp Pro Tyr Pro
                85                  90                  95

His Lys Phe His Val Asp Ile Ser Leu Thr Asp Phe Ile Gln Lys Tyr
            100                 105                 110

Ser His Leu Gln Pro Gly Asp His Leu Thr Asp Ile Thr Leu Lys Val
        115                 120                 125

Ala Gly Arg Ile His Ala Lys Arg Ala Ser Gly Gly Lys Leu Ile Phe
    130                 135                 140

Tyr Asp Leu Arg Gly Glu Gly Val Lys Leu Gln Val Met Ala Asn Ser
145                 150                 155                 160

-continued

Arg Asn Tyr Lys Ser Glu Glu Phe Ile His Ile Asn Asn Lys Leu
            165                 170                 175

Arg Arg Gly Asp Ile Ile Gly Val Gln Gly Asn Pro Gly Lys Thr Lys
            180                 185                 190

Lys Gly Glu Leu Ser Ile Ile Pro Tyr Glu Ile Thr Leu Leu Ser Pro
            195                 200                 205

Cys Leu His Met Leu Pro His Leu His Phe Gly Leu Lys Asp Lys Glu
        210                 215                 220

Thr Arg Tyr Arg Gln Arg Tyr Leu Asp Leu Ile Leu Asn Asp Phe Val
225                 230                 235                 240

Arg Gln Lys Phe Ile Ile Arg Ser Lys Ile Ile Thr Tyr Ile Arg Ser
                245                 250                 255

Phe Leu Asp Glu Leu Gly Phe Leu Glu Ile Glu Thr Pro Met Met Asn
            260                 265                 270

Ile Ile Pro Gly Gly Ala Val Ala Lys Pro Phe Ile Thr Tyr His Asn
        275                 280                 285

Glu Leu Asp Met Asn Leu Tyr Met Arg Ile Ala Pro Glu Leu Tyr His
        290                 295                 300

Lys Met Leu Val Val Gly Gly Ile Asp Arg Val Tyr Glu Ile Gly Arg
305                 310                 315                 320

Gln Phe Arg Asn Glu Gly Ile Asp Leu Thr His Asn Pro Glu Phe Thr
                325                 330                 335

Thr Cys Glu Phe Tyr Met Ala Tyr Ala Asp Tyr His Asp Leu Met Glu
            340                 345                 350

Ile Thr Glu Lys Met Val Ser Gly Met Val Lys His Ile Thr Gly Ser
        355                 360                 365

Tyr Lys Val Thr Tyr His Pro Asp Gly Pro Glu Gly Gln Ala Tyr Asp
        370                 375                 380

Val Asp Phe Thr Pro Pro Phe Arg Arg Ile Asn Met Val Glu Glu Leu
385                 390                 395                 400

Glu Lys Ala Leu Gly Met Lys Leu Pro Glu Thr Asn Leu Phe Glu Thr
                405                 410                 415

Glu Glu Thr Arg Lys Ile Leu Asp Asp Ile Cys Val Ala Lys Ala Val
            420                 425                 430

Glu Cys Pro Pro Pro Arg Thr Thr Ala Arg Leu Leu Asp Lys Leu Val
        435                 440                 445

Gly Glu Phe Leu Glu Val Thr Cys Ile Asn Pro Thr Phe Ile Cys Asp
        450                 455                 460

His Pro Gln Ile Met Ser Pro Leu Ala Lys Trp His Arg Ser Lys Glu
465                 470                 475                 480

Gly Leu Thr Glu Arg Phe Glu Leu Phe Val Met Lys Lys Glu Ile Cys
                485                 490                 495

Asn Ala Tyr Thr Glu Leu Asn Asp Pro Met Arg Gln Arg Gln Leu Phe
            500                 505                 510

Glu Glu Gln Ala Lys Ala Lys Ala Gly Asp Asp Glu Ala Met Phe
        515                 520                 525

Ile Asp Glu Asn Phe Cys Thr Ala Leu Glu Tyr Gly Leu Pro Pro Thr
        530                 535                 540

Ala Gly Trp Gly Met Gly Ile Asp Arg Val Ala Met Phe Leu Thr Asp
545                 550                 555                 560

Ser Asn Asn Ile Lys Glu Val Leu Leu Phe Pro Ala Met Lys Pro Glu
                565                 570                 575

Asp Lys Lys Glu Asn Val Ala Thr Thr Asp Thr Leu Glu Ser Thr Thr
            580                 585                 590

Val Gly Thr Ser Val
        595

<210> SEQ ID NO 77
<211> LENGTH: 446
<212> TYPE: PRT
<213> ORGANISM: Artificial Sequence
<220> FEATURE:
<223> OTHER INFORMATION: Description of Artificial Sequence: Synthetic
      N3 IgG heavy chain

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Gly Asn Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

```
Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 78
<211> LENGTH: 1338
<212> TYPE: DNA
<213> ORGANISM: Artificial Sequence
<220> FEATURE:
<223> OTHER INFORMATION: Description of Artificial Sequence: Synthetic
    N3 IgG heavy chain

<400> SEQUENCE: 78

```
gaggtgcagc tgttggagtc tgggggaggc ttggtacagc ctggggggtc cctgagactc      60
tcctgtgcag cctctggatt caccttagc agttatgata tgagctgggt ccgccaggct     120
ccagggaagg gctggagtg gtctcagcg atctcttatg ataatggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgattccg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggaccctga ggtcacatgc     780 gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc tcccgtgct ggactccgac    1200 ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                  1338
```

<210> SEQ ID NO 79
<211> LENGTH: 217
<212> TYPE: PRT
<213> ORGANISM: Artificial Sequence
<220> FEATURE:
<223> OTHER INFORMATION: Description of Artificial Sequence: Synthetic
   N3 IgG light chain

<400> SEQUENCE: 79

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
            20                  25                  30

Tyr Val Thr Trp Tyr Gln Gln Leu Pro Gly Thr Ala Pro Lys Leu Leu
        35                  40                  45

Ile Tyr Asp Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Ala Tyr Val Phe Gly Gly Gly Thr Lys Leu Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 80
<211> LENGTH: 651
<212> TYPE: DNA
<213> ORGANISM: Artificial Sequence
<220> FEATURE:
<223> OTHER INFORMATION: Description of Artificial Sequence: Synthetic
   N3 IgG light chain

<400> SEQUENCE: 80
cagtctgtgc tgactcagcc accctcagcg tctgggaccc ccgggcagag ggtcaccatc      60
tcttgtactg gctcttcatc taatattggc agtaattatg tcacctggta ccagcagctc     120
ccaggaacgg cccccaaact cctcatctat gataatagta atcggccaag cggggtccct     180
gaccgattct ctggctccaa gtctggcacc tcagcctccc tggccatcag tgggctccgg     240
tccgaggatg aggctgatta ttactgtgct tcttgggatg atagcctgag tgcttatgtc     300
ttcggcggag gcaccaagct gacggtccta cgtacggtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480

```
aactcccagg agagtgtcac agagcaggac agcaaggaca gcacctacag cctcagcagc      540
accctgacgc tgagcaaagc agactacgag aaacacaaag tctacgcctg cgaagtcacc      600
catcagggcc tgagctcgcc cgtcacaaag agcttcaaca ggggagagtg t               651
```

<210> SEQ ID NO 81
<211> LENGTH: 446
<212> TYPE: PRT
<213> ORGANISM: Artificial Sequence
<220> FEATURE:
<223> OTHER INFORMATION: Description of Artificial Sequence: Synthetic
    N5 IgG heavy chain

<400> SEQUENCE: 81

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Trp Ile Tyr Ser Gly Ser Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
```

```
                    325                 330                 335
Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 82
<211> LENGTH: 1338
<212> TYPE: DNA
<213> ORGANISM: Artificial Sequence
<220> FEATURE:
<223> OTHER INFORMATION: Description of Artificial Sequence: Synthetic
      N5 IgG heavy chain

<400> SEQUENCE: 82
gaggtgcagc tgttggagtc tgggggaggc ttggtacagc ctggggggtc cctgagactc      60
tcctgtgcag cctctggatt cacctttagc gattatgcta tgagctgggt ccgccaggct     120
ccagggaaag gctggagtg gtctcatgg atctattctg gtagtggtaa taaatattac       180
gctgattctg taaaaggtcg gttcaccatc tccagagaca attccaagaa cacgctgtat     240
ctgcaaatga acagcctgag agccgaggac acggccgtgt attactgtgc gagaatgggt     300
ttggatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                   1338
```

<210> SEQ ID NO 83
<211> LENGTH: 217
<212> TYPE: PRT
<213> ORGANISM: Artificial Sequence
<220> FEATURE:
<223> OTHER INFORMATION: Description of Artificial Sequence: Synthetic
      N5 IgG light chain

<400> SEQUENCE: 83

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Asp Ser Leu
                85                  90                  95

Ser Ala Tyr Val Phe Gly Gly Gly Thr Lys Leu Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 84
<211> LENGTH: 651
<212> TYPE: DNA
<213> ORGANISM: Artificial Sequence
<220> FEATURE:
<223> OTHER INFORMATION: Description of Artificial Sequence: Synthetic
      N5 IgG light chain

<400> SEQUENCE: 84
cagtctgtgc tgactcagcc accctcagcg tctgggaccc ccgggcagag ggtcaccatc    60
tcttgtactg gctcttcatc taatattggc aataattatg tctcctggta ccagcagctc   120
ccaggaacgg ccccaaaact cctcatctat gatgataatc agcggccaag cggggtccct   180
gaccgattct ctggctccaa gtctggcacc tcagcctccc tggccatcag tgggctccgg   240
tccgaggatg aggctgatta ttactgtggt acttgggatg atagcctgag tgcttatgtc   300
ttcggcggag gcaccaagct gacggtccta cgtacggtgg ctgcaccatc tgtcttcatc   360
ttcccgccat ctgatgagca gttgaaatct ggaactgcct ctgttgtgtg cctgctgaat   420

```
aacttctatc cagagaggc caaagtacag tggaaggtgg ataacgccct ccaatcgggt      480
aactcccagg agagtgtcac agagcaggac agcaaggaca gcacctacag cctcagcagc      540
accctgacgc tgagcaaagc agactacgag aaacacaaag tctacgcctg cgaagtcacc      600
catcagggcc tgagctcgcc cgtcacaaag agcttcaaca ggggagagtg t              651
```

<210> SEQ ID NO 85
<211> LENGTH: 446
<212> TYPE: PRT
<213> ORGANISM: Artificial Sequence
<220> FEATURE:
<223> OTHER INFORMATION: Description of Artificial Sequence: Synthetic
    N7 IgG heavy chain

<400> SEQUENCE: 85

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Ser Gly Thr Gly Ser Ile Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Pro Pro Tyr His Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 86
<211> LENGTH: 1338
<212> TYPE: DNA
<213> ORGANISM: Artificial Sequence
<220> FEATURE:
<223> OTHER INFORMATION: Description of Artificial Sequence: Synthetic
      N7 IgG heavy chain

<400> SEQUENCE: 86

```
gaggtgcagc tgttggagtc ggggggaggc ttggtacagc ctgggggtc cctgagactc      60 tcctgtgcag cctctggatt caccttttagc gattattata tgagctgggt ccgccaggct    120
ccagggaagg gctggagtg gtctcaggg atctattctg gtactggtag tatatattac      180
gctgattctg tagaaggtcg gttcaccatc tccagagaca attccaagaa cacgctgtat    240
ctgcaaatga acagcctgag agccgaggac acggccgtgt attactctgc gagacctccg    300
tatcatttcg actactgggg ccagggtaca ctggtcaccg tgagctcagc ctccaccaag    360
ggcccatcgg tcttccccct ggcaccctcc tccaagagca cctctggggg cacagcggcc    420
ctgggctgcc tggtcaagga ctacttcccc gaaccggtga cggtgtcgtg aactcaggc     480 gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtatacccctg cccccatccc gggatgagct gaccaagaac   1080
caggtcagcc tgacctgcct ggtcaaaggc ttctatccca gcgacatcgc cgtggagtgg   1140
gagagcaatg gcagccgga gaacaactac aagaccacgc ctcccgtgct ggactccgac    1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
```
tccctgtccc cgggtaaa                                              1338

<210> SEQ ID NO 87
<211> LENGTH: 217
<212> TYPE: PRT
<213> ORGANISM: Artificial Sequence
<220> FEATURE:
<223> OTHER INFORMATION: Description of Artificial Sequence: Synthetic
      N7 IgG light chain

<400> SEQUENCE: 87

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Asp Ser Leu
                85                  90                  95

Ser Ala Tyr Val Phe Gly Gly Gly Thr Lys Leu Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 88
<211> LENGTH: 651
<212> TYPE: DNA
<213> ORGANISM: Artificial Sequence
<220> FEATURE:
<223> OTHER INFORMATION: Description of Artificial Sequence: Synthetic
      N7 IgG light chain

<400> SEQUENCE: 88
cagtctgtgc tgactcagcc accctcagcg tctgggaccc ccgggcagag ggtcaccatc     60
tcttgtactg gctcttcatc taatattggc agtaattatg tcacctggta ccagcagctc    120
ccaggaacgg cccccaaact cctcatctat gctgatagta tcggccaag cggggtccct     180 gaccgattct ctggctccaa gtctggcacc tcagcctccc tggccatcag tgggctccgg    240
tccgaggacg aggctgatta ttactgtggt gcttgggatt atagcctgag tggttatgtc    300
ttcggcggag gcaccaagct gacggtccta cgtacggtgg ctgcaccatc tgtcttcatc    360
ttcccgccat ctgatgagca gttgaaatct ggaactgcct ctgttgtgtg cctgctgaat    420

-continued

```
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t             651
```

<210> SEQ ID NO 89
<211> LENGTH: 446
<212> TYPE: PRT
<213> ORGANISM: Artificial Sequence
<220> FEATURE:
<223> OTHER INFORMATION: Description of Artificial Sequence: Synthetic
    N9 IgG heavy chain

<400> SEQUENCE: 89

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Trp Ile Tyr Ser Gly Asp Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Glu Thr Arg Thr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 90
<211> LENGTH: 1338
<212> TYPE: DNA
<213> ORGANISM: Artificial Sequence
<220> FEATURE:
<223> OTHER INFORMATION: Description of Artificial Sequence: Synthetic
      N9 IgG heavy chain

<400> SEQUENCE: 90

| | | | | | |
|---|---|---|---|---|---|
| gaggtgcagc | tgttggagtc | tgggggaggc | ttggtacagc | ctgggggtc | cctgagactc | 60 |
| tcctgtgcag | cctctggatt | cacctttagc | aattatgata | tgagctgggt | ccgccaggct | 120 |
| ccagggaagg | gctggagtg | gtctcatgg | atctattctg | gtgatagtag | taaatattac | 180 |
| gctgattctg | taaaaggtcg | gttcaccatc | tccagagaca | attccaagaa | cacgctgtat | 240 |
| ctgcaaatga | acagcctgag | agccgaggac | acggccgtgt | attactctgc | gagagagacg | 300 |
| cggacgttcg | actactgggg | ccagggtaca | ctggtcaccg | tgagctcagc | ctccaccaag | 360 |
| ggcccatcgg | tcttcccct | ggcaccctcc | tccaagagca | cctctggggg | cacagcggcc | 420 |
| ctgggctgcc | tggtcaagga | ctacttcccc | gaaccggtga | cggtgtcgtg | gaactcaggc | 480 |
| gccctgacca | gcggcgtgca | caccttcccg | gctgtcctac | agtcctcagg | actctactcc | 540 |
| ctcagcagcg | tggtgaccgt | gccctccagc | agcttgggca | cccagaccta | catctgcaac | 600 |
| gtgaatcaca | agcccagcaa | caccaaggtg | gacaagaaag | ttgagcccaa | atcttgtgac | 660 |
| aaaactcaca | catgcccacc | gtgcccagca | cctgaactcc | tggggggacc | gtcagtcttc | 720 |
| ctcttccccc | caaaacccaa | ggacaccctc | atgatctccc | ggaccctga | ggtcacatgc | 780 |
| gtggtggtgg | acgtgagcca | cgaagaccct | gaggtcaagt | tcaactggta | cgtggacggc | 840 |
| gtggaggtgc | ataatgccaa | gacaaagccg | cgggaggagc | agtacaacag | cacgtaccgt | 900 |
| gtggtcagcg | tcctcaccgt | cctgcaccag | gactggctga | atggcaagga | gtacaagtgc | 960 |
| aaggtctcca | acaaagccct | cccagccccc | atcgagaaaa | ccatctccaa | agccaaaggg | 1020 |
| cagccccgag | aaccacaggt | gtataccctg | cccccatccc | gggatgagct | gaccaagaac | 1080 |
| caggtcagcc | tgacctgcct | ggtcaaaggc | ttctatccca | gcgacatcgc | cgtggagtgg | 1140 |
| gagagcaatg | ggcagccgga | gaacaactac | aagaccacgc | ctcccgtgct | ggactccgac | 1200 |
| ggctccttct | tcctctacag | caagctcacc | gtggacaaga | gcaggtggca | gcaggggaac | 1260 |
| gtcttctcat | gctccgtgat | gcatgaggct | ctgcacaacc | actacacgca | gaagagcctc | 1320 | tccctgtccc cgggtaaa                                              1338

<210> SEQ ID NO 91
<211> LENGTH: 217
<212> TYPE: PRT
<213> ORGANISM: Artificial Sequence
<220> FEATURE:
<223> OTHER INFORMATION: Description of Artificial Sequence: Synthetic
      N9 IgG light chain

<400> SEQUENCE: 91

Gln Ser Val Leu Thr Gln Pro Pro Ser Ala Ser Gly Thr Pro Gly Gln
1               5                   10                  15

Arg Val Thr Ile Ser Cys Thr Gly Ser Ser Phe Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Tyr Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Ser Gly Tyr Val Phe Gly Gly Gly Thr Lys Leu Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 92
<211> LENGTH: 651
<212> TYPE: DNA
<213> ORGANISM: Artificial Sequence
<220> FEATURE:
<223> OTHER INFORMATION: Description of Artificial Sequence: Synthetic
      N9 IgG light chain

<400> SEQUENCE: 92
cagtctgtgc tgactcagcc accctcagcg tctgggaccc ccgggcagag ggtcaccatc    60
tcttgtactg gctcttcatt taatattggc agtaatgctg tctactggta ccagcagctc   120
ccaggaacgg ccccaaaact cctcatctat tataatagtc agcggccaag cggggtccct   180
gaccgattct ctggctccaa gtctggcacc tcagcctccc tggccatcag tgggctccgg   240
tccgaggatg aggctgatta ttactgtggc tcttgggatg ctagcctgag tggttatgtc   300
ttcggcggag gcaccaagct gacggtccta cgtacggtgg ctgcaccatc tgtcttcatc   360

```
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t            651

<210> SEQ ID NO 93
<211> LENGTH: 34
<212> TYPE: DNA
<213> ORGANISM: Artificial Sequence
<220> FEATURE:
<223> OTHER INFORMATION: Description of Artificial Sequence: Synthetic
      scFv VH primer Forward

<400> SEQUENCE: 93
agagagtgta cactcccagg cggccgaggt gcag                                34

<210> SEQ ID NO 94
<211> LENGTH: 42
<212> TYPE: DNA
<213> ORGANISM: Artificial Sequence
<220> FEATURE:
<223> OTHER INFORMATION: Description of Artificial Sequence: Synthetic
      scFv VH primer Reverse

<400> SEQUENCE: 94
cgccgctggg cccttggtgg aggctgagct cacggtgacc ag                       42

<210> SEQ ID NO 95
<211> LENGTH: 89
<212> TYPE: DNA
<213> ORGANISM: Artificial Sequence
<220> FEATURE:
<223> OTHER INFORMATION: Description of Artificial Sequence: Synthetic
      scFv VL primer Forward

<400> SEQUENCE: 95
aagcggccgc caccatggga tggagctgta tcatcctctt cttggtagca acagctacag    60
gtgtacactc ccagtctgtg ctgactcag                                      89

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
      scFv VL primer Reverse

<400> SEQUENCE: 96
cgccgccgta cgtaggaccg tcagcttggt                                     30

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      main binding site of N3 Ab

<400> SEQUENCE: 97

Lys Leu Ser Lys Asn Glu Leu Lys Arg Arg Leu Lys Ala
1               5                   10
```

-continued

```
<210> SEQ ID NO 98
<211> LENGTH: 29
<212> TYPE: PRT
<213> ORGANISM: Artificial Sequence
<220> FEATURE:
<223> OTHER INFORMATION: Description of Artificial Sequence: Synthetic
      N3 epitope F1

<400> SEQUENCE: 98

Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala
            20                  25

<210> SEQ ID NO 99
<211> LENGTH: 30
<212> TYPE: PRT
<213> ORGANISM: Artificial Sequence
<220> FEATURE:
<223> OTHER INFORMATION: Description of Artificial Sequence: Synthetic
      N3 epitope F2

<400> SEQUENCE: 99

Gln Ala Ala Glu Val Lys Val Asp Gly Ser Glu Pro Lys Leu Ser Lys
1               5                   10                  15

Asn Glu Leu Lys Arg Arg Leu Lys Ala Glu Lys Lys Val Ala
            20                  25                  30

<210> SEQ ID NO 100
<211> LENGTH: 29
<212> TYPE: PRT
<213> ORGANISM: Artificial Sequence
<220> FEATURE:
<223> OTHER INFORMATION: Description of Artificial Sequence: Synthetic
      N3 epitope F3

<400> SEQUENCE: 100

Lys Val Asp Gly Ser Glu Pro Lys Leu Ser Lys Asn Glu Leu Lys Arg
1               5                   10                  15

Arg Leu Lys Ala Glu Lys Lys Val Ala Glu Lys Glu Ala
            20                  25

<210> SEQ ID NO 101
<211> LENGTH: 28
<212> TYPE: PRT
<213> ORGANISM: Artificial Sequence
<220> FEATURE:
<223> OTHER INFORMATION: Description of Artificial Sequence: Synthetic
      N3 epitope F4

<400> SEQUENCE: 101

Glu Pro Lys Leu Ser Lys Asn Glu Leu Lys Arg Arg Leu Lys Ala Glu
1               5                   10                  15

Lys Lys Val Ala Glu Lys Glu Ala Lys Gln Lys Glu
            20                  25

<210> SEQ ID NO 102
<211> LENGTH: 26
<212> TYPE: PRT
<213> ORGANISM: Artificial Sequence
<220> FEATURE:
<223> OTHER INFORMATION: Description of Artificial Sequence: Synthetic
      N3 epitope F5

<400> SEQUENCE: 102

Lys Arg Arg Leu Lys Ala Glu Lys Lys Val Ala Glu Lys Glu Ala Lys
```

```
                 1               5                  10                 15

Gln Lys Glu Leu Ser Glu Lys Gln Leu Ser
                20                  25

<210> SEQ ID NO 103
<211> LENGTH: 28
<212> TYPE: PRT
<213> ORGANISM: Artificial Sequence
<220> FEATURE:
<223> OTHER INFORMATION: Description of Artificial Sequence: Synthetic
      mouse N3 epitope F1(mF1)

<400> SEQUENCE: 103

Met Ala Thr Leu Gln Glu Ser Glu Val Lys Val Asp Gly Glu Gln Lys
1               5                   10                  15

Leu Ser Lys Asn Glu Leu Lys Arg Arg Leu Lys Ala
                20                  25

<210> SEQ ID NO 104
<211> LENGTH: 29
<212> TYPE: PRT
<213> ORGANISM: Artificial Sequence
<220> FEATURE:
<223> OTHER INFORMATION: Description of Artificial Sequence: Synthetic
      mouse N3 epitope F2(mF2)

<400> SEQUENCE: 104

Gln Glu Ser Glu Val Lys Val Asp Gly Glu Gln Lys Leu Ser Lys Asn
1               5                   10                  15

Glu Leu Lys Arg Arg Leu Lys Ala Glu Lys Lys Leu Ala
                20                  25

<210> SEQ ID NO 105
<211> LENGTH: 28
<212> TYPE: PRT
<213> ORGANISM: Artificial Sequence
<220> FEATURE:
<223> OTHER INFORMATION: Description of Artificial Sequence: Synthetic
      mouse N3 epitope F3(mF3)

<400> SEQUENCE: 105

Lys Val Asp Gly Glu Gln Lys Leu Ser Lys Asn Glu Leu Lys Arg Arg
1               5                   10                  15

Leu Lys Ala Glu Lys Lys Leu Ala Glu Lys Glu Ala
                20                  25

<210> SEQ ID NO 106
<211> LENGTH: 27
<212> TYPE: PRT
<213> ORGANISM: Artificial Sequence
<220> FEATURE:
<223> OTHER INFORMATION: Description of Artificial Sequence: Synthetic
      mouse N3 epitope F4(mF4)

<400> SEQUENCE: 106

Gln Lys Leu Ser Lys Asn Glu Leu Lys Arg Arg Leu Lys Ala Glu Lys
1               5                   10                  15

Lys Leu Ala Glu Lys Glu Ala Lys Gln Lys Glu
                20                  25

<210> SEQ ID NO 107
<211> LENGTH: 25
<212> TYPE: PRT
<213> ORGANISM: Artificial Sequence
<220> FEATURE:
```

```
<223> OTHER INFORMATION: Description of Artificial Sequence: Synthetic
      mouse N3 epitope F5(mF5)

<400> SEQUENCE: 107

Arg Arg Leu Lys Ala Glu Lys Lys Leu Ala Glu Lys Glu Ala Lys Gln
1               5                   10                  15

Lys Glu Leu Ser Glu Lys Gln Leu Asn
            20                  25

<210> SEQ ID NO 108
<211> LENGTH: 28
<212> TYPE: PRT
<213> ORGANISM: Artificial Sequence
<220> FEATURE:
<223> OTHER INFORMATION: Description of Artificial Sequence: Synthetic
      rat N3 epitope F1(rF1)

<400> SEQUENCE: 108

Met Ala Thr Leu Arg Glu Gly Glu Val Lys Leu Asp Gly Glu Pro Lys
1               5                   10                  15

Leu Ser Lys Asn Glu Leu Lys Arg Arg Leu Lys Ala
            20                  25

<210> SEQ ID NO 109
<211> LENGTH: 29
<212> TYPE: PRT
<213> ORGANISM: Artificial Sequence
<220> FEATURE:
<223> OTHER INFORMATION: Description of Artificial Sequence: Synthetic
      rat N3 epitope F2(rF2)

<400> SEQUENCE: 109

Arg Glu Gly Glu Val Lys Leu Asp Gly Glu Pro Lys Leu Ser Lys Asn
1               5                   10                  15

Glu Leu Lys Arg Arg Leu Lys Ala Glu Lys Lys Leu Ala
            20                  25

<210> SEQ ID NO 110
<211> LENGTH: 28
<212> TYPE: PRT
<213> ORGANISM: Artificial Sequence
<220> FEATURE:
<223> OTHER INFORMATION: Description of Artificial Sequence: Synthetic
      rat N3 epitope F3(rF3)

<400> SEQUENCE: 110

Lys Leu Asp Gly Glu Pro Lys Leu Ser Lys Asn Glu Leu Lys Arg Arg
1               5                   10                  15

Leu Lys Ala Glu Lys Lys Leu Ala Glu Lys Glu Ala
            20                  25

<210> SEQ ID NO 111
<211> LENGTH: 27
<212> TYPE: PRT
<213> ORGANISM: Artificial Sequence
<220> FEATURE:
<223> OTHER INFORMATION: Description of Artificial Sequence: Synthetic
      rat N3 epitope F4(rF4)

<400> SEQUENCE: 111

Pro Lys Leu Ser Lys Asn Glu Leu Lys Arg Arg Leu Lys Ala Glu Lys
1               5                   10                  15

Lys Leu Ala Glu Lys Glu Ala Lys Gln Lys Glu
            20                  25
```

```
<210> SEQ ID NO 112
<211> LENGTH: 25
<212> TYPE: PRT
<213> ORGANISM: Artificial Sequence
<220> FEATURE:
<223> OTHER INFORMATION: Description of Artificial Sequence: Synthetic
      rat N3 epitope F5(rF5)

<400> SEQUENCE: 112

Arg Arg Leu Lys Ala Glu Lys Lys Leu Ala Glu Lys Glu Ala Lys Gln
1               5                   10                  15

Lys Glu Leu Ser Glu Lys Gln Leu Asn
            20                  25

<210> SEQ ID NO 113
<211> LENGTH: 48
<212> TYPE: PRT
<213> ORGANISM: Artificial Sequence
<220> FEATURE:
<223> OTHER INFORMATION: Description of Artificial Sequence: Synthetic
      Lysyl-tRNA synthetase N-term(mouse)

<400> SEQUENCE: 113

Met Ala Thr Leu Gln Glu Ser Glu Val Lys Val Asp Gly Glu Gln Lys
1               5                   10                  15

Leu Ser Lys Asn Glu Leu Lys Arg Arg Leu Lys Ala Glu Lys Lys Leu
            20                  25                  30

Ala Glu Lys Glu Ala Lys Gln Lys Glu Leu Ser Glu Lys Gln Leu Asn
        35                  40                  45

<210> SEQ ID NO 114
<211> LENGTH: 48
<212> TYPE: PRT
<213> ORGANISM: Artificial Sequence
<220> FEATURE:
<223> OTHER INFORMATION: Description of Artificial Sequence: Synthetic
      Lysyl-tRNA synthetase N-term(rat)

<400> SEQUENCE: 114

Met Ala Thr Leu Arg Glu Gly Glu Val Lys Leu Asp Gly Glu Pro Lys
1               5                   10                  15

Leu Ser Lys Asn Glu Leu Lys Arg Arg Leu Lys Ala Glu Lys Lys Leu
            20                  25                  30

Ala Glu Lys Glu Ala Lys Gln Lys Glu Leu Ser Glu Lys Gln Leu Asn
        35                  40                  45

<210> SEQ ID NO 115
<211> LENGTH: 1823
<212> TYPE: PRT
<213> ORGANISM: Artificial Sequence
<220> FEATURE:
<223> OTHER INFORMATION: Description of Artificial Sequence: Synthetic
      Amino acid sequence of Laminin subunit alpha-4 (Homo sapiens)

<400> SEQUENCE: 115

Met Ala Leu Ser Ser Ala Trp Arg Ser Val Leu Pro Leu Trp Leu Leu
1               5                   10                  15

Trp Ser Ala Ala Cys Ser Arg Ala Ala Ser Gly Asp Asp Asn Ala Phe
            20                  25                  30

Pro Phe Asp Ile Glu Gly Ser Ser Ala Val Gly Arg Gln Asp Pro Pro
        35                  40                  45

Glu Thr Ser Glu Pro Arg Val Ala Leu Gly Arg Leu Pro Pro Ala Ala
    50                  55                  60
```

```
Glu Lys Cys Asn Ala Gly Phe Phe His Thr Leu Ser Gly Glu Cys Val
 65                  70                  75                  80

Pro Cys Asp Cys Asn Gly Asn Ser Asn Glu Cys Leu Asp Gly Ser Gly
                 85                  90                  95

Tyr Cys Val His Cys Gln Arg Asn Thr Thr Gly Glu His Cys Glu Lys
            100                 105                 110

Cys Leu Asp Gly Tyr Ile Gly Asp Ser Ile Arg Gly Ala Pro Gln Phe
        115                 120                 125

Cys Gln Pro Cys Pro Cys Pro Leu Pro His Leu Ala Asn Phe Ala Glu
    130                 135                 140

Ser Cys Tyr Arg Lys Asn Gly Ala Val Arg Cys Ile Cys Asn Glu Asn
145                 150                 155                 160

Tyr Ala Gly Pro Asn Cys Glu Arg Cys Ala Pro Gly Tyr Tyr Gly Asn
                165                 170                 175

Pro Leu Leu Ile Gly Ser Thr Cys Lys Lys Cys Asp Cys Ser Gly Asn
            180                 185                 190

Ser Asp Pro Asn Leu Ile Phe Glu Asp Cys Asp Glu Val Thr Gly Gln
        195                 200                 205

Cys Arg Asn Cys Leu Arg Asn Thr Thr Gly Phe Lys Cys Glu Arg Cys
    210                 215                 220

Ala Pro Gly Tyr Tyr Gly Asp Ala Arg Ile Ala Lys Asn Cys Ala Val
225                 230                 235                 240

Cys Asn Cys Gly Gly Gly Pro Cys Asp Ser Val Thr Gly Glu Cys Leu
                245                 250                 255

Glu Glu Gly Phe Glu Pro Pro Thr Gly Met Asp Cys Pro Thr Ile Ser
            260                 265                 270

Cys Asp Lys Cys Val Trp Asp Leu Thr Asp Ala Leu Arg Leu Ala Ala
        275                 280                 285

Leu Ser Ile Glu Glu Gly Lys Ser Gly Val Leu Ser Val Ser Ser Gly
    290                 295                 300

Ala Ala Ala His Arg His Val Asn Glu Ile Asn Ala Thr Ile Tyr Leu
305                 310                 315                 320

Leu Lys Thr Lys Leu Ser Glu Arg Glu Asn Gln Tyr Ala Leu Arg Lys
                325                 330                 335

Ile Gln Ile Asn Asn Ala Glu Asn Thr Met Lys Ser Leu Leu Ser Asp
            340                 345                 350

Val Glu Glu Leu Val Glu Lys Glu Asn Gln Ala Ser Arg Lys Gly Gln
        355                 360                 365

Leu Val Gln Lys Glu Ser Met Asp Thr Ile Asn His Ala Ser Gln Leu
    370                 375                 380

Val Glu Gln Ala His Asp Met Arg Asp Lys Ile Gln Glu Ile Asn Asn
385                 390                 395                 400

Lys Met Leu Tyr Tyr Gly Glu Glu His Glu Leu Ser Pro Lys Glu Ile
                405                 410                 415

Ser Glu Lys Leu Val Leu Ala Gln Lys Met Leu Glu Glu Ile Arg Ser
            420                 425                 430

Arg Gln Pro Phe Phe Thr Gln Arg Glu Leu Val Asp Glu Glu Ala Asp
        435                 440                 445

Glu Ala Tyr Glu Leu Leu Ser Gln Ala Glu Ser Trp Gln Arg Leu His
    450                 455                 460

Asn Glu Thr Arg Thr Leu Phe Pro Val Val Leu Glu Gln Leu Asp Asp
465                 470                 475                 480
```

-continued

```
Tyr Asn Ala Lys Leu Ser Asp Leu Gln Glu Ala Leu Asp Gln Ala Leu
            485                 490                 495

Asn Tyr Val Arg Asp Ala Glu Asp Met Asn Arg Ala Thr Ala Ala Arg
        500                 505                 510

Gln Arg Asp His Glu Lys Gln Gln Glu Arg Val Arg Glu Gln Met Glu
    515                 520                 525

Val Val Asn Met Ser Leu Ser Thr Ser Ala Asp Ser Leu Thr Thr Pro
530                 535                 540

Arg Leu Thr Leu Ser Glu Leu Asp Asp Ile Ile Lys Asn Ala Ser Gly
545                 550                 555                 560

Ile Tyr Ala Glu Ile Asp Gly Ala Lys Ser Glu Leu Gln Val Lys Leu
            565                 570                 575

Ser Asn Leu Ser Asn Leu Ser His Asp Leu Val Gln Glu Ala Ile Asp
        580                 585                 590

His Ala Gln Asp Leu Gln Gln Glu Ala Asn Glu Leu Ser Arg Lys Leu
    595                 600                 605

His Ser Ser Asp Met Asn Gly Leu Val Gln Lys Ala Leu Asp Ala Ser
610                 615                 620

Asn Val Tyr Glu Asn Ile Val Asn Tyr Val Ser Glu Ala Asn Glu Thr
625                 630                 635                 640

Ala Glu Phe Ala Leu Asn Thr Thr Asp Arg Ile Tyr Asp Ala Val Ser
            645                 650                 655

Gly Ile Asp Thr Gln Ile Ile Tyr His Lys Asp Glu Ser Glu Asn Leu
        660                 665                 670

Leu Asn Gln Ala Arg Glu Leu Gln Ala Lys Ala Glu Ser Ser Ser Asp
    675                 680                 685

Glu Ala Val Ala Asp Thr Ser Arg Arg Val Gly Gly Ala Leu Ala Arg
690                 695                 700

Lys Ser Ala Leu Lys Thr Arg Leu Ser Asp Ala Val Lys Gln Leu Gln
705                 710                 715                 720

Ala Ala Glu Arg Gly Asp Ala Gln Gln Arg Leu Gly Gln Ser Arg Leu
            725                 730                 735

Ile Thr Glu Glu Ala Asn Arg Thr Thr Met Glu Val Gln Gln Ala Thr
        740                 745                 750

Ala Pro Met Ala Asn Asn Leu Thr Asn Trp Ser Gln Asn Leu Gln His
    755                 760                 765

Phe Asp Ser Ser Ala Tyr Asn Thr Ala Val Asn Ser Ala Arg Asp Ala
770                 775                 780

Val Arg Asn Leu Thr Glu Val Val Pro Gln Leu Leu Asp Gln Leu Arg
785                 790                 795                 800

Thr Val Glu Gln Lys Arg Pro Ala Ser Asn Val Ser Ala Ser Ile Gln
            805                 810                 815

Arg Ile Arg Glu Leu Ile Ala Gln Thr Arg Ser Val Ala Ser Lys Ile
        820                 825                 830

Gln Val Ser Met Met Phe Asp Gly Gln Ser Ala Val Glu Val His Ser
    835                 840                 845

Arg Thr Ser Met Asp Asp Leu Lys Ala Phe Thr Ser Leu Ser Leu Tyr
850                 855                 860

Met Lys Pro Pro Val Lys Arg Pro Glu Leu Thr Glu Thr Ala Asp Gln
865                 870                 875                 880

Phe Ile Leu Tyr Leu Gly Ser Lys Asn Ala Lys Lys Glu Tyr Met Gly
            885                 890                 895

Leu Ala Ile Lys Asn Asp Asn Leu Val Tyr Val Tyr Asn Leu Gly Thr
```

```
                900             905             910
Lys Asp Val Glu Ile Pro Leu Asp Ser Lys Pro Val Ser Ser Trp Pro
            915                 920                 925

Ala Tyr Phe Ser Ile Val Lys Ile Glu Arg Val Gly Lys His Gly Lys
            930                 935             940

Val Phe Leu Thr Val Pro Ser Leu Ser Ser Thr Ala Glu Glu Lys Phe
945             950                 955                 960

Ile Lys Lys Gly Glu Phe Ser Gly Asp Asp Ser Leu Leu Asp Leu Asp
                965                 970                 975

Pro Glu Asp Thr Val Phe Tyr Val Gly Gly Val Pro Ser Asn Phe Lys
            980                 985                 990

Leu Pro Thr Ser Leu Asn Leu Pro Gly Phe Val Gly Cys Leu Glu Leu
        995                 1000                1005

Ala Thr Leu Asn Asn Asp Val Ile Ser Leu Tyr Asn Phe Lys His
        1010                1015                1020

Ile Tyr Asn Met Asp Pro Ser Thr Ser Val Pro Cys Ala Arg Asp
    1025                1030                1035

Lys Leu Ala Phe Thr Gln Ser Arg Ala Ala Ser Tyr Phe Phe Asp
    1040                1045                1050

Gly Ser Gly Tyr Ala Val Val Arg Asp Ile Thr Arg Arg Gly Lys
    1055                1060                1065

Phe Gly Gln Val Thr Arg Phe Asp Ile Glu Val Arg Thr Pro Ala
    1070                1075                1080

Asp Asn Gly Leu Ile Leu Leu Met Val Asn Gly Ser Met Phe Phe
    1085                1090                1095

Arg Leu Glu Met Arg Asn Gly Tyr Leu His Val Phe Tyr Asp Phe
    1100                1105                1110

Gly Phe Ser Gly Gly Pro Val His Leu Glu Asp Thr Leu Lys Lys
    1115                1120                1125

Ala Gln Ile Asn Asp Ala Lys Tyr His Glu Ile Ser Ile Ile Tyr
    1130                1135                1140

His Asn Asp Lys Lys Met Ile Leu Val Val Asp Arg Arg His Val
    1145                1150                1155

Lys Ser Met Asp Asn Glu Lys Met Lys Ile Pro Phe Thr Asp Ile
    1160                1165                1170

Tyr Ile Gly Gly Ala Pro Pro Glu Ile Leu Gln Ser Arg Ala Leu
    1175                1180                1185

Arg Ala His Leu Pro Leu Asp Ile Asn Phe Arg Gly Cys Met Lys
    1190                1195                1200

Gly Phe Gln Phe Gln Lys Lys Asp Phe Asn Leu Leu Glu Gln Thr
    1205                1210                1215

Glu Thr Leu Gly Val Gly Tyr Gly Cys Pro Glu Asp Ser Leu Ile
    1220                1225                1230

Ser Arg Arg Ala Tyr Phe Asn Gly Gln Ser Phe Ile Ala Ser Ile
    1235                1240                1245

Gln Lys Ile Ser Phe Phe Asp Gly Phe Glu Gly Gly Phe Asn Phe
    1250                1255                1260

Arg Thr Leu Gln Pro Asn Gly Leu Leu Phe Tyr Tyr Ala Ser Gly
    1265                1270                1275

Ser Asp Val Phe Ser Ile Ser Leu Asp Asn Gly Thr Val Ile Met
    1280                1285                1290

Asp Val Lys Gly Ile Lys Val Gln Ser Val Asp Lys Gln Tyr Asn
    1295                1300                1305
```

-continued

Asp Gly Leu Ser His Phe Val Ile Ser Ser Val Ser Pro Thr Arg
1310                1315                1320

Tyr Glu Leu Ile Val Asp Lys Ser Arg Val Gly Ser Lys Asn Pro
1325                1330                1335

Thr Lys Gly Lys Ile Glu Gln Thr Gln Ala Ser Glu Lys Lys Phe
1340                1345                1350

Tyr Phe Gly Gly Ser Pro Ile Ser Ala Gln Tyr Ala Asn Phe Thr
1355                1360                1365

Gly Cys Ile Ser Asn Ala Tyr Phe Thr Arg Val Asp Arg Asp Val
1370                1375                1380

Glu Val Glu Asp Phe Gln Arg Tyr Thr Glu Lys Val His Thr Ser
1385                1390                1395

Leu Tyr Glu Cys Pro Ile Glu Ser Ser Pro Leu Phe Leu Leu His
1400                1405                1410

Lys Lys Gly Lys Asn Leu Ser Lys Pro Lys Ala Ser Gln Asn Lys
1415                1420                1425

Lys Gly Gly Lys Ser Lys Asp Ala Pro Ser Trp Asp Pro Val Ala
1430                1435                1440

Leu Lys Leu Pro Glu Arg Asn Thr Pro Arg Asn Ser His Cys His
1445                1450                1455

Leu Ser Asn Ser Pro Arg Ala Ile Glu His Ala Tyr Gln Tyr Gly
1460                1465                1470

Gly Thr Ala Asn Ser Arg Gln Glu Phe Glu His Leu Lys Gly Asp
1475                1480                1485

Phe Gly Ala Lys Ser Gln Phe Ser Ile Arg Leu Arg Thr Arg Ser
1490                1495                1500

Ser His Gly Met Ile Phe Tyr Val Ser Asp Gln Glu Glu Asn Asp
1505                1510                1515

Phe Met Thr Leu Phe Leu Ala His Gly Arg Leu Val Tyr Met Phe
1520                1525                1530

Asn Val Gly His Lys Lys Leu Lys Ile Arg Ser Gln Glu Lys Tyr
1535                1540                1545

Asn Asp Gly Leu Trp His Asp Val Ile Phe Ile Arg Glu Arg Ser
1550                1555                1560

Ser Gly Arg Leu Val Ile Asp Gly Leu Arg Val Leu Glu Glu Ser
1565                1570                1575

Leu Pro Pro Thr Glu Ala Thr Trp Lys Ile Lys Gly Pro Ile Tyr
1580                1585                1590

Leu Gly Gly Val Ala Pro Gly Lys Ala Val Lys Asn Val Gln Ile
1595                1600                1605

Asn Ser Ile Tyr Ser Phe Ser Gly Cys Leu Ser Asn Leu Gln Leu
1610                1615                1620

Asn Gly Ala Ser Ile Thr Ser Ala Ser Gln Thr Phe Ser Val Thr
1625                1630                1635

Pro Cys Phe Glu Gly Pro Met Glu Thr Gly Thr Tyr Phe Ser Thr
1640                1645                1650

Glu Gly Gly Tyr Val Val Leu Asp Glu Ser Phe Asn Ile Gly Leu
1655                1660                1665

Lys Phe Glu Ile Ala Phe Glu Val Arg Pro Arg Ser Ser Ser Gly
1670                1675                1680

Thr Leu Val His Gly His Ser Val Asn Gly Glu Tyr Leu Asn Val
1685                1690                1695

```
His Met Lys Asn Gly Gln Val Ile Val Lys Val Asn Asn Gly Ile
    1700                1705                1710

Arg Asp Phe Ser Thr Ser Val Thr Pro Lys Gln Ser Leu Cys Asp
    1715                1720                1725

Gly Arg Trp His Arg Ile Thr Val Ile Arg Asp Ser Asn Val Val
    1730                1735                1740

Gln Leu Asp Val Asp Ser Glu Val Asn His Val Gly Pro Leu
    1745                1750                1755

Asn Pro Lys Pro Ile Asp His Arg Glu Pro Val Phe Val Gly Gly
    1760                1765                1770

Val Pro Glu Ser Leu Leu Thr Pro Arg Leu Ala Pro Ser Lys Pro
    1775                1780                1785

Phe Thr Gly Cys Ile Arg His Phe Val Ile Asp Gly His Pro Val
    1790                1795                1800

Ser Phe Ser Lys Ala Ala Leu Val Ser Gly Ala Val Ser Ile Asn
    1805                1810                1815

Ser Cys Pro Ala Ala
    1820

<210> SEQ ID NO 116
<211> LENGTH: 5472
<212> TYPE: DNA
<213> ORGANISM: Artificial Sequence
<220> FEATURE:
<223> OTHER INFORMATION: Description of Artificial Sequence: Synthetic
      DNA sequence of Laminin subunit alpha-4 (Homo sapiens)

<400> SEQUENCE: 116
atggctttga gctcagcctg cgctcggtt ctgcctctgt ggctcctctg gagcgctgcc      60
tgctcccgcg ccgcgtccgg ggacgacaac gcttttcctt ttgacattga agggagctca    120
gcggttggca ggcaagaccc gcctgagacg agcgaacccc gcgtggctct gggacgcctg    180
ccgcctgcgg ccgagaaatg caatgctgga ttctttcaca ccctgtcggg agaatgtgtg    240
ccctgcgact gtaatggcaa ttccaacgag tgtttggacg gctcaggata ctgtgtgcac    300
tgccagcgga acacaacagg agagcactgt gaaaagtgtc tggatggtta tatcggagat    360
tccatcaggg gagcacccca attctgccag ccgtgcccct gtccctgcc ccacttggcc    420 aattttgcag aatcctgcta taggaaaaat ggagctgttc ggtgcatttg taacgaaaat    480
tatgctggac taactgtga agatgtgct cccggttact atggaaaccc cttactcatt    540
ggaagcacct gtaagaaatg tgactgcagt ggaaattcag atcccaacct gatctttgaa    600
gattgtgatg aagtcactgg ccagtgtagg aattgcttac gcaacaccac cggattcaag    660
tgtgaacgtt gcgctcctgg ctactatggg acgccagga tagccaagaa ctgtgcagtg    720
tgcaactgcg ggggaggccc atgtgacagt gtaaccggag aatgcttgga agaaggtttt    780 gaaccccta caggcatgga ctgcccaacc ataagtgctg taagtgcgt ctgggacctg    840 actgatgacc tgcggttagc agcgctctcc atcgaggaag gcaaatccgg ggtgctgagc    900
gtatcctctg ggccgccgc tcataggcac gtgaatgaaa tcaacgccac catctacctc    960
ctcaaaacaa aattgtcaga aagagaaaac caatacgccc taagaaagat acaaatcaac   1020
aatgctgaga acacgatgaa aagccttctg tctgactag aggaattagt tgaaaaggaa   1080
aatcaagcct ccagaaaagg acaacttgtt cagaaggaaa gcatggacac cattaaccac   1140
gcaagtcagc tggtagagca agcccatgat atgaggata aaatccaaga gatcaacaac   1200
aagatgctct attatgggga agagcatgaa cttagcccca ggaaatctc tgagaagctg   1260
```

```
gtgttggccc agaagatgct tgaagagatt agaagccgtc aaccattttt cacccaacgg    1320
gagctcgtgg atgaggaggc agatgaggct tacgaactac tgagccaggc tgagagctgg    1380
cagcggctgc acaatgagac ccgcactctg tttcctgtcg tcctggagca gctggatgac    1440
tacaatgcta agttgtcaga tctccaggaa gcacttgacc aggcccttaa ctatgtcagg    1500
gatgccgaag acatgaacag gccacagca gccaggcagc gggaccatga aaacaacag     1560 gaaagagtga gggaacaaat ggaagtggtg aacatgtctc tgagcacatc tgcggactct    1620
ctgacaacac ctcgtctaac tctttcagaa cttgatgata aataaagaa tgcgtcaggg     1680 atttatgcag aaatagatgg agccaaaagt gaactacaag taaaactatc taacctaagt    1740
aacctcagcc atgatttagt ccaagaagct attgaccatg cacaggacct tcaacaagaa    1800
gctaatgaat tgagcaggaa gttgcacagt tcagatatga acgggctggt acagaaggct    1860
ttggatgcat caaatgtcta tgaaaatatt gttaattatg ttagtgaagc caatgaaaca    1920
gcagaatttg cttttgaacac cactgaccga atttatgatg cggtgagtgg gattgatact    1980
caaatcattt accataaaga tgaaagtgag aacctcctca atcaagccag agaactgcaa    2040
gcaaaggcag agtctagcag tgatgaagca gtggctgaca ctagcaggcg tgtgggtgga    2100
gccctagcaa ggaaaagtgc ccttaaaacc agactcagtg atgccgttaa gcaactacaa    2160
gcagcagaga gaggggatgc ccagcagcgc ctggggcagt ctagactgat caccgaggaa    2220
gccaacagga cgacgatgga ggtgcagcag gccactgccc ccatggccaa caatctaacc    2280
aactggtcac agaatcttca acattttgac tcttctgctt acaacactgc agtgaactct    2340
gctagggatg cagtaagaaa tctgaccgag gttgtccctc agctcctgga tcagcttcgt    2400
acggttgagc agaagcgacc tgcaagcaac gtttctgcca gcatccagag gatccgagag    2460
ctcattgctc agaccagaag tgttgccagc aagatccaag tctccatgat gtttgatggc    2520
cagtcagctg tggaagtgca ctcgagaacc agtatggatg acttaaaggc cttcacgtct    2580
ctgagcctgt acatgaaacc ccctgtgaag cggccggaac tgaccgagac tgcagatcag    2640
tttatcctgt acctcggaag caaaaacgcc aaaaaagagt atatgggtct tgcaatcaaa    2700
aatgataatc tggtatacgt ctataatttg ggaactaaaa atgtggagat tcccctggac    2760
tccaagcccg tcagttcctg gcctgcttac ttcagcattg tcaagattga aaggggtggga    2820 aaacatggaa aggtgttttt aacagtcccg agtctaagta gcacagcaga ggaaaagttc    2880
attaaaaagg gggaattttc gggagatgac tctctgctgg acctggaccc tgaggacaca    2940
gtgttttatg ttggtggagt gccttccaac ttcaagctcc ctaccagctt aaacctgcct    3000
ggctttgttg gctgcctgga actggccact ttgaataatg atgtgatcag cttgtacaac    3060
tttaagcaca tctataatat ggaccccctcc acatcagtgc catgtgcccg agataagctg    3120
gccttcactc agagtcgggc tgccagttac ttcttcgatg gctccggtta tgccgtggtg    3180
agagacatca aaggagagg gaaatttggt caggtgactc gctttgacat agaagttcga    3240
acaccagctg acaacggcct tattctcctg atggtcaatg aagtatgtt tttcagactg    3300 gaaatgcgca atggttacct acatgtgttc tatgattttg gattcagcgg tggccctgtg    3360
catcttgaag atacgttaaa gaaagctcaa attaatgatg caaaatacca tgagatctca    3420
atcatttacc acaatgataa gaaaatgatc ttggtagttg acagaaggca tgtcaagagc    3480
atggataatg aaaagatgaa aataccttt acagatatat acattggagg agctcctcca    3540
gaaatcttac aatccagggc cctcagagca caccttcccc tagatatcaa cttcagagga    3600
```

| | | |
|---|---|---|
| tgcatgaagg gcttccagtt ccaaaagaag gacttcaatt tactggagca gacagaaacc | 3660 | |
| ctgggagttg gttatggatg cccagaagac tcacttatat ctcgcagagc atatttcaat | 3720 | |
| ggacagagct tcattgcttc aattcagaaa atatctttct ttgatggctt tgaaggaggt | 3780 | |
| tttaatttcc gaacattaca accaaatggg ttactattct attatgcttc agggtcagac | 3840 | |
| gtgttctcca tctcactgga taatggtact gtcatcatgg atgtaaaggg aatcaaagtt | 3900 | |
| cagtcagtag ataagcagta caatgatggg ctgtcccact tcgtcattag ctctgtctca | 3960 | |
| cccacaagat atgaactgat agtagataaa agcagagttg ggagtaagaa tcctaccaaa | 4020 | |
| gggaaaatag aacagacaca agcaagtgaa aagaagtttt acttcggtgg ctcaccaatc | 4080 | |
| agtgctcagt atgctaattt cactggctgc ataagtaatg cctactttac cagggtggat | 4140 | |
| agagatgtgg aggttgaaga tttccaacgg tatactgaaa aggtccacac ttctctttat | 4200 | |
| gagtgtccca ttgagtcttc accattgttt ctcctccata aaaaaggaaa aaatttatcc | 4260 | |
| aagcctaaag caagtcagaa taaaaaggga gggaaaagta aagatgcacc ttcatgggat | 4320 | |
| cctgttgctc tgaaactccc agagcggaat actccaagaa actctcattg ccaccttttcc | 4380 | |
| aacagcccta gagcaataga gcacgcctat caatatggag aacagccaa cagccgccaa | 4440 | |
| gagtttgaac acttaaaagg agattttggt gccaaatctc agttttccat tcgtctgaga | 4500 | |
| actcgttcct cccatggcat gatcttctat gtctcagatc aagaagagaa tgacttcatg | 4560 | |
| actctatttt tggcccatgg ccgcttggtt tacatgttta atgttggtca caaaaaactg | 4620 | |
| aagattagaa gccaggagaa atacaatgat ggcctgtggc atgatgtgat atttattcga | 4680 | |
| gaaaggagca gtggccgact ggtaattgat ggtctccgag tcctagaaga aagtcttcct | 4740 | |
| cctactgaag ctacctggaa aatcaagggt cccatttatt gggaggtgt ggctcctgga | 4800 | |
| aaggctgtga aaaatgttca gattaactcc atctacagtt ttagtggctg tctcagcaat | 4860 | |
| ctccagctca atggggcctc catcacctct gcttctcaga cattcagtgt gaccccttgc | 4920 | |
| tttgaaggcc ccatggaaac aggaacttac ttttcaacag aaggaggata cgtggttcta | 4980 | |
| gatgaatctt tcaatattgg attgaagttt gaaattgcat ttgaagtccg tcccagaagc | 5040 | |
| agttccggaa ccctggtcca cggccacagt gtcaatgggg agtacctaaa tgttcacatg | 5100 | |
| aaaaatggac aggtcatagt gaaagtcaat aatggcatca gagattttc cacctcagtt | 5160 | |
| acacccaagc agagtctctg tgatggcaga tggcacagaa ttacagttat tagagattct | 5220 | |
| aatgtggttc agttggatgt ggactctgaa gtgaaccatg tggttggacc cctgaatcca | 5280 | |
| aaaccaattg atcacaggga gcctgtgttt gttggaggtg ttccagaatc tctactgaca | 5340 | |
| ccacgcttgg cccccagcaa acccttcaca ggctgcatac gccactttgt gattgatgga | 5400 | |
| cacccagtga gcttcagtaa agcagccctg gtcagcggcg ccgtaagcat caactcctgt | 5460 | |
| ccagcagcct ga | 5472 | |

<210> SEQ ID NO 117
<211> LENGTH: 1798
<212> TYPE: PRT
<213> ORGANISM: Artificial Sequence
<220> FEATURE:
<223> OTHER INFORMATION: Description of Artificial Sequence: Synthetic
    Amino acid sequence of Laminin subunit beta-2 (Homo sapiens)

<400> SEQUENCE: 117

Met Glu Leu Thr Ser Arg Glu Arg Gly Arg Gly Gln Pro Leu Pro Trp
1               5                   10                  15

Glu Leu Arg Leu Gly Leu Leu Leu Ser Val Leu Ala Ala Thr Leu Ala

```
                20                  25                  30
       Gln Ala Pro Ala Pro Asp Val Pro Gly Cys Ser Arg Gly Ser Cys Tyr
                    35                  40                  45

Pro Ala Thr Gly Asp Leu Leu Val Gly Arg Ala Asp Arg Leu Thr Ala
                50                  55                  60

Ser Ser Thr Cys Gly Leu Asn Gly Pro Gln Pro Tyr Cys Ile Val Ser
        65                  70                  75                  80

His Leu Gln Asp Glu Lys Lys Cys Phe Leu Cys Asp Ser Arg Arg Pro
                        85                  90                  95

Phe Ser Ala Arg Asp Asn Pro His Ser His Arg Ile Gln Asn Val Val
                       100                 105                 110

Thr Ser Phe Ala Pro Gln Arg Ala Ala Trp Trp Gln Ser Glu Asn
                   115                 120                 125

Gly Ile Pro Ala Val Thr Ile Gln Leu Asp Leu Glu Ala Glu Phe His
                   130                 135                 140

Phe Thr His Leu Ile Met Thr Phe Lys Thr Phe Arg Pro Ala Ala Met
       145                 150                 155                 160

Leu Val Glu Arg Ser Ala Asp Phe Gly Arg Thr Trp His Val Tyr Arg
                       165                 170                 175

Tyr Phe Ser Tyr Asp Cys Gly Ala Asp Phe Pro Gly Val Pro Leu Ala
                       180                 185                 190

Pro Pro Arg His Trp Asp Asp Val Val Cys Glu Ser Arg Tyr Ser Glu
                       195                 200                 205

Ile Glu Pro Ser Thr Glu Gly Glu Val Ile Tyr Arg Val Leu Asp Pro
                       210                 215                 220

Ala Ile Pro Ile Pro Asp Pro Tyr Ser Ser Arg Ile Gln Asn Leu Leu
       225                 230                 235                 240

Lys Ile Thr Asn Leu Arg Val Asn Leu Thr Arg Leu His Thr Leu Gly
                       245                 250                 255

Asp Asn Leu Leu Asp Pro Arg Arg Glu Ile Arg Glu Lys Tyr Tyr Tyr
                       260                 265                 270

Ala Leu Tyr Glu Leu Val Val Arg Gly Asn Cys Phe Cys Tyr Gly His
                       275                 280                 285

Ala Ser Glu Cys Ala Pro Ala Pro Gly Ala Pro Ala His Ala Glu Gly
                       290                 295                 300

Met Val His Gly Ala Cys Ile Cys Lys His Asn Thr Arg Gly Leu Asn
       305                 310                 315                 320

Cys Glu Gln Cys Gln Asp Phe Tyr Arg Asp Leu Pro Trp Arg Pro Ala
                       325                 330                 335

Glu Asp Gly His Ser His Ala Cys Arg Lys Cys Glu Cys His Gly His
                       340                 345                 350

Thr His Ser Cys His Phe Asp Met Ala Val Tyr Leu Ala Ser Gly Asn
                       355                 360                 365

Val Ser Gly Gly Val Cys Asp Gly Cys Gln His Asn Thr Ala Gly Arg
                       370                 375                 380

His Cys Glu Leu Cys Arg Pro Phe Phe Tyr Arg Asp Pro Thr Lys Asp
       385                 390                 395                 400

Leu Arg Asp Pro Ala Val Cys Arg Ser Cys Asp Cys Asp Pro Met Gly
                       405                 410                 415

Ser Gln Asp Gly Gly Arg Cys Asp Ser His Asp Asp Pro Ala Leu Gly
                       420                 425                 430

Leu Val Ser Gly Gln Cys Arg Cys Lys Glu His Val Val Gly Thr Arg
                       435                 440                 445
```

```
Cys Gln Gln Cys Arg Asp Gly Phe Phe Gly Leu Ser Ile Ser Asp Arg
        450                 455                 460

Leu Gly Cys Arg Arg Cys Gln Cys Asn Ala Arg Gly Thr Val Pro Gly
465                 470                 475                 480

Ser Thr Pro Cys Asp Pro Asn Ser Gly Ser Cys Tyr Cys Lys Arg Leu
                485                 490                 495

Val Thr Gly Arg Gly Cys Asp Arg Cys Leu Pro Gly His Trp Gly Leu
                500                 505                 510

Ser His Asp Leu Leu Gly Cys Arg Pro Cys Asp Cys Asp Val Gly Gly
            515                 520                 525

Ala Leu Asp Pro Gln Cys Asp Glu Gly Thr Gly Gln Cys His Cys Arg
530                 535                 540

Gln His Met Val Gly Arg Arg Cys Glu Gln Val Gln Pro Gly Tyr Phe
545                 550                 555                 560

Arg Pro Phe Leu Asp His Leu Ile Trp Glu Ala Glu Asp Thr Arg Gly
                565                 570                 575

Gln Val Leu Asp Val Val Glu Arg Leu Val Thr Pro Gly Glu Thr Pro
                580                 585                 590

Ser Trp Thr Gly Ser Gly Phe Val Arg Leu Gln Glu Gly Gln Thr Leu
        595                 600                 605

Glu Phe Leu Val Ala Ser Val Pro Lys Ala Met Asp Tyr Asp Leu Leu
        610                 615                 620

Leu Arg Leu Glu Pro Gln Val Pro Glu Gln Trp Ala Glu Leu Glu Leu
625                 630                 635                 640

Ile Val Gln Arg Pro Gly Pro Val Pro Ala His Ser Leu Cys Gly His
                645                 650                 655

Leu Val Pro Lys Asp Asp Arg Ile Gln Gly Thr Leu Gln Pro His Ala
                660                 665                 670

Arg Tyr Leu Ile Phe Pro Asn Pro Val Cys Leu Glu Pro Gly Ile Ser
            675                 680                 685

Tyr Lys Leu His Leu Lys Leu Val Arg Thr Gly Gly Ser Ala Gln Pro
        690                 695                 700

Glu Thr Pro Tyr Ser Gly Pro Gly Leu Leu Ile Asp Ser Leu Val Leu
705                 710                 715                 720

Leu Pro Arg Val Leu Val Leu Glu Met Phe Ser Gly Gly Asp Ala Ala
                725                 730                 735

Ala Leu Glu Arg Gln Ala Thr Phe Glu Arg Tyr Gln Cys His Glu Glu
                740                 745                 750

Gly Leu Val Pro Ser Lys Thr Ser Pro Ser Glu Ala Cys Ala Pro Leu
        755                 760                 765

Leu Ile Ser Leu Ser Thr Leu Ile Tyr Asn Gly Ala Leu Pro Cys Gln
        770                 775                 780

Cys Asn Pro Gln Gly Ser Leu Ser Ser Glu Cys Asn Pro His Gly Gly
785                 790                 795                 800

Gln Cys Leu Cys Lys Pro Gly Val Val Gly Arg Arg Cys Asp Leu Cys
                805                 810                 815

Ala Pro Gly Tyr Tyr Gly Phe Gly Pro Thr Gly Cys Gln Ala Cys Gln
                820                 825                 830

Cys Ser His Glu Gly Ala Leu Ser Ser Leu Cys Glu Lys Thr Ser Gly
            835                 840                 845

Gln Cys Leu Cys Arg Thr Gly Ala Phe Gly Leu Arg Cys Asp Arg Cys
        850                 855                 860
```

```
Gln Arg Gly Gln Trp Gly Phe Pro Ser Cys Arg Pro Cys Val Cys Asn
865                 870                 875                 880

Gly His Ala Asp Glu Cys Asn Thr His Thr Gly Ala Cys Leu Gly Cys
                885                 890                 895

Arg Asp His Thr Gly Gly Glu His Cys Glu Arg Cys Ile Ala Gly Phe
            900                 905                 910

His Gly Asp Pro Arg Leu Pro Tyr Gly Gly Gln Cys Arg Pro Cys Pro
        915                 920                 925

Cys Pro Glu Gly Pro Gly Ser Gln Arg His Phe Ala Thr Ser Cys His
930                 935                 940

Gln Asp Glu Tyr Ser Gln Gln Ile Val Cys His Cys Arg Ala Gly Tyr
945                 950                 955                 960

Thr Gly Leu Arg Cys Glu Ala Cys Ala Pro Gly His Phe Gly Asp Pro
            965                 970                 975

Ser Arg Pro Gly Gly Arg Cys Gln Leu Cys Glu Cys Ser Gly Asn Ile
        980                 985                 990

Asp Pro Met Asp Pro Asp Ala Cys Asp Pro His Thr Gly Gln Cys Leu
    995                 1000                1005

Arg Cys Leu His His Thr Glu Gly Pro His Cys Ala His Cys Lys
1010            1015                1020

Pro Gly Phe His Gly Gln Ala Ala Arg Gln Ser Cys His Arg Cys
1025            1030                1035

Thr Cys Asn Leu Leu Gly Thr Asn Pro Gln Gln Cys Pro Ser Pro
1040            1045                1050

Asp Gln Cys His Cys Asp Pro Ser Ser Gly Gln Cys Pro Cys Leu
1055            1060                1065

Pro Asn Val Gln Gly Pro Ser Cys Asp Arg Cys Ala Pro Asn Phe
1070            1075                1080

Trp Asn Leu Thr Ser Gly His Gly Cys Gln Pro Cys Ala Cys His
1085            1090                1095

Pro Ser Arg Ala Arg Gly Pro Thr Cys Asn Glu Phe Thr Gly Gln
1100            1105                1110

Cys His Cys Arg Ala Gly Phe Gly Gly Arg Thr Cys Ser Glu Cys
1115            1120                1125

Gln Glu Leu His Trp Gly Asp Pro Gly Leu Gln Cys His Ala Cys
1130            1135                1140

Asp Cys Asp Ser Arg Gly Ile Asp Thr Pro Gln Cys His Arg Phe
1145            1150                1155

Thr Gly His Cys Ser Cys Arg Pro Gly Val Ser Gly Val Arg Cys
1160            1165                1170

Asp Gln Cys Ala Arg Gly Phe Ser Gly Ile Phe Pro Ala Cys His
1175            1180                1185

Pro Cys His Ala Cys Phe Gly Asp Trp Asp Arg Val Val Gln Asp
1190            1195                1200

Leu Ala Ala Arg Thr Gln Arg Leu Glu Gln Arg Ala Gln Glu Leu
1205            1210                1215

Gln Gln Thr Gly Val Leu Gly Ala Phe Glu Ser Ser Phe Trp His
1220            1225                1230

Met Gln Glu Lys Leu Gly Ile Val Gln Gly Ile Val Gly Ala Arg
1235            1240                1245

Asn Thr Ser Ala Ala Ser Thr Ala Gln Leu Val Glu Ala Thr Glu
1250            1255                1260

Glu Leu Arg Arg Glu Ile Gly Glu Ala Thr Glu His Leu Thr Gln
```

-continued

```
            1265                1270                1275
Leu Glu Ala Asp Leu Thr Asp Val Gln Asp Asn Phe Asn Ala
        1280                1285                1290
Asn His Ala Leu Ser Gly Leu Glu Arg Asp Arg Leu Ala Leu Asn
        1295                1300                1305
Leu Thr Leu Arg Gln Leu Asp Gln His Leu Asp Leu Leu Lys His
        1310                1315                1320
Ser Asn Phe Leu Gly Ala Tyr Asp Ser Ile Arg His Ala His Ser
        1325                1330                1335
Gln Ser Ala Glu Ala Glu Arg Arg Ala Asn Thr Ser Ala Leu Ala
        1340                1345                1350
Val Pro Ser Pro Val Ser Asn Ser Ala Ser Ala Arg His Arg Thr
        1355                1360                1365
Glu Ala Leu Met Asp Ala Gln Lys Glu Asp Phe Asn Ser Lys His
        1370                1375                1380
Met Ala Asn Gln Arg Ala Leu Gly Lys Leu Ser Ala His Thr His
        1385                1390                1395
Thr Leu Ser Leu Thr Asp Ile Asn Glu Leu Val Cys Gly Ala Pro
        1400                1405                1410
Gly Asp Ala Pro Cys Ala Thr Ser Pro Cys Gly Gly Ala Gly Cys
        1415                1420                1425
Arg Asp Glu Asp Gly Gln Pro Arg Cys Gly Gly Leu Ser Cys Asn
        1430                1435                1440
Gly Ala Ala Thr Ala Asp Leu Ala Leu Gly Arg Ala Arg His
        1445                1450                1455
Thr Gln Ala Glu Leu Gln Arg Ala Leu Ala Glu Gly Gly Ser Ile
        1460                1465                1470
Leu Ser Arg Val Ala Glu Thr Arg Arg Gln Ala Ser Glu Ala Gln
        1475                1480                1485
Gln Arg Ala Gln Ala Ala Leu Asp Lys Ala Asn Ala Ser Arg Gly
        1490                1495                1500
Gln Val Glu Gln Ala Asn Gln Glu Leu Gln Glu Leu Ile Gln Ser
        1505                1510                1515
Val Lys Asp Phe Leu Asn Gln Glu Gly Ala Asp Pro Asp Ser Ile
        1520                1525                1530
Glu Met Val Ala Thr Arg Val Leu Glu Leu Ser Ile Pro Ala Ser
        1535                1540                1545
Ala Glu Gln Ile Gln His Leu Ala Gly Ala Ile Ala Glu Arg Val
        1550                1555                1560
Arg Ser Leu Ala Asp Val Asp Ala Ile Leu Ala Arg Thr Val Gly
        1565                1570                1575
Asp Val Arg Arg Ala Glu Gln Leu Leu Gln Asp Ala Arg Arg Ala
        1580                1585                1590
Arg Ser Trp Ala Glu Asp Glu Lys Gln Lys Ala Glu Thr Val Gln
        1595                1600                1605
Ala Ala Leu Glu Glu Ala Gln Arg Ala Gln Gly Ile Ala Gln Gly
        1610                1615                1620
Ala Ile Arg Gly Ala Val Ala Asp Thr Arg Asp Thr Glu Gln Thr
        1625                1630                1635
Leu Tyr Gln Val Gln Glu Arg Met Ala Gly Ala Glu Arg Ala Leu
        1640                1645                1650
Ser Ser Ala Gly Glu Arg Ala Arg Gln Leu Asp Ala Leu Leu Glu
        1655                1660                1665
```

Ala Leu Lys Leu Lys Arg Ala Gly Asn Ser Leu Ala Ala Ser Thr
1670                1675                1680

Ala Glu Glu Thr Ala Gly Ser Ala Gln Gly Arg Ala Gln Glu Ala
    1685                1690                1695

Glu Gln Leu Leu Arg Gly Pro Leu Gly Asp Gln Tyr Gln Thr Val
    1700                1705                1710

Lys Ala Leu Ala Glu Arg Lys Ala Gln Gly Val Leu Ala Ala Gln
    1715                1720                1725

Ala Arg Ala Glu Gln Leu Arg Asp Glu Ala Arg Asp Leu Leu Gln
    1730                1735                1740

Ala Ala Gln Asp Lys Leu Gln Arg Leu Gln Glu Leu Glu Gly Thr
    1745                1750                1755

Tyr Glu Glu Asn Glu Arg Ala Leu Glu Ser Lys Ala Ala Gln Leu
    1760                1765                1770

Asp Gly Leu Glu Ala Arg Met Arg Ser Val Leu Gln Ala Ile Asn
    1775                1780                1785

Leu Gln Val Gln Ile Tyr Asn Thr Cys Gln
    1790                1795

<210> SEQ ID NO 118
<211> LENGTH: 5397
<212> TYPE: DNA
<213> ORGANISM: Artificial Sequence
<220> FEATURE:
<223> OTHER INFORMATION: Description of Artificial Sequence: Synthetic
      DNA sequence of Laminin subunit beta-2 (Homo sapiens)

<400> SEQUENCE: 118

```
atggagctga cctcaaggga aagagggagg ggacagcctc tgccctggga acttcgactg      60
ggcctactgc taagcgtgct ggctgccaca ctggcacagg cccctgcccc ggatgtgcct     120
ggctgttcca ggggaagctg ctaccccgcc acgggcgacc tgctggtggg ccgagctgac     180
agactgactg cctcatccac ttgtggcctg aatggccccc agccctactg catcgtcagt     240
cacctgcagg acgaaaagaa gtgcttcctt tgtgactccc ggcgcccctt ctctgctaga     300
gacaacccac acagccatcg catccagaat gtagtcacca gctttgcacc acagcggcgg     360
gcagcctggt ggcagtcaga gaatggtatc cctgcggtca ccatccagct ggacctggag     420
gctgagtttc atttcacaca cctcattatg accttcaaga catttcgccc tgctgccatg     480
ctggtggaac gctcagcaga ctttggccgc acctggcatg tgtaccgata tttctcctat     540
gactgtgggg ctgacttccc aggagtccca ctagcacccc cacggcactg ggatgatgta     600
gtctgtgagt cccgctactc agagattgag ccatccactg aaggcgaggt catctatcgt     660
gtgctggacc ctgccatccc tatcccagac ccctacagct cacggattca gaacctgttg     720
aagatcacca acctacgggt gaacctgact cgtctacaca cgttgggaga caacctactc     780
gacccacgga gggagatccg agagaagtac tactatgccc tctatgagct ggttgtacgt     840
ggcaactgct tctgctacgg acacgcctca gagtgtgcac ccgccccagg ggcaccagcc     900
catgctgagg gcatggtgca cggagcttgc atctgcaaac acaacacacg tggcctcaac     960
tgcgagcagt gtcaggattt ctatcgtgac ctgccctggc gtccggctga ggacggccat    1020
agtcatgcct gtaggaagtg tgagtgccat gggcacaccc acagctgcca cttcgacatg    1080
gccgtatacc tggcatctgg caatgtgagt ggaggtgtgt gtgatggatg tcagcataac    1140
acagctgggc gccactgtga gctctgtcgg cccttcttct accgtgaccc aaccaaggac    1200
```

-continued

```
ctgcgggatc cggctgtgtg ccgctcctgt gattgtgacc ccatgggttc tcaagacggt     1260
ggtcgctgtg attcccatga tgaccctgca ctgggactgg tctccggcca gtgtcgctgc     1320
aaagaacatg tggtgggcac tcgctgccag caatgccgtg atggcttctt tgggctcagc     1380
atcagtgacc gtctgggctg ccggcgatgt caatgtaatg cacggggcac agtgcctggg     1440
agcactcctt gtgaccccaa cagtggatcc tgttactgca aacgtctagt gactggacgt     1500
ggatgtgacc gctgcctgcc tggccactgg ggcctgagcc acgacctgct cggctgccgc     1560
ccctgtgact gcgacgtggg tggtgctttg gatccccagt gtgatgaggg cacaggtcaa     1620
tgccactgcc gccagcacat ggttgggcga cgctgtgagc aggtgcaacc tggctacttc     1680
cggcccttcc tggaccacct aatttgggag gctgaggaca cccgagggca ggtgctcgat     1740
gtggtggagc gcctggtgac ccccggggaa actccatcct ggactggctc aggcttcgtg     1800
cggctacagg aaggtcagac cctggagttc ctggtggcct ctgtgccgaa ggctatggac     1860
tatgacctgc tgctgcgctt agagccccag gtccctgagc aatgggcaga gttggaactg     1920
attgtgcagc gtccagggcc tgtgcctgcc cacagcctgt gtgggcattt ggtgcccaag     1980
gatgatcgca tccaagggac tctgcaacca catgccaggt acttgatatt tcctaatcct     2040
gtctgccttg agcctggtat ctcctacaag ctgcatctga agctggtacg gacagggggga    2100 agtgcccagc ctgagactcc ctactctgga cctggcctgc tcattgactc gctggtgctg     2160
ctgccccgtg tcctggtgct agagatgttt agtgggggtg atgctgctgc cctggagcgc     2220
caggccacct ttgaacgcta ccaatgccat gaggagggtc tggtgcccag caagacttct     2280
ccctctgagg cctgcgcacc cctcctcatc agcctgtcca ccctcatcta caatggtgcc     2340
ctgccatgtc agtgcaaccc tcaaggttca ctgagttctg agtgcaaccc tcatggtggt     2400
cagtgcctgt gcaagcctgg agtggttggg cgccgctgtg acctctgtgc ccctggctac     2460
tatggctttg gccccacagg ctgtcaagcc tgccagtgca gccacgaggg ggcactcagc     2520
agtctctgtg aaaagaccag tgggcaatgt ctctgtcgaa ctggtgcctt tgggcttcgc     2580
tgtgaccgct gccagcgtgg ccagtgggga ttccctagct gccggccatg tgtctgcaat     2640
gggcatgcag atgagtgcaa cacccacaca ggcgcttgcc tgggctgccg tgatcacaca     2700
gggggtgagc actgtgaaag gtgcattgct ggtttccacg gggacccacg gctgccatat     2760
gggggccagt gccggccctg tccctgtcct gaaggccctg ggagccaacg gcactttgct     2820
acttcttgcc accaggatga atattcccag cagattgtgt gccactgccg ggcaggctat     2880
acggggctgc gatgtgaagc ttgtgcccct gggcactttg gggacccatc aaggccaggt     2940
ggccggtgcc aactgtgtga gtgcagtggg aacattgacc caatggatcc tgatgcctgt     3000
gacccccaca cggggcaatg cctgcgctgt ttacaccaca cagagggtcc acactgtgcc     3060
cactgcaagc ctggcttcca tgggcaggct gcccgacaga gctgtcaccg ctgcacatgc     3120
aacctgctgg gcacaaatcc gcagcagtgc ccatctcctg accagtgcca ctgtgatcca     3180
agcagtgggc agtgcccatg cctccccaat gtccagggcc ctagctgtga ccgctgtgcc     3240
cccaacttct ggaacctcac cagtggccat ggttgccagc cttgtgcctg ccacccaagc     3300
cgggccagag gccccacctg caacgagttc acagggcagt gccactgccg tgccggcttt     3360
ggagggcgga cttgttctga gtgccaagag ctccactggg gagaccctgg gttgcagtgc     3420
catgcctgtg attgtgactc tcgtggaata gataccctcc agtgtcaccg cttcacaggt     3480
cactgcagct gccgcccagg ggtgtctggt gtgcgctgtg accagtgtgc ccgtggcttc     3540
tcaggaatct ttcctgcctg ccatccctgc catgcatgct tcgggggattg ggaccgagtg     3600
```

```
gtgcaggact tggcagcccg tacacagcgc ctagagcagc gggcgcagga gttgcaacag    3660
acgggtgtgc tgggtgcctt tgagagcagc ttctggcaca tgcaggagaa gctgggcatt    3720
gtgcagggca tcgtaggtgc ccgcaacacc tcagccgcct ccactgcaca gcttgtggag    3780
gcccacagag agctgcggcg tgaaattggg gaggccactg agcacctgac tcagctcgag    3840
gcagacctga cagatgtgca agatgagaac ttcaatgcca accatgcact aagtggtctg    3900
gagcgagata ggcttgcact taatctcaca ctgcggcagc tcgaccagca tcttgacttg    3960
ctcaaacatt caaacttcct gggtgcctat gacagcatcc ggcatgccca tagccagtct    4020
gcagaggcag aacgtcgtgc caatacctca gccctggcag tacctagccc tgtgagcaac    4080
tcggcaagtg ctcggcatcg gacagaggca ctgatggatg ctcagaagga ggacttcaac    4140
agcaaacaca tggccaacca gcgggcactt ggcaagctct ctgcccatac ccacaccctg    4200
agcctgacag acataaatga gctggtgtgt ggggcaccag gggatgcacc ctgtgctaca    4260
agcccttgtg ggggtgccgg ctgtcgagat gaggatgggc agccgcgctg tgggggcctc    4320
agctgcaatg gggcagcggc tacagcagac ctagcactgg gccgggcccg gcacacacag    4380
gcagagctgc agcgggcact ggcagaaggt ggtagcatcc tcagcagagt ggctgagact    4440
cgtcggcagg caagcgaggc acagcagcgg gcccaggcag ccctggacaa ggctaatgct    4500
tccaggggac aggtggaaca ggccaaccag gaacttcaag aacttatcca gagtgtgaag    4560
gacttcctca accaggaggg ggctgatcct gatagcattg aaatggtggc cacacgggtg    4620
ctagagctct ccatcccagc ttcagctgag cagatccagc acctggcggg tgcgattgca    4680
gagcgagtcc ggagcctggc agatgtggat gcgatcctgg cacgtactgt aggagatgtg    4740
cgtcgtgccg agcagctact gcaggatgca cggcgggcaa ggagctgggc tgaggatgag    4800
aaacagaagg cagagacagt acaggcagca ctggaggagg cccagcgggc acagggtatt    4860
gcccagggtg ccatccgggg ggcagtggct gacacacggg acacagagca gaccctgtac    4920
caggtacagg agaggatggc aggtgcagag cgggcactga gctctgcagg tgaaagggct    4980
cggcagttgg atgctctcct ggaggctctg aaattgaaac gggcaggaaa tagtctggca    5040
gcctctacag cagaagaaac ggcaggcagt gcccagggtc gtgcccagga ggctgagcag    5100
ctgctacgcg gtcctctggg tgatcagtac cagacggtga aggccctagc tgagcgcaag    5160
gcccaaggtg tgctggctgc acaggcaagg cagaacaac tgcgggatga ggctcgggac    5220
ctgttgcaag ccgctcagga caagctgcag cggctacagg aattggaagg cacctatgag    5280
gaaaatgagc gggcactgga gagtaaggca gcccagttgg acgggttgga ggccaggatg    5340
cgcagcgtgc ttcaagccat caacttgcag gtgcagatct acaacacctg ccagtga      5397
```

<210> SEQ ID NO 119
<211> LENGTH: 1609
<212> TYPE: PRT
<213> ORGANISM: Artificial Sequence
<220> FEATURE:
<223> OTHER INFORMATION: Description of Artificial Sequence: Synthetic
      Amino acid sequence of Laminin subunit gamma-1 (Homo sapiens)

<400> SEQUENCE: 119

Met Arg Gly Ser His Arg Ala Ala Pro Ala Leu Arg Pro Arg Gly Arg
1               5                   10                  15

Leu Trp Pro Val Leu Ala Val Leu Ala Ala Ala Ala Ala Gly Cys
            20                  25                  30

Ala Gln Ala Ala Met Asp Glu Cys Thr Asp Glu Gly Gly Arg Pro Gln

```
            35                  40                  45
Arg Cys Met Pro Glu Phe Val Asn Ala Ala Phe Asn Val Thr Val
 50                  55                  60
Ala Thr Asn Thr Cys Gly Thr Pro Glu Glu Tyr Cys Val Gln Thr
 65                  70                  75                  80
Gly Val Thr Gly Val Thr Lys Ser Cys His Leu Cys Asp Ala Gly
                     85                  90                  95
Pro His Leu Gln His Gly Ala Ala Phe Leu Thr Asp Tyr Asn Asn Gln
                    100                 105                 110
Ala Asp Thr Thr Trp Trp Gln Ser Gln Thr Met Leu Ala Gly Val Gln
                115                 120                 125
Tyr Pro Ser Ser Ile Asn Leu Thr Leu His Leu Gly Lys Ala Phe Asp
            130                 135                 140
Ile Thr Tyr Val Arg Leu Lys Phe His Thr Ser Arg Pro Glu Ser Phe
145                 150                 155                 160
Ala Ile Tyr Lys Arg Thr Arg Glu Asp Gly Pro Trp Ile Pro Tyr Gln
                165                 170                 175
Tyr Tyr Ser Gly Ser Cys Glu Asn Thr Tyr Ser Lys Ala Asn Arg Gly
                180                 185                 190
Phe Ile Arg Thr Gly Gly Asp Glu Gln Gln Ala Leu Cys Thr Asp Glu
            195                 200                 205
Phe Ser Asp Ile Ser Pro Leu Thr Gly Gly Asn Val Ala Phe Ser Thr
            210                 215                 220
Leu Glu Gly Arg Pro Ser Ala Tyr Asn Phe Asp Asn Ser Pro Val Leu
225                 230                 235                 240
Gln Glu Trp Val Thr Ala Thr Asp Ile Arg Val Thr Leu Asn Arg Leu
                245                 250                 255
Asn Thr Phe Gly Asp Glu Val Phe Asn Asp Pro Lys Val Leu Lys Ser
                260                 265                 270
Tyr Tyr Tyr Ala Ile Ser Asp Phe Ala Val Gly Gly Arg Cys Lys Cys
            275                 280                 285
Asn Gly His Ala Ser Glu Cys Met Lys Asn Glu Phe Asp Lys Leu Val
            290                 295                 300
Cys Asn Cys Lys His Asn Thr Tyr Gly Val Asp Cys Glu Lys Cys Leu
305                 310                 315                 320
Pro Phe Phe Asn Asp Arg Pro Trp Arg Arg Ala Thr Ala Glu Ser Ala
                325                 330                 335
Ser Glu Cys Leu Pro Cys Asp Cys Asn Gly Arg Ser Gln Glu Cys Tyr
                340                 345                 350
Phe Asp Pro Glu Leu Tyr Arg Ser Thr Gly His Gly Gly His Cys Thr
            355                 360                 365
Asn Cys Gln Asp Asn Thr Asp Gly Ala His Cys Glu Arg Cys Arg Glu
            370                 375                 380
Asn Phe Phe Arg Leu Gly Asn Asn Glu Ala Cys Ser Ser Cys His Cys
385                 390                 395                 400
Ser Pro Val Gly Ser Leu Ser Thr Gln Cys Asp Ser Tyr Gly Arg Cys
                405                 410                 415
Ser Cys Lys Pro Gly Val Met Gly Asp Lys Cys Asp Arg Cys Gln Pro
            420                 425                 430
Gly Phe His Ser Leu Thr Glu Ala Gly Cys Arg Pro Cys Ser Cys Asp
            435                 440                 445
Pro Ser Gly Ser Ile Asp Glu Cys Asn Ile Glu Thr Gly Arg Cys Val
450                 455                 460
```

```
Cys Lys Asp Asn Val Glu Gly Phe Asn Cys Glu Arg Cys Lys Pro Gly
465                 470                 475                 480

Phe Phe Asn Leu Glu Ser Ser Asn Pro Arg Gly Cys Thr Pro Cys Phe
            485                 490                 495

Cys Phe Gly His Ser Ser Val Cys Thr Asn Ala Val Gly Tyr Ser Val
            500                 505                 510

Tyr Ser Ile Ser Ser Thr Phe Gln Ile Asp Glu Asp Gly Trp Arg Ala
            515                 520                 525

Glu Gln Arg Asp Gly Ser Glu Ala Ser Leu Glu Trp Ser Ser Glu Arg
            530                 535                 540

Gln Asp Ile Ala Val Ile Ser Asp Ser Tyr Phe Pro Arg Tyr Phe Ile
545                 550                 555                 560

Ala Pro Ala Lys Phe Leu Gly Lys Gln Val Leu Ser Tyr Gly Gln Asn
                565                 570                 575

Leu Ser Phe Ser Phe Arg Val Asp Arg Arg Asp Thr Arg Leu Ser Ala
            580                 585                 590

Glu Asp Leu Val Leu Glu Gly Ala Gly Leu Arg Val Ser Val Pro Leu
            595                 600                 605

Ile Ala Gln Gly Asn Ser Tyr Pro Ser Glu Thr Thr Val Lys Tyr Val
610                 615                 620

Phe Arg Leu His Glu Ala Thr Asp Tyr Pro Trp Arg Pro Ala Leu Thr
625                 630                 635                 640

Pro Phe Glu Phe Gln Lys Leu Leu Asn Asn Leu Thr Ser Ile Lys Ile
                645                 650                 655

Arg Gly Thr Tyr Ser Glu Arg Ser Ala Gly Tyr Leu Asp Asp Val Thr
            660                 665                 670

Leu Ala Ser Ala Arg Pro Gly Pro Gly Val Pro Ala Thr Trp Val Glu
            675                 680                 685

Ser Cys Thr Cys Pro Val Gly Tyr Gly Gly Gln Phe Cys Glu Met Cys
            690                 695                 700

Leu Ser Gly Tyr Arg Arg Glu Thr Pro Asn Leu Gly Pro Tyr Ser Pro
705                 710                 715                 720

Cys Val Leu Cys Ala Cys Asn Gly His Ser Glu Thr Cys Asp Pro Glu
                725                 730                 735

Thr Gly Val Cys Asn Cys Arg Asp Asn Thr Ala Gly Pro His Cys Glu
            740                 745                 750

Lys Cys Ser Asp Gly Tyr Tyr Gly Asp Ser Thr Ala Gly Thr Ser Ser
            755                 760                 765

Asp Cys Gln Pro Cys Pro Cys Pro Gly Gly Ser Ser Cys Ala Val Val
            770                 775                 780

Pro Lys Thr Lys Glu Val Val Cys Thr Asn Cys Pro Thr Gly Thr Thr
785                 790                 795                 800

Gly Lys Arg Cys Glu Leu Cys Asp Asp Gly Tyr Phe Gly Asp Pro Leu
                805                 810                 815

Gly Arg Asn Gly Pro Val Arg Leu Cys Arg Leu Cys Gln Cys Ser Asp
            820                 825                 830

Asn Ile Asp Pro Asn Ala Val Gly Asn Cys Asn Arg Leu Thr Gly Glu
            835                 840                 845

Cys Leu Lys Cys Ile Tyr Asn Thr Ala Gly Phe Tyr Cys Asp Arg Cys
            850                 855                 860

Lys Asp Gly Phe Phe Gly Asn Pro Leu Ala Pro Asn Pro Ala Asp Lys
865                 870                 875                 880
```

Cys Lys Ala Cys Asn Cys Asn Leu Tyr Gly Thr Met Lys Gln Gln Ser
                885                 890                 895

Ser Cys Asn Pro Val Thr Gly Gln Cys Glu Cys Leu Pro His Val Thr
        900                 905                 910

Gly Gln Asp Cys Gly Ala Cys Asp Pro Gly Phe Tyr Asn Leu Gln Ser
        915                 920                 925

Gly Gln Gly Cys Glu Arg Cys Asp Cys His Ala Leu Gly Ser Thr Asn
    930                 935                 940

Gly Gln Cys Asp Ile Arg Thr Gly Gln Cys Glu Cys Gln Pro Gly Ile
945                 950                 955                 960

Thr Gly Gln His Cys Glu Arg Cys Glu Val Asn His Phe Gly Phe Gly
                965                 970                 975

Pro Glu Gly Cys Lys Pro Cys Asp Cys His Pro Glu Gly Ser Leu Ser
            980                 985                 990

Leu Gln Cys Lys Asp Asp Gly Arg Cys Glu Cys Arg Glu Gly Phe Val
        995                 1000                1005

Gly Asn Arg Cys Asp Gln Cys Glu Glu Asn Tyr Phe Tyr Asn Arg
    1010                1015                1020

Ser Trp Pro Gly Cys Gln Glu Cys Pro Ala Cys Tyr Arg Leu Val
    1025                1030                1035

Lys Asp Lys Val Ala Asp His Arg Val Lys Leu Gln Glu Leu Glu
    1040                1045                1050

Ser Leu Ile Ala Asn Leu Gly Thr Gly Asp Glu Met Val Thr Asp
    1055                1060                1065

Gln Ala Phe Glu Asp Arg Leu Lys Glu Ala Glu Arg Glu Val Met
    1070                1075                1080

Asp Leu Leu Arg Glu Ala Gln Asp Val Lys Asp Val Asp Gln Asn
    1085                1090                1095

Leu Met Asp Arg Leu Gln Arg Val Asn Asn Thr Leu Ser Ser Gln
    1100                1105                1110

Ile Ser Arg Leu Gln Asn Ile Arg Asn Thr Ile Glu Glu Thr Gly
    1115                1120                1125

Asn Leu Ala Glu Gln Ala Arg Ala His Val Glu Asn Thr Glu Arg
    1130                1135                1140

Leu Ile Glu Ile Ala Ser Arg Glu Leu Glu Lys Ala Lys Val Ala
    1145                1150                1155

Ala Ala Asn Val Ser Val Thr Gln Pro Glu Ser Thr Gly Asp Pro
    1160                1165                1170

Asn Asn Met Thr Leu Leu Ala Glu Glu Ala Arg Lys Leu Ala Glu
    1175                1180                1185

Arg His Lys Gln Glu Ala Asp Asp Ile Val Arg Val Ala Lys Thr
    1190                1195                1200

Ala Asn Asp Thr Ser Thr Glu Ala Tyr Asn Leu Leu Leu Arg Thr
    1205                1210                1215

Leu Ala Gly Glu Asn Gln Thr Ala Phe Glu Ile Glu Glu Leu Asn
    1220                1225                1230

Arg Lys Tyr Glu Gln Ala Lys Asn Ile Ser Gln Asp Leu Glu Lys
    1235                1240                1245

Gln Ala Ala Arg Val His Glu Glu Ala Lys Arg Ala Gly Asp Lys
    1250                1255                1260

Ala Val Glu Ile Tyr Ala Ser Val Ala Gln Leu Ser Pro Leu Asp
    1265                1270                1275

Ser Glu Thr Leu Glu Asn Glu Ala Asn Asn Ile Lys Met Glu Ala

```
            1280            1285            1290
Glu Asn Leu Glu Gln Leu Ile Asp Gln Lys Leu Lys Asp Tyr Glu
    1295            1300            1305
Asp Leu Arg Glu Asp Met Arg Gly Lys Glu Leu Glu Val Lys Asn
    1310            1315            1320
Leu Leu Glu Lys Gly Lys Thr Glu Gln Gln Thr Ala Asp Gln Leu
    1325            1330            1335
Leu Ala Arg Ala Asp Ala Ala Lys Ala Leu Ala Glu Glu Ala Ala
    1340            1345            1350
Lys Lys Gly Arg Asp Thr Leu Gln Glu Ala Asn Asp Ile Leu Asn
    1355            1360            1365
Asn Leu Lys Asp Phe Asp Arg Arg Val Asn Asp Asn Lys Thr Ala
    1370            1375            1380
Ala Glu Glu Ala Leu Arg Lys Ile Pro Ala Ile Asn Gln Thr Ile
    1385            1390            1395
Thr Glu Ala Asn Glu Lys Thr Arg Glu Ala Gln Gln Ala Leu Gly
    1400            1405            1410
Ser Ala Ala Ala Asp Ala Thr Glu Ala Lys Asn Lys Ala His Glu
    1415            1420            1425
Ala Glu Arg Ile Ala Ser Ala Val Gln Lys Asn Ala Thr Ser Thr
    1430            1435            1440
Lys Ala Glu Ala Glu Arg Thr Phe Ala Glu Val Thr Asp Leu Asp
    1445            1450            1455
Asn Glu Val Asn Asn Met Leu Lys Gln Leu Gln Glu Ala Glu Lys
    1460            1465            1470
Glu Leu Lys Arg Lys Gln Asp Asp Ala Asp Gln Asp Met Met Met
    1475            1480            1485
Ala Gly Met Ala Ser Gln Ala Ala Gln Glu Ala Glu Ile Asn Ala
    1490            1495            1500
Arg Lys Ala Lys Asn Ser Val Thr Ser Leu Leu Ser Ile Ile Asn
    1505            1510            1515
Asp Leu Leu Glu Gln Leu Gly Gln Leu Asp Thr Val Asp Leu Asn
    1520            1525            1530
Lys Leu Asn Glu Ile Glu Gly Thr Leu Asn Lys Ala Lys Asp Glu
    1535            1540            1545
Met Lys Val Ser Asp Leu Asp Arg Lys Val Ser Asp Leu Glu Asn
    1550            1555            1560
Glu Ala Lys Lys Gln Glu Ala Ala Ile Met Asp Tyr Asn Arg Asp
    1565            1570            1575
Ile Glu Glu Ile Met Lys Asp Ile Arg Asn Leu Glu Asp Ile Arg
    1580            1585            1590
Lys Thr Leu Pro Ser Gly Cys Phe Asn Thr Pro Ser Ile Glu Lys
    1595            1600            1605
Pro
```

<210> SEQ ID NO 120
<211> LENGTH: 4830
<212> TYPE: DNA
<213> ORGANISM: Artificial Sequence
<220> FEATURE:
<223> OTHER INFORMATION: Description of Artificial Sequence: Synthetic
      DNA sequence of Laminin subunit gamma-1 (Homo sapiens)

<400> SEQUENCE: 120
atgagaggga gccatcgggc cgcgccggcc ctgcggcccc gggggcggct ctggcccgtg    60

```
ctggccgtgc tggcggcggc cgccgcggcg ggctgtgccc aggcagccat ggacgagtgc    120
acggacgagg gcgggcggcc gcagcgctgc atgcccgagt tcgtcaacgc cgccttcaac    180
gtgactgtgg tggccaccaa cacgtgtggg actccgcccg aggaatactg tgtgcagacc    240
ggggtgaccg gggtcaccaa gtcctgtcac ctgtgcgacg ccgggcagcc ccacctgcag    300
cacggggcag ccttcctgac cgactacaac aaccaggccg acaccacctg gtggcaaagc    360
cagaccatgc tggccggggt gcagtacccc agctccatca acctcacgct gcacctggga    420
aaagcttttg acatcaccta tgtgcgtctc aagttccaca ccagccgccc ggagagcttt    480
gccatttaca agcgcacacg ggaagacggg ccctggattc cttaccagta ctacagtggt    540
tcctgtgaga cacctactc caaggcaaac cgcggcttca tcaggacagg aggggacgag    600
cagcaggcct tgtgtactga tgaattcagt gacatttctc ccctcactgg gggcaacgtg    660
gccttttcta ccctggaagg aaggcccagc gcctataact ttgacaatag ccctgtgctg    720
caggaatggg taactgccac tgacatcaga gtaactctta atcgcctgaa cacttttgga    780
gatgaagtgt ttaacgatcc caaagttctc aagtcctatt attatgccat ctctgatttt    840
gctgtaggtg gcagatgtaa atgtaatgga cacgcaagcg agtgtatgaa gaacgaattt    900
gataagctgg tgtgtaattg caaacataac acatatggag tagactgtga aaagtgtctt    960
cctttcttca atgaccggcc gtggaggagg caactgcgg aaagtgccag tgaatgcctg    1020
ccctgtgatt gcaatggtcg atcccaggaa tgctacttcg accctgaact ctatcgttcc    1080
actggccatg ggggccactg taccaactgc caggataaca cagatggcgc ccactgtgag    1140
aggtgccgag agaacttctt ccgccttggc aacaatgaag cctgctcttc atgccactgt    1200
agtcctgtgg gctctctaag cacacagtgt gatagttacg gcagatgcag ctgtaagcca    1260
ggagtgatgg gggacaaatg tgaccgttgc cagcctggat tccattctct cactgaagca    1320
ggatgcaggc catgctcttg tgatccctct ggcagcatag atgaatgtaa tattgaaaca    1380
ggaagatgtg tttgcaaaga caatgtcgaa ggcttcaatt gtgaaagatg caaacctgga    1440 tttttaatc tggaatcatc taatcctcgg ggttgcacac cctgcttctg ctttgggcat    1500
tcttctgtct gtacaaacgc tgttggctac agtgtttatt ctatctcctc tacctttcag    1560
attgatgagg atgggtggcg tgcggaacag agagatggct ctgaagcatc tctcgagtgg    1620
tcctctgaga ggcaagatat cgccgtgatc tcagacagct actttcctcg gtacttcatt    1680
gctcctgcaa agttcttggg caagcaggtg ttgagttatg gtcagaacct ctccttctcc    1740
tttcgagtgg acaggcgaga tactcgcctc tctgcagaag accttgtgct gagggagct    1800 ggcttaagag tatctgtacc cttgatcgct cagggcaatt cctatccaag tgagaccact    1860
gtgaagtatg tcttcaggct ccatgaagca acagattacc cttggaggcc tgctcttacc    1920
ccttttgaat tcagaagct cctaaacaac ttgacctcta tcaagatacg tgggacatac    1980
agtgagagaa gtgctggata tttggatgat gtcaccctgg caagtgctcg tcctgggcct    2040
ggagtccctg caacttgggt ggagtcctgc acctgtcctg tgggatatgg agggcagttt    2100
tgtgagatgt gcctctcagg ttacagaaga gaaactccta atcttggacc atacagtcca    2160
tgtgtgcttt gcgcctgcaa tggacacagc gagacctgta tcctgagac aggtgttgt    2220 aactgcagag acaatacggc tggcccgcac tgtgagaagt gcagtgatgg gtactatgga    2280
gattcaactg caggcacctc ctccgattgc caacctgtc cgtgtcctgg aggttcaagt    2340
tgtgctgttg ttcccaagac aaaggaggtg gtgtgcacca actgtcctac tggcaccact    2400
```

```
ggtaagagat gtgagctctg tgatgatggc tactttggag accccctggg tagaaacggc   2460
cctgtgagac tttgccgcct gtgccagtgc agtgacaaca tcgatcccaa tgcagttgga   2520
aattgcaatc gcttgacggg agaatgcctg aagtgcatct ataacactgc tggcttctat   2580
tgtgaccggt gcaaagacgg attttttgga atcccctgg ctcccaatcc agcagacaaa    2640
tgcaaagcct gcaattgcaa tctgtatggg accatgaagc agcagagcag ctgtaacccc   2700 gtgacgggc agtgtgaatg tttgcctcac gtgactggcc aggactgtgg tgcttgtgac    2760
cctggattct acaatctgca gagtgggcaa ggctgtgaga ggtgtgactg ccatgccttg   2820
ggctccacca atgggcagtg tgacatccgc accggccagt gtgagtgcca gcccggcatc   2880
actggtcagc actgtgagcg ctgtgaggtc aaccactttg ggtttggacc tgaaggctgc   2940
aaaccctgtg actgtcatcc tgagggatct ctttcacttc agtgcaaaga tgatggtcgc   3000
tgtgaatgca gagaaggctt tgtgggaaat cgctgtgacc agtgtgaaga aaactatttc   3060
tacaatcggt cttggcctgg ctgccaggaa tgtccagctt gttaccggct ggtaaaggat   3120
aaggttgctg atcatagagt gaagctccag gaattagaga gtctcatagc aaaccttgga   3180
actggggatg agatggtgac agatcaagcc ttcgaggata gactaaagga agcagagagg   3240
gaagttatgg acctccttcg tgaggcccag gatgtcaaag atgttgacca gaatttgatg   3300
gatcgcctac agagagtgaa taacactctg tccagccaaa ttagccgttt acagaatatc   3360
cggaatacca ttgaagagac tggaaacttg gctgaacaag cgcgtgccca tgtagagaac   3420
acagagcggt tgattgaaat cgcatccaga gaacttgaga agcaaaagt cgctgctgcc    3480 aatgtgtcag tcactcagcc agaatctaca ggggacccaa acaacatgac tcttttggca   3540
gaagaggctc gaaagcttgc tgaacgtcat aaacaggaag ctgatgacat tgttcgagtg   3600
gcaaagacag ccaatgatac gtcaactgag gcatacaacc tgcttctgag gacactggca   3660
ggagaaaatc aaacagcatt tgagattgaa gagcttaata ggaagtatga acaagcgaag   3720
aacatctcac aggatctgga aaaacaagct gcccgagtac atgaggaggc caaagggcc    3780 ggtgacaaag ctgtggagat ctatgccagc gtggctcagc tgagccctt ggactctgag    3840 acactggaga atgaagcaaa taacataaag atggaagctg agaatctgga caactgatt    3900 gaccagaaat taaagatta tgaggacctc agagaagata tgagagggaa ggaacttgaa    3960
gtcaagaacc ttctggagaa aggcaagact gaacagcaga ccgcagacca actcctagcc   4020
cgagctgatg ctgccaaggc cctcgctgaa gaagctgcaa agaagggacg ggataccta    4080 caagaagcta atgacattct caacaacctg aaagattttg ataggcgtgt gaacgataac   4140
aagacggccg cagaggaggc actaaggaag attcctgcca tcaaccagac catcactgaa   4200
gccaatgaaa agaccagaga agcccagcag gccctgggca gtgctgcggc ggatgccaca   4260
gaggccaaga caaggccca tgaggcggag aggatcgcga gcgctgtcca aaagaatgcc     4320
accagcacca aggcagaagc tgaaagaact tttgcagaag ttacagatct ggataatgag   4380
gtgaacaata tgttgaagca actgcaggaa gcagaaaaag agctaaagag aaaacaagat   4440
gacgctgacc aggacatgat gatggcaggg atggcttcac aggctgctca agaagccgag   4500
atcaatgcca gaaaagccaa aaactctgtt actagcctcc tcagcattat taatgacctc   4560
ttggagcagc tggggcagct ggatacagtg gacctgaata agctaaacga gattgaaggc   4620
accctaaaca aagccaaaga tgaaatgaag gtcagcgatc ttgataggaa agtgtctgac   4680
ctggagaatg aagccaagaa gcaggaggct gccatcatgg actataaccg agatatcgag   4740
gagatcatga aggacattcg caatctggag gacatcagga gaccttacc atctggctgc   4800
```
ttcaacaccc cgtccattga aaagccctag                        4830

<210> SEQ ID NO 121
<211> LENGTH: 3122
<212> TYPE: PRT
<213> ORGANISM: Artificial Sequence
<220> FEATURE:
<223> OTHER INFORMATION: Description of Artificial Sequence: Synthetic
    Amino acid sequence of Laminin subunit alpha-2 (Homo sapiens)

<400> SEQUENCE: 121

Met Pro Gly Ala Ala Gly Val Leu Leu Leu Leu Leu Ser Gly Gly
1               5                   10                  15

Leu Gly Gly Val Gln Ala Gln Arg Pro Gln Gln Arg Gln Ser Gln
                20                  25                  30

Ala His Gln Gln Arg Gly Leu Phe Pro Ala Val Leu Asn Leu Ala Ser
                35                  40                  45

Asn Ala Leu Ile Thr Thr Asn Ala Thr Cys Gly Glu Lys Gly Pro Glu
        50                  55                  60

Met Tyr Cys Lys Leu Val Glu His Val Pro Gly Gln Pro Val Arg Asn
65              70                  75                  80

Pro Gln Cys Arg Ile Cys Asn Gln Asn Ser Asn Pro Asn Gln Arg
                85                  90                  95

His Pro Ile Thr Asn Ala Ile Asp Gly Lys Asn Thr Trp Trp Gln Ser
                100                 105                 110

Pro Ser Ile Lys Asn Gly Ile Glu Tyr His Tyr Val Thr Ile Thr Leu
            115                 120                 125

Asp Leu Gln Gln Val Phe Gln Ile Ala Tyr Val Ile Val Lys Ala Ala
        130                 135                 140

Asn Ser Pro Arg Pro Gly Asn Trp Ile Leu Glu Arg Ser Leu Asp Asp
145                 150                 155                 160

Val Glu Tyr Lys Pro Trp Gln Tyr His Ala Val Thr Asp Thr Glu Cys
                165                 170                 175

Leu Thr Leu Tyr Asn Ile Tyr Pro Arg Thr Gly Pro Pro Ser Tyr Ala
            180                 185                 190

Lys Asp Asp Glu Val Ile Cys Thr Ser Phe Tyr Ser Lys Ile His Pro
        195                 200                 205

Leu Glu Asn Gly Glu Ile His Ile Ser Leu Ile Asn Gly Arg Pro Ser
    210                 215                 220

Ala Asp Asp Pro Ser Pro Glu Leu Leu Glu Phe Thr Ser Ala Arg Tyr
225                 230                 235                 240

Ile Arg Leu Arg Phe Gln Arg Ile Arg Thr Leu Asn Ala Asp Leu Met
                245                 250                 255

Met Phe Ala His Lys Asp Pro Arg Glu Ile Asp Pro Ile Val Thr Arg
            260                 265                 270

Arg Tyr Tyr Tyr Ser Val Lys Asp Ile Ser Val Gly Gly Met Cys Ile
        275                 280                 285

Cys Tyr Gly His Ala Arg Ala Cys Pro Leu Asp Pro Ala Thr Asn Lys
    290                 295                 300

Ser Arg Cys Glu Cys Glu His Asn Thr Cys Gly Asp Ser Cys Asp Gln
305                 310                 315                 320

Cys Cys Pro Gly Phe His Gln Lys Pro Trp Arg Ala Gly Thr Phe Leu
                325                 330                 335

Thr Lys Thr Glu Cys Glu Ala Cys Asn Cys His Gly Lys Ala Glu Glu
            340                 345                 350

```
Cys Tyr Tyr Asp Glu Asn Val Ala Arg Arg Asn Leu Ser Leu Asn Ile
            355                 360                 365

Arg Gly Lys Tyr Ile Gly Gly Val Cys Ile Asn Cys Thr Gln Asn
370                 375                 380

Thr Ala Gly Ile Asn Cys Glu Thr Cys Thr Asp Gly Phe Phe Arg Pro
385                 390                 395                 400

Lys Gly Val Ser Pro Asn Tyr Pro Arg Pro Cys Gln Pro Cys His Cys
                405                 410                 415

Asp Pro Ile Gly Ser Leu Asn Glu Val Cys Val Lys Asp Glu Lys His
            420                 425                 430

Ala Arg Arg Gly Leu Ala Pro Gly Ser Cys His Cys Lys Thr Gly Phe
            435                 440                 445

Gly Gly Val Ser Cys Asp Arg Cys Ala Arg Gly Tyr Thr Gly Tyr Pro
            450                 455                 460

Asp Cys Lys Ala Cys Asn Cys Ser Gly Leu Gly Ser Lys Asn Glu Asp
465                 470                 475                 480

Pro Cys Phe Gly Pro Cys Ile Cys Lys Glu Asn Val Glu Gly Gly Asp
                485                 490                 495

Cys Ser Arg Cys Lys Ser Gly Phe Phe Asn Leu Gln Glu Asp Asn Trp
            500                 505                 510

Lys Gly Cys Asp Glu Cys Phe Cys Ser Gly Val Ser Asn Arg Cys Gln
            515                 520                 525

Ser Ser Tyr Trp Thr Tyr Gly Lys Ile Gln Asp Met Ser Gly Trp Tyr
            530                 535                 540

Leu Thr Asp Leu Pro Gly Arg Ile Arg Val Ala Pro Gln Gln Asp Asp
545                 550                 555                 560

Leu Asp Ser Pro Gln Gln Ile Ser Ile Ser Asn Ala Glu Ala Arg Gln
                565                 570                 575

Ala Leu Pro His Ser Tyr Tyr Trp Ser Ala Pro Ala Pro Tyr Leu Gly
            580                 585                 590

Asn Lys Leu Pro Ala Val Gly Gly Gln Leu Thr Phe Thr Ile Ser Tyr
            595                 600                 605

Asp Leu Glu Glu Glu Glu Glu Asp Thr Glu Arg Val Leu Gln Leu Met
            610                 615                 620

Ile Ile Leu Glu Gly Asn Asp Leu Ser Ile Ser Thr Ala Gln Asp Glu
625                 630                 635                 640

Val Tyr Leu His Pro Ser Glu Glu His Thr Asn Val Leu Leu Leu Lys
                645                 650                 655

Glu Glu Ser Phe Thr Ile His Gly Thr His Phe Pro Val Arg Arg Lys
            660                 665                 670

Glu Phe Met Thr Val Leu Ala Asn Leu Lys Arg Val Leu Leu Gln Ile
            675                 680                 685

Thr Tyr Ser Phe Gly Met Asp Ala Ile Phe Arg Leu Ser Ser Val Asn
            690                 695                 700

Leu Glu Ser Ala Val Ser Tyr Pro Thr Asp Gly Ser Ile Ala Ala Ala
705                 710                 715                 720

Val Glu Val Cys Gln Cys Pro Pro Gly Tyr Thr Gly Ser Ser Cys Glu
                725                 730                 735

Ser Cys Trp Pro Arg His Arg Arg Val Asn Gly Thr Ile Phe Gly Gly
            740                 745                 750

Ile Cys Glu Pro Cys Gln Cys Phe Gly His Ala Glu Ser Cys Asp Asp
            755                 760                 765
```

```
Val Thr Gly Glu Cys Leu Asn Cys Lys Asp His Thr Gly Gly Pro Tyr
770                 775                 780
Cys Asp Lys Cys Leu Pro Gly Phe Tyr Gly Glu Pro Thr Lys Gly Thr
785                 790                 795                 800
Ser Glu Asp Cys Gln Pro Cys Ala Cys Pro Leu Asn Ile Pro Ser Asn
            805                 810                 815
Asn Phe Ser Pro Thr Cys His Leu Asp Arg Ser Leu Gly Leu Ile Cys
                820                 825                 830
Asp Gly Cys Pro Val Gly Tyr Thr Gly Pro Arg Cys Glu Arg Cys Ala
            835                 840                 845
Glu Gly Tyr Phe Gly Gln Pro Ser Val Pro Gly Gly Ser Cys Gln Pro
850                 855                 860
Cys Gln Cys Asn Asp Asn Leu Asp Phe Ser Ile Pro Gly Ser Cys Asp
865                 870                 875                 880
Ser Leu Ser Gly Ser Cys Leu Ile Cys Lys Pro Gly Thr Thr Gly Arg
                885                 890                 895
Tyr Cys Glu Leu Cys Ala Asp Gly Tyr Phe Gly Asp Ala Val Asp Ala
            900                 905                 910
Lys Asn Cys Gln Pro Cys Arg Cys Asn Ala Gly Gly Ser Phe Ser Glu
            915                 920                 925
Val Cys His Ser Gln Thr Gly Gln Cys Glu Cys Arg Ala Asn Val Gln
930                 935                 940
Gly Gln Arg Cys Asp Lys Cys Lys Ala Gly Thr Phe Gly Leu Gln Ser
945                 950                 955                 960
Ala Arg Gly Cys Val Pro Cys Asn Cys Asn Ser Phe Gly Ser Lys Ser
                965                 970                 975
Phe Asp Cys Glu Glu Ser Gly Gln Cys Trp Cys Gln Pro Gly Val Thr
            980                 985                 990
Gly Lys Lys Cys Asp Arg Cys Ala  His Gly Tyr Phe Asn  Phe Gln Glu
            995                 1000                1005
Gly Gly Cys Thr Ala Cys Glu  Cys Ser His Leu Gly  Asn Asn Cys
1010                1015                1020
Asp Pro Lys Thr Gly Arg Cys  Ile Cys Pro Pro Asn  Thr Ile Gly
1025                1030                1035
Glu Lys Cys Ser Lys Cys Ala  Pro Asn Thr Trp Gly  His Ser Ile
1040                1045                1050
Thr Thr Gly Cys Lys Ala Cys  Asn Cys Ser Thr Val  Gly Ser Leu
1055                1060                1065
Asp Phe Gln Cys Asn Val Asn  Thr Gly Gln Cys Asn  Cys His Pro
1070                1075                1080
Lys Phe Ser Gly Ala Lys Cys  Thr Glu Cys Ser Arg  Gly His Trp
1085                1090                1095
Asn Tyr Pro Arg Cys Asn Leu  Cys Asp Cys Phe Leu  Pro Gly Thr
1100                1105                1110
Asp Ala Thr Thr Cys Asp Ser  Glu Thr Lys Lys Cys  Ser Cys Ser
1115                1120                1125
Asp Gln Thr Gly Gln Cys Thr  Cys Lys Val Asn Val  Glu Gly Ile
1130                1135                1140
His Cys Asp Arg Cys Arg Pro  Gly Lys Phe Gly Leu  Asp Ala Lys
1145                1150                1155
Asn Pro Leu Gly Cys Ser Ser  Cys Tyr Cys Phe Gly  Thr Thr Thr
1160                1165                1170
Gln Cys Ser Glu Ala Lys Gly  Leu Ile Arg Thr Trp  Val Thr Leu
```

-continued

```
            1175                1180                1185

Lys Ala Glu Gln Thr Ile Leu Pro Leu Val Asp Glu Ala Leu Gln
            1190                1195                1200

His Thr Thr Thr Lys Gly Ile Val Phe Gln His Pro Glu Ile Val
            1205                1210                1215

Ala His Met Asp Leu Met Arg Glu Asp Leu His Leu Glu Pro Phe
            1220                1225                1230

Tyr Trp Lys Leu Pro Glu Gln Phe Glu Gly Lys Lys Leu Met Ala
            1235                1240                1245

Tyr Gly Gly Lys Leu Lys Tyr Ala Ile Tyr Phe Glu Ala Arg Glu
            1250                1255                1260

Glu Thr Gly Phe Ser Thr Tyr Asn Pro Gln Val Ile Ile Arg Gly
            1265                1270                1275

Gly Thr Pro Thr His Ala Arg Ile Ile Val Arg His Met Ala Ala
            1280                1285                1290

Pro Leu Ile Gly Gln Leu Thr Arg His Glu Ile Glu Met Thr Glu
            1295                1300                1305

Lys Glu Trp Lys Tyr Tyr Gly Asp Asp Pro Arg Val His Arg Thr
            1310                1315                1320

Val Thr Arg Glu Asp Phe Leu Asp Ile Leu Tyr Asp Ile His Tyr
            1325                1330                1335

Ile Leu Ile Lys Ala Thr Tyr Gly Asn Phe Met Arg Gln Ser Arg
            1340                1345                1350

Ile Ser Glu Ile Ser Met Glu Val Ala Glu Gln Gly Arg Gly Thr
            1355                1360                1365

Thr Met Thr Pro Pro Ala Asp Leu Ile Glu Lys Cys Asp Cys Pro
            1370                1375                1380

Leu Gly Tyr Ser Gly Leu Ser Cys Glu Ala Cys Leu Pro Gly Phe
            1385                1390                1395

Tyr Arg Leu Arg Ser Gln Pro Gly Gly Arg Thr Pro Gly Pro Thr
            1400                1405                1410

Leu Gly Thr Cys Val Pro Cys Gln Cys Asn Gly His Ser Ser Leu
            1415                1420                1425

Cys Asp Pro Glu Thr Ser Ile Cys Gln Asn Cys Gln His His Thr
            1430                1435                1440

Ala Gly Asp Phe Cys Glu Arg Cys Ala Leu Gly Tyr Tyr Gly Ile
            1445                1450                1455

Val Lys Gly Leu Pro Asn Asp Cys Gln Gln Cys Ala Cys Pro Leu
            1460                1465                1470

Ile Ser Ser Ser Asn Asn Phe Ser Pro Ser Cys Val Ala Glu Gly
            1475                1480                1485

Leu Asp Asp Tyr Arg Cys Thr Ala Cys Pro Arg Gly Tyr Glu Gly
            1490                1495                1500

Gln Tyr Cys Glu Arg Cys Ala Pro Gly Tyr Thr Gly Ser Pro Gly
            1505                1510                1515

Asn Pro Gly Gly Ser Cys Gln Glu Cys Glu Cys Asp Pro Tyr Gly
            1520                1525                1530

Ser Leu Pro Val Pro Cys Asp Pro Val Thr Gly Phe Cys Thr Cys
            1535                1540                1545

Arg Pro Gly Ala Thr Gly Arg Lys Cys Asp Gly Cys Lys His Trp
            1550                1555                1560

His Ala Arg Glu Gly Trp Glu Cys Val Phe Cys Gly Asp Glu Cys
            1565                1570                1575
```

```
Thr Gly Leu Leu Leu Gly Asp Leu Ala Arg Leu Glu Gln Met Val
    1580            1585                1590

Met Ser Ile Asn Leu Thr Gly Pro Leu Pro Ala Pro Tyr Lys Met
    1595            1600                1605

Leu Tyr Gly Leu Glu Asn Met Thr Gln Glu Leu Lys His Leu Leu
    1610            1615                1620

Ser Pro Gln Arg Ala Pro Glu Arg Leu Ile Gln Leu Ala Glu Gly
    1625            1630                1635

Asn Leu Asn Thr Leu Val Thr Glu Met Asn Glu Leu Leu Thr Arg
    1640            1645                1650

Ala Thr Lys Val Thr Ala Asp Gly Glu Gln Thr Gly Gln Asp Ala
    1655            1660                1665

Glu Arg Thr Asn Thr Arg Ala Lys Ser Leu Gly Glu Phe Ile Lys
    1670            1675                1680

Glu Leu Ala Arg Asp Ala Glu Ala Val Asn Glu Lys Ala Ile Lys
    1685            1690                1695

Leu Asn Glu Thr Leu Gly Thr Arg Asp Glu Ala Phe Glu Arg Asn
    1700            1705                1710

Leu Glu Gly Leu Gln Lys Glu Ile Asp Gln Met Ile Lys Glu Leu
    1715            1720                1725

Arg Arg Lys Asn Leu Glu Thr Gln Lys Glu Ile Ala Glu Asp Glu
    1730            1735                1740

Leu Val Ala Ala Glu Ala Leu Leu Lys Lys Val Lys Lys Leu Phe
    1745            1750                1755

Gly Glu Ser Arg Gly Glu Asn Glu Glu Met Glu Lys Asp Leu Arg
    1760            1765                1770

Glu Lys Leu Ala Asp Tyr Lys Asn Lys Val Asp Asp Ala Trp Asp
    1775            1780                1785

Leu Leu Arg Glu Ala Thr Asp Lys Ile Arg Glu Ala Asn Arg Leu
    1790            1795                1800

Phe Ala Val Asn Gln Lys Asn Met Thr Ala Leu Glu Lys Lys Lys
    1805            1810                1815

Glu Ala Val Glu Ser Gly Lys Arg Gln Ile Glu Asn Thr Leu Lys
    1820            1825                1830

Glu Gly Asn Asp Ile Leu Asp Glu Ala Asn Arg Leu Ala Asp Glu
    1835            1840                1845

Ile Asn Ser Ile Ile Asp Tyr Val Glu Asp Ile Gln Thr Lys Leu
    1850            1855                1860

Pro Pro Met Ser Glu Glu Leu Asn Asp Lys Ile Asp Asp Leu Ser
    1865            1870                1875

Gln Glu Ile Lys Asp Arg Lys Leu Ala Glu Lys Val Ser Gln Ala
    1880            1885                1890

Glu Ser His Ala Ala Gln Leu Asn Asp Ser Ser Ala Val Leu Asp
    1895            1900                1905

Gly Ile Leu Asp Glu Ala Lys Asn Ile Ser Phe Asn Ala Thr Ala
    1910            1915                1920

Ala Phe Lys Ala Tyr Ser Asn Ile Lys Asp Tyr Ile Asp Glu Ala
    1925            1930                1935

Glu Lys Val Ala Lys Glu Ala Lys Asp Leu Ala His Glu Ala Thr
    1940            1945                1950

Lys Leu Ala Thr Gly Pro Arg Gly Leu Leu Lys Glu Asp Ala Lys
    1955            1960                1965
```

```
Gly Cys Leu Gln Lys Ser Phe Arg Ile Leu Asn Glu Ala Lys Lys
    1970                1975                1980

Leu Ala Asn Asp Val Lys Glu Asn Glu Asp His Leu Asn Gly Leu
    1985                1990                1995

Lys Thr Arg Ile Glu Asn Ala Asp Ala Arg Asn Gly Asp Leu Leu
    2000                2005                2010

Arg Thr Leu Asn Asp Thr Leu Gly Lys Leu Ser Ala Ile Pro Asn
    2015                2020                2025

Asp Thr Ala Ala Lys Leu Gln Ala Val Lys Asp Lys Ala Arg Gln
    2030                2035                2040

Ala Asn Asp Thr Ala Lys Asp Val Leu Ala Gln Ile Thr Glu Leu
    2045                2050                2055

His Gln Asn Leu Asp Gly Leu Lys Lys Asn Tyr Asn Lys Leu Ala
    2060                2065                2070

Asp Ser Val Ala Lys Thr Asn Ala Val Val Lys Asp Pro Ser Lys
    2075                2080                2085

Asn Lys Ile Ile Ala Asp Ala Asp Ala Thr Val Lys Asn Leu Glu
    2090                2095                2100

Gln Glu Ala Asp Arg Leu Ile Asp Lys Leu Lys Pro Ile Lys Glu
    2105                2110                2115

Leu Glu Asp Asn Leu Lys Lys Asn Ile Ser Glu Ile Lys Glu Leu
    2120                2125                2130

Ile Asn Gln Ala Arg Lys Gln Ala Asn Ser Ile Lys Val Ser Val
    2135                2140                2145

Ser Ser Gly Gly Asp Cys Ile Arg Thr Tyr Lys Pro Glu Ile Lys
    2150                2155                2160

Lys Gly Ser Tyr Asn Asn Ile Val Val Asn Val Lys Thr Ala Val
    2165                2170                2175

Ala Asp Asn Leu Leu Phe Tyr Leu Gly Ser Ala Lys Phe Ile Asp
    2180                2185                2190

Phe Leu Ala Ile Glu Met Arg Lys Gly Lys Val Ser Phe Leu Trp
    2195                2200                2205

Asp Val Gly Ser Gly Val Gly Arg Val Glu Tyr Pro Asp Leu Thr
    2210                2215                2220

Ile Asp Asp Ser Tyr Trp Tyr Arg Ile Val Ala Ser Arg Thr Gly
    2225                2230                2235

Arg Asn Gly Thr Ile Ser Val Arg Ala Leu Asp Gly Pro Lys Ala
    2240                2245                2250

Ser Ile Val Pro Ser Thr His His Ser Thr Ser Pro Pro Gly Tyr
    2255                2260                2265

Thr Ile Leu Asp Val Asp Ala Asn Ala Met Leu Phe Val Gly Gly
    2270                2275                2280

Leu Thr Gly Lys Leu Lys Lys Ala Asp Ala Val Arg Val Ile Thr
    2285                2290                2295

Phe Thr Gly Cys Met Gly Glu Thr Tyr Phe Asp Asn Lys Pro Ile
    2300                2305                2310

Gly Leu Trp Asn Phe Arg Glu Lys Glu Gly Asp Cys Lys Gly Cys
    2315                2320                2325

Thr Val Ser Pro Gln Val Glu Asp Ser Glu Gly Thr Ile Gln Phe
    2330                2335                2340

Asp Gly Glu Gly Tyr Ala Leu Val Ser Arg Pro Ile Arg Trp Tyr
    2345                2350                2355

Pro Asn Ile Ser Thr Val Met Phe Lys Phe Arg Thr Phe Ser Ser
```

```
                2360                2365                2370

Ser Ala Leu Leu Met Tyr Leu Ala Thr Arg Asp Leu Arg Asp Phe
    2375                2380                2385

Met Ser Val Glu Leu Thr Asp Gly His Ile Lys Val Ser Tyr Asp
    2390                2395                2400

Leu Gly Ser Gly Met Ala Ser Val Val Ser Asn Gln Asn His Asn
    2405                2410                2415

Asp Gly Lys Trp Lys Ser Phe Thr Leu Ser Arg Ile Gln Lys Gln
    2420                2425                2430

Ala Asn Ile Ser Ile Val Asp Ile Asp Thr Asn Gln Glu Glu Asn
    2435                2440                2445

Ile Ala Thr Ser Ser Ser Gly Asn Asn Phe Gly Leu Asp Leu Lys
    2450                2455                2460

Ala Asp Asp Lys Ile Tyr Phe Gly Gly Leu Pro Thr Leu Arg Asn
    2465                2470                2475

Leu Ser Met Lys Ala Arg Pro Glu Val Asn Leu Lys Lys Tyr Ser
    2480                2485                2490

Gly Cys Leu Lys Asp Ile Glu Ile Ser Arg Thr Pro Tyr Asn Ile
    2495                2500                2505

Leu Ser Ser Pro Asp Tyr Val Gly Val Thr Lys Gly Cys Ser Leu
    2510                2515                2520

Glu Asn Val Tyr Thr Val Ser Phe Pro Lys Pro Gly Phe Val Glu
    2525                2530                2535

Leu Ser Pro Val Pro Ile Asp Val Gly Thr Glu Ile Asn Leu Ser
    2540                2545                2550

Phe Ser Thr Lys Asn Glu Ser Gly Ile Ile Leu Leu Gly Ser Gly
    2555                2560                2565

Gly Thr Pro Ala Pro Pro Arg Arg Lys Arg Arg Gln Thr Gly Gln
    2570                2575                2580

Ala Tyr Tyr Ala Ile Leu Leu Asn Arg Gly Arg Leu Glu Val His
    2585                2590                2595

Leu Ser Thr Gly Ala Arg Thr Met Arg Lys Ile Val Ile Arg Pro
    2600                2605                2610

Glu Pro Asn Leu Phe His Asp Gly Arg Glu His Ser Val His Val
    2615                2620                2625

Glu Arg Thr Arg Gly Ile Phe Thr Val Gln Val Asp Glu Asn Arg
    2630                2635                2640

Arg Tyr Met Gln Asn Leu Thr Val Glu Gln Pro Ile Glu Val Lys
    2645                2650                2655

Lys Leu Phe Val Gly Gly Ala Pro Pro Glu Phe Gln Pro Ser Pro
    2660                2665                2670

Leu Arg Asn Ile Pro Pro Phe Glu Gly Cys Ile Trp Asn Leu Val
    2675                2680                2685

Ile Asn Ser Val Pro Met Asp Phe Ala Arg Pro Val Ser Phe Lys
    2690                2695                2700

Asn Ala Asp Ile Gly Arg Cys Ala His Gln Lys Leu Arg Glu Asp
    2705                2710                2715

Glu Asp Gly Ala Ala Pro Ala Glu Ile Val Ile Gln Pro Glu Pro
    2720                2725                2730

Val Pro Thr Pro Ala Phe Pro Thr Pro Thr Pro Val Leu Thr His
    2735                2740                2745

Gly Pro Cys Ala Ala Glu Ser Glu Pro Ala Leu Leu Ile Gly Ser
    2750                2755                2760
```

```
Lys Gln Phe Gly Leu Ser Arg Asn Ser His Ile Ala Ile Ala Phe
    2765                2770                2775

Asp Asp Thr Lys Val Lys Asn Arg Leu Thr Ile Glu Leu Glu Val
    2780                2785                2790

Arg Thr Glu Ala Glu Ser Gly Leu Leu Phe Tyr Met Ala Arg Ile
    2795                2800                2805

Asn His Ala Asp Phe Ala Thr Val Gln Leu Arg Asn Gly Leu Pro
    2810                2815                2820

Tyr Phe Ser Tyr Asp Leu Gly Ser Gly Asp Thr His Thr Met Ile
    2825                2830                2835

Pro Thr Lys Ile Asn Asp Gly Gln Trp His Lys Ile Lys Ile Met
    2840                2845                2850

Arg Ser Lys Gln Glu Gly Ile Leu Tyr Val Asp Gly Ala Ser Asn
    2855                2860                2865

Arg Thr Ile Ser Pro Lys Lys Ala Asp Ile Leu Asp Val Val Gly
    2870                2875                2880

Met Leu Tyr Val Gly Gly Leu Pro Ile Asn Tyr Thr Thr Arg Arg
    2885                2890                2895

Ile Gly Pro Val Thr Tyr Ser Ile Asp Gly Cys Val Arg Asn Leu
    2900                2905                2910

His Met Ala Glu Ala Pro Ala Asp Leu Glu Gln Pro Thr Ser Ser
    2915                2920                2925

Phe His Val Gly Thr Cys Phe Ala Asn Ala Gln Arg Gly Thr Tyr
    2930                2935                2940

Phe Asp Gly Thr Gly Phe Ala Lys Ala Val Gly Gly Phe Lys Val
    2945                2950                2955

Gly Leu Asp Leu Leu Val Glu Phe Glu Phe Arg Thr Thr Thr Thr
    2960                2965                2970

Thr Gly Val Leu Leu Gly Ile Ser Ser Gln Lys Met Asp Gly Met
    2975                2980                2985

Gly Ile Glu Met Ile Asp Glu Lys Leu Met Phe His Val Asp Asn
    2990                2995                3000

Gly Ala Gly Arg Phe Thr Ala Val Tyr Asp Ala Gly Val Pro Gly
    3005                3010                3015

His Leu Cys Asp Gly Gln Trp His Lys Val Thr Ala Asn Lys Ile
    3020                3025                3030

Lys His Arg Ile Glu Leu Thr Val Asp Gly Asn Gln Val Glu Ala
    3035                3040                3045

Gln Ser Pro Asn Pro Ala Ser Thr Ser Ala Asp Thr Asn Asp Pro
    3050                3055                3060

Val Phe Val Gly Gly Phe Pro Asp Asp Leu Lys Gln Phe Gly Leu
    3065                3070                3075

Thr Thr Ser Ile Pro Phe Arg Gly Cys Ile Arg Ser Leu Lys Leu
    3080                3085                3090

Thr Lys Gly Thr Gly Lys Pro Leu Glu Val Asn Phe Ala Lys Ala
    3095                3100                3105

Leu Glu Leu Arg Gly Val Gln Pro Val Ser Cys Pro Ala Asn
    3110                3115                3120

<210> SEQ ID NO 122
<211> LENGTH: 3695
<212> TYPE: PRT
<213> ORGANISM: Artificial Sequence
<220> FEATURE:
```

<223> OTHER INFORMATION: Description of Artificial Sequence: Synthetic
      Amino acid sequence of Laminin subunit alpha-5 (Homo sapiens)

<400> SEQUENCE: 122

```
Met Ala Lys Arg Leu Cys Ala Gly Ser Ala Leu Cys Val Arg Gly Pro
1               5                   10                  15

Arg Gly Pro Ala Pro Leu Leu Val Gly Leu Ala Leu Leu Gly Ala
            20                  25                  30

Ala Arg Ala Arg Glu Glu Ala Gly Gly Phe Ser Leu His Pro Pro
        35                  40                  45

Tyr Phe Asn Leu Ala Glu Gly Ala Arg Ile Ala Ala Ser Ala Thr Cys
    50                  55                  60

Gly Glu Glu Ala Pro Ala Arg Gly Ser Pro Arg Pro Thr Glu Asp Leu
65                  70                  75                  80

Tyr Cys Lys Leu Val Gly Gly Pro Val Ala Gly Gly Asp Pro Asn Gln
                85                  90                  95

Thr Ile Arg Gly Gln Tyr Cys Asp Ile Cys Thr Ala Ala Asn Ser Asn
                100                 105                 110

Lys Ala His Pro Ala Ser Asn Ala Ile Asp Gly Thr Glu Arg Trp Trp
            115                 120                 125

Gln Ser Pro Pro Leu Ser Arg Gly Leu Glu Tyr Asn Glu Val Asn Val
        130                 135                 140

Thr Leu Asp Leu Gly Gln Val Phe His Val Ala Tyr Val Leu Ile Lys
145                 150                 155                 160

Phe Ala Asn Ser Pro Arg Pro Asp Leu Trp Val Leu Glu Arg Ser Met
                165                 170                 175

Asp Phe Gly Arg Thr Tyr Gln Pro Trp Gln Phe Phe Ala Ser Ser Lys
            180                 185                 190

Arg Asp Cys Leu Glu Arg Phe Gly Pro Gln Thr Leu Glu Arg Ile Thr
        195                 200                 205

Arg Asp Asp Ala Ala Ile Cys Thr Thr Glu Tyr Ser Arg Ile Val Pro
    210                 215                 220

Leu Glu Asn Gly Glu Ile Val Val Ser Leu Val Asn Gly Arg Pro Gly
225                 230                 235                 240

Ala Met Asn Phe Ser Tyr Ser Pro Leu Leu Arg Glu Phe Thr Lys Ala
                245                 250                 255

Thr Asn Val Arg Leu Arg Phe Leu Arg Thr Asn Thr Leu Leu Gly His
            260                 265                 270

Leu Met Gly Lys Ala Leu Arg Asp Pro Thr Val Thr Arg Arg Tyr Tyr
        275                 280                 285

Tyr Ser Ile Lys Asp Ile Ser Ile Gly Gly Arg Cys Val Cys His Gly
    290                 295                 300

His Ala Asp Ala Cys Asp Ala Lys Asp Pro Thr Asp Pro Phe Arg Leu
305                 310                 315                 320

Gln Cys Thr Cys Gln His Asn Thr Cys Gly Gly Thr Cys Asp Arg Cys
                325                 330                 335

Cys Pro Gly Phe Asn Gln Gln Pro Trp Lys Pro Ala Thr Ala Asn Ser
            340                 345                 350

Ala Asn Glu Cys Gln Ser Cys Asn Cys Tyr Gly His Ala Thr Asp Cys
        355                 360                 365

Tyr Tyr Asp Pro Glu Val Asp Arg Arg Arg Ala Ser Gln Ser Leu Asp
    370                 375                 380

Gly Thr Tyr Gln Gly Gly Gly Val Cys Ile Asp Cys Gln His His Thr
385                 390                 395                 400
```

```
Thr Gly Val Asn Cys Glu Arg Cys Leu Pro Gly Phe Tyr Arg Ser Pro
                405                 410                 415

Asn His Pro Leu Asp Ser Pro His Val Cys Arg Arg Cys Asn Cys Glu
            420                 425                 430

Ser Asp Phe Thr Asp Gly Thr Cys Glu Asp Leu Thr Gly Arg Cys Tyr
        435                 440                 445

Cys Arg Pro Asn Phe Ser Gly Glu Arg Cys Asp Val Cys Ala Glu Gly
    450                 455                 460

Phe Thr Gly Phe Pro Ser Cys Tyr Pro Thr Pro Ser Ser Ser Asn Asp
465                 470                 475                 480

Thr Arg Glu Gln Val Leu Pro Ala Gly Gln Ile Val Asn Cys Asp Cys
                485                 490                 495

Ser Ala Ala Gly Thr Gln Gly Asn Ala Cys Arg Lys Asp Pro Arg Val
            500                 505                 510

Gly Arg Cys Leu Cys Lys Pro Asn Phe Gln Gly Thr His Cys Glu Leu
        515                 520                 525

Cys Ala Pro Gly Phe Tyr Gly Pro Gly Cys Gln Pro Cys Gln Cys Ser
    530                 535                 540

Ser Pro Gly Val Ala Asp Asp Arg Cys Asp Pro Asp Thr Gly Gln Cys
545                 550                 555                 560

Arg Cys Arg Val Gly Phe Glu Gly Ala Thr Cys Asp Arg Cys Ala Pro
                565                 570                 575

Gly Tyr Phe His Phe Pro Leu Cys Gln Leu Cys Gly Cys Ser Pro Ala
            580                 585                 590

Gly Thr Leu Pro Glu Gly Cys Asp Glu Ala Gly Arg Cys Leu Cys Gln
        595                 600                 605

Pro Glu Phe Ala Gly Pro His Cys Asp Arg Cys Arg Pro Gly Tyr His
    610                 615                 620

Gly Phe Pro Asn Cys Gln Ala Cys Thr Cys Asp Pro Arg Gly Ala Leu
625                 630                 635                 640

Asp Gln Leu Cys Gly Ala Gly Leu Cys Arg Cys Arg Pro Gly Tyr
                645                 650                 655

Thr Gly Thr Ala Cys Gln Glu Cys Ser Pro Gly Phe His Gly Phe Pro
            660                 665                 670

Ser Cys Val Pro Cys His Cys Ser Ala Glu Gly Ser Leu His Ala Ala
        675                 680                 685

Cys Asp Pro Arg Ser Gly Gln Cys Ser Cys Arg Pro Arg Val Thr Gly
    690                 695                 700

Leu Arg Cys Asp Thr Cys Val Pro Gly Ala Tyr Asn Phe Pro Tyr Cys
705                 710                 715                 720

Glu Ala Gly Ser Cys His Pro Ala Gly Leu Ala Pro Val Asp Pro Ala
                725                 730                 735

Leu Pro Glu Ala Gln Val Pro Cys Met Cys Arg Ala His Val Glu Gly
            740                 745                 750

Pro Ser Cys Asp Arg Cys Lys Pro Gly Phe Trp Gly Leu Ser Pro Ser
        755                 760                 765

Asn Pro Glu Gly Cys Thr Arg Cys Ser Cys Asp Leu Arg Gly Thr Leu
    770                 775                 780

Gly Gly Val Ala Glu Cys Gln Pro Gly Thr Gly Gln Cys Phe Cys Lys
785                 790                 795                 800

Pro His Val Cys Gly Gln Ala Cys Ala Ser Cys Lys Asp Gly Phe Phe
                805                 810                 815
```

Gly Leu Asp Gln Ala Asp Tyr Phe Gly Cys Arg Ser Cys Arg Cys Asp
            820                 825                 830

Ile Gly Gly Ala Leu Gly Gln Ser Cys Glu Pro Arg Thr Gly Val Cys
            835                 840                 845

Arg Cys Arg Pro Asn Thr Gln Gly Pro Thr Cys Ser Glu Pro Ala Arg
850                 855                 860

Asp His Tyr Leu Pro Asp Leu His His Leu Arg Leu Glu Leu Glu Glu
865                 870                 875                 880

Ala Ala Thr Pro Glu Gly His Ala Val Arg Phe Gly Phe Asn Pro Leu
            885                 890                 895

Glu Phe Glu Asn Phe Ser Trp Arg Gly Tyr Ala Gln Met Ala Pro Val
            900                 905                 910

Gln Pro Arg Ile Val Ala Arg Leu Asn Leu Thr Ser Pro Asp Leu Phe
            915                 920                 925

Trp Leu Val Phe Arg Tyr Val Asn Arg Gly Ala Met Ser Val Ser Gly
            930                 935                 940

Arg Val Ser Val Arg Glu Glu Gly Arg Ser Ala Thr Cys Ala Asn Cys
945                 950                 955                 960

Thr Ala Gln Ser Gln Pro Val Ala Phe Pro Pro Ser Thr Glu Pro Ala
            965                 970                 975

Phe Ile Thr Val Pro Gln Arg Gly Phe Gly Glu Pro Phe Val Leu Asn
            980                 985                 990

Pro Gly Thr Trp Ala Leu Arg Val Glu Ala Glu Gly Val Leu Leu Asp
            995                 1000                1005

Tyr Val Val Leu Leu Pro Ser Ala Tyr Tyr Glu Ala Ala Leu Leu
    1010                1015                1020

Gln Leu Arg Val Thr Glu Ala Cys Thr Tyr Arg Pro Ser Ala Gln
    1025                1030                1035

Gln Ser Gly Asp Asn Cys Leu Leu Tyr Thr His Leu Pro Leu Asp
    1040                1045                1050

Gly Phe Pro Ser Ala Ala Gly Leu Glu Ala Leu Cys Arg Gln Asp
    1055                1060                1065

Asn Ser Leu Pro Arg Pro Cys Pro Thr Glu Gln Leu Ser Pro Ser
    1070                1075                1080

His Pro Pro Leu Ile Thr Cys Thr Gly Ser Asp Val Asp Val Gln
    1085                1090                1095

Leu Gln Val Ala Val Pro Gln Pro Gly Arg Tyr Ala Leu Val Val
    1100                1105                1110

Glu Tyr Ala Asn Glu Asp Ala Arg Gln Glu Val Gly Val Ala Val
    1115                1120                1125

His Thr Pro Gln Arg Ala Pro Gln Gln Gly Leu Leu Ser Leu His
    1130                1135                1140

Pro Cys Leu Tyr Ser Thr Leu Cys Arg Gly Thr Ala Arg Asp Thr
    1145                1150                1155

Gln Asp His Leu Ala Val Phe His Leu Asp Ser Glu Ala Ser Val
    1160                1165                1170

Arg Leu Thr Ala Glu Gln Ala Arg Phe Phe Leu His Gly Val Thr
    1175                1180                1185

Leu Val Pro Ile Glu Glu Phe Ser Pro Glu Phe Val Glu Pro Arg
    1190                1195                1200

Val Ser Cys Ile Ser Ser His Gly Ala Phe Gly Pro Asn Ser Ala
    1205                1210                1215

Ala Cys Leu Pro Ser Arg Phe Pro Lys Pro Pro Gln Pro Ile Ile

```
              1220              1225              1230
Leu Arg Asp Cys Gln Val Ile Pro Leu Pro Pro Gly Leu Pro Leu
    1235              1240              1245
Thr His Ala Gln Asp Leu Thr Pro Ala Met Ser Pro Ala Gly Pro
    1250              1255              1260
Arg Pro Arg Pro Pro Thr Ala Val Asp Pro Asp Ala Glu Pro Thr
    1265              1270              1275
Leu Leu Arg Glu Pro Gln Ala Thr Val Val Phe Thr Thr His Val
    1280              1285              1290
Pro Thr Leu Gly Arg Tyr Ala Phe Leu Leu His Gly Tyr Gln Pro
    1295              1300              1305
Ala His Pro Thr Phe Pro Val Glu Val Leu Ile Asn Ala Gly Arg
    1310              1315              1320
Val Trp Gln Gly His Ala Asn Ala Ser Phe Cys Pro His Gly Tyr
    1325              1330              1335
Gly Cys Arg Thr Leu Val Val Cys Glu Gly Gln Ala Leu Leu Asp
    1340              1345              1350
Val Thr His Ser Glu Leu Thr Val Thr Val Arg Val Pro Lys Gly
    1355              1360              1365
Arg Trp Leu Trp Leu Asp Tyr Val Leu Val Val Pro Glu Asn Val
    1370              1375              1380
Tyr Ser Phe Gly Tyr Leu Arg Glu Glu Pro Leu Asp Lys Ser Tyr
    1385              1390              1395
Asp Phe Ile Ser His Cys Ala Ala Gln Gly Tyr His Ile Ser Pro
    1400              1405              1410
Ser Ser Ser Ser Leu Phe Cys Arg Asn Ala Ala Ala Ser Leu Ser
    1415              1420              1425
Leu Phe Tyr Asn Asn Gly Ala Arg Pro Cys Gly Cys His Glu Val
    1430              1435              1440
Gly Ala Thr Gly Pro Thr Cys Glu Pro Phe Gly Gly Gln Cys Pro
    1445              1450              1455
Cys His Ala His Val Ile Gly Arg Asp Cys Ser Arg Cys Ala Thr
    1460              1465              1470
Gly Tyr Trp Gly Phe Pro Asn Cys Arg Pro Cys Asp Cys Gly Ala
    1475              1480              1485
Arg Leu Cys Asp Glu Leu Thr Gly Gln Cys Ile Cys Pro Pro Arg
    1490              1495              1500
Thr Ile Pro Pro Asp Cys Leu Leu Cys Gln Pro Gln Thr Phe Gly
    1505              1510              1515
Cys His Pro Leu Val Gly Cys Glu Glu Cys Asn Cys Ser Gly Pro
    1520              1525              1530
Gly Ile Gln Glu Leu Thr Asp Pro Thr Cys Asp Thr Asp Ser Gly
    1535              1540              1545
Gln Cys Lys Cys Arg Pro Asn Val Thr Gly Arg Arg Cys Asp Thr
    1550              1555              1560
Cys Ser Pro Gly Phe His Gly Tyr Pro Arg Cys Arg Pro Cys Asp
    1565              1570              1575
Cys His Glu Ala Gly Thr Ala Pro Gly Val Cys Asp Pro Leu Thr
    1580              1585              1590
Gly Gln Cys Tyr Cys Lys Glu Asn Val Gln Gly Pro Lys Cys Asp
    1595              1600              1605
Gln Cys Ser Leu Gly Thr Phe Ser Leu Asp Ala Ala Asn Pro Lys
    1610              1615              1620
```

Gly Cys Thr Arg Cys Phe Cys Phe Gly Ala Thr Glu Arg Cys Arg
1625                1630                 1635

Ser Ser Ser Tyr Thr Arg Gln Glu Phe Val Asp Met Glu Gly Trp
1640                1645                 1650

Val Leu Leu Ser Thr Asp Arg Gln Val Val Pro His Glu Arg Gln
1655                1660                 1665

Pro Gly Thr Glu Met Leu Arg Ala Asp Leu Arg His Val Pro Glu
1670                1675                 1680

Ala Val Pro Glu Ala Phe Pro Glu Leu Tyr Trp Gln Ala Pro Pro
1685                1690                 1695

Ser Tyr Leu Gly Asp Arg Val Ser Ser Tyr Gly Gly Thr Leu Arg
1700                1705                 1710

Tyr Glu Leu His Ser Glu Thr Gln Arg Gly Asp Val Phe Val Pro
1715                1720                 1725

Met Glu Ser Arg Pro Asp Val Val Leu Gln Gly Asn Gln Met Ser
1730                1735                 1740

Ile Thr Phe Leu Glu Pro Ala Tyr Pro Thr Pro Gly His Val His
1745                1750                 1755

Arg Gly Gln Leu Gln Leu Val Glu Gly Asn Phe Arg His Thr Glu
1760                1765                 1770

Thr Arg Asn Thr Val Ser Arg Glu Glu Leu Met Met Val Leu Ala
1775                1780                 1785

Ser Leu Glu Gln Leu Gln Ile Arg Ala Leu Phe Ser Gln Ile Ser
1790                1795                 1800

Ser Ala Val Phe Leu Arg Arg Val Ala Leu Glu Val Ala Ser Pro
1805                1810                 1815

Ala Gly Gln Gly Ala Leu Ala Ser Asn Val Glu Leu Cys Leu Cys
1820                1825                 1830

Pro Ala Ser Tyr Arg Gly Asp Ser Cys Gln Glu Cys Ala Pro Gly
1835                1840                 1845

Phe Tyr Arg Asp Val Lys Gly Leu Phe Leu Gly Arg Cys Val Pro
1850                1855                 1860

Cys Gln Cys His Gly His Ser Asp Arg Cys Leu Pro Gly Ser Gly
1865                1870                 1875

Val Cys Val Asp Cys Gln His Asn Thr Glu Gly Ala His Cys Glu
1880                1885                 1890

Arg Cys Gln Ala Gly Phe Val Ser Ser Arg Asp Asp Pro Ser Ala
1895                1900                 1905

Pro Cys Val Ser Cys Pro Cys Pro Leu Ser Val Pro Ser Asn Asn
1910                1915                 1920

Phe Ala Glu Gly Cys Val Leu Arg Gly Gly Arg Thr Gln Cys Leu
1925                1930                 1935

Cys Lys Pro Gly Tyr Ala Gly Ala Ser Cys Glu Arg Cys Ala Pro
1940                1945                 1950

Gly Phe Phe Gly Asn Pro Leu Val Leu Gly Ser Ser Cys Gln Pro
1955                1960                 1965

Cys Asp Cys Ser Gly Asn Gly Asp Pro Asn Leu Leu Phe Ser Asp
1970                1975                 1980

Cys Asp Pro Leu Thr Gly Ala Cys Arg Gly Cys Leu Arg His Thr
1985                1990                 1995

Thr Gly Pro Arg Cys Glu Ile Cys Ala Pro Gly Phe Tyr Gly Asn
2000                2005                 2010

-continued

Ala Leu Leu Pro Gly Asn Cys Thr Arg Cys Asp Cys Thr Pro Cys
2015                2020                2025

Gly Thr Glu Ala Cys Asp Pro His Ser Gly His Cys Leu Cys Lys
2030                2035                2040

Ala Gly Val Thr Gly Arg Arg Cys Asp Arg Cys Gln Glu Gly His
2045                2050                2055

Phe Gly Phe Asp Gly Cys Gly Gly Cys Arg Pro Cys Ala Cys Gly
2060                2065                2070

Pro Ala Ala Glu Gly Ser Glu Cys His Pro Gln Ser Gly Gln Cys
2075                2080                2085

His Cys Arg Pro Gly Thr Met Gly Pro Gln Cys Arg Glu Cys Ala
2090                2095                2100

Pro Gly Tyr Trp Gly Leu Pro Glu Gln Gly Cys Arg Arg Cys Gln
2105                2110                2115

Cys Pro Gly Gly Arg Cys Asp Pro His Thr Gly Arg Cys Asn Cys
2120                2125                2130

Pro Pro Gly Leu Ser Gly Glu Arg Cys Asp Thr Cys Ser Gln Gln
2135                2140                2145

His Gln Val Pro Val Pro Gly Gly Pro Val Gly His Ser Ile His
2150                2155                2160

Cys Glu Val Cys Asp His Cys Val Val Leu Leu Leu Asp Asp Leu
2165                2170                2175

Glu Arg Ala Gly Ala Leu Leu Pro Ala Ile His Glu Gln Leu Arg
2180                2185                2190

Gly Ile Asn Ala Ser Ser Met Ala Trp Ala Arg Leu His Arg Leu
2195                2200                2205

Asn Ala Ser Ile Ala Asp Leu Gln Ser Gln Leu Arg Ser Pro Leu
2210                2215                2220

Gly Pro Arg His Glu Thr Ala Gln Gln Leu Glu Val Leu Glu Gln
2225                2230                2235

Gln Ser Thr Ser Leu Gly Gln Asp Ala Arg Arg Leu Gly Gly Gln
2240                2245                2250

Ala Val Gly Thr Arg Asp Gln Ala Ser Gln Leu Leu Ala Gly Thr
2255                2260                2265

Glu Ala Thr Leu Gly His Ala Lys Thr Leu Leu Ala Ala Ile Arg
2270                2275                2280

Ala Val Asp Arg Thr Leu Ser Glu Leu Met Ser Gln Thr Gly His
2285                2290                2295

Leu Gly Leu Ala Asn Ala Ser Ala Pro Ser Gly Glu Gln Leu Leu
2300                2305                2310

Arg Thr Leu Ala Glu Val Glu Arg Leu Leu Trp Glu Met Arg Ala
2315                2320                2325

Arg Asp Leu Gly Ala Pro Gln Ala Ala Ala Glu Ala Glu Leu Ala
2330                2335                2340

Ala Ala Gln Arg Leu Leu Ala Arg Val Gln Glu Gln Leu Ser Ser
2345                2350                2355

Leu Trp Glu Glu Asn Gln Ala Leu Ala Thr Gln Thr Arg Asp Arg
2360                2365                2370

Leu Ala Gln His Glu Ala Gly Leu Met Asp Leu Arg Glu Ala Leu
2375                2380                2385

Asn Arg Ala Val Asp Ala Thr Arg Glu Ala Gln Glu Leu Asn Ser
2390                2395                2400

Arg Asn Gln Glu Arg Leu Glu Glu Ala Leu Gln Arg Lys Gln Glu

```
                2405                2410                2415
Leu Ser Arg Asp Asn Ala Thr Leu Gln Ala Thr Leu His Ala Ala
        2420                2425                2430

Arg Asp Thr Leu Ala Ser Val Phe Arg Leu Leu His Ser Leu Asp
        2435                2440                2445

Gln Ala Lys Glu Glu Leu Glu Arg Leu Ala Ala Ser Leu Asp Gly
        2450                2455                2460

Ala Arg Thr Pro Leu Leu Gln Arg Met Gln Thr Phe Ser Pro Ala
        2465                2470                2475

Gly Ser Lys Leu Arg Leu Val Glu Ala Ala Glu Ala His Ala Gln
        2480                2485                2490

Gln Leu Gly Gln Leu Ala Leu Asn Leu Ser Ser Ile Ile Leu Asp
        2495                2500                2505

Val Asn Gln Asp Arg Leu Thr Gln Arg Ala Ile Glu Ala Ser Asn
        2510                2515                2520

Ala Tyr Ser Arg Ile Leu Gln Ala Val Gln Ala Ala Glu Asp Ala
        2525                2530                2535

Ala Gly Gln Ala Leu Gln Gln Ala Asp His Thr Trp Ala Thr Val
        2540                2545                2550

Val Arg Gln Gly Leu Val Asp Arg Ala Gln Gln Leu Leu Ala Asn
        2555                2560                2565

Ser Thr Ala Leu Glu Glu Ala Met Leu Gln Glu Gln Arg Leu
        2570                2575                2580

Gly Leu Val Trp Ala Ala Leu Gln Gly Ala Arg Thr Gln Leu Arg
        2585                2590                2595

Asp Val Arg Ala Lys Lys Asp Gln Leu Glu Ala His Ile Gln Ala
        2600                2605                2610

Ala Gln Ala Met Leu Ala Met Asp Thr Asp Glu Thr Ser Lys Lys
        2615                2620                2625

Ile Ala His Ala Lys Ala Val Ala Ala Glu Ala Gln Asp Thr Ala
        2630                2635                2640

Thr Arg Val Gln Ser Gln Leu Gln Ala Met Gln Glu Asn Val Glu
        2645                2650                2655

Arg Trp Gln Gly Gln Tyr Glu Gly Leu Arg Gly Gln Asp Leu Gly
        2660                2665                2670

Gln Ala Val Leu Asp Ala Gly His Ser Val Ser Thr Leu Glu Lys
        2675                2680                2685

Thr Leu Pro Gln Leu Leu Ala Lys Leu Ser Ile Leu Glu Asn Arg
        2690                2695                2700

Gly Val His Asn Ala Ser Leu Ala Leu Ser Ala Ser Ile Gly Arg
        2705                2710                2715

Val Arg Glu Leu Ile Ala Gln Ala Arg Gly Ala Ala Ser Lys Val
        2720                2725                2730

Lys Val Pro Met Lys Phe Asn Gly Arg Ser Gly Val Gln Leu Arg
        2735                2740                2745

Thr Pro Arg Asp Leu Ala Asp Leu Ala Ala Tyr Thr Ala Leu Lys
        2750                2755                2760

Phe Tyr Leu Gln Gly Pro Glu Pro Glu Pro Gly Gln Gly Thr Glu
        2765                2770                2775

Asp Arg Phe Val Met Tyr Met Gly Ser Arg Gln Ala Thr Gly Asp
        2780                2785                2790

Tyr Met Gly Val Ser Leu Arg Asp Lys Lys Val His Trp Val Tyr
        2795                2800                2805
```

```
Gln Leu Gly Glu Ala Gly Pro Ala Val Leu Ser Ile Asp Glu Asp
2810                2815                2820

Ile Gly Glu Gln Phe Ala Ala Val Ser Leu Asp Arg Thr Leu Gln
2825                2830                2835

Phe Gly His Met Ser Val Thr Val Glu Arg Gln Met Ile Gln Glu
2840                2845                2850

Thr Lys Gly Asp Thr Val Ala Pro Gly Ala Glu Gly Leu Leu Asn
2855                2860                2865

Leu Arg Pro Asp Asp Phe Val Phe Tyr Val Gly Gly Tyr Pro Ser
2870                2875                2880

Thr Phe Thr Pro Pro Pro Leu Arg Phe Pro Gly Tyr Arg Gly
2885                2890                2895

Cys Ile Glu Met Asp Thr Leu Asn Glu Glu Val Val Ser Leu Tyr
2900                2905                2910

Asn Phe Glu Arg Thr Phe Gln Leu Asp Thr Ala Val Asp Arg Pro
2915                2920                2925

Cys Ala Arg Ser Lys Ser Thr Gly Asp Pro Trp Leu Thr Asp Gly
2930                2935                2940

Ser Tyr Leu Asp Gly Thr Gly Phe Ala Arg Ile Ser Phe Asp Ser
2945                2950                2955

Gln Ile Ser Thr Thr Lys Arg Phe Glu Gln Glu Leu Arg Leu Val
2960                2965                2970

Ser Tyr Ser Gly Val Leu Phe Phe Leu Lys Gln Gln Ser Gln Phe
2975                2980                2985

Leu Cys Leu Ala Val Gln Glu Gly Ser Leu Val Leu Leu Tyr Asp
2990                2995                3000

Phe Gly Ala Gly Leu Lys Lys Ala Val Pro Leu Gln Pro Pro Pro
3005                3010                3015

Pro Leu Thr Ser Ala Ser Lys Ala Ile Gln Val Phe Leu Leu Gly
3020                3025                3030

Gly Ser Arg Lys Arg Val Leu Val Arg Val Glu Arg Ala Thr Val
3035                3040                3045

Tyr Ser Val Glu Gln Asp Asn Asp Leu Glu Leu Ala Asp Ala Tyr
3050                3055                3060

Tyr Leu Gly Gly Val Pro Pro Asp Gln Leu Pro Pro Ser Leu Arg
3065                3070                3075

Arg Leu Phe Pro Thr Gly Gly Ser Val Arg Gly Cys Val Lys Gly
3080                3085                3090

Ile Lys Ala Leu Gly Lys Tyr Val Asp Leu Lys Arg Leu Asn Thr
3095                3100                3105

Thr Gly Val Ser Ala Gly Cys Thr Ala Asp Leu Leu Val Gly Arg
3110                3115                3120

Ala Met Thr Phe His Gly His Gly Phe Leu Arg Leu Ala Leu Ser
3125                3130                3135

Asn Val Ala Pro Leu Thr Gly Asn Val Tyr Ser Gly Phe Gly Phe
3140                3145                3150

His Ser Ala Gln Asp Ser Ala Leu Leu Tyr Tyr Arg Ala Ser Pro
3155                3160                3165

Asp Gly Leu Cys Gln Val Ser Leu Gln Gln Gly Arg Val Ser Leu
3170                3175                3180

Gln Leu Leu Arg Thr Glu Val Lys Thr Gln Ala Gly Phe Ala Asp
3185                3190                3195
```

```
Gly Ala Pro His Tyr Val Ala Phe Tyr Ser Asn Ala Thr Gly Val
    3200                3205                3210

Trp Leu Tyr Val Asp Asp Gln Leu Gln Gln Met Lys Pro His Arg
3215                3220                3225

Gly Pro Pro Pro Glu Leu Gln Pro Gln Pro Gly Pro Pro Arg
    3230                3235                3240

Leu Leu Leu Gly Gly Leu Pro Glu Ser Gly Thr Ile Tyr Asn Phe
3245                3250                3255

Ser Gly Cys Ile Ser Asn Val Phe Val Gln Arg Leu Leu Gly Pro
    3260                3265                3270

Gln Arg Val Phe Asp Leu Gln Gln Asn Leu Gly Ser Val Asn Val
3275                3280                3285

Ser Thr Gly Cys Ala Pro Ala Leu Gln Ala Gln Thr Pro Gly Leu
    3290                3295                3300

Gly Pro Arg Gly Leu Gln Ala Thr Ala Arg Lys Ala Ser Arg Arg
3305                3310                3315

Ser Arg Gln Pro Ala Arg His Pro Ala Cys Met Leu Pro Pro His
    3320                3325                3330

Leu Arg Thr Thr Arg Asp Ser Tyr Gln Phe Gly Gly Ser Leu Ser
3335                3340                3345

Ser His Leu Glu Phe Val Gly Ile Leu Ala Arg His Arg Asn Trp
    3350                3355                3360

Pro Ser Leu Ser Met His Val Leu Pro Arg Ser Ser Arg Gly Leu
3365                3370                3375

Leu Leu Phe Thr Ala Arg Leu Arg Pro Gly Ser Pro Ser Leu Ala
    3380                3385                3390

Leu Phe Leu Ser Asn Gly His Phe Val Ala Gln Met Glu Gly Leu
3395                3400                3405

Gly Thr Arg Leu Arg Ala Gln Ser Arg Gln Arg Ser Arg Pro Gly
    3410                3415                3420

Arg Trp His Lys Val Ser Val Arg Trp Glu Lys Asn Arg Ile Leu
3425                3430                3435

Leu Val Thr Asp Gly Ala Arg Ala Trp Ser Gln Glu Gly Pro His
    3440                3445                3450

Arg Gln His Gln Gly Ala Glu His Pro Gln Pro His Thr Leu Phe
3455                3460                3465

Val Gly Gly Leu Pro Ala Ser Ser His Ser Ser Lys Leu Pro Val
    3470                3475                3480

Thr Val Gly Phe Ser Gly Cys Val Lys Arg Leu Arg Leu His Gly
3485                3490                3495

Arg Pro Leu Gly Ala Pro Thr Arg Met Ala Gly Val Thr Pro Cys
    3500                3505                3510

Ile Leu Gly Pro Leu Glu Ala Gly Leu Phe Phe Pro Gly Ser Gly
3515                3520                3525

Gly Val Ile Thr Leu Asp Leu Pro Gly Ala Thr Leu Pro Asp Val
    3530                3535                3540

Gly Leu Glu Leu Glu Val Arg Pro Leu Ala Val Thr Gly Leu Ile
3545                3550                3555

Phe His Leu Gly Gln Ala Arg Thr Pro Pro Tyr Leu Gln Leu Gln
    3560                3565                3570

Val Thr Glu Lys Gln Val Leu Leu Arg Ala Asp Asp Gly Ala Gly
3575                3580                3585

Glu Phe Ser Thr Ser Val Thr Arg Pro Ser Val Leu Cys Asp Gly
```

```
                    3590                3595                3600
Gln Trp His Arg Leu Ala Val Met Lys Ser Gly Asn Val Leu Arg
    3605                3610                3615

Leu Glu Val Asp Ala Gln Ser Asn His Thr Val Gly Pro Leu Leu
    3620                3625                3630

Ala Ala Ala Ala Gly Ala Pro Ala Pro Leu Tyr Leu Gly Gly Leu
    3635                3640                3645

Pro Glu Pro Met Ala Val Gln Pro Trp Pro Pro Ala Tyr Cys Gly
    3650                3655                3660

Cys Met Arg Arg Leu Ala Val Asn Arg Ser Pro Val Ala Met Thr
    3665                3670                3675

Arg Ser Val Glu Val His Gly Ala Val Gly Ala Ser Gly Cys Pro
    3680                3685                3690

Ala Ala
    3695

<210> SEQ ID NO 123
<211> LENGTH: 1786
<212> TYPE: PRT
<213> ORGANISM: Artificial Sequence
<220> FEATURE:
<223> OTHER INFORMATION: Description of Artificial Sequence: Synthetic
      Amino acid sequence of Laminin subunit beta-1 (Homo sapiens)

<400> SEQUENCE: 123

Met Gly Leu Leu Gln Leu Leu Ala Phe Ser Phe Leu Ala Leu Cys Arg
1               5                   10                  15

Ala Arg Val Arg Ala Gln Glu Pro Glu Phe Ser Tyr Gly Cys Ala Glu
            20                  25                  30

Gly Ser Cys Tyr Pro Ala Thr Gly Asp Leu Leu Ile Gly Arg Ala Gln
        35                  40                  45

Lys Leu Ser Val Thr Ser Thr Cys Gly Leu His Lys Pro Glu Pro Tyr
    50                  55                  60

Cys Ile Val Ser His Leu Gln Glu Asp Lys Lys Cys Phe Ile Cys Asn
65                  70                  75                  80

Ser Gln Asp Pro Tyr His Glu Thr Leu Asn Pro Asp Ser His Leu Ile
                85                  90                  95

Glu Asn Val Val Thr Thr Phe Ala Pro Asn Arg Leu Lys Ile Trp Trp
            100                 105                 110

Gln Ser Glu Asn Gly Val Glu Asn Val Thr Ile Gln Leu Asp Leu Glu
        115                 120                 125

Ala Glu Phe His Phe Thr His Leu Ile Met Thr Phe Lys Thr Phe Arg
    130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ala Ser Phe Pro Gly
                165                 170                 175

Ile Ser Thr Gly Pro Met Lys Lys Val Asp Asp Ile Ile Cys Asp Ser
            180                 185                 190

Arg Tyr Ser Asp Ile Glu Pro Ser Thr Glu Gly Glu Val Ile Phe Arg
        195                 200                 205

Ala Leu Asp Pro Ala Phe Lys Ile Glu Asp Pro Tyr Ser Pro Arg Ile
    210                 215                 220

Gln Asn Leu Leu Lys Ile Thr Asn Leu Arg Ile Lys Phe Val Lys Leu
225                 230                 235                 240
```

His Thr Leu Gly Asp Asn Leu Leu Asp Ser Arg Met Glu Ile Arg Glu
            245                 250                 255

Lys Tyr Tyr Tyr Ala Val Tyr Asp Met Val Val Arg Gly Asn Cys Phe
        260                 265                 270

Cys Tyr Gly His Ala Ser Glu Cys Ala Pro Val Asp Gly Phe Asn Glu
        275                 280                 285

Glu Val Glu Gly Met Val His Gly His Cys Met Cys Arg His Asn Thr
    290                 295                 300

Lys Gly Leu Asn Cys Glu Leu Cys Met Asp Phe Tyr His Asp Leu Pro
305                 310                 315                 320

Trp Arg Pro Ala Glu Gly Arg Asn Ser Asn Ala Cys Lys Lys Cys Asn
                325                 330                 335

Cys Asn Glu His Ser Ile Ser Cys His Phe Asp Met Ala Val Tyr Leu
            340                 345                 350

Ala Thr Gly Asn Val Ser Gly Val Cys Asp Asp Cys Gln His Asn
        355                 360                 365

Thr Met Gly Arg Asn Cys Glu Gln Cys Lys Pro Phe Tyr Tyr Gln His
    370                 375                 380

Pro Glu Arg Asp Ile Arg Asp Pro Asn Phe Cys Glu Arg Cys Thr Cys
385                 390                 395                 400

Asp Pro Ala Gly Ser Gln Asn Glu Gly Ile Cys Asp Ser Tyr Thr Asp
                405                 410                 415

Phe Ser Thr Gly Leu Ile Ala Gly Gln Cys Arg Cys Lys Leu Asn Val
            420                 425                 430

Glu Gly Glu His Cys Asp Val Cys Lys Glu Gly Phe Tyr Asp Leu Ser
        435                 440                 445

Ser Glu Asp Pro Phe Gly Cys Lys Ser Cys Ala Cys Asn Pro Leu Gly
    450                 455                 460

Thr Ile Pro Gly Gly Asn Pro Cys Asp Ser Glu Thr Gly His Cys Tyr
465                 470                 475                 480

Cys Lys Arg Leu Val Thr Gly Gln His Cys Asp Gln Cys Leu Pro Glu
                485                 490                 495

His Trp Gly Leu Ser Asn Asp Leu Asp Gly Cys Arg Pro Cys Asp Cys
            500                 505                 510

Asp Leu Gly Gly Ala Leu Asn Asn Ser Cys Phe Ala Glu Ser Gly Gln
        515                 520                 525

Cys Ser Cys Arg Pro His Met Ile Gly Arg Gln Cys Asn Glu Val Glu
    530                 535                 540

Pro Gly Tyr Tyr Phe Ala Thr Leu Asp His Tyr Leu Tyr Glu Ala Glu
545                 550                 555                 560

Glu Ala Asn Leu Gly Pro Gly Val Ser Ile Val Glu Arg Gln Tyr Ile
                565                 570                 575

Gln Asp Arg Ile Pro Ser Trp Thr Gly Ala Gly Phe Val Arg Val Pro
            580                 585                 590

Glu Gly Ala Tyr Leu Glu Phe Phe Ile Asp Asn Ile Pro Tyr Ser Met
        595                 600                 605

Glu Tyr Asp Ile Leu Ile Arg Tyr Glu Pro Gln Leu Pro Asp His Trp
    610                 615                 620

Glu Lys Ala Val Ile Thr Val Gln Arg Pro Gly Arg Ile Pro Thr Ser
625                 630                 635                 640

Ser Arg Cys Gly Asn Thr Ile Pro Asp Asp Asn Gln Val Val Ser
                645                 650                 655

Leu Ser Pro Gly Ser Arg Tyr Val Val Leu Pro Arg Pro Val Cys Phe

```
            660                 665                 670
Glu Lys Gly Thr Asn Tyr Thr Val Arg Leu Glu Leu Pro Gln Tyr Thr
            675                 680                 685

Ser Ser Asp Ser Asp Val Glu Ser Pro Tyr Thr Leu Ile Asp Ser Leu
    690                 695                 700

Val Leu Met Pro Tyr Cys Lys Ser Leu Asp Ile Phe Thr Val Gly Gly
705                 710                 715                 720

Ser Gly Asp Gly Val Val Thr Asn Ser Ala Trp Glu Thr Phe Gln Arg
                725                 730                 735

Tyr Arg Cys Leu Glu Asn Ser Arg Ser Val Val Lys Thr Pro Met Thr
            740                 745                 750

Asp Val Cys Arg Asn Ile Ile Phe Ser Ile Ser Ala Leu Leu His Gln
            755                 760                 765

Thr Gly Leu Ala Cys Glu Cys Asp Pro Gln Gly Ser Leu Ser Ser Val
            770                 775                 780

Cys Asp Pro Asn Gly Gly Gln Cys Gln Cys Arg Pro Asn Val Val Gly
785                 790                 795                 800

Arg Thr Cys Asn Arg Cys Ala Pro Gly Thr Phe Gly Phe Gly Pro Ser
                805                 810                 815

Gly Cys Lys Pro Cys Glu Cys His Leu Gln Gly Ser Val Asn Ala Phe
                820                 825                 830

Cys Asn Pro Val Thr Gly Gln Cys His Cys Phe Gln Gly Val Tyr Ala
            835                 840                 845

Arg Gln Cys Asp Arg Cys Leu Pro Gly His Trp Gly Phe Pro Ser Cys
            850                 855                 860

Gln Pro Cys Gln Cys Asn Gly His Ala Asp Asp Cys Asp Pro Val Thr
865                 870                 875                 880

Gly Glu Cys Leu Asn Cys Gln Asp Tyr Thr Met Gly His Asn Cys Glu
                885                 890                 895

Arg Cys Leu Ala Gly Tyr Tyr Gly Asp Pro Ile Ile Gly Ser Gly Asp
                900                 905                 910

His Cys Arg Pro Cys Pro Cys Pro Asp Gly Pro Asp Ser Gly Arg Gln
            915                 920                 925

Phe Ala Arg Ser Cys Tyr Gln Asp Pro Val Thr Leu Gln Leu Ala Cys
            930                 935                 940

Val Cys Asp Pro Gly Tyr Ile Gly Ser Arg Cys Asp Asp Cys Ala Ser
945                 950                 955                 960

Gly Tyr Phe Gly Asn Pro Ser Glu Val Gly Gly Ser Cys Gln Pro Cys
                965                 970                 975

Gln Cys His Asn Asn Ile Asp Thr Thr Asp Pro Glu Ala Cys Asp Lys
            980                 985                 990

Glu Thr Gly Arg Cys Leu Lys Cys Leu Tyr His Thr Glu Gly Glu His
            995                 1000                1005

Cys Gln Phe Cys Arg Phe Gly Tyr Tyr Gly Asp Ala Leu Gln Gln
            1010                1015                1020

Asp Cys Arg Lys Cys Val Cys Asn Tyr Leu Gly Thr Val Gln Glu
            1025                1030                1035

His Cys Asn Gly Ser Asp Cys Gln Cys Asp Lys Ala Thr Gly Gln
            1040                1045                1050

Cys Leu Cys Leu Pro Asn Val Ile Gly Gln Asn Cys Asp Arg Cys
            1055                1060                1065

Ala Pro Asn Thr Trp Gln Leu Ala Ser Gly Thr Gly Cys Asp Pro
            1070                1075                1080
```

```
Cys Asn Cys Asn Ala Ala His Ser Phe Gly Pro Ser Cys Asn Glu
    1085                1090                1095

Phe Thr Gly Gln Cys Gln Cys Met Pro Gly Phe Gly Gly Arg Thr
    1100                1105                1110

Cys Ser Glu Cys Gln Glu Leu Phe Trp Gly Asp Pro Asp Val Glu
    1115                1120                1125

Cys Arg Ala Cys Asp Cys Asp Pro Arg Gly Ile Glu Thr Pro Gln
    1130                1135                1140

Cys Asp Gln Ser Thr Gly Gln Cys Val Cys Val Glu Gly Val Glu
    1145                1150                1155

Gly Pro Arg Cys Asp Lys Cys Thr Arg Gly Tyr Ser Gly Val Phe
    1160                1165                1170

Pro Asp Cys Thr Pro Cys His Gln Cys Phe Ala Leu Trp Asp Val
    1175                1180                1185

Ile Ile Ala Glu Leu Thr Asn Arg Thr His Arg Phe Leu Glu Lys
    1190                1195                1200

Ala Lys Ala Leu Lys Ile Ser Gly Val Ile Gly Pro Tyr Arg Glu
    1205                1210                1215

Thr Val Asp Ser Val Glu Arg Lys Val Ser Glu Ile Lys Asp Ile
    1220                1225                1230

Leu Ala Gln Ser Pro Ala Ala Glu Pro Leu Lys Asn Ile Gly Asn
    1235                1240                1245

Leu Phe Glu Glu Ala Glu Lys Leu Ile Lys Asp Val Thr Glu Met
    1250                1255                1260

Met Ala Gln Val Glu Val Lys Leu Ser Asp Thr Thr Ser Gln Ser
    1265                1270                1275

Asn Ser Thr Ala Lys Glu Leu Asp Ser Leu Gln Thr Glu Ala Glu
    1280                1285                1290

Ser Leu Asp Asn Thr Val Lys Glu Leu Ala Glu Gln Leu Glu Phe
    1295                1300                1305

Ile Lys Asn Ser Asp Ile Arg Gly Ala Leu Asp Ser Ile Thr Lys
    1310                1315                1320

Tyr Phe Gln Met Ser Leu Glu Ala Glu Glu Arg Val Asn Ala Ser
    1325                1330                1335

Thr Thr Glu Pro Asn Ser Thr Val Glu Gln Ser Ala Leu Met Arg
    1340                1345                1350

Asp Arg Val Glu Asp Val Met Met Glu Arg Glu Ser Gln Phe Lys
    1355                1360                1365

Glu Lys Gln Glu Glu Gln Ala Arg Leu Leu Asp Glu Leu Ala Gly
    1370                1375                1380

Lys Leu Gln Ser Leu Asp Leu Ser Ala Ala Ala Glu Met Thr Cys
    1385                1390                1395

Gly Thr Pro Pro Gly Ala Ser Cys Ser Glu Thr Glu Cys Gly Gly
    1400                1405                1410

Pro Asn Cys Arg Thr Asp Glu Gly Glu Arg Lys Cys Gly Gly Pro
    1415                1420                1425

Gly Cys Gly Gly Leu Val Thr Val Ala His Asn Ala Trp Gln Lys
    1430                1435                1440

Ala Met Asp Leu Asp Gln Asp Val Leu Ser Ala Leu Ala Glu Val
    1445                1450                1455

Glu Gln Leu Ser Lys Met Val Ser Glu Ala Lys Leu Arg Ala Asp
    1460                1465                1470
```

```
Glu Ala Lys Gln Ser Ala Glu Asp Ile Leu Leu Lys Thr Asn Ala
    1475                1480                1485

Thr Lys Glu Lys Met Asp Lys Ser Asn Glu Glu Leu Arg Asn Leu
    1490                1495                1500

Ile Lys Gln Ile Arg Asn Phe Leu Thr Gln Asp Ser Ala Asp Leu
    1505                1510                1515

Asp Ser Ile Glu Ala Val Ala Asn Glu Val Leu Lys Met Glu Met
    1520                1525                1530

Pro Ser Thr Pro Gln Gln Leu Gln Asn Leu Thr Glu Asp Ile Arg
    1535                1540                1545

Glu Arg Val Glu Ser Leu Ser Gln Val Glu Val Ile Leu Gln His
    1550                1555                1560

Ser Ala Ala Asp Ile Ala Arg Ala Glu Met Leu Leu Glu Glu Ala
    1565                1570                1575

Lys Arg Ala Ser Lys Ser Ala Thr Asp Val Lys Val Thr Ala Asp
    1580                1585                1590

Met Val Lys Glu Ala Leu Glu Glu Ala Glu Lys Ala Gln Val Ala
    1595                1600                1605

Ala Glu Lys Ala Ile Lys Gln Ala Asp Glu Asp Ile Gln Gly Thr
    1610                1615                1620

Gln Asn Leu Leu Thr Ser Ile Glu Ser Glu Thr Ala Ala Ser Glu
    1625                1630                1635

Glu Thr Leu Phe Asn Ala Ser Gln Arg Ile Ser Glu Leu Glu Arg
    1640                1645                1650

Asn Val Glu Glu Leu Lys Arg Lys Ala Ala Gln Asn Ser Gly Glu
    1655                1660                1665

Ala Glu Tyr Ile Glu Lys Val Val Tyr Thr Val Lys Gln Ser Ala
    1670                1675                1680

Glu Asp Val Lys Lys Thr Leu Asp Gly Glu Leu Asp Glu Lys Tyr
    1685                1690                1695

Lys Lys Val Glu Asn Leu Ile Ala Lys Lys Thr Glu Glu Ser Ala
    1700                1705                1710

Asp Ala Arg Arg Lys Ala Glu Met Leu Gln Asn Glu Ala Lys Thr
    1715                1720                1725

Leu Leu Ala Gln Ala Asn Ser Lys Leu Gln Leu Leu Lys Asp Leu
    1730                1735                1740

Glu Arg Lys Tyr Glu Asp Asn Gln Arg Tyr Leu Glu Asp Lys Ala
    1745                1750                1755

Gln Glu Leu Ala Arg Leu Gly Glu Val Arg Ser Leu Leu Lys
    1760                1765                1770

Asp Ile Ser Gln Lys Val Ala Val Tyr Ser Thr Cys Leu
    1775                1780                1785

<210> SEQ ID NO 124
<211> LENGTH: 72
<212> TYPE: PRT
<213> ORGANISM: Artificial
<220> FEATURE:
<223> OTHER INFORMATION: human(h) KRS N terminal peptide fragments

<400> SEQUENCE: 124

Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
            20                  25                  30
```

```
Val Ala Glu Lys Glu Ala Lys Gln Lys Glu Leu Ser Glu Lys Gln Leu
            35                  40                  45

Ser Gln Ala Thr Ala Ala Ala Thr Asn His Thr Thr Asp Asn Gly Val
    50                  55                  60

Gly Pro Glu Glu Glu Ser Val Asp
65                  70

<210> SEQ ID NO 125
<211> LENGTH: 72
<212> TYPE: PRT
<213> ORGANISM: Artificial
<220> FEATURE:
<223> OTHER INFORMATION: mouse(m) KRS N terminal peptide fragments

<400> SEQUENCE: 125

Met Ala Thr Leu Gln Glu Ser Glu Val Lys Val Asp Gly Glu Gln Lys
1               5                   10                  15

Leu Ser Lys Asn Glu Leu Lys Arg Arg Leu Lys Ala Glu Lys Lys Leu
            20                  25                  30

Ala Glu Lys Glu Ala Lys Gln Lys Glu Leu Ser Glu Lys Gln Leu Asn
            35                  40                  45

Gln Thr Ala Ser Ala Pro Asn His Thr Ala Asp Asn Gly Val Gly Ala
    50                  55                  60

Glu Glu Glu Thr Leu Asp Pro Asn
65                  70

<210> SEQ ID NO 126
<211> LENGTH: 72
<212> TYPE: PRT
<213> ORGANISM: Artificial
<220> FEATURE:
<223> OTHER INFORMATION: rat(r) KRS N terminal peptide fragments

<400> SEQUENCE: 126

Met Ala Thr Leu Arg Glu Gly Glu Val Lys Leu Asp Gly Glu Pro Lys
1               5                   10                  15

Leu Ser Lys Asn Glu Leu Lys Arg Arg Leu Lys Ala Glu Lys Lys Leu
            20                  25                  30

Ala Glu Lys Glu Ala Lys Gln Lys Glu Leu Ser Glu Leu Gln Leu Asn
            35                  40                  45

Gln Thr Thr Ala Ala Ala Thr Asn His Thr Ala Asp Asn Gly Val
    50                  55                  60

Gly Ala Glu Glu Glu Thr Leu Asp
65                  70
```